US011560373B2

(12) United States Patent
Adam et al.

(10) Patent No.: US 11,560,373 B2
(45) Date of Patent: Jan. 24, 2023

(54) COMPOUNDS AND THEIR USE AS PDE4 ACTIVATORS

(71) Applicant: Mironid Limited, North Lanarkshire (GB)

(72) Inventors: Julia Mary Adam, North Lanarkshire (GB); David Roger Adams, North Lanarkshire (GB); Santosh Shripad Kulkarni, Bangalore (IN); Rahul Shripad Nandurdikar, Bangalore (IN)

(73) Assignee: Mironid Limited, North Lanarkshire (GB)

( * ) Notice: Subject to any disclaimer, the term of this patent is extended or adjusted under 35 U.S.C. 154(b) by 0 days.

(21) Appl. No.: 17/044,007

(22) PCT Filed: Apr. 4, 2019

(86) PCT No.: PCT/GB2019/050976
§ 371 (c)(1),
(2) Date: Sep. 30, 2020

(87) PCT Pub. No.: WO2019/193342
PCT Pub. Date: Oct. 10, 2019

(65) Prior Publication Data
US 2021/0032231 A1 Feb. 4, 2021

(30) Foreign Application Priority Data
Apr. 4, 2018 (GB) .................... 1805527

(51) Int. Cl.
| C07D 413/12 | (2006.01) |
| C07D 249/08 | (2006.01) |
| C07D 401/12 | (2006.01) |
| C07D 403/12 | (2006.01) |
| C07D 405/12 | (2006.01) |

(52) U.S. Cl.
CPC ......... *C07D 413/12* (2013.01); *C07D 249/08* (2013.01); *C07D 401/12* (2013.01); *C07D 403/12* (2013.01); *C07D 405/12* (2013.01)

(58) Field of Classification Search
CPC .. C07D 413/12; C07D 249/08; C07D 401/12; C07D 403/12
See application file for complete search history.

(56) References Cited

U.S. PATENT DOCUMENTS

| 7,726,930 | B2 | 6/2010 | Simpson et al. |
| 10,385,027 | B2 | 8/2019 | Adam |
| 2004/0192743 | A1 | 9/2004 | Mjalli et al. |
| 2005/0137168 | A1 | 6/2005 | Gobbi et al. |
| 2009/0186900 | A1 | 7/2009 | Vicker et al. |
| 2010/0144733 | A1 | 6/2010 | Doyle et al. |
| 2010/0222336 | A1 | 9/2010 | Konetzki et al. |
| 2010/0267741 | A1 | 10/2010 | Penrose et al. |
| 2012/0053218 | A1 | 3/2012 | Bruggemeier et al. |
| 2013/0150341 | A1 | 6/2013 | Grauert et al. |
| 2013/0184248 | A1 | 7/2013 | Grauert et al. |
| 2014/0302988 | A1 | 10/2014 | Gienckle et al. |
| 2020/0002296 | A1 | 1/2020 | Adam |

FOREIGN PATENT DOCUMENTS

| EP | 0936221 A1 | 8/1999 |
| JP | 2006518738 A | 8/2004 |
| JP | 2006523719 A | 10/2006 |
| JP | S51082269 | 6/2018 |
| WO | 2004071447 A2 | 8/2004 |
| WO | 2004094411 A1 | 11/2004 |
| WO | 2007097927 A3 | 1/2008 |
| WO | 2009131956 A1 | 10/2009 |
| WO | 2010131194 A1 | 11/2010 |
| WO | 2010131195 A1 | 11/2010 |
| WO | 2010059838 A3 | 12/2010 |
| WO | 2011127019 A2 | 10/2011 |
| WO | 2013021044 A1 | 2/2013 |
| WO | 2014150326 A1 | 9/2014 |
| WO | 2015175956 A1 | 11/2015 |
| WO | 2016151300 A1 | 9/2016 |
| WO | 2017044828 A1 | 3/2017 |
| WO | 2018060704 A1 | 4/2018 |

OTHER PUBLICATIONS

Aandahl et al., Protein kinase A type I antagonist restores immune responses of T cells from HIV-infected patients; The FASEB Journal, vol. 12, Jul. 1, 1998 pp. 855-862.

Agarwal et al., Cyclic AMP intoxication of macrophages by a *Mycobacterium tuberculosis* adenylate cyclase; Nature, vol. 460, Jul. 2, 2009 pp. 98-102.

Ahuja et al., The Adenylate Cyclase Toxins; Critical Reviews in Microbiology, vol. 30, Oct. 19, 2008 pp. 187-196.

Almahariq et al., A novel EPAC-specific inhibitor suppresses pancreatic cancer cell migration and invasion; Molecular Pharmacology, vol. 83, Jan. 2013 pp. 122-128.

Arturi et al., Thyroid hyperfunctioning adenomas with and without Gsp/TSH receptor mutations show similar clinical features; Experimental and Clinical Endocrinology & Diabetes, vol. 106, 1998 pp. 234-236.

Azevedo et al., The transcriptome that mediates increased cyclic adenosine monophosphate signaling in PRKAR1A defects and other settings; Endocrine Practice, vol. 17, Jul. 2011 pp. 2-7.

Baljinnyam et al., Epac1 promotes melanoma metastasis via modification of heparan sulfate; Pigment Cell & Melanoma Research, vol. 24, Apr. 19, 2011 pp. 680-687.

Belibi et al., Novel targets for the treatment of autosomal dominant polycystic kidney disease; Expert Opinion on Investigational Drugs, vol. 19, Mar. 2010 pp. 315-328.

(Continued)

*Primary Examiner* — Samira J Jean-Louis
(74) *Attorney, Agent, or Firm* — McNeill Baur PLLC

(57) ABSTRACT

The present invention relates to compounds as defined herein, which are activators of long form cyclic nucleotide phosphodiesterase-4 (PDE4) enzymes (isoforms) and to therapies using these activators. In particular, the invention relates to these activator compounds for use in a method for the treatment or prevention of disorders requiring a reduction of second messenger responses mediated by cyclic 3',5'-adenosine monophosphate (cAMP).

24 Claims, 3 Drawing Sheets

(56) References Cited

OTHER PUBLICATIONS

Biebermann et al., The First Activating TSH Receptor Mutation in Transmembrane Domain 1 Identified in a Family with Nonautoimmune Hyperthyroidism; The Journal of Clinical Endocrinology & Metabolism, vol. 86. Sep. 1, 2001 pp. 4429-4433.
Bolger et al., Dimerization of cAMP phosphodiesterase-4 (PDE4) in living cells requires interfaces located in both the UCR1 and catalytic unit domains; Cellular Signalling, vol. 27, Apr. 2015 pp. 756-769.
Breckler et al., Rap-linked cAMP signaling Epac proteins: compartmentation, functioning and disease implications; Cellular Signalling, vol. 23, Aug. 2011 pp. 1257-1266.
Burgin et al., Design of phosphodiesterase 4D (PDE4D) allosteric modulators for enhancing cognition with improved safety; Nature Biotechnology, vol. 28, Jan. 28, 2010 pp. 63-70.
Calvi et al., The PTH/PTHrP receptor in Jansen's metaphyseal chondrodysplasia; Journal of Endocrinological Investigation, vol. 23, Sep. 2000 pp. 545-554.
Cho et al., CREB and Leukemogenesis; Critical reviews in oncogenesis, vol. 16, 2011 pp. 37-46.
Crans-Vargas et al., Expression of cyclic adenosine monophosphate response-element binding protein in acute leukemia; Blood, vol. 99, May 2002 pp. 2617-2619.
Diaz et al., McCune-Albright Syndrome and Disorders Due to Activating Mutations of GNAS1; Journal of Pediatric Endocrinology and Metabolism, vol. 20, Apr. 4, 2007 pp. 853-880.
Duprez et al., Germline mutations in the thyrotropin receptor gene cause non-autoimmune autosomal dominant hyperthyroidism; Nature Genetics, vol. 7, Jul. 1994 pp. 396-401.
Francis, et al. A Convenient Synthesis of 3, 5-Disubstituted-1, 2, 4-Triazoles; Tetrahedron Letters, Pergamon, GB, vol. 28, No. 43 Jan. 1, 1987 pp. 5133-5136.
Gattone et al., Inhibition of renal cystic disease development and progression by a vasopressin V2 receptor antagonist; Nature Medicine, vol. 9, Oct. 2003 pp. 1323-1326.
Gevers et al., Somatostatin analogues for treatment of polycystic liver disease; Current Opinion in Gastroenterology, vol. 27, May 2011 pp. 294-300.
Gong et al., Somatostatin stimulates ductal bile absorption and inhibits ductal bile secretion in mice via SSTR2 on cholangiocytes; American Journal of Physiology—Cell Physiology, vol. 284, May 1, 2003 pp. C1205-1214.
Grange et al., The cAMP-specific Phosphodiesterase PDE4D3 is Regulated by Phosphatidic Acid Binding; Journal of Biological Chemistry, vol. 275, Aug. 9, 2000 pp. 33379-33387.
Gurney et al., Small molecule allosteric modulators of phosphodiesterase 4; Handbook of Experimental Pharmacology, vol. 204, 2011 pp. 167-192.
Henderson et al., The cAMP phosphodiesterase-4D7 (PDE4D7) is downregulated in androgen-independent prostate cancer cells and mediates proliferation by compartmentalising cAMP at the plasma membrane of VCaP prostate cancer cells; British Journal of Cancer, vol. 110, Mar. 4, 2014 pp. 1278-1287.
Holm et al., Impaired Secretion of IL-10 by T Cells from Patients with Common Variable Immunodeficiency-Involvement of Protein Kinase A Type I; Journal of Immunology, vol. 170, Jun. 1, 2003 pp. 5772-5777.
Horvath et al., A cAMP-specific phosphodiesterase (PDE8B) that is mutated in adrenal hyperplasia is expressed widely in human and mouse tissues: a novel PDE8B isoform in human adrenal cortex; European Journal of Human Genetics, vol. 16, Oct. 2008 pp. 1245-1253.
Horvath et al., A genome-wide scan identifies mutations in the gene encoding phosphodiesterase 11A4 (PDE11A) in individuals with adrenocortical hyperplasia; Nature Genetics, vol. 38, Jun. 11, 2006 pp. 794-800.
Horvath et al., Adrenal Hyperplasia and Adenomas are Associated with Inhibition of Phosphodiesterase 11A in Carriers of PDE11A Sequence Variants that are Frequent in the Population; Cancer Research, vol. 66, Dec. 2006 pp. 11571-11575.
Horvath et al., Functional Phosphodiesterase 11A Mutations May Modify the Risk of Familial and Bilateral Testicular Germ Cell Tumors; Cancer Research, vol. 69, Jul. 2009 pp. 5301-5306.
Horvath et al., Mutation in PDE8B, a cyclic AMP-specific phosphodiesterase in adrenal hyperplasia; The New England Journal of Medicine, vol. 358, Feb. 2008 pp. 750-752.
Houslay et al., The Multienzyme PDE4 Cyclic Adenosine Monophosphate-Specific Phosphodiesterase Family: Intracellular Targeting, Regulation, and Selective Inhibition by Compounds Exerting Anti-inflammatory and Antidepressant Actions; Advances in Pharmacology vol. 44, 1998 pp. 225-234.
Houslay, et al., cAMP-Specific phosphodiesterase-4 enzymes in the cardiovascular system: a molecular toolbox for generating compartmentalized cAMP signalling; Circulation Research, vol. 100, Apr. 13, 2007 pp. 950-966.
Houslay, et al., Phosphodiesterase-4 as a therapeutic target; Drug Discovery Today, vol. 10, No. 22, Nov. 2005 pp. 1503-1519.
Houslay, M.D., PDE4 cAMP-specific phosphodiesterases; Progress in Nucleic Acid Research and Molecular Biology, vol. 69, May 7, 2001 pp. 249-315.
International Search Report of International Application No. PCT/GB2016/050766 dated May 13, 2016; 13 pages.
International Search Report of International Application No. PCT/GB2017/052898 dated Dec. 5, 2017, 14 pages.
International Search Report of International Application No. PCT/GB2019/050976 dated May 23, 2019, 6 pages.
Janssen et al., Congenital disorders of glycosylation in hepatology: the example of polycystic liver disease; Journal of Hepatology, vol. 52, Mar. 2010 pp. 432-440.
Karges et al., TSH receptor mutation V509A causes familial hyperthyroidism by release of interhelical constraints between transmembrane helices TMH3 and TMH5; Journal of Endocrinology, vol. 186, Aug. 2005 pp. 377-385.
Kosugi et al., Characterization of heterogeneous mutations causing constitutive activation of the luteinizing hormone receptor in familial male precocious puberty; Human Molecular Genetics, vol. 4, Feb. 1, 1995 pp. 183-188.
Lania et al., cAMP pathway and pituitary tumorigenesis; Annales d'Endocrinologie, vol. 73, Apr. 2012 pp. 73-75.
Lania et al., G protein mutations in endocrine diseases; European Journal of Endocrinology, vol. 145, Nov. 2001 pp. 543-559.
Latronico et al., A novel mutation of the luteinizing hormone receptor gene causing male gonadotropin-independent precocious puberty; The Journal of Clinical Endocrinology and Metabolism, vol. 80, Aug. 1, 1995 pp. 2490-2494.
Lau et al., Development of a novel in vitro model to predict hepatic clearance using fresh, cryopreserved, and sandwich-cultured hepatocytes; Drug Metabolism and Disposition, vol. 30, Aug. 20, 2002 pp. 1446-1454.
Levy et al., Phosphodiesterase function and endocrine cells: links to human disease and roles in tumor development and treatment; Current Opinion in Pharmacology, vol. 11, Dec. 2011 pp. 689-697.
Libé et al., Frequent Phosphodiesterase 11A Gene (PDE11A) Defects in Patients with Carney Complex (CNC) Caused by PRKAR1A Mutations: PDE11A May Contribute to Adrenal and Testicular Tumors in CNC as a Modifier of the Phenotype; The Journal of Clinical Endocrinology and Metabolism, vol. 96, Jan. 1, 2011 pp. E208-214.
Libé et al., Phosphodiesterase 11A (PDE11A) and Genetic Predisposition to Adrenocortical Tumors; Cancer Research, vol. 14, Jun. 2008 pp. 4016-4024.
Lorenz et al., The cAMP/Epac1/Rap1 Pathway in Pancreatic Carcinoma; Pancreas, vol. 37, Jul. 2008 pp. 102-103.
Lugnier, C., Cyclic nucleotide phosphodiesterase (PDE) superfamily: A new target for the development of specific therapeutic agents; Pharmacology & Therapeutics, vol. 109, 2006 pp. 366-398.
Ma et al., Mutations of HNF-1? inhibit epithelial morphogenesis through dysregulation of SOCS-3; Proceedings of the National Academy of Sciences of the United States of America, vol. 104, Dec. 18, 2007 pp. 20386-20391.

(56) References Cited

OTHER PUBLICATIONS

Mackenzie et al., Long PDE4 cAMP specific phosphodiesterases are activated by protein kinase A-mediated phosphorylation of a single serine residue in Upstream Conserved Region 1 (UCR1); British Journal of Pharmacology, vol. 136, Jun. 2002 pp. 421-433.

Mancusi et al., HNF-1β mutation affects PKD2 and SOCS3 expression causing renal cysts and diabetes in MODY5 kindred; Journal of Nephrology, vol. 26, Jan. 2013 pp. 207-212.

Mao et al., Thiazolidinediones inhibit MDCK cyst growth through disrupting orientated cell division and apicobasal polarity; American Journal of Physiology—Renal Physiology, vol. 300(6), Jun. 2011 pp. F1375-F1384.

Marchmont et al., A peripheral and an intrinsic enzyme constitute the cyclic AMP phosphodiesterase activity of rat iver plasma membranes; Biochemical Journal, vol. 187, May 1, 1980 pp. 381-392.

Masoumi et al., Potential pharmacological interventions in polycystic kidney disease; Drugs, vol. 67, Jan. 1, 2007 pp. 2495-2510.

Masyuk et al., Octreotide inhibits hepatic cystogenesis in a rodent model of polycystic liver disease by reducing cholangiocyte adenosine 3′,5′-cyclic monophosphate; Gastroenterology, vol. 132, Mar. 2007 pp. 1104-1116.

Meng et al., "An Efficient and Recyclable Heterogeneous Catalytic System for the Synthesis of 1, 2, 4-triazoles using air as the oxidant" RSC Advances: An International Journal to Further Chemical Sciences, vol. 4, No. 17, Jan. 1, 2014 pp. 8612.

Merkle et al., Roles of cAMP and cAMP-dependent protein kinase in the progression of prostate cancer: cross-talk with the androgen receptor; Cellular Signalling, vol. 23, Mar. 2011 pp. 507-515.

Misra et al., Epac1?induced cellular proliferation in prostate cancer cells is mediated by B?Raf/ERK and mTOR signaling cascades; Journal of Cellular Biochemistry, vol. 108, Sep. 1, 2009 pp. 998-1011.

Misra et al., Upregulation of mTORC2 activation by the selective agonist of EPAC, 8-CPT-2Me-cAMP, in prostate cancer cells: Assembly of a multiprotein signaling complex; Journal of Cellular Biochemistry, vol. 113, 2012 pp. 1488-1500.

Nayjib et al., In vivo administration of a PKA type I inhibitor (Rp-8-Br-cAMPS) restores T-cell responses in retrovirus-infected mice; The Open Immunology Journal, vol. 170, 2008 pp. 20-24.

Parker et al., Insulin-like growth factor-1 induces hyperproliferation of PKD1 cystic cells via a Ras/Raf dependent signalling pathway; Kidney International, vol. 72(2), Mar. 28, 2007 pp. 157-165.

Persani et al., Induction of Specific Phosphodiesterase Isoforms by Constitutive Activation of the cAMP Pathway in Autonomous Thyroid Adenomas; The Journal of Clinical Endocrinology & Metabolism, vol. 85, Aug. 1, 2000 pp. 2872-2878.

Richter, et al., Dimerization of the Type 4 cAMP-specific Phosphodiesterases is Mediated by the Upstream Conserved Regions (UCRs)*; The Journal of Biological Chemistry, vol. 277, Oct. 25, 2002 pp. 40212-40221.

Shankar et al., The role of CREB as a proto-oncogene in hematopoiesis and in acute myeloid leukemia; Cancer Cell, vol. 7, Apr. 2005 pp. 351-362.

Strazzabosco et al., polycystic liver diseases: congenital disorders of cholangiocyte signaling; Gastroenterology, vol. 140, Jun. 1, 2011 pp. 1855-1859.

Sun et al., Drug discovery for polycystic kidney disease; Acta Pharmacologica Sinica, vol. 32, Jun. 1, 2011 pp. 805-816.

Sussman et al., Phosphodiesterase 1A Modulates Cystogenesis in Zebrafish; Journal of the American Society of Nephrology, vol. 25, Oct. 2014 pp. 2222-2230.

Takiar et al., Polycystic kidney disease: pathogenesis and potential therapies; Biochimica et Biophysica Acta, vol. 1812, Oct. 2011 pp. 1337-1343.

Thompson et al., G protein-coupled receptors disrupted in human genetic disease; Methods in Molecular Biology, vol. 448, Jan. 1, 2008 pp. 109-137.

Thompson et al., Multiple cyclic nucleotide phosphodiesterase activities from rat brain; Biochemistry, vol. 10, Jan. 19, 1971 pp. 311-316.

Torres et al., Effective treatment of an orthologous model of autosomal dominant polycystic kidney disease; Nature Medicine, vol. 10, Apr. 2004 pp. 363-364.

Tritos et al., Advances in medical therapies for Cushing's syndrome; Discovery Medicine, vol. 13, Feb. 2012 pp. 171-179.

United Kingdom Search Report issued in Application No. GB1504763.2, dated Dec. 15, 2015, 5 pages.

United Kingdom Search Report issued in Application No. GB1616439.4 dated Jul. 17, 2017, 4 pages.

United Kingdom Search Report issued in Application No. GB1805527.7 dated Nov. 28, 2018, 5 pages.

Vezzosi et al., Phosphodiesterases in endocrine physiology and disease; European Journal of Endocrinology, vol. 165, Aug. 2011 pp. 177-188.

Wade et al. Synthesis of the Triazolo[5,1-a][2,4] benzodiazepine Ring System; The Journal of Organic Chemistry, vol. 44, No. 1, Jan. 1, 1979 pp. 84-88.

Wallace, D., Cyclic AMP-mediated cyst expansion; Biochimica et Biophysica Acta, vol. 1812, Oct. 2011 pp. 1291-1300.

Wang et al., UCR1C is a novel activator of phosphodiesterase 4 (PDE4) long isoforms and attenuates cardiomyocyte hypertrophy; Cellular Signalling, vol. 27, May 2015 908-922.

Weinstein et al., Minireview: GNAS: Normal and Abnormal Functions; Endocrinology, vol. 145, Dec. 1, 2004 pp. 5459-5464.

Yamaguchi et al., cAMP stimulates the in vitro proliferation of renal cyst epithelial cells by activating the extracellular signal-regulated kinase pathway; Kidney International, vol. 57, Apr. 2000 pp. 1460-1471.

STN International, CAS Registry No. 1390593-23-3, 1389982-71-1, 1389956-05-1, 1387237-35-5, 1387237-06-0, 1386599-13-8, 1385933-63-0, 1355855-72-9, 1333866-08-2, 1333722-54-5, 1290014-46-8, 1279953-11-5, 1386223-24-0, File Registry (online), Entered STN, Aug. 12, 2021.

COMPOUNDS AND THEIR USE AS PDE4 ACTIVATORS

FIELD OF THE INVENTION

The present invention relates to compounds as defined herein, which are activators of long form cyclic nucleotide phosphodiesterase-4 (PDE4) enzymes (isoforms) and to therapies using these activators. In particular, the invention relates to these activator compounds for use in a method for the treatment or prevention of disorders requiring a reduction of second messenger responses mediated by cyclic 3',5'-adenosine monophosphate (cAMP).

BACKGROUND TO THE INVENTION

Cyclic 3',5'-adenosine monophosphate—"cAMP"—is a critical intracellular biochemical messenger that is involved in the transduction of the cellular effects of a variety of hormones, neurotransmitters, and other extracellular biological factors in most animal and human cells.

The intracellular concentration of cAMP is controlled by the relative balance between its rate of production and degradation. cAMP is generated by biosynthetic enzymes of the adenylyl cyclase superfamily and degraded by members of the cyclic nucleotide phosphodiesterase (PDE) superfamily. Certain members of the PDE superfamily, such as PDE4, specifically degrade cAMP, while others either specifically degrade cyclic guanosine monophosphate (cGMP) or degrade both cAMP and cGMP. PDE4 enzymes inactivate cAMP, thereby terminating its signalling, by hydrolysing cAMP to 5'-AMP (Lugnier, C. *Pharmacol Ther.* 109: 366-398, 2006).

Four PDE4 genes (PDE4A, PDE4B, PDE4C and PDE4D) have been identified, each of which encodes a number of different enzyme isoforms through the use of alternative promoters and mRNA splicing. On the basis of their primary structures, the catalytically active PDE4 splice variants can be classified as "long", "short" or "super-short" forms (Houslay, M. D. *Prog Nucleic Acid Res Mol Biol.* 69: 249-315, 2001). A "dead short" form also exists, which is not catalytically active (Houslay, M. D., Baillie, G. S. and Maurice, D. H. *Circ Res.* 100: 950-66, 2007). PDE4 long forms have two regulatory regions, called upstream conserved regions 1 and 2 (UCR1 and UCR2), located between their isoform-specific N-terminal portion and the catalytic domain. The UCR1 domain is absent in short forms, whereas the super-short forms not only lack UCR1, but also have a truncated UCR2 domain (Houslay, M. D., Schafer, P. and Zhang, K. *Drug Discovery Today* 10: 1503-1519, 2005).

PDE4 long forms, but not short forms, associate into dimers within cells (Richter, W and Conti, M. *J. Biol. Chem.* 277: 40212-40221, 2002; Bolger, G. B. et al., *Cell. Signal.* 27: 756-769, 2015). A proposed negative allosteric modulation of PDE4 long forms by small molecules has been reported (Burgin A. B. et al., *Nat. Biotechnol.* 28: 63-70, 2010; Gurney M. E. et al., *Handb. Exp. Pharmacol.* 204: 167-192, 2011).

It is known in the art that PDE4 long forms may be activated by endogenous cellular mechanisms, such as phosphorylation (MacKenzie, S. J. et al., *Br. J. Pharmacol.* 136: 421-433, 2002) and phosphatidic acid (Grange et al., *J. Biol. Chem.* 275: 33379-33387, 2000). Activation of PDE4 long forms by ectopic expression of a 57 amino acid protein (called 'UCR1C') whose precise sequence reflects part of that of the upstream conserved region 1 of PDE4D ('UCR1C' sequence reflects that of amino acids 80-136 while UCR is amino acids 17-136: numbering based on the PDE4D3 long isoform) has recently been reported (Wang, L. et al., *Cell. Signal.* 27: 908-922, 2015: "UCR1C is a novel activator of phosphodiesterase 4 (PDE4) long isoforms and attenuates cardiomyocyte hypertrophy"). The authors hypothesised that PDE4 activation might be used as a potential therapeutic strategy for preventing cardiac hypertrophy.

The first small molecules that act as activators of PDE4 long forms were disclosed in WO2016151300. No small molecule activators of PDE4 long forms have yet been reported in clinical development. There remains a need for further, structurally distinct small molecule activators of PDE4 long forms for potential development as therapeutic agents.

It is amongst the objects of the present invention to provide new small molecule activators of at least one of the long forms of PDE4 for use in a method of therapy, as well as specific disease treatment or prevention.

SUMMARY OF THE INVENTION

In a first aspect of the invention, there is provided a compound for use in therapy, wherein the compound is a compound of Formula I:

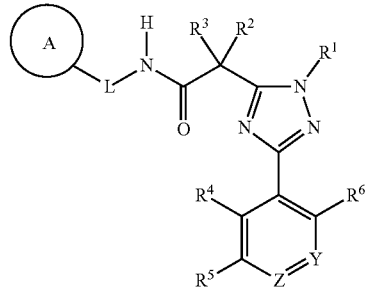

Formula I or a pharmaceutically acceptable salt or derivative thereof, wherein:

$R^1$ is (C1-6)alkyl, (C3-7)cycloalkyl, —C(O)X or —S(O)$_2$X, the (C1-6)alkyl and (C3-7)cycloalkyl groups being optionally substituted with one or more substituents (for example 1 to 3 substituents) independently selected from OH, (C1-4)alkyloxy, (C1-4)alkylsulfonyl, C(O)—NR$^9$R$^{10}$, C(O)—OR$^9$, S(O)$_2$—NR$^9$R$^{10}$, CN and halogen, the (C1-4)alkyloxy and (C1-4)alkylsulfonyl groups being optionally substituted with one or more fluoros;

X, when present, is (C1-6)alkyl or NR$^9$R$^{10}$, the (C1-6)alkyl group being optionally substituted with one or more substituents (for example 1 to 3 substituents) independently selected from OH, (C1-4)alkyloxy, CN and halogen;

$R^2$ and $R^3$ are independently selected from H, fluoro and (C1-4)alkyl, the (C1-4)alkyl being optionally substituted with one or more fluoros;

L is a linker —CR$^7$R$^8$— or L is absent;

$R^7$ and $R^8$ are independently selected from H and (C1-4)alkyl or $R^7$ and $R^8$, together with the carbon atom to which they are bonded, form a cyclopropyl, cyclobutyl or cyclopentyl group;

A is selected from a 6-membered aromatic ring, a 6-membered heteroaromatic ring that contains one to three N atoms, a 5-membered heteroaromatic ring that contains 1 to 3 heteroatoms selected from O, S and N, a fused 10-membered bicyclic aromatic ring system or heteroaromatic ring system that contains one to three N atoms, a fused 9-membered bicyclic heteroaromatic ring system that contains 1 to 3 heteroatoms selected from O, S and N, and a fused 9- or 10-membered bicyclic ring system that contains an aromatic or heteroaromatic ring fused to a non-aromatic carbocyclic or heterocyclic ring;

wherein A is optionally substituted with one or more substituents (for example 1 to 5 substituents) independently selected from (C1-4)alkyl, (C1-4)alkyloxy, (C1-4)alkylsulfonyl, C(O)—NR$^9$R$^{10}$, S(O)$_2$—NR$^9$R$^{10}$, OH, CN and halogen, the (C1-4)alkyl, (C1-4)alkyloxy and (C1-4)alkylsulfonyl groups being optionally substituted with one or more fluoros;

R$^4$ and R$^6$ are independently selected from H, (C1-4)alkyl, (C1-4)alkyloxy, CN and halogen, the (C1-4)alkyl and (C1-4)alkyloxy groups being optionally substituted with one or more fluoros;

R$^5$ is selected from H, (C1-4)alkyl, (C1-4)alkyloxy, —O—(CH$_2$)$_n$—O—(CH$_2$)$_m$CH$_3$, CN and halogen, the (C1-4)alkyl, (C1-4)alkyloxy and —O—(CH$_2$)$_n$—O—(CH$_2$)$_m$CH$_3$ groups being optionally substituted with OH or one or more fluoros;

Y and Z are independently selected from N and CR$^{11}$;

each R$^{11}$, when present, is independently selected from H, (C1-4)alkyl, (C1-4)alkyloxy, (C1-4)alkylsulfonyl, —O—(CH$_2$)$_n$—O—(CH$_2$)$_m$CH$_3$, CN and halogen, the (C1-4)alkyl, (C1-4)alkyloxy, (C1-4)alkylsulfonyl, and —O—(CH$_2$)$_n$—O—(CH$_2$)$_m$CH$_3$ groups being optionally substituted with OH or one or more fluoros;

each n is, independently, 1, 2, 3 or 4;

each m is, independently, 0 or 1; and each R$^9$ and R$^{10}$, when present, is independently selected from H and (C1-6)alkyl.

Compounds of Formula I are shown in the Examples to activate PDE4 long form enzymes.

In one aspect, the present invention provides a compound of Formula I for use in therapy. In an embodiment, the therapy is the treatment or prevention of a disease or disorder mediated by excessive intracellular cAMP signalling. In these diseases, a reduction of second messenger responses mediated by cyclic 3',5'-adenosine monophosphate (cAMP) should provide a therapeutic benefit. Also provided is a method of treating or preventing a disease or disorder mediated by excessive intracellular cAMP signalling, comprising the step of administering an effective amount of a compound of Formula I to a patient in need thereof. Also provided is the use of a compound of Formula I in the manufacture of a medicament for treating or preventing a disease or disorder mediated by excessive intracellular cAMP signalling.

A compound of Formula I can be provided in a pharmaceutical composition comprising a pharmaceutically acceptable excipient.

In certain embodiments of the foregoing aspects, the compounds of the invention are provided for the treatment or prevention of a condition selected from hyperthyroidism, Jansens's metaphyseal chondrodysplasia, hyperparathyroidism, familial male-limited precocious puberty, pituitary adenomas, Cushing's disease, polycystic kidney disease, polycystic liver disease, McCune-Albright syndrome, cholera, whooping cough, anthrax, tuberculosis, HIV, AIDS, Common Variable Immunodeficiency (CVID), melanoma, pancreatic cancer, leukaemia, prostate cancer, adrenocortical tumours, testicular cancer, primary pigmented nodular adrenocortical diseases (PPNAD), Carney Complex, autosomal dominant polycystic kidney disease (ADPKD), autosomal recessive polycystic kidney disease (ARPKD), maturity onset diabetes of young type 5 (MODY5), or cardiac hypertrophy.

DETAILED DESCRIPTION

Figure 1:
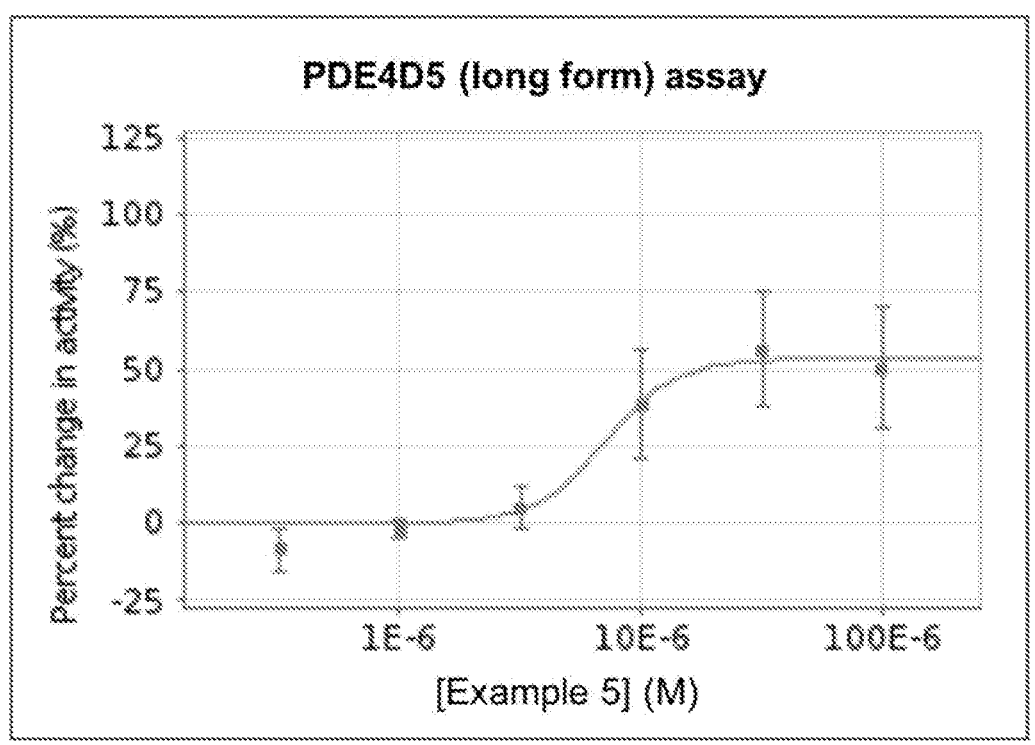
FIG. 1 shows dose-dependent activation of a PDE4 long form, PDE4D5, by Example 5.

The invention is based on the surprising identification of new compounds that are able to activate long isoforms of PDE4 enzymes. The compounds are small molecules and so are expected to be easier and cheaper to make and formulate into pharmaceuticals than large biological molecules such as polypeptides, proteins or antibodies. The compounds can be chemically synthesized, as demonstrated in the Examples.

The Examples demonstrate that a number of compounds of Formula I are able to activate long isoforms of PDE4. The Examples go on to demonstrate that certain tested compounds of the invention do not activate a short form of PDE4, thereby demonstrating selectivity for activation of PDE4 long forms over PDE4 short forms. The Examples further demonstrate that PDE4 long form activators reduce cAMP levels in a cellular assay.

Various aspects and embodiments are disclosed herein. It will be recognised that features specified in each embodiment may be combined with other specified features to provide further embodiments.

A first aspect provides a compound of Formula I, or a pharmaceutically acceptable salt or derivative thereof, as set out above.

In the compounds of Formula I, R$^1$ is (C1-6)alkyl, (C3-7)cycloalkyl, —C(O)X or —S(O)$_2$X, the (C1-6)alkyl and (C3-7)cycloalkyl groups being optionally substituted with one or more substituents independently selected from OH, (C1-4)alkyloxy, (C1-4)alkylsulfonyl, C(O)—NR$^9$R$^{10}$, C(O)—OR$^9$, S(O)$_2$—NR$^9$R$^{10}$, CN and halogen, the (C1-4)alkyloxy and (C1-4)alkylsulfonyl groups being optionally substituted with one or more fluoros. R$^1$ may, for example, be (C1-6)alkyl, (C3-7)cycloalkyl, —C(O)X or —S(O)$_2$X, the (C1-6)alkyl and (C3-7)cycloalkyl groups being optionally substituted with 1 to 3 substituents independently selected from OH, (C1-4)alkyloxy, (C1-4)alkylsulfonyl, C(O)—NR$^9$R$^{10}$, C(O)—OR$^9$, S(O)$_2$—NR$^9$R$^{10}$, CN and halogen, the (C1-4)alkyloxy and (C1-4)alkylsulfonyl groups being optionally substituted with one or more fluoros. In a further embodiment, R$^1$ is (C1-6)alkyl, (C3-7)cycloalkyl, or —S(O)$_2$X, the (C1-6)alkyl and (C3-7)cycloalkyl groups being optionally substituted with one or more (for example 1 to 3) substituents independently selected from OH, (C1-4)alkyloxy, (C1-4)alkylsulfonyl, C(O)—NR$^9$R$^{10}$, C(O)—OR$^9$, S(O)$_2$—NR$^9$R$^{10}$, CN and halogen, the (C1-4)alkyloxy and (C1-4)alkylsulfonyl groups being optionally substituted with one or more fluoros; and X, when present, is (C1-6)alkyl, the (C1-6)alkyl group being optionally substituted with 1 to 3 substituents independently selected from OH, (C1-4)alkyloxy, CN and halogen. In yet a further embodiment, $R^1$ is (C1-6)alkyl, (C3-7)cycloalkyl, or —S(O)$_2$X, the (C1-6)alkyl and (C3-7)cycloalkyl groups being optionally substituted with 1 to 3 substituents independently selected from OH, (C1-4)alkyloxy, (C1-4)alkylsulfonyl, C(O)—NR$^9$R$^{10}$, C(O)—OR$^9$, S(O)$_2$—NR$^9$R$^{10}$, CN and halogen, the (C1-4)alkyloxy and (C1-4)alkylsulfonyl groups being optionally substituted with one or more fluoros; and X, when present, is (C1-6)alkyl, the (C1-6)alkyl group being optionally substituted with one or more (for example 1 to 3) substituents independently selected from OH, (C1-4)alkyloxy, CN and halogen. In a further embodiment, $R^1$ is (C11-6)alkyl or (C3-7)cycloalkyl, the (C1-6)alkyl and (C3-7)cycloalkyl groups being optionally substituted with 1 to 3 substituents independently selected from OH, (C1-4)alkyloxy, C(O)—OR$^9$, CN and halogen, the (C1-4)alkyloxy group being optionally substituted with one or more fluoros. In a further embodiment, $R^1$ is (C1-6)alkyl or (C3-7)cycloalkyl, the (C1-6)alkyl and (C3-7)cycloalkyl groups being optionally substituted with 1 to 3 substituents independently selected from OH, (C1-4)alkyloxy, CN and halogen, the (C1-4)alkyloxy group being optionally substituted with one or more fluoros. In a further embodiment, $R^1$ is (C1-6)alkyl, optionally substituted with 1 to 3 substituents independently selected from OH, —C(O)OH, —C(O)OMe, —C(O)OEt, (C1-4)alkyloxy, CN and halogen. In a further embodiment, $R^1$ is (C1-6)alkyl, optionally substituted with 1 to 3 substituents independently selected from OH, (C1-4)alkyloxy, CN and halogen. In a further embodiment, $R^1$ is (C1-4)alkyl, optionally substituted with 1 to 3 substituents independently selected from OH, —C(O)OH, —C(O)OMe, —C(O)OEt, and (C1-2)alkyloxy. In a further embodiment, $R^1$ is (C1-4)alkyl, optionally substituted with 1 to 3 substituents independently selected from OH and (C1-2)alkyloxy. Exemplary $R^1$ moieties for a compound as disclosed herein include —CH$_3$, —CH$_2$CH$_3$, —CH$_2$CH$_2$OCH$_3$, —CH$_2$CH$_2$OH, —S(O)$_2$CH$_3$, —CH$_2$(cyclopropyl), —CH$_2$C(O)OCH$_3$, —CH$_2$C(O)OH, —CH$_2$CH$_2$C(O)OCH$_3$, —(CH$_2$)$_3$C(O)OCH$_2$CH$_3$, —CH$_2$CH$_2$C(O)OH and —(CH$_2$)$_3$C(O)OH. Exemplary $R^1$ moieties for a compound as disclosed herein include —CH$_3$, —CH$_2$CH$_3$, —CH$_2$CH$_2$OCH$_3$, —CH$_2$CH$_2$OH, —S(O)$_2$CH$_3$ and —CH$_2$(cyclopropyl). The remaining moieties may be as defined for any aspect or embodiment of Formula I described herein, mutatis mutandis.

In the compounds of Formula I, each $R^9$ and $R^{10}$, when present, is independently selected from H and (C1-6)alkyl. In an embodiment of the compounds of Formula I, including any of the embodiments thereof described above, each $R^9$ and $R^{10}$, when present, is independently selected from H and (C1-4)alkyl. In a further embodiment of the compounds of Formula I, including any of the embodiments thereof described above, each $R^9$ and $R^{10}$, when present, is independently selected from H and (C1-2)alkyl. The remaining moieties may be as defined for any aspect or embodiment of Formula I described herein, mutatis mutandis.

In the compounds of Formula I, $R^2$ and $R^3$ are independently selected from H, fluoro and (C1-4)alkyl, the (C1-4)alkyl being optionally substituted with one or more fluoros. In an embodiment of the compounds of Formula I, including any of the embodiments thereof described above, $R^2$ and $R^3$ are independently selected from H and (C1-4)alkyl. In an embodiment of the compounds of Formula I, including any of the embodiments thereof described above mutatis mutandis, $R^2$ and $R^3$ are independently selected from H, F and methyl. In an embodiment of the compounds of Formula I, including any of the embodiments thereof described above, $R^2$ and $R^3$ are independently selected from H and methyl. In a further embodiment of the compounds of Formula I, including any of the embodiments thereof described above mutatis mutandis, $R^2$ and $R^3$ are both H, $R^2$ and $R^3$ are both F or one of $R^2$ and $R^3$ is H and the other is methyl. In a further embodiment of the compounds of Formula I, including any of the embodiments thereof described above, $R^2$ and $R^3$ are both H, or one of $R^2$ and $R^3$ is H and the other is methyl. In an embodiment of the compounds of Formula I, including any of the embodiments thereof described above, $R^2$ and $R^3$ are H. The remaining moieties may be as defined for any aspect or embodiment of Formula I described herein, mutatis mutandis.

In the compounds of Formula I, $R^4$ and $R^6$ are independently selected from H, (C1-4)alkyl, (C1-4)alkyloxy, CN and halogen, the (C1-4)alkyl and (C1-4)alkyloxy groups being optionally substituted with one or more fluoros. In an embodiment of the compounds of Formula I, including any of the embodiments thereof described above, $R^4$ and $R^6$ are independently selected from H and F. In a further embodiment of the compounds of Formula I, including any of the embodiments thereof described above, $R^4$ and $R^6$ are H. The remaining moieties may be as defined for any aspect or embodiment of Formula I described herein, mutatis mutandis.

In the compounds of Formula I, $R^5$ is selected from H, (C1-4)alkyl, (C1-4)alkyloxy, —O—(CH$_2$)$_{n'}$—O—(CH$_2$)$_{m'}$CH$_3$, CN and halogen, the (C1-4)alkyl, (C1-4)alkyloxy and —O—(CH$_2$)$_{n'}$—O—(CH$_2$)$_{m'}$CH$_3$ groups being optionally substituted with OH or one or more fluoros. In an embodiment of the compounds of Formula I, including any of the embodiments thereof described above, $R^5$ is selected from H, (C1-4)alkyl, (C1-4)alkyloxy, CN and halogen, the (C1-4)alkyl and (C1-4)alkyloxy groups being optionally substituted with one or more fluoros. In an embodiment of the compounds of Formula I, including any of the embodiments thereof described above mutatis mutandis, $R^5$ is selected from H, (C1-3)alkyl, (C1-3)alkyloxy, —O—(CH$_2$)$_{n'}$—O—(CH$_2$)$_{m'}$CH$_3$, CN and halogen, the (C1-3)alkyl, (C1-3)alkyloxy and —O—(CH$_2$)$_{n'}$O—(CH$_2$)$_{m'}$CH$_3$ groups being optionally substituted with one or more fluoros, wherein n' is 1 or 2 and m' is 0. In an embodiment of the compounds of Formula I, including any of the embodiments thereof described above, $R^5$ is selected from H, (C1-2)alkyl, (C1-2)alkyloxy, CN and halogen, the (C1-2)alkyl and (C1-2)alkyloxy groups being optionally substituted with one or more fluoros. In a further embodiment of the compounds of Formula I, including any of the embodiments thereof described above, $R^5$ is H or F. In a further embodiment of the compounds of Formula I, including any of the embodiments thereof described above, $R^4$, $R^5$ and $R^6$ are, independently, H or F. In a further embodiment of the compounds of Formula I, including any of the embodiments thereof described above, $R^4$ and $R^6$ are H and $R^5$ is H or F. In a further embodiment of the compounds of Formula I, including any of the embodiments thereof described above, $R^4$, $R^5$ and $R^6$ are H. The remaining moieties may be as defined for any aspect or embodiment of Formula I described herein, mutatis mutandis.

In the compounds of Formula I, Y and Z are independently selected from N and CR$^{11}$, wherein R$^{11}$ is as defined herein. In a further embodiment of a compound of Formula I, including any of the embodiments thereof described above, Y is N and Z is CR$^{11}$. In a further embodiment, Y is CR$^{11}$ and Z is N. In a further embodiment, Y and Z are both CR$^{11}$. The remaining moieties may be as defined for any aspect or embodiment of Formula I described herein, mutatis mutandis. In the compounds of Formula I, each R$^{11}$, when present, is independently selected from H, (C1-4)alkyl, (C1-4)alkyloxy, (C1-4)alkylsulfonyl, —O—$(CH_2)_n$—O—$(CH_2)_m CH_3$, CN and halogen, the (C1-4)alkyl, (C1-4)alkyloxy, (C1-4)alkylsulfonyl, and —O—$(CH_2)_n$—O—$(CH_2)_m CH_3$ groups being optionally substituted with OH or one or more fluoros. In an embodiment of a compound of Formula I, including any of the embodiments thereof described above, each $R^{11}$, when present, is independently selected from H, (C1-4)alkyl, (C1-4)alkyloxy, (C1-4)alkylsulfonyl, CN and halogen, the (C1-4)alkyl, (C1-4)alkyloxy and (C1-4)alkylsulfonyl groups being optionally substituted with one or more fluoros. In an embodiment of a compound of Formula I, including any of the embodiments thereof described above, each $R^{11}$, when present, is independently selected from H, (C1-4)alkyl, (C1-4)alkyloxy, CN and halogen, the (C1-4)alkyl and (C1-4)alkyloxy groups being optionally substituted with 1 to 3 flouros. In an embodiment of the compounds of Formula I, including any of the embodiments thereof described above mutatis mutandis, $R^{11}$ is selected from H, (C1-3)alkyl, (C1-3)alkyloxy, —O—$(CH_2)_n$O—$(CH_2)_m CH_3$, CN and halogen, the (C1-3)alkyl, (C1-3)alkyloxy and —O—$(CH_2)_n$—O—$(CH_2)_m CH_3$ groups being optionally substituted with one or more fluoros, wherein n' is 1 or 2 and m' is 0. In a further embodiment of a compound of Formula I, including any of the embodiments thereof described above, each $R^{11}$, when present, is independently selected from H, (C1-2)alkyl, (C1-2)alkyloxy, CN and halogen, the (C1-2)alkyl and (C1-2)alkyloxy groups being optionally substituted with one or more fluoros. In a further embodiment of a compound of Formula I, including any of the embodiments thereof described above, each $R^{11}$, when present, is independently selected from H and halogen. The remaining moieties may be as defined for any aspect or embodiment of Formula I described herein, mutatis mutandis.

In an embodiment of a compound of Formula I, including any of the embodiments thereof described above, at least one instance of $R^5$ and $R^{11}$ is not H. In an embodiment of a compound of Formula I, including any of the embodiments thereof described above, at least one instance of $R^5$ and $R^{11}$ is H. In a further embodiment of a compound of Formula I, including any of the embodiments thereof described above, at least one instance of $R^5$ and $R^{11}$ is not H and at least one instance of $R^5$ and $R^{11}$ is H. In a further embodiment of a compound of Formula I, including any of the embodiments thereof described above, Y and Z are both $CR^{11}$, and (a) one instance of $R^5$ and $R^{11}$ is H and the remaining instances of $R^5$ and $R^{11}$ are independently selected from any option defined herein for $R^5$ and $R^{11}$, respectively, except for H; or (b) two instances of $R^5$ and $R^{11}$ are H and the remaining instance of $R^5$ and $R^{11}$ is selected from any option defined herein for $R^5$ and $R^{11}$, respectively, except for H. In a further embodiment of a compound of Formula I, including any of the embodiments thereof described above, Y and Z are both $CR^{11}$, $R^5$ is H and (a) each instance of $R^{11}$ is independently selected from (C1-4)alkyl, (C1-4)alkyloxy, —O—$(CH_2)_n$—O—$(CH_2)_m CH_3$, CN and halogen, the (C1-4)alkyl, (C1-4) alkyloxy, and —O—$(CH_2)_n$—O—$(CH_2)_m CH_3$ groups being optionally substituted with one or more fluoros; or (b) one instance of $R^{11}$ is H and the other instance of $R^{11}$ is selected from ((C1-4)alkyl, (C1-4)alkyloxy, —O—$(CH_2)_n$—O—$(CH_2)_m CH_3$, CN and halogen, the (C1-4)alkyl, (C1-4)alkyloxy, and —O—$(CH_2)_n$—O—$(CH_2)_m CH_3$ groups being optionally substituted with one or more fluoros. In a further embodiment of a compound of Formula I, including any of the embodiments thereof described above, Y and Z are both $CR^{11}$, $R^5$ is H and (a) each instance of $R^{11}$ is independently selected from (C1-3)alkyl, (C1-3)alkyloxy, —O—$(CH_2)_n$—O—$(CH_2)_m CH_3$, CN and halogen, the (C1-3)alkyl, (C1-3)alkyloxy and —O—$(CH_2)_n$—O—$(CH_2)_m$—$CH_3$ groups being optionally substituted with one or more fluoros wherein n' is 1 or 2 and m' is 0; or (b) one instance of $R^{11}$ is H and the other instance of $R^{11}$ is selected from (C1-3)alkyl, (C1-3)alkyloxy, —O—$(CH_2)_n$—O—$(CH_2)_m CH_3$, CN and halogen, the (C1-3)alkyl, (C1-3)alkyloxy and —O—$(CH_2)_n$—O—$(CH_2)_m CH_3$ groups being optionally substituted with one or more fluoros, wherein n' is 1 or 2 and m' is 0. In a further embodiment of a compound of Formula I, including any of the embodiments thereof described above, Y and Z are both $CR^{11}$, $R^5$ is H and (a) each instance of $R^{11}$ is independently selected from (C1-2)alkyl, (C1-2) alkyloxy, CN and halogen, the (C1-2)alkyl and (C1-2) alkyloxy groups being optionally substituted with one or more fluoros; or (b) one instance of $R^{11}$ is H and the other instance of $R^{11}$ is selected from (C1-2)alkyl, (C1-2)alkyloxy, CN and halogen, the (C1-2)alkyl and (C1-2)alkyloxy groups being optionally substituted with one or more fluoros. In a further embodiment of a compound of Formula I, including any of the embodiments thereof described above, Z is $CR^{11a}$, wherein $R^{11a}$ is selected from (C1-2)alkyl, (C1-2)alkyloxy, CN and halogen, the (C1-2)alkyl and (C1-2)alkyloxy groups being optionally substituted with one or more fluoros. In a further embodiment of a compound of Formula I, including any of the embodiments thereof described above, Z is $CR^{11a}$, wherein $R^{11a}$ is selected from methyl, methoxy, CN and halogen, the methyl and methoxy groups being optionally substituted with one to three fluoros. In a further embodiment of a compound of Formula I, including any of the embodiments thereof described above, Z is $CR^{11a}$, wherein $R^{11a}$ is selected from methyl, methoxy, CN and chloro, the methyl and methoxy groups being optionally substituted with one to three fluoros. The remaining moieties may be as defined for any aspect or embodiment of Formula I described herein, mutatis mutandis.

In the compounds of Formula I, L is a linker —$CR^7R^8$— or L is absent. $R^7$ and $R^8$ are independently selected from H and (C1-4)alkyl or $R^7$ and Re, together with the carbon atom to which they are bonded, form a cyclopropyl, cyclobutyl or cyclopentyl group. In an embodiment of a compound of Formula I, including any of the embodiments thereof described above, L is a linker —$CR^7R^8$— where $R^7$ and $R^8$ are independently selected from H and (C1-4)alkyl or L is absent. In an embodiment of a compound of Formula I, including any of the embodiments thereof described above, L is a linker —$CR^7R^8$— and $R^7$ and $R^8$ are both H.

In the compounds of Formula I, A is selected from a 6-membered aromatic ring, a 6-membered heteroaromatic ring that contains one to three N atoms, a 5-membered heteroaromatic ring that contains 1 to 3 heteroatoms selected from O, S and N, a fused 10-membered bicyclic aromatic ring system or heteroaromatic ring system that contains one to three N atoms, a fused 9-membered bicyclic heteroaromatic ring system that contains 1 to 3 heteroatoms selected from O, S and N, and a fused 9- or 10-membered bicyclic ring system that contains an aromatic or heteroaromatic ring fused to a non-aromatic carbocyclic or heterocyclic ring; wherein A is optionally substituted with one or more (for example one to five, one to three or one to two) substituents independently selected from (C1-4)alkyl, (C1-4)alkyloxy, (C1-4)alkylsulfonyl, C(O)—$NR^9R^{10}$, $S(O)_2$—$NR^9R^{10}$, OH, CN and halogen, the (C1-4)alkyl, (C1-4)alkyloxy and (C1-4)alkylsulfonyl groups being optionally substituted with one or more fluoros. In a further embodiment of a compound of Formula I, including any of the embodiments thereof described above, A is selected from a 6-membered aromatic ring, a 6-membered heteroaromatic ring that contains one to three N atoms, a 5-membered heteroaromatic ring that contains 1 to 3 heteroatoms selected from O, S and N, a fused 10-membered bicyclic aromatic ring system or heteroaromatic ring system that contains one to three N atoms, and a fused 9-membered bicyclic heteroaromatic ring system that contains 1 to 3 heteroatoms selected from O, S and N; wherein A is optionally substituted with one or more (for example one to five, one to three or one to two) substituents independently selected from (C1-4)alkyl, (C1-4)alkyloxy, (C1-4)alkylsulfonyl, C(O)—NR$^9$R$^{10}$, S(O)$_2$—NR$^9$R$^{10}$, OH, CN and halogen, the (C1-4)alkyl, (C1-4)alkyloxy and (C1-4)alkylsulfonyl groups being optionally substituted with one or more fluoros. In a further embodiment of a compound of Formula I, including any of the embodiments thereof described above, A is optionally substituted with one to three substituents independently selected from (C1-4)alkyl, (C1-4)alkyloxy, (C1-4)alkylsulfonyl, C(O)—NR$^9$R$^{10}$, S(O)$_2$—NR$^9$R$^{10}$, OH, CN and halogen, the (C1-4)alkyl, (C1-4) alkyloxy and (C1-4)alkylsulfonyl groups being optionally substituted with one or more fluoros, for example with 1 to 3 fluoros. In yet a further embodiment of a compound of Formula I, including any of the embodiments thereof described above, A is optionally substituted with one to three substituents independently selected from (C1-4)alkyl, (C1-4)alkyloxy, CN and halogen, the (C1-4)alkyl and (C1-4)alkyloxy groups being optionally substituted as described above, e.g. with 1 to 3 fluoros. In yet a further embodiment of a compound of Formula I, including any of the embodiments thereof described above, A is optionally substituted with one to three substituents independently selected from (C1-2)alkyl, (C1-2)alkyloxy, OH and halogen, the (C1-2) alkyl and (C1-2)alkyloxy groups being optionally substituted with one or more fluoros. In yet a further embodiment of a compound of Formula I, including any of the embodiments thereof described above, A is optionally substituted with one or two substituents as defined in any of the embodiments above. The remaining moieties may be as defined for any aspect or embodiment of Formula I described herein, mutatis mutandis.

In a further embodiment of a compound of Formula I, including any of the embodiments thereof described above mutatis mutandis, wherein A may be a fused 9- or 10-membered bicyclic ring system that contains an aromatic or heteroaromatic ring fused to a non-aromatic carbocyclic or heterocyclic ring, the fused 9- or 10-membered bicyclic ring system contains a 6-membered aromatic ring or a 6-membered heteroaromatic ring that contains 1 or 2 N atoms fused to a 5- or 6-membered non-aromatic carbocyclic ring or a 5- or 6-membered non-aromatic heterocyclic ring that contains 1 or 2 N, O or S atoms, and wherein A is optionally substituted as defined in relation to any of the embodiments above. In a further embodiment of a compound of formula I, including any of the embodiments thereof described above mutatis mutandis, A may be a fused 9- or 10-membered bicyclic ring system that contains a 6-membered aromatic ring or a 6-membered heteroaromatic ring that contains 1 or 2 N atoms fused to a 5- or 6-membered non-aromatic carbocyclic ring or a 5- or 6-membered non-aromatic heterocyclic ring that contains 1 O atom, and wherein A is optionally substituted as defined in relation to any of the embodiments above.

In a further embodiment of a compound of formula I, including any of the embodiments thereof described above mutatis mutandis, A may be a fused 9- or 10-membered bicyclic ring system that contains a 6-membered aromatic ring or a 6-membered heteroaromatic ring that contains 1 or 2 N atoms fused to a 5- or 6-membered non-aromatic carbocyclic ring or a 6-membered non-aromatic heterocyclic ring that contains 1 O atom, for example indane, chromane or 7-aza-2,3-dihydro-1H-indene, and wherein A is optionally substituted as defined in relation to any of the embodiments above. The remaining moieties may be as defined for any aspect or embodiment of Formula I described herein, mutatis mutandis.

In a further embodiment of a compound of Formula I, including any of the embodiments thereof described above, A is selected from a 6-membered heteroaromatic ring that contains one to three N atoms, a 5-membered heteroaromatic ring that contains 1 to 3 heteroatoms selected from O, S and N, a fused 10-membered bicyclic aromatic ring system or heteroaromatic ring system that contains one to three N atoms, and a fused 9-membered bicyclic heteroaromatic ring system that contains 1 to 3 heteroatoms selected from O, S and N, for example wherein A is benzimidazole, indazole, isoxazole or pyridine, and wherein A is optionally substituted as defined in relation to any of the embodiments above. The remaining moieties may be as defined for any aspect or embodiment of Formula I described herein, mutatis mutandis.

In a further embodiment of a compound of Formula I, including any of the embodiments thereof described above, A is a 6-membered aromatic ring, a 6-membered heteroaromatic ring that contains one or two N atoms, or a 5-membered heteroaromatic ring that contains one to three heteroatoms selected from O, S and N, wherein A is optionally substituted as defined for any of embodiments above, for example with one to three substituents independently selected from (C1-4)alkyl, (C1-4)alkyloxy, (C1-4)alkylsulfonyl, C(O)—NR$^9$R$^{10}$, S(O)$_2$—NR$^9$R$^{10}$, OH, CN and halogen, the (C1-4)alkyl, (C1-4)alkyloxy and (C1-4)alkylsulfonyl groups being optionally substituted with 1 to 3 fluoros. In a further embodiment, A is optionally substituted with one to three substituents independently selected from (C1-4)alkyl, (C1-4)alkyloxy, CN and halogen, the (C1-4) alkyl and (C1-4)alkyloxy groups being optionally substituted with 1 to 3 fluoros. In yet a further embodiment of a compound of Formula I, including any of the embodiments thereof described above, A is optionally substituted with one or two substituents as defined in any of the embodiments above. The remaining moieties may be as defined for any aspect or embodiment of Formula I described herein, mutatis mutandis.

In a further embodiment of a compound of Formula I, including any of the embodiments thereof described above, A is a phenyl or pyridyl ring, optionally substituted with one to three (or one to two) substituents independently selected from (C1-4)alkyl, (C1-4)alkyloxy, (C1-4)alkylsulfonyl, C(O)—NR$^9$R$^{10}$, S(O)$_2$—NR$^9$R$^{10}$, OH, CN and halogen, the (C1-4)alkyl, (C1-4)alkyloxy and (C1-4)alkylsulfonyl groups being optionally substituted with 1 to 3 fluoros. In a further embodiment of a compound of Formula I, including any of the embodiments thereof described above, A is:

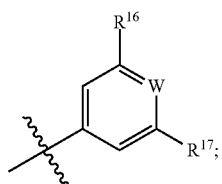

$R^{16}$ and $R^{17}$ are, independently selected from H, (C1-2)alkyl, (C1-2)alkyloxy, OH and halogen, the (C1-2)alkyl and (C1-2)alkyloxy groups being optionally substituted with one or more fluoros; W is $CR^{18}$ or N; and $R^{18}$ is selected from H, (C11-2)alkyl, (C1-2)alkyloxy, OH and halogen, the (C1-2)alkyl and (C1-2)alkyloxy groups being optionally substituted with one or more fluoros. In some embodiments, $R^{16}$ and $R^{17}$ are independently selected from H, (C1-2)alkyl, (C1-2)alkyloxy, OH and halogen, the (C1-2)alkyl and (C1-2)alkyloxy groups being optionally substituted with one or more fluoros; and W is N. In further embodiments, $R^{16}$ is H, $R^{17}$ is selected from (C1-2)alkyl, (C1-2)alkyloxy, OH and halogen, the (C1-2)alkyl and (C1-2)alkyloxy groups being optionally substituted with one or more fluoros, and W is N. In another embodiment, $R^{16}$ and $R^{17}$ are independently selected from (C1-2)alkyl, (C1-2)alkyloxy, OH and halogen, the (C1-2)alkyl and (C1-2)alkyloxy groups being optionally substituted with one or more fluoros; and W is N. The remaining moieties may be as defined for any aspect or embodiment of Formula I described herein, mutatis mutandis.

In a further embodiment A is a 4-pyridyl ring, optionally substituted with one to three (or one to two) substituents independently selected from (C1-4)alkyl, (C1-4)alkyloxy, CN and halogen, the (C1-4)alkyl and (C1-4)alkyloxy groups being optionally substituted with 1 to 3 fluoros. The remaining moieties may be as defined for any aspect or embodiment of Formula I described herein, mutatis mutandis.

In an embodiment of a compound of Formula I, $R^1$ is (C1-6)alkyl, (C3-7)cycloalkyl, —C(O)X or —S(O)$_2$X, the (C1-6)alkyl and (C3-7)cycloalkyl groups being optionally substituted with one or more substituents independently selected from OH, (C1-4)alkyloxy, (C1-4)alkylsulfonyl, C(O)—$NR^9R^{10}$, C(O)—$OR^9$, S(O)$_2$—$NR^9R^{10}$, CN and halogen, the (C1-4)alkyloxy and (C1-4)alkylsulfonyl groups being optionally substituted with one or more fluoros; X, when present, is (C1-6)alkyl or $NR^9R^{10}$, the (C1-6)alkyl group being optionally substituted with one or more substituents independently selected from OH, (C1-4)alkyloxy, CN and halogen; $R^2$ and $R^3$ are independently selected from H and (C1-4)alkyl; L is a linker —$CR^7R^8$— where $R^7$ and $R^8$ are independently selected from H and (C1-4)alkyl or L is absent; A is selected from a 6-membered aromatic ring, a 6-membered heteroaromatic ring that contains one to three N atoms, a 5-membered heteroaromatic ring that contains 1 to 3 heteroatoms selected from O, S and N, a fused 10-membered bicyclic aromatic ring system or heteroaromatic ring system that contains one to three N atoms, and a fused 9-membered bicyclic heteroaromatic ring system that contains 1 to 3 heteroatoms selected from O, S and N; wherein A is optionally substituted with one or more substituents independently selected from (C1-4)alkyl, (C1-4)alkyloxy, (C1-4)alkylsulfonyl, C(O)—$NR^9R^{10}$, S(O)$_2$—$NR^9R^{10}$, $NR^9R^{10}$, OH, CN and halogen, the (C1-4)alkyl, (C1-4)alkyloxy and (C1-4)alkylsulfonyl groups being optionally substituted with one or more fluoros; $R^4$ and $R^6$ are independently selected from H, (C1-4)alkyl, (C1-4)alkyloxy, CN and halogen, the (C1-4)alkyl and (C1-4)alkyloxy groups being optionally substituted with one or more fluoros; $R^5$ is selected from H, (C1-4)alkyl, (C1-4)alkyloxy, CN and halogen, the (C1-4)alkyl and (C1-4)alkyloxy groups being optionally substituted with OH or one or more fluoros; Y and Z are independently selected from N and $CR^{11}$; each $R^{11}$, when present, is independently selected from H, (C1-4)alkyl, (C1-4)alkyloxy, (C1-4)alkylsulfonyl, CN and halogen, the (C1-4)alkyl, (C1-4)alkyloxy and (C1-4)alkylsulfonyl groups being optionally substituted with OH or one or more fluoros; and each $R^9$ and $R^{10}$, when present, is independently selected from H and (C1-6)alkyl. In further embodiments, any of $R^1$ to $R^{10}$ may, independently, be as defined for any aspect or embodiment of Formula I described herein, mutatis mutandis.

In a further embodiment of a compound of Formula I, including any of the embodiments thereof described above, one or more hydrogen atoms are replaced by $^2$H. The remaining moieties may be as defined for any aspect or embodiment of Formula I described herein, mutatis mutandis.

It will be appreciated that the moieties described herein for aspects and embodiments of Formula I may be present in combination in a compound of Formula I, mutatis mutandis.

In an embodiment, the compound of Formula I is selected from:

2-[3-(4-chloro-3-fluorophenyl)-1-ethyl-1H-1,2,4-triazol-5-yl]-N-(3-fluorobenzyl)acetamide;
2-[3-(4-chloro-3-fluorophenyl)-1-ethyl-1H-1,2,4-triazol-5-yl]-N-(3-methoxybenzyl)acetamide;
2-[3-(4-chloro-3-fluorophenyl)-1-ethyl-1H-1,2,4-triazol-5-yl]-N-[(2,6-dimethylpyridin-4-yl)methyl]acetamide;
2-[3-(4-chloro-3-fluorophenyl)-1-ethyl-1H-1,2,4-triazol-5-yl]-N-[(1H-indazol-7-yl)methyl]acetamide;
2-[3-(4-chloro-3-fluorophenyl)-1-ethyl-1H-1,2,4-triazol-5-yl]-N-(3,5-dichlorobenzyl)acetamide;
2-[3-(4-chloro-3-fluorophenyl)-1-ethyl-1H-1,2,4-triazol-5-yl]-N-(5-methyl-1,2-oxazol-3-yl) acetamide;
2-[3-(4-chloro-3-fluorophenyl)-1-ethyl-1H-1,2,4-triazol-5-yl]-N-[(1H-indazol-5-yl)methyl]acetamide;
2-[3-(4-chloro-3-fluorophenyl)-1-ethyl-1H-1,2,4-triazol-5-yl]-N-(pyrazin-2-yl)acetamide;
2-[3-(4-chloro-3-fluorophenyl)-1-ethyl-1H-1,2,4-triazol-5-yl]-N-[(2-oxo-2,3-dihydro-1H-benzo[d]imidazol-5-yl)methyl]acetamide;
2-[3-(4-chloro-3-fluorophenyl)-1-ethyl-1H-1,2,4-triazol-5-yl]-N-[(3-chloro-5-methylphenyl)methyl] acetamide;
2-[3-(4-chloro-3-fluorophenyl)-1-ethyl-1H-1,2,4-triazol-5-yl]-N-[(3-fluoro-5-methylphenyl)methyl] acetamide;
2-[3-(4-chloro-3-fluorophenyl)-1-ethyl-1H-1,2,4-triazol-5-yl]-N-[(3,5-dimethylphenyl)methyl]acetamide;
2-[3-(4-chloro-3-fluorophenyl)-1-ethyl-1H-1,2,4-triazol-5-yl]-N-[(2,3-difluorophenyl)methyl]acetamide;
2-[3-(4-chloro-3-fluorophenyl)-1-ethyl-1H-1,2,4-triazol-5-yl]-N-[(3-ethoxyphenyl)methyl]acetamide;
2-[3-(4-chloro-3-fluorophenyl)-1-ethyl-1H-1,2,4-triazol-5-yl]-N-[(3,5-dimethoxyphenyl)methyl] acetamide;
2-[3-(4-chloro-3-fluorophenyl)-1-ethyl-1H-1,2,4-triazol-5-yl]-N-[(4-methoxyphenyl)methyl]acetamide;
2-[3-(4-chloro-3-fluorophenyl)-1-ethyl-1H-1,2,4-triazol-5-yl]-N-[(6-methoxypyridin-3-yl)methyl] acetamide;
2-[3-(4-chloro-3-fluorophenyl)-1-methyl-1H-1,2,4-triazol-5-yl]-N-[(3,5-dichlorophenyl)methyl]acetamide;
2-[3-(4-chloro-3-fluorophenyl)-1-methyl-1H-1,2,4-triazol-5-yl]-N-[(3-methoxyphenyl)methyl]acetamide;
2-[3-(4-chloro-3-fluorophenyl)-1-methyl-1H-1,2,4-triazol-5-yl]-N-[(3-fluorophenyl)methyl]acetamide;
2-[3-(4-chloro-3-fluorophenyl)-1-methyl-1H-1,2,4-triazol-5-yl]-N-[(1H-indazol-5-yl)methyl]acetamide;
2-[3-(4-chloro-3-fluorophenyl)-1-(2-methoxyethyl)-1H-1,2,4-triazol-5-yl]-N-[(3,5-dichlorophenyl)methyl] acetamide;
2-[3-(4-chloro-3-fluorophenyl)-1-(2-hydroxyethyl)-1H-1,2,4-triazol-5-yl]-N-[(3,5-dichlorophenyl)methyl] acetamide;
2-[3-(4-chloro-3-fluorophenyl)-1-ethyl-1H-1,2,4-triazol-5-yl]-N-[(3-fluorophenyl)methyl]propanamide;

2-[3-(4-chloro-3-fluorophenyl)-1-methanesulfonyl-1H-1,2,4-triazol-5-yl]-N-[(3-fluorophenyl)methyl]acetamide;
2-[3-(4-chloro-3-fluorophenyl)-1-(cyclopropylmethyl)-1H-1,2,4-triazol-5-yl]-N-[(2,6-dimethylpyridin-4-yl)methyl]acetamide;
2-[3-(4-chloro-3-fluorophenyl)-1-(cyclopropylmethyl)-1H-1,2,4-triazol-5-yl]-N-[(1H-indazol-5-yl)methyl]acetamide;
N-[(3,5-dichlorophenyl)methyl]-2-{1-ethyl-3-[4-(trifluoromethoxy)phenyl]-1H-1,2,4-triazol-5-yl}acetamide;
2-[3-(4-chloro-3-methoxyphenyl)-1-ethyl-1H-1,2,4-triazol-5-yl]-N-[(3,5-dichlorophenyl)methyl] acetamide;
2-[3-(4-cyanophenyl)-1-ethyl-1H-1,2,4-triazol-5-yl]-N-[(3,5-dichlorophenyl)methyl]acetamide;
2-[3-(4-chloro-3-fluorophenyl)-1-ethyl-1H-1,2,4-triazol-5-yl]-N-[(2,6-dimethyl-1-oxidopyridin-4-yl)methyl]acetamide;
2-[3-(4-chloro-3-ethoxyphenyl)-1-ethyl-1H-1,2,4-triazol-5-yl]-N-[(3,5-dichlorophenyl)methyl]acetamide;
2-{3-[4-chloro-3-(2-methoxyethoxy)phenyl]-1-ethyl-1H-1,2,4-triazol-5-yl}-N-[(3,5-dichlorophenyl)methyl]acetamide;
2-[3-(4-chloro-3-isopropyloxyphenyl)-1-ethyl-1H-1,2,4-triazol-5-yl]-N-[(3,5-dichlorophenyl)methyl]acetamide;
2-[3-(4-chloro-3-isopropyloxyphenyl)-1-ethyl-1H-1,2,4-triazol-5-yl]-N-[(2,6-dimethylpyridin-4-yl)methyl]acetamide;
2-[3-(4-chloro-3-isopropyloxyphenyl)-1-ethyl-1H-1,2,4-triazol-5-yl]-N-[(1S)-2,3-dihydro-1H-inden-1-yl]acetamide;
2-[3-(4-chloro-3-isopropyloxyphenyl)-1-ethyl-1H-1,2,4-triazol-5-yl]-N-[(3-cyanophenyl)methyl]acetamide;
2-[3-(4-chloro-3-isopropyloxyphenyl)-1-ethyl-1H-1,2,4-triazol-5-yl]-N-[(1H-indazol-5-yl)methyl]acetamide;
2-[3-(4-chloro-3-isopropyloxyphenyl)-1-ethyl-1H-1,2,4-triazol-5-yl]-N-[(4S)-3,4-dihydro-2H-1-benzopyran-4-yl]acetamide;
N-[(4S)-6-chloro-3,4-dihydro-2H-1-benzopyran-4-yl]-2-[3-(4-chloro-3-isopropyloxyphenyl)-1-ethyl-1H-1,2,4-triazol-5-yl]acetamide;
N-[(4R)-6-chloro-3,4-dihydro-2H-1-benzopyran-4-yl]-2-[3-(4-chloro-3-isopropyloxyphenyl)-1-ethyl-1H-1,2,4-triazol-5-yl]acetamide;
2-[3(4-chloro-3-isopropyloxyphenyl)-1-ethyl-1H-1,2,4-triazol-5-yl]-N-[(5S)-5H,6H,7H-cyclopenta[b]pyridin-5-yl]acetamide;
2-[3-(4-chloro-3-isopropyloxyphenyl)-1-methyl-1H-1,2,4-triazol-5-yl]-N-[(3,5-dichlorophenyl)methyl]acetamide;
2-[3-(4-chloro-3-isopropyloxyphenyl)-1-methyl-1H-1,2,4-triazol-5-yl]-N-[(1S)-2,3-dihydro-1H-inden-1-yl]acetamide;
2-[3-(4-chloro-3-isopropyloxyphenyl)-1-methyl-1H-1,2,4-triazol-5-yl]-N-[(2,6-dimethylpyridin-4-yl)methyl]acetamide;
2-[3-(4-chloro-3-isopropyloxyphenyl)-1-methyl-1H-1,2,4-triazol-5-yl]-N-[(3-fluorophenyl)methyl]acetamide;
2-[3-(4-chloro-3-isopropyloxyphenyl)-1-methyl-1H-1,2,4-triazol-5-yl]-N-[(4R)-3,4-dihydro-2H-1-benzopyran-4-yl]acetamide;
2-[3-(4-chloro-3-isopropyloxyphenyl)-1-methyl-1H-1,2,4-triazol-5-yl]-N-[(4S)-3,4-dihydro-2H-1-benzopyran-4-yl]acetamide;
N-[(4R)-6-chloro-3,4-dihydro-2H-1-benzopyran-4-yl]-2-[3-(4-chloro-3-isopropyloxyphenyl)-1-methyl-1H-1,2,4-triazol-5-yl]acetamide;
2-[3-(4-chloro-3-fluorophenyl)-1-ethyl-1H-1,2,4-triazol-5-yl]-N-[(3,5-dichlorophenyl)methyl]-2,2-difluoroacetamide;
2-[3-(4-chloro-3-fluorophenyl)-1-ethyl-1H-1,2,4-triazol-5-yl]-N-[(2,6-dimethylpyridin-4-yl)methyl]-2,2-difluoroacetamide;
2-[3-(4-chloro-3-fluorophenyl)-1-ethyl-1H-1,2,4-triazol-5-yl]-2,2-difluoro-N-[(2-methyl-1H-1,3-benzimidazol-5-yl)methyl]acetamide;
N-[(4S)-6-chloro-3,4-dihydro-2H-1-benzopyran-4-yl]-2-[3-(4-chloro-3-fluorophenyl)-1-ethyl-1H-1,2,4-triazol-5-yl]-2,2-difluoroacetamide;
methyl 2-[3-(4-chloro-3-fluorophenyl)-5-({[(3,5-dichlorophenyl)methyl] carbamoyl}methyl)-1H-1,2,4-triazol-1-yl]acetate;
methyl 3-[3-(4-chloro-3-fluorophenyl)-5-({[(3,5-dichlorophenyl)methyl] carbamoyl}methyl)-1H-1,2,4-triazol-1-yl]propanoate;
ethyl 4-[3-(4-chloro-3-fluorophenyl)-5-({[(3,5-dichlorophenyl)methyl] carbamoyl}methyl)-1H-1,2,4-triazol-1-yl]butanoate;
2-[3-(4-chloro-3-fluorophenyl)-5-({[(3,5-dichlorophenyl)methyl] carbamoyl}methyl)-1H-1,2,4-triazol-1-yl]acetic acid;
3-[3-(4-chloro-3-fluorophenyl)-5-({[(3,5-dichlorophenyl)methyl] carbamoyl}methyl)-1H-1,2,4-triazol-1-yl]propanoic acid;
4-[3-(4-chloro-3-fluorophenyl)-5-({[(3,5-dichlorophenyl)methyl] carbamoyl}methyl)-1H-1,2,4-triazol-1-yl]butanoic acid;
2-[3-(4-chloro-3-fluorophenyl)-1-ethyl-1H-1,2,4-triazol-5-yl]-N-[(1R)-2,3-dihydro-1H-inden-1-yl]acetamide;
2-[3-(4-chloro-3-fluorophenyl)-1-ethyl-1H-1,2,4-triazol-5-yl]-N-[(1S)-2,3-dihydro-1H-inden-1-yl]acetamide;
2-[3-(4-chloro-3-fluorophenyl)-1-ethyl-1H-1,2,4-triazol-5-yl]-N-[(1R,2S)-2-hydroxy-2,3-dihydro-1H-inden-1-yl]acetamide;
2-[3-(4-chloro-3-fluorophenyl)-1-ethyl-1H-1,2,4-triazol-5-yl]-N-[(1S,2R)-2-hydroxy-2,3-dihydro-1H-inden-1-yl]acetamide;
2-[3-(4-chloro-3-fluorophenyl)-1-ethyl-1H-1,2,4-triazol-5-yl]-N-[(1S,2S)-2-hydroxy-2,3-dihydro-1H-inden-1-yl]acetamide;
2-[3-(4-chloro-3-fluorophenyl)-1-ethyl-1H-1,2,4-triazol-5-yl]-N-[(1R,2R)-2-hydroxy-2,3-dihydro-1H-inden-1-yl]acetamide;
2-[3-(4-chloro-3-fluorophenyl)-1-ethyl-1H-1,2,4-triazol-5-yl]-N-(2,3-dihydro-1H-inden-2-yl)acetamide;
2-[3-(4-chloro-3-fluorophenyl)-1-ethyl-1H-1,2,4-triazol-5-yl]-N-[(1S,3R)-3-hydroxy-2,3-dihydro-1H-inden-1-yl]acetamide;
2-[3-(4-chloro-3-fluorophenyl)-1-ethyl-1H-1,2,4-triazol-5-yl]-N-[(1S,3S)-3-hydroxy-2,3-dihydro-1H-inden-1-yl]acetamide;
2-[3-(4-chloro-3-fluorophenyl)-1-ethyl-1H-1,2,4-triazol-5-yl]-N-[(1R,3R)-3-hydroxy-2,3-dihydro-1H-inden-1-yl]acetamide;
2-[3-(4-chloro-3-fluorophenyl)-1-ethyl-1H-1,2,4-triazol-5-yl]-N-[(1R,3S)-3-hydroxy-2,3-dihydro-1H-inden-1-yl]acetamide;
2-[3-(4-chloro-3-fluorophenyl)-1-(cyclopropylmethyl)-1H-1,2,4-triazol-5-yl]-N-[(5S)-5H,6H,7H-cyclopenta[b]pyridin-5-yl]acetamide;
2-[3-(4-chloro-3-fluorophenyl)-1-(cyclopropylmethyl)-1H-1,2,4-triazol-5-yl]-N-[(1S)-2,3-dihydro-1H-inden-1-yl]acetamide;

2-[3-(4-chloro-3-fluorophenyl)-1-ethyl-1H-1,2,4-triazol-5-yl]-N-[(2-oxo-2,3-dihydro-1,3-benzoxazol-5-yl)methyl]acetamide;
2-[3-(4-chloro-3-fluorophenyl)-1-ethyl-1H-1,2,4-triazol-5-yl]-N-[(4S)-3,4-dihydro-2H-1-benzopyran-4-yl]acetamide;
2-[3-(4-chloro-3-fluorophenyl)-1-ethyl-1H-1,2,4-triazol-5-yl]-N-[(4R)-3,4-dihydro-2H-1-benzopyran-4-yl]acetamide;
N-[(4S)-6-chloro-3,4-dihydro-2H-1-benzopyran-4-yl]-2-[3-(4-chloro-3-fluorophenyl)-1-ethyl-1H-1,2,4-triazol-5-yl]acetamide;
N-[(4R)-6-chloro-3,4-dihydro-2H-1-benzopyran-4-yl]-2-[3-(4-chloro-3-fluorophenyl)-1-ethyl-1H-1,2,4-triazol-5-yl]acetamide;
N-[(4S)-6-chloro-3,4-dihydro-2H-1-benzopyran-4-yl]-2-[3-(4-chloro-3-fluorophenyl)-1-(cyclopropylmethyl)-1H-1,2,4-triazol-5-yl]acetamide;
2-[3-(4-chloro-3-fluorophenyl)-1-ethyl-1H-1,2,4-triazol-5-yl]-N-{pyrazolo[1,5-a]pyridin-3-yl}acetamide;
2-[3-(4-chloro-3-fluorophenyl)-1-ethyl-1H-1,2,4-triazol-5-yl]-N-[(2,6-diethylpyridin-4-yl)methyl]acetamide;
2-[3-(4-chloro-3-fluorophenyl)-1-ethyl-1H-1,2,4-triazol-5-yl]-N-[(4,6-dimethylpyridin-2-yl)methyl]acetamide;
2-[3-(4-chloro-3-isopropyloxyphenyl)-1-ethyl-1H-1,2,4-triazol-5-yl]-N-[(4,6-dimethylpyridin-2-yl)methyl]acetamide;
2-[3-(4-chloro-3-fluorophenyl)-1-ethyl-1H-1,2,4-triazol-5-yl]-N-{[2-(trifluoromethyl)pyridin-4-yl]methyl}acetamide;
2-[3-(4-chloro-3-fluorophenyl)-1-ethyl-1H-1,2,4-triazol-5-yl]-N-{[2-(difluoromethyl)pyridin-4-yl]methyl}acetamide;
N-{[2,6-bis(difluoromethyl)pyridin-4-yl]methyl}-2-[3-(4-chloro-3-fluorophenyl)-1-ethyl-1H-1,2,4-triazol-5-yl]acetamide;
2-[3-(4-chloro-3-fluorophenyl)-1-ethyl-1H-1,2,4-triazol-5-yl]-N-[1-(2,6-dimethylpyridin-4-yl)cyclopropyl]acetamide;
2-[3-(4-chloro-3-fluorophenyl)-1-(cyclopropylmethyl)-1H-1,2,4-triazol-5-yl]-N-[1-(2,6-dimethylpyridin-4-yl)cyclopropyl]acetamide;
2-[3-(4-chloro-3-fluorophenyl)-1-ethyl-1H-1,2,4-triazol-5-yl]-N-{[2,6-di($^2$H$_3$)methylpyridin-4-yl]methyl}acetamide;
2-[3-(4-chloro-3-fluorophenyl)-1-ethyl-1H-1,2,4-triazol-5-yl]-N-{[2,6-di($^2$H$_3$)methylpyridin-4-yl]methyl}-2,2-difluoroacetamide;
2-[3-(4-chloro-3-fluorophenyl)-1-ethyl-1H-1,2,4-triazol-5-yl]-N-[(2,6-dimethylpyridin-4-yl)($^2$H$_2$)methyl]($^2$H$_2$)acetamide;
and pharmaceutically acceptable salts thereof.

Definitions

The term "aromatic ring" refers to an aromatic carbocyclic ring system. The term "heteroaromatic ring" refers to an aromatic ring system wherein one or more of the ring-forming atoms is a heteroatom such as O, S or N. In the definition of Formula I, in some embodiments A is an optionally substituted 6-membered aromatic ring. This aromatic ring is an optionally substituted phenyl ring. Alternatively, A may be a 6-membered heteroaromatic ring that contains one to three N atoms or a 5-membered heteroaromatic ring that contains one to three heteroatoms selected from O, S and N. Examples of such 6- or 5-membered heteroaromatic rings include pyridine, pyridazine, pyrazine, pyrimidine, thiophene, furan, thiazole, thiadiazole, oxazole, oxadiazole, imidazole, triazole and their isomers including isothiazole, isothiadiazole, isoxazole and isoxadiazole. Alternatively, in some embodiments A may be a fused 10-membered bicyclic aromatic ring system or heteroaromatic ring system that contains one to three N atoms, or a fused 9-membered bicyclic heteroaromatic ring system that contains 1 to 3 heteroatoms selected from O, S and N. Examples of such fused bicyclic ring systems include indazole, indole, naphthalene, quinoline, isoquinoline and benzimidazole. In all instances described above, A is optionally substituted as defined herein.

The term "carbocyclic ring" refers to a ring system with may be saturated, partially unsaturated or aromatic and wherein all ring forming atoms are carbon. The term "heterocyclic ring" refers to a ring system with may be saturated, partially unsaturated or aromatic and wherein one or more of the ring-forming atoms is a heteroatom such as O, S or N. A "non-aromatic carbocyclic or heterocyclic ring" may be saturated or partially unsaturated. In the definition of Formula I, in some embodiments A is an optionally substituted fused 9- or 10-membered bicyclic ring system that contains an aromatic or heteroaromatic ring fused to a non-aromatic carbocyclic or heterocyclic ring. Examples of such fused bicyclic ring systems include indane, chromane or 7-aza-2,3-dihydro-1H-indene. In all instances described above, A is optionally substituted as defined herein.

Unless otherwise defined, the term "alkyl" as used herein refers to a saturated hydrocarbon which may be straight-chain, branched, cyclic or a combination thereof. Alkyl groups include linear, branched or cyclic alkyl groups and hybrids thereof, such as (cycloalkyl)alkyl. The term "(C1-6)alkyl" as used herein means an alkyl group having 1-6 carbon atoms, which may be branched or unbranched and optionally contains a ring. Examples of (C1-6)alkyl include hexyl, cyclohexyl, pentyl, cyclopentyl, butyl, isobutyl, cyclobutyl, tertiary butyl, propyl, isopropyl, cyclopropyl, cyclopropylmethyl, ethyl and methyl. The term "(C1-4)alkyl" as used herein means a branched or unbranched alkyl group having 1-4 carbon atoms, optionally containing a ring. Examples of (C1-4)alkyl include butyl, isobutyl, cyclobutyl, tertiary butyl, propyl, isopropyl, cyclopropyl, cyclopropylmethyl, ethyl and methyl. A (C1-4)alkyl as referenced herein may preferably be a (C1-2)alkyl. Where specified in the formulae above, (C1-4)alkyl may be substituted, for example with 1 to 3 fluoros. A particularly preferred example of a substituted (C1-4)alkyl is trifluoromethyl. Alternatively (C1-4)alkyl may be unsubstituted.

The term "cycloalkyl" refers to a cyclic alkyl group, for example cycloheptyl, cyclohexyl, cyclopentyl, cyclobutyl or cyclopropyl.

The term "alkyloxy" means —O-alkyl wherein alkyl has the meaning as defined above. Examples of (C1-4)alkyloxy include methoxy, ethoxy, propoxy, isopropoxy, butoxy, isobutoxy and tertiary butoxy. A (C1-4)alkyloxy as referenced herein may preferably be a (C1-2)alkyloxy. Where specified in the formulae above, (C1-4)alkyloxy may be substituted, for example with 1 to 3 fluoros. A particularly preferred example of a substituted (C1-4)alkyloxy is trifluoromethoxy. Alternatively, (C1-4)alkyloxy may be unsubstituted. In the present invention, alkyloxy is attached to the rest of the molecule by the "oxy" moiety.

The term "alkylsulfonyl" means —S(O)$_2$-alkyl wherein alkyl has the meaning as defined above. In the present invention, alkylsulfonyl is attached to the rest of the molecule by the "sulfonyl" moiety.

The term "halogen" means F, Cl, Br or I. F and Cl are particularly preferred.

The 1,2,4-triazole derivatives of Formula I may be prepared by methods known in the art of organic chemistry in general. Suitable methods for constructing 1,2,4-triazole rings are, for example, described in the general reference Katritzky, A. R.: Comprehensive heterocyclic chemistry (First Edition, Pergamon Press, 1984, see especially Volume 5, Part 4A, Five-membered rings with two or more nitrogen atoms). Suitable protecting groups for functional groups which are to be temporarily protected during syntheses are known in the art, for example from Wuts, P. G. M. and Greene, T. W.: Protective Groups in Organic Synthesis, Fourth Edition, Wiley, New York, 2006.

Compounds of Formula I may be prepared by amide coupling of an amine (A-L-NH$_2$) with an appropriate carboxylic acid (see Experimental Details). Amines (A-L-NH$_2$) may be obtained from commercial sources or prepared by methods known in the art of organic chemistry in general. Certain chiral amines (A-L-NH$_2$) may be prepared in enantiomerically enriched form using methods described in Colyer et al, *J. Org. Chem.*, 71: 6859-6862, 2006. Examples of such chiral amines are 1-aminoindane, chroman-4-ylamine, 6,7-dihydro-5H-cyclopenta(b)pyridin-5-amine and substituted derivatives thereof.

Activation of Long PDE4 Isoforms

PDE4 long isoforms have two regulatory regions, upstream conserved region 1 (UCR1) and upstream conserved region 2 (UCR2). These are between the isoform-specific N-terminal portion and the catalytic domain. The UCR1 domain is missing in the short forms, whereas the super-short forms not only lack UCR1, but also have a N-terminal truncated UCR2 domain (Houslay, M. D., Schafer, P. and Zhang, K. *Drug Discovery Today* 10: 1503-1519, 2005).

There are four PDE4 families, PDE4A, PDE4B, PDE4C and PDE4D. The present invention concerns compounds that are capable of activating one or more of the long isoforms from one or more of these four families. The long isoform PDE4 may therefore be long isoform PDE4A, long isoform PDE4B, long isoform PDE4C or long isoform PDE4D. For the avoidance of doubt, a long isoform PDE4 contains a UCR1 region. In some embodiments, a long isoform PDE4 as referred to herein is human. UCR1 is conserved within mammalian species (Houslay, M D, Sullivan, M and Bolger G B *Adv. Pharmacol.* 44: 225-342, 1998), so in other embodiments, the long isoform PDE4 can be from a non-human mammal.

Without wishing to be bound by theory, PDE4 long form activators of Formula I of the present invention are small molecules that are believed to bind directly to PDE4 long forms and induce structural changes that increase, stabilise, uncover and/or maintain the catalytic activity of these enzymes. In the field of pharmacology, and as used herein, a small molecule is defined as a low molecular weight organic compound that may serve as a regulator of biological processes. Preferred small molecule activators according to the present invention have a molecular weight of less than or equal to 700 Daltons. This allows for the possibility to rapidly diffuse across cell membranes and reach intracellular sites of action (Veber, D. F. et al., *J. Med. Chem.* 45: 2615-2623, 2002). Especially preferred small molecule activators according to the present invention have molecular weights of greater than or equal to 250 Daltons and less than or equal to 500 Daltons (Lipinski, C. A. *Drug Discovery Today*: Technologies 1: 337-341, 2004).

One suitable method of detecting whether or not a compound is capable of serving as an activator of a PDE4 long form is using a two-step radio-assay procedure described in Experiment 1. In summary, the method involves incubating a PDE4 long form with a test small molecule activator, together with [$^3$H]-labelled cAMP to assess alterations in the breakdown of cAMP to the 5'-adenosine monophosphate (5'-AMP) product. A sample of the reaction mixture from such an incubation is subsequently treated with snake venom 5'-nucleotidase to allow conversion of the nucleotide [$^3$H]-labelled 5'-AMP to the uncharged nucleoside [$^3$H]-labelled adenosine, which can be separated and quantified to assess PDE4 activity and the effect of the test compound (Thompson, W. J. and Appleman, M. M. *Biochemistry* 10: 311-316, 1971, with some modifications as described in: Marchmont, R. J. and Houslay, M. D. *Biochem J.* 187: 381-92, 1980).

Using the above assay procedure, as described in detail in Experiment 1, preferred small molecule activators according to the present invention produce an increase in the background activity of one or more PDE4 long forms of more than 50% at a test compound concentration of 100 micromolar or less. Especially preferred small molecule activators according to the present invention produce an increase in the background activity of one or more PDE4 long forms of more than 50% at a test compound concentration of 10 micromolar, or less, for example 3 micromolar.

The compounds of the present invention may be selective for the long form of the PDE4 enzyme and, as such, do not act or act to a lesser extent as activators of the short or super-short isoforms of the PDE4 enzyme. The short or super-short isoform PDE4 may be short or super-short isoform PDE4A, short or super-short isoform PDE4B, short or super-short isoform PDE4C, or short or super-short isoform PDE4D. For the avoidance of doubt, short and super-short isoforms of PDE4 lack a UCR1 domain. Super-short isoforms are characterised by a truncated UCR2 domain and lack of a UCR1 domain. The short or super-short isoform PDE4 is, for example, human, but may also be from other mammalian species (where UCR2 is conserved, see Houslay, M D, Sullivan, M and Bolger GB *Adv. Pharmacol.* 44: 225-342, 1998).

Under the same assay conditions, as described in Experiment 1, the small molecule activators according to the present invention may produce a less than 50% increase in the background activity of the short or super-short forms of the PDE4A, PDE4B, PDE4C or PDE4D enzymes at a test compound concentration of 100 micromolar, or less.

Compounds of the invention may therefore provide a positive result in an assay for activation of a long form PDE4 and a negative result in an assay for activation of a short form (or super-short form) of PDE4.

PDE4 long isoforms include those now known as PDE4A4, PDE4A4/5, PDE4A5, PDE4A8, PDE4A10, PDE4A11, PDE4B1, PDE4B3, PDE4B4, PDE4C1, PDE4C2, PDE4C3, PDE4D3, PDE4D4, PDE4D5, PDE4D7, PDE4D8, PDE4D9 and PDE4D11. Further long isoforms may be or have already been identified or called by different nomenclature from any of the four PDE4 sub-families.

PDE4 short isoforms include PDE4A1, PDE4B2, PDE4D1 and PDE4D2. Further short isoforms may be or have already been identified or called by different nomenclature from any of the four PDE4 sub-families.

PDE4 super-short isoforms include PDE4B5, PDE4D6 and PDE4D10. Further super-short isoforms may be or have already been identified or called by different nomenclature from any of the four PDE4 sub-families.

The Examples below exemplify activity of compounds in the human PDE4D5 and PDE4B1 long isoforms and a lack of activity in the human PDE4B2 short isoform. Details of these isoforms and a number of the other known isoforms, including GenBank accession numbers, are provided in Tables A to D immediately below.

TABLE A

Examples of known PDE4A isoforms
PDE4A

| Isoform | accession | calculated size | SDS-PAGE (kDa) | Type |
|---|---|---|---|---|
| A1 (human) | U97583 | | 83 | S |
| A1 (rodent) | M26715, L27062 | | 76 | S |
| A4* (humanA5) | L20965 | | 125 | L |
| A5 (rodentA4) | L27057 | | 107 | L |
| A7** (human) | U18088 | | 37 | DS |
| A8 (rodent) | L36467 | 88 kDa | 98 | L |
| A10 (human) | AF110461 | 91 kDa | 121 | L |
| A11 (human) | AY618547 | 95 kDa | 126 | L |

L = Long; S = short; SS = Super-short; D = Dead short
*Note that the PDE4A4B clone is correct while PDE4A4A has a cloning artefact and PDE4A4C is a truncation artefact.
**Note that this species is C- as well as N-terminally truncated and so will NOT be detected by pan PDE4A antisera that detect all active forms.

TABLE B

Examples of known PDE4B Isoforms
PDE4B

| Isoform | accession | SDS-PAGE (kDa) | Type |
|---|---|---|---|
| B1 | L20966 | 104 | L |
| B2 | M97515, L20971 | 68 | S |
| B3 | U85048 | 103 | L |
| B4 | AF202733 | 84 | L |
| B5 | EF595686 | 58 | SS |

L = Long; S = short; SS = Super-short; D = Dead short

TABLE C

Examples of known PDE4C Isoforms
PDE4C

| Isoform Name | GenBank | Size (aa) |
|---|---|---|
| PDE4C1 (partial clone) | L20968 | 251 (partial) |
| PDE4C1 | Z46632 | 712 (Long) |
| PDE4C2 | U88712 | 606 (Long) |
| PDE4C3 | U88713 | 700 (Long) |
| PDE4C4 | U66346 | 791 (Long) |
| PDE4C5 | U66347 | 426 |
| PDE4C6 | U66348 | 518 |
| PDE4C7 | U66349 | 427 |

TABLE D

Examples of known PDE4D Isoforms
PDE4D

| Isoform | accession | calculated | SDS-PAGE (kDa) | Type |
|---|---|---|---|---|
| D1 | U50157, U79571 | 66 kDa | 68 | S |
| D2 | U50158, AFO12074 | 66 kDa | 68 | S |
| D3 | L20970, U50159 | 77 kDa | 95 | L |
| D4 | L20969 | 91 kDa | 119 | L |
| D5 | AFO12073 | 84 kDa | 105 | L |
| D6 (m) | AF536975 | 59 kDa | 59 | SS |
| D7 | AF536976 | 85 kDa | 103 | L |
| D8* | AF536977 | 78 kDa | 96 | L |
| D9 | AY245867 | 77 kDa | 95 | L |
| D10 | DQ665896 | 58 kDa | 58 | SS |
| D11 | EU489880 | 79 kDa | 95 | L |

L = Long; S = short; SS = Super-short; D = Dead short
*nb D8 was originally called PDE4D6 in the literature
(m) Memory clones are (AY245867, AF536977, AF536976)

Reduction of cAMP Levels

Without wishing to be bound by theory, the compounds of the present invention may function by reducing cAMP levels in one or more intracellular compartments. The PDE4 long form activators of the present invention may thus provide a means to regulate certain cellular processes that are dependent upon cAMP. Excessive intracellular cAMP signalling mediates a number of diseases and disorders. Therefore, the compounds of the invention are expected to be of utility for the treatment of diseases associated with abnormally elevated cAMP levels, increased cAMP-mediated signalling and/or reduced cAMP elimination, enzymatic or otherwise (e.g. via efflux). The treatment is typically of a human, but may also be of a non-human animal, such as a non-human mammal (e.g. veterinary treatment).

In one aspect, the present invention provides a small molecule activator of a PDE4 long form of Formula I, for use in a method for the treatment or prevention of disorders where a reduction of second messenger responses mediated by cyclic 3',5'-adenosine monophosphate (cAMP) is required.

For example, gain-of-function gene mutations in proteins involved in driving cAMP signalling upstream of adenylyl cyclase, such as GPCRs and Gsα, can lead to abnormal excessive cAMP activity with pathological consequences (Lania A, Mantovani G, Spada A. *Ann Endocrinol* (Paris). 73: 73-75, 2012; Thompson, M. D. et al., *Methods Mol. Biol.* 448: 109-137, 2008; Weinstein L S, Liu J, Sakamoto A, Xie T, Chen M. *Endocrinology.* 145: 5459-5464, 2004; Lania A, Mantovani G, Spada A. *Eur J Endocrinol.* 145: 543-559, 2001). PDE4 long form activators of the present invention, possessing the ability to accelerate the termination of cAMP action, would therefore be expected to be effective in the treatment, prevention or partial control of diseases characterised by undesirably high cAMP levels, or activity, as detailed below.

Diseases Characterised by Elevated cAMP Levels

Hyperthyroidism

Stimulation of the thyroid-stimulating hormone (TSH) receptor (TSHR) leads to increased generation and release of thyroid hormones, thyroxine and triiodothyronine, through a cAMP-dependent signalling mechanism involving Gsα-mediated activation of adenylyl cyclase. Gain-of-function mutations in the TSHR have been reported to be involved in the development of hyperthyroidism (Duprez, L. et al., *Nat. Genet.* 7: 396-401, 1994; Biebermann, H. et al., *J. Clin. Endocrinol. Metab.* 86: 4429-4433, 2001; Karges, B. et al., *J. Endocrinol.* 186: 377-385, 2005). Activating mutations of both TSHR and Gsα have also been found in goitre and thyroid adenomas (Arturi, F. et al., *Exp. Clin. Endocrinol. Diabetes* 106: 234-236, 1998). The increased cAMP activity in thyroid adenomas, as a result of the activating TSHR or Gsα mutations, has been reported to produce a protective adaptive increase in PDE4 activity to counteract abnormal rise in cAMP levels and signal transduction (Persani, L. et al., *J. Clin. Endocrinol. Metab.* 85: 2872-2878, 2000).

The most common cause of hyperthyroidism is Graves' disease, an autoimmune disorder in which antibodies mimic TSH action at the TSHR, leading to excessive cAMP activity in thyroid follicle cells and consequently a state of hyperthyroidism.

PDE4 long form activators of the present invention are therefore expected to be effective in the treatment, prevention or partial control of hyperthyroidism. In one embodiment, the hyperthyroidism is associated with Graves' disease.

Jansens's Metaphyseal Chondrodysplasia and Hyperparathyroidism

Jansens's Metaphyseal Chondrodysplasia (JMC) is a very rare disease resulting from gain-of-function mutations of the parathyroid hormone (PTH) receptor 1 (PTHR1) (Thompson, M. D. et al., *Methods Mol. Biol.* 448: 109-137, 2008). The constitutive activation of the PTHR1 which couples to adenylyl cyclase as effector is associated with excessive cAMP signalling primarily in bone and kidney, leading to dysregulation of ion homeostasis characterised by hypercalcemia and hypophosphatemia (Calvi, L. M. and Schipani, E. *J. Endocrinol. Invest.* 23: 545-554, 2000) and developmental (e.g. short stature) and physical (e.g. protruding eyes) abnormalities.

Primary hyperparathyroidism results from excessive release of PTH from the parathyroid gland due to tissue enlargement or non-cancerous adenoma. The resulting excessive stimulation of the PTHR1 receptor causes disruption of plasma ion homeostasis with patients showing hypercalcemia and hypophosphatemia. PDE4 long form activators of the present invention are therefore expected to be effective in the treatment, prevention or partial control of JMC and hyperparathyroidism.

Familial Male Precocious Puberty (Testotoxicosis)

Familial male-limited precocious puberty (FMPP), also known as familial sexual precocity or gonadotropin-independent testotoxicosis, is a disorder in which boys generally develop signs of precocious puberty in early childhood.

The spinal length in boys may be short due to a rapid advance in epiphyseal maturation. FMPP is an autosomal dominant condition with constitutively activating mutations in the luteinizing hormone (LH) receptor, which leads to increased cAMP production, associated with Leydig cell hyperplasia and low sperm cell count (Latronico, A. C. et al., *J Clin. Endocrinol. Metab.* 80: 2490-2494, 1995; Kosugi, S. et al., *Hum. Mol. Genet.* 4: 183-188, 1995). PDE4 long form activators of the present invention are therefore expected to be effective in the treatment, prevention or partial control of FMPP.

Pituitary Adenomas and Cushing's Disease

Non-cancerous tumours of the pituitary gland are collectively referred to as pituitary adenomas and can lead to hypersecretion of adenohypophyseal hormones (e.g. growth hormone, thyroid stimulating hormone, luteinizing hormone, follicle stimulating hormone and adrenocorticotrophic hormone), which exert their action through GPCRs coupled to Gs and cAMP generation. Thus pituitary adenomas can lead to a state of enhanced cAMP mediated signalling in a variety of endocrine tissues which can precipitate a number of hormonal disorders such as acromegly (mainly due to excess growth hormone secretion), Cushing's disease (due to overproduction of adrenocorticotrophic hormone (ACTH) and the subsequent hypercortisolemia) and/or general hyperpituitarism (associated with excess release of multiple anterior pituitary hormones). Current treatment options for pituitary adenomas include treatment with dopamine receptor agonists, which reduce tumour size and lower pituitary hormonal output through a mechanism involving lowering of intracellular cAMP levels. PDE4 long form activators of the present invention may also be expected to attenuate the pathological effects of pituitary hormones in their target tissues, such as the adrenal glands.

In Cushing's disease, pituitary adenoma related overproduction of ACTH can lead to hypercortisolemia through an overactivation of melanocortin 2 receptor (MC2) and subsequent cAMP mediated stimulation of steroidogenesis and release of cortisol from the adrenal cortex (Tritos, N. A. and Biller, B. M. *Discov. Med.* 13: 171-179, 2012). PDE4 long form activators of the present invention are therefore expected to be effective in the treatment, prevention or partial control of Cushing's disease.

Polycystic Kidney Disease

Polycystic kidney disease (PKD) is a genetic disorder of the kidneys characterised by development of pathological cysts, which damage renal structure and compromise kidney function (Takiar, V. and Caplan, M. *J. Biochim. Biophys. Acta.* 1812: 1337-1343, 2011; Masoumi, A. et al., *Drugs* 67: 2495-2510, 2007). There are two types of PKD: autosomal dominant polycystic kidney disease (ADPKD) and autosomal recessive polycystic kidney disease (ARPKD). ADPKD affects between 0.1% and 0.2% of the population worldwide and is characterized by progressive cyst development and enlarged kidneys. Approximately 50% of people with this disease will develop end stage kidney disease, usually between 40 and 70 years of age and require dialysis or kidney transplantation. ARPKD affects around 1:20,000 live births and is typically identified in the first few weeks after birth. Pulmonary hypoplasia results in a 30-50% death rate in neonates with ARPKD.

Defects in two genes are thought to be responsible for ADPKD. In around 85% of patients, development of ADPKD can be linked to mutations in the gene PKD1, encoding polycystin-1 (PC-1); in around 15% of patients mutations in PKD2, encoding polycystin-2 (PC-2) are implicated. Cyclic AMP has been identified as an important stimulus for proliferation and cyst expansion in polycystic kidney cells but not in normal human kidney cells (Yamaguchi, T. et al., *Kidney Int.* 57: 1460-1471, 2000). A considerable body of evidence has now developed to implicate cAMP as an important facilitator of renal cystogenesis (Masoumi, A. et al., *Drugs* 67: 2495-2510, 2007; Wallace, D. P. *Biochim. Biophys. Acta.* 1812: 1291-1300, 2011). Consistent with the role of cAMP in cyst formation, agents that lower cAMP levels (e.g. vasopressin V2 receptor antagonists and the somatostatin receptor agonist octreotide) showed efficacy in rodent models of PKD (Torres, V. E. et al., *Nat. Med.* 10: 363-364, 2004; Gattone, V. H. $2^{nd}$ et al., *Nat. Med.* 9: 1323-1326, 2003; Belibi, F. A. and Edelstein, C. L. *Expert Opin. Investig. Drugs.* 19: 315-328, 2010). In zebrafish embryos, depletion of a cAMP-hydrolysing PDE enzyme subtype, PDE1A, resulted in development of a cystic phenotype, while PDE1A over-expression partially rescued cystic phenotypes resulting from PC2 depletion (Sussman, C. R., Ward, C. J., Leightner, A. C., Smith, J. L., Agarwal, R., Harris, P. C., Torres, V. E. *J. Am. Soc. Nephrol.* 25: 2222-2230, 2014). Phosphodiesterase activation has been suggested as a therapeutic strategy for PKD treatment (Sun, Y., Zhou, H. and Yang, B-X. *Acta Pharmacologica Sinica* 32: 805-816, 2011).

PDE4 long form activators of the present invention are therefore expected to be effective in the treatment, prevention or partial control of polycystic kidney disease.

Polycystic Liver Disease

Polycystic liver disease (PLD) is a rare inherited condition associated with hepatic cystogenesis (usually defined when number of cysts exceeds 20), which often occurs in association with ADPKD (Strazzabosco, M. and Somlo, S. Gastroenterology 140: 1855-1859, 2011; Gevers, T. J. and Drenth, J. P. Curr. Opin. Gastroenterol. 27: 294-300, 2010). PLD may have a different genetic pathology when compared to ADPKD, driven by mutated proteins associated with the endoplasmic reticulum and the cilium. Increased cholangiocyte proliferation, neovascularisation and elevated fluid secretion act to drive liver cyst formation through dysregulation of multiple signal transduction pathways, including cAMP-mediated signalling. Elevation of hepatic cAMP levels stimulates cAMP-dependent chloride and fluid secretion in biliary epithelial cells and increases cholangiocyte proliferation (Janssen, M. J. et al., J. Hepatol. 52: 432-440, 2010). Somatostatin, which acts through a Gi-coupled mechanism to lower cAMP levels, reduced cholangiocyte proliferation and fluid secretion (Gong, A. Y. et al., Am. J. Physiol. Cell. Physiol. 284: C1205-1214, 2003). Furthermore, the synthetic somatostatin analogue, octreotide, showed efficacy in an animal model of PLD through a mechanism involving reduction in cAMP signalling (Masyuk, T. V. et al., Gastroenterology 132: 1104-1116, 2007). PDE4 long form activators of the present invention may therefore be effective in the treatment, prevention or partial control of polycystic liver disease due at least in part to cAMP.

Maturity Onset Diabetes of Young Type 5 (MODY5)

MODY5 is a form of non-insulin-dependent diabetes mellitus associated with renal cysts. It is an autosomal dominant disorder caused by mutations in the gene encoding hepatocyte nuclear factor-1β (HNF-1β). The predominant clinical feature of patients affected by MODY5 is renal dysfunction, frequently diagnosed before the onset of diabetes. In some patients, HNF-1β mutations can result in additional phenotypic features, such as pancreatic atrophy, abnormal liver function and genital tract abnormalities. Studies in mice suggest that the mechanism responsible for renal cyst formation, associated with mutations of HNF-1β, involves a severe defect of the transcriptional activation of PKD2, in addition to effects on uromodulin (UMOD) and PKD1 genes. Down-regulation of PKD1 and PKD2 is associated with cAMP-driven formation of renal cysts (Mancusi, S. et al., J. Nephrol. 26: 207-12, 2013). HNF-1β also binds to the PDE4C promoter and regulates the expression of PDE4C (Ma et al., PNAS 104: 20386, 2007).

PDE4 long form activators of the present invention are therefore expected to be effective in the treatment, prevention or partial control of the symptoms of MODY5.

Cardiac Hypertrophy, Heart Failure and Arrhythmia

Localized regulation and integration of cAMP signalling are important for proper cardiac function and perturbation of this signalling can lead to heart failure. Upon chronic p-adrenergic receptor stimulation, cardiomyocyte hypertrophy is induced via elevated cAMP and activation of its downstream effectors, including PKA and Epac (Wang, L. et al., Cell. Signal. 27: 908-922, 2015 and references therein). Cardiomyocyte hypertrophy increases the risk of heart failure and arrhythmia.

PDE4 long form activators of the present invention may therefore be effective in the treatment, prevention or partial control of cardiac hypertrophy, heart failure and/or arrhythmia.

Diseases Associated with Increased cAMP-Mediated Signalling

Disorders Associated with Activating Mutations of the Alpha Subunit of the G Protein (GNAS1)

The G-protein Gs acts as a transducer for GPCRs that stimulate adenylyl cyclase activity and exert their biological effects by increasing intracellular cAMP levels. Gs is a heterotrimeric protein composed of a, p and y subunits. Activating mutations in the gene, GNAS1, for the a-subunit have been identified which lead to exaggerated abnormal cAMP signalling in a variety of tissues and give rise to a range of disorders.

McCune-Albright Syndrome

McCune-Albright syndrome (MAS) is a rare genetic disorder typically characterised by three dominating features of precocious puberty, fibrous dysplasia of bone and café au lait lesions. The underlying molecular pathology for MAS involves an activating mutation of the GNAS1 gene (Diaz, A. Danon, M. and Crawford, J. J. Pediatr. Endocrinol. Metab. 20: 853-880, 2007). PDE4 long form activators of the present invention would therefore be expected to be effective in the treatment, prevention or partial control of disorders associated with activating mutations of GNAS1, including McCune-Albright syndrome.

Amelioration of Toxin-Induced Increases in Adenylyl Cyclase Activity in Infectious Diseases.

Adenylyl cyclase, the enzyme responsible for production of cAMP, is a key biological target thought to be involved in mediating the effects of many bacterial toxins (Ahuja et al., Critical Reviews in Microbiology, 30: 187-196, 2004). These toxins produce their effects by raising cAMP levels through enhancement of host immune cell and/or pathogen related adenylyl cyclase activity. PDE4 long form activators of the present invention, by reducing cAMP levels, would therefore be expected to be of utility in the treatment or partial control of symptoms of infectious diseases that are associated with elevated cAMP activity. The following are some examples of such infectious diseases:

Cholera

Vibrio cholerae produces cholera toxin, which through adenosine disphosphate ribosylation of the a subunit of Gs leads to host cell adenylyl cyclase activation and cAMP production. Diarrhoea caused by cholera toxin is believed to be a result of excessive cAMP accumulation in the cells of the gastrointestinal tract.

Whooping Cough

Bordetella pertussis is the pathogen responsible for the childhood disease whooping cough. Bordetella pertussis toxin stimulates adenosine disphosphate ribosylation of the a subunit of Gi and indirectly augments cAMP levels in target cells. The bacterium also secretes an invasive adenylyl cyclase, which produces toxic cAMP levels and impairs host immune defence.

Anthrax

Anthrax is caused by Bacillus anthracis and whilst it is primarily an animal disease it can be transmitted to humans through contact. Anthrax infections are associated with widespread oedema, the development of which is thought to be driven by oedema toxin. The latter is an adenylyl cyclase and is activated by host calmodulin to produce abnormally high levels of cAMP that have a toxic effect on host immune cells.

Tuberculosis

*Mycobactrium tuberculosis* expresses a large and diverse range of adenylyl cyclases, which may play a role in virulence and generation of disease pathology. One adenylyl cyclase subtype, RV0386, has been demonstrated to enter host macrophages and elevate intracellular cAMP to cause toxicity (Agarwal et al., *Nature*, 460: 98-102, 2009).

PDE4 long form activators of the present invention may therefore be effective in the treatment, prevention or partial control of infectious diseases such as cholera, whooping cough, anthrax and tuberculosis.

Diseases Dependent Upon Activation of PKA by Elevated cAMP.

In eukaryotes, cAMP activates protein kinase A (PKA), which is also known as cAMP-dependent protein kinase. PKA is normally inactive as a tetrameric holoenzyme, consisting of two catalytic and two regulatory units, with the regulatory units blocking the catalytic centres of the catalytic units. cAMP binds to specific locations on the regulatory units of PKA and causes dissociation between the regulatory and catalytic units, thus activating the catalytic units. The active catalytic units catalyse the transfer of phosphate from ATP to specific residues of protein substrates, which may modulate the function of those protein substrates.

PDE4 long form activation reduces cAMP levels and cAMP mediated activation of PKA. PDE4 long form activators of the present invention would therefore be expected to be of utility in the treatment or partial control of disorders where inhibitors of PKA show evidence of therapeutic effects.

Disorders that are dependent upon activation of PKA by cAMP may be identified by their response to PKA inhibitors such as Rp-8-Br-cAMPS. Rp-8-Br-cAMPS is an analogue of cAMP that occupies the cAMP binding sites of PKA, preventing its dissociation and activation.

HIV Infection and AIDS

T cells from HIV-infected patients have increased levels of cAMP and are more sensitive to inhibition by Rp-8-Br-cAMPS than are normal T cells. Excessive activation of PKA by cAMP has been associated with the progressive T cell dysfunction in HIV infection (Aandahl, E. M. et al., *FASEB J.* 12: 855-862, 1998). Furthermore, in vivo administration of Rp-8-Br-cAMPS has been shown to restore T cell responses in retrovirus-infected mice (Nayjib, B. et al., *The Open Immunology Journal*, 1: 20-24, 2008). PDE4 long form activators of the present invention are therefore expected to be of utility in the treatment, prevention or partial control of HIV infection and AIDS.

Common Variable Immunodeficiency (CVID)

In vitro administration of Rp-8-Br-cAMPS has been shown to correct impaired secretion of the cytokine IL-10 by T cells from patients with Common Variable Immunodeficiency (CVID) (Holm, A. M. et al., *J. Immunol.* 170: 5772-5777, 2003). PDE4 long form activators of the present invention are therefore expected to be of utility in the treatment, prevention or partial control of CVID.

Diseases Dependent Upon Activation of Either or Both of Epac1 and Epac2 by Elevated cAMP.

In addition to PKA, cAMP activates another intracellular receptor, known as exchange protein directly activated by cAMP (Epac). There are two isoforms of Epac, Epac1 and Epac2, both consisting of a regulatory region that binds cAMP and a catalytic region that promotes the exchange of GDP for GTP on the small G proteins, Rap1 and Rap2 of the Ras family. In addition, Epac proteins exert their functions through interactions with a number of other cellular partners at specific cellular loci. Pathophysiological changes in Epac signalling have been associated with a wide range of diseases (Breckler, M. et al., *Cell. Signal.* 23: 1257-1266, 2011).

Relevant disorders that are dependent upon activation of Epac proteins by cAMP may be identified by their response to Epac inhibitors, such as ESI-09, a novel non-cyclic nucleotide Epac1 and Epac2 antagonist that is capable of specifically blocking intracellular Epac-mediated Rap1 activation and Akt phosphorylation, as well as Epac-mediated insulin secretion in pancreatic beta cells (Almahariq, M. et al., *Mol. Pharmacol.* 83: 122-128, 2013).

Melanoma

Epac1 has been implicated in promoting migration and metastasis in melanoma (Baljinnyam, E. et al., *Pigment Cell Melanoma Res.* 24: 680-687, 2011 and references cited therein). PDE4 long form activators of the present invention are therefore expected to be of utility in the treatment, prevention or partial control of melanoma.

Pancreatic Cancer

It has recently been shown that Epac1 is markedly elevated in human pancreatic cancer cells as compared with normal pancreas or surrounding tissue (Lorenz, R. et al., *Pancreas* 37: 102-103, 2008).

Pancreatic cancer is often resistant to treatments that are usually effective for other types of cancer. Using the Epac inhibitor ESI-09, a functional role of Epac1 overexpression in pancreatic cancer cell migration and invasion was demonstrated (Almahariq, M. et al., *Mol. Pharmacol.* 83: 122-128, 2013). These findings are consistent with results based on RNAi silencing techniques and suggest that inhibition of Epac1 signalling could be an effective therapeutic strategy for pancreatic cancer.

PDE4 long form activators of the present invention would therefore be expected to be of utility in the treatment, prevention or partial control of pancreatic cancer.

Diseases Dependent Upon Modulation of cAMP-Gated Ion Channels by Elevated cAMP.

In addition to activation of PKA and Epac, another effector pathway for elevated cAMP is the activation of cAMP-gated ion channels. PDE4 long form activators of the present invention would therefore be expected to be of utility in the treatment of disorders where inhibitors of cAMP-gated ion channels show evidence of therapeutic effects.

Diseases Associated with Increased Activity of cAMP Response Element Binding Protein.

The cAMP response element binding protein (CREB) is an important transcription factor involved in the regulation of a variety of cellular functions such as cell proliferation, differentiation, survival, and apoptosis (Cho et al., *Crit Rev Oncog,* 16: 37-46, 2011). CREB activity is regulated by kinase dependant phosphorylation through a range of extracellular signals, such as stress, growth factors and neurotransmitters. Phosphorylation leads to dimerisation of CREB, and together with other co-activator partner proteins, enables it to bind to promoter regions of target genes containing the cAMP response element (CRE sites) and initiate transcriptional activity. The cAMP pathway (e.g. through cAMP-dependant protein kinase mediated phosphorylation) is an important positive modulator of CREB mediated biological activity. PDE4 long form activators of the present invention are therefore expected to be of utility in the treatment, prevention or partial control of disorders associated with elevated CREB activity.

Leukaemia

Bone marrow cells from acute lymphoid and myeloid leukaemia patients have been reported to overexpress CREB protein and mRNA (Crans-Vargas et al., *Blood*, 99: 2617-9, 2002; Cho et al., *Crit Rev Oncog*, 16: 37-46, 2011). Furthermore, the increased CREB level correlates with poor clinical response in subjects with acute myeloid leukaemia (Crans-Vargas et al., *Blood*, 99: 2617-9, 2002; Shankar et al., *Cancer Cell*, 7:351-62, 2005). Upregulation of CREB is associated with stimulation of human leukaemia cell growth whilst downregulation inhibits myeloid cell proliferation and survival. PDE4 long form activators of the present invention would be expected to reduce CREB activity and function through attenuation of cAMP mediated stimulation of CREB and therefore expected to have utility in the treatment, prevention or partial control of acute lymphoid and myeloid leukaemia.

Prostate Cancer

Abnormal excessive androgen activity is an important driver in the development of prostate cancer as it stimulates the development of intraepithelial neoplasias (Merkle et al., *Cellular Signalling*, 23: 507-515, 2011). This is strongly supported by the use of androgen ablation approaches, involving chemical or surgical castration, in the treatment of prostate cancer. Cyclic AMP elevating agents such as forskolin can enhance androgen receptor activity through multiple intracellular mechanisms including androgen receptor activation through phosphorylation and/or interaction with CREB. Epac1 activation has also been implicated in promoting cellular proliferation in prostate cancer (Misra, U. K. and Pizzo, S. V. *J. Cell. Biochem.* 108: 998-1011, 2009; Misra, U. K. and Pizzo, S. V. *J. Cell. Biochem.* 113: 1488-1500, 2012). PDE4 long form activators of the present invention are therefore expected to have utility in the treatment, prevention or partial control of prostate cancer.

Diseases associated with reduced activity of cAMP-hydrolysing PDE enzymes Loss-of-function mutations in gene(s) for cAMP-hydrolysing PDE isoforms other than PDE4, such as PDE8 and PDE11, have been detected in a number of diseases (Vezzosi, D. and Berthenat, J., *Eur. J. Endocrinol.* 165: 177-188, 2011; Levy, I. et al., *Curr. Opin. Pharmacol.* 11: 689-697, 2011; Azevedo, M. F. and Stratakis, C. A. *Endocr. Pract.* 17 Suppl 3: 2-7, 2011). These mutations can lead to abnormally high cAMP levels and/or duration of cAMP action with pathological consequences as detailed below. PDE4 long form activators of the present invention are therefore expected to be of utility in the treatment, prevention or partial control of these diseases, such as adrenocortical tumours, testicular cancer, PPNAD and Carney Complex.

Adrenocortical Tumours

Adrenocortical tumours associated with an inactivating point mutation in the gene encoding PDE11A4 have decreased expression of PDE11A4 and increased cAMP levels (Horvath, A. et al., *Nat Genet.* 38: 794-800, 2006; Horvath, A. et al., *Cancer Res.* 66:11571-11575, 2006; Libe, R., et al., *Clin. Cancer Res.* 14: 4016-4024, 2008).

Testicular Cancer

Mutations that reduce PDE11A activity and increase cAMP levels have been observed in some forms of testicular cancer (Horvath. A. et al., *Cancer Res.* 69: 5301-5306, 2009).

Primary Pigmented Nodular Adrenocortical Diseases (PPNAD)

Mutations in the PDE8B gene have also been identified as a predisposing factor for PPNAD and the mutant protein shows reduced ability to degrade cAMP (Horvath, A., Mericq, V. and Stratakis, C. A. *N. Engl. J. Med.* 358: 750-752, 2008; Horvath, A. et al., *Eur. J. Hum. Genet.* 16: 1245-1253, 2008).

Carney Complex

In Carney Complex (CNC) caused by PRKAR1A mutations, some patients also have defects in PDE11A that may exert a synergistic effect to enhance abnormal activation of the cAMP signal transduction pathway, leading to adrenal and testicular cancer (Libe, R. et al., *J. Clin. Endocrinol. Metab.* 96: E208-214, 2011).

Treatment and Posology

By "treatment" herein is meant the treatment by therapy, whether of a human or a non-human animal (e.g., in veterinary applications) typically a non-human mammal, in which some desired therapeutic effect on the condition is achieved; for example, the inhibition of the progress of the disorder, including a reduction in the rate of progress, a halt in the rate of progress, amelioration of the disorder or cure of the condition. Treatment as a prophylactic measure is also included. References herein to prevention or prophylaxis do not indicate or require complete prevention of a condition; its manifestation may instead be reduced or delayed via prophylaxis or prevention according to the present invention.

By a "therapeutically effective amount" herein is meant an amount of the one or more compounds of the invention or a pharmaceutical formulation comprising such one or more compounds, which is effective for producing such a therapeutic effect, commensurate with a reasonable benefit/risk ratio.

It will be appreciated that appropriate dosages of the compounds of the invention may vary from patient to patient. Determining the optimal dosage will generally involve the balancing of the level of therapeutic benefit against any risk or deleterious side effects of the treatments of the present invention. The selected dosage level will depend on a variety of factors including the activity of the particular compound, the route of administration, the time of administration, the rate of excretion of the compound, the duration of the treatment, other drugs, compounds or materials used in combination and the age, sex, weight, condition, general health and prior medical history of the patient. The amount of compound(s) and route of administration will ultimately be at the discretion of the physician, although generally the dosage will be to achieve local concentrations at the site of action so as to achieve the desired effect. Administration in vivo can be effected in one dose, continuously or intermittently throughout the course of treatment. Methods of determining the most effective means and dosage of administration are well known to a person skilled in the art and will vary with the formulation used for therapy, the purpose of the therapy, the target cell being treated, and the subject being treated. Single or multiple administrations can be carried out with the dose level and pattern being selected by the treating physician. In general, a suitable dose of the one or more compounds of the invention may be in the range of about 0.001 to 50 mg/kg body weight of the subject per day, preferably in a dosage of 0.01-25 mg per kg body weight per day, e.g., 0.01, 0.05, 0.10, 0.25, 0.50, 1.0, 2.5, 10 or 25 mg/kg per day. Where the compound(s) is a salt, solvate, prodrug or the like, the amount administered may be calculated on the basis of the parent compound and so the actual weight to be used may be increased proportionately.

Combination Therapies

The compounds of the invention may also find application in mimicking or enhancing the effects of drugs known to produce their therapeutic effect through lowering of intracellular cAMP levels.

A number of therapeutically beneficial drugs have a primary mode of action involving lowering intracellular cAMP levels and/or cAMP-mediated activity, as summarised below. Since PDE4 long form activators of the present invention will also act to lower cAMP levels it is expected that these agents will mimic and/or augment the pharmacological properties and therapeutic utility of drugs operating through a down-regulation of cAMP-mediated signalling. In certain embodiments, a compound of the invention is therefore provided as part of a combination therapy with another agent that lowers intracellular cAMP levels and/or cAMP-mediated activity. The combination therapy may be administered simultaneously, contemporaneously, sequentially or separately. In one embodiment, the compound of the invention and the separate cAMP lowering agent are provided in a single composition, as described in more detail below. The combination therapy may comprise a compound of the invention and one or more of:

(i) a presynaptic α-2 adrenergic receptor agonist, optionally clonidine, dexmedetomidine, or guanfacine;

(ii) a β-1 Adrenergic receptor antagonist ("beta-blocker"), optionally Atenolol, Metoprolol, Bisoprolol, Acebutolol, or Betaxolol.

Combination with α-2 Adrenergic Receptor Agonist

α-2 Adrenergic receptor stimulation is known to reduce cAMP levels through a Gi protein-mediated inhibition of adenylyl cyclase activity in a broad range of tissues. In noradrenergic neurones in the brain and peripheral sympathetic nervous system, presynaptic α-2 adrenergic receptor activation inhibits noradrenaline release and noradrenergic activity. Drugs (e.g. clonidine, dexmedetomidine, guanfacine) that act as agonists at these receptors are effective in the treatment of a variety of clinical conditions. Clonidine, the prototypic agent, has shown therapeutic utility in the treatment of hypertension, neuropathic pain, opioid detoxification, insomnia, ADHD, Tourette syndrome, sleep hyperhidrosis, addiction (narcotic, alcohol and nicotine withdrawal symptoms), migraine, hyperarousal, anxiety and also as a veterinary anaesthetic. Lowering of cAMP levels by PDE4 long form activation may be expected to yield similar effects to drugs acting through α-2 adrenergic receptor stimulation. Furthermore, PDE4 long form activators of the present invention may be expected to potentiate the pharmacodynamic effects of α-2 adrenergic receptor agonists when used in combination.

Combination with A-1 Adrenergic Receptor Antagonist

β-1 Adrenergic receptor antagonists are used in the treatment a range of cardiovascular indications including hypertension, cardiac arrhythmias and cardioprotection following myocardial infarction. Their primary mechanism of action involves reducing the effects of excessive circulating adrenaline and sympathetic activity, mediated by noradrenaline, particularly at cardiac β-1 adrenergic receptors. Endogenous and synthetic β-1 adrenergic receptor agonists stimulate adenylyl cyclase activity through Gs activation and raise intracellular cAMP levels in a variety of tissues such as heart and kidney. Consequently, drugs that block β-1 adrenergic receptor mediated activity exert their pharmacological effects by attenuating the increase in cAMP mediated signalling. Given that PDE4 long form activation will also lower cAMP concentration and transduction in cardiac tissue, PDE4 long form activators of the present invention may be expected to find utility in the treatment or partial control of hypertension, cardiac arrhythmias, congestive heart failure and cardioprotection. Additional non-cardiovascular therapeutic utility may be expected in disorders such as post-traumatic stress related disorder, anxiety, essential tremor and glaucoma, which also respond to β-1 adrenergic antagonist treatment. Furthermore, PDE4 long form activators of the present invention may be expected to potentiate the pharmacodynamic effects of β-1 adrenergic receptor antagonists when used in combination.

Methods of Treatment

In a further aspect, the present invention provides a small molecule activator of a PDE4 long form of Formula I for use in a method for the treatment or prevention of a disease or disorder in a patient in need of such therapy. The invention also provides a method of treating or preventing a disease or disorder in a patient in need thereof, comprising administering to a patient in need thereof an effective amount of a compound if the invention. The disease or disorder may be any disease of disorder described herein, including: a disease associated with increased cAMP production and signalling (such as hyperthyroidism, Jansens's metaphyseal chondrodysplasia, hyperparathyroidism, familial male-limited precocious puberty, pituitary adenomas, Cushing's disease, polycystic kidney disease, polycystic liver disease, MODY5 and cardiac hypertrophy); diseases known to be associated with increased cAMP-mediated signalling, including disorders associated with activating mutations of the alpha subunit of the G protein (GNAS1) (such as McCune-Albright syndrome); amelioration of toxin-induced increases in adenylyl cyclase activity in infectious diseases (such as cholera, whooping cough, anthrax, and tuberculosis); treatment of diseases known to be dependent upon activation of PKA by elevated cAMP (such as HIV infection and AIDS, and Common Variable Immunodeficiency (CVID)); treatment of diseases known to be dependent upon activation of either or both of Epac1 and Epac2 by elevated cAMP (such as melanoma and pancreatic cancer); treatment of diseases dependent upon modulation of cAMP-gated ion channels by elevated cAMP; treatment of diseases known to be associated with increased activity of cAMP response element binding protein (such as leukaemia and prostate cancer); treatment of diseases known to be associated with reduced activity of cAMP-hydrolysing PDE enzymes (such as adrenocortical tumours, testicular cancer, primary pigmented nodular adrenocortical diseases (PPNAD) and Carney Complex); and mimicking or enhancing the effects of drugs known to produce their therapeutic effect through lowering of intracellular cAMP levels.

As used herein, the terms "compound of the invention", "compound of the disclosure" and "compound of Formula I" and the like include polymorphs, isomers (e.g. stereoisomers and tautomers) and isotopically labelled variants thereof (e.g. deuterated forms thereof). Also included where a "compound of the invention", "compound of the disclosure", "compound of Formula I" and the like are referred to are pharmaceutically acceptable derivatives. For example, reference to compounds of Formula I and the like also includes pharmaceutically acceptable salts thereof. Furthermore, these terms include all the sub-embodiments of those compounds disclosed herein.

Pharmaceutically Acceptable Derivatives

Pharmaceutically acceptable derivatives of a compound of the invention include pharmaceutically acceptable salts, solvates, esters, hydrates, amides, or prodrugs (e.g. a pyridine N-oxide) thereof. The present invention further provides pharmaceutical compositions comprising a compound of the invention, including a pharmaceutically acceptable salt, solvate, ester, hydrate or amide thereof, in admixture with a pharmaceutically acceptable excipient(s), and optionally other therapeutic agents. The term "acceptable" means being compatible with the other ingredients of the composition and not deleterious to the recipient thereof. Compositions include e.g. those suitable for oral, sublingual, subcutaneous, intravenous, epidural, intrathecal, intramuscular, transdermal, intranasal, pulmonary, topical, local, or rectal administration, and the like, typically in unit dosage forms for administration.

The term "pharmaceutically acceptable salt" includes a salt prepared from pharmaceutically acceptable non-toxic acids or bases including inorganic or organic acids and bases. Compounds of the invention which contain basic, e.g. amino, groups are capable of forming pharmaceutically acceptable salts with acids. Examples of pharmaceutically acceptable acid addition salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Compounds of the invention which contain acidic, e.g. carboxyl, groups are capable of forming pharmaceutically acceptable salts with bases. Pharmaceutically acceptable basic salts of the compounds of the invention include, but are not limited to metal salts such as alkali metal or alkaline earth metal salts (e.g. sodium, potassium, magnesium or calcium salts) and zinc or aluminium salts and salts formed with ammonia or pharmaceutically acceptable organic amines or heterocyclic bases such as ethanolamines (e.g. diethanolamine), benzylamines, N-methyl-glucamine, amino acids (e.g. lysine) or pyridine. Hemisalts of acids and bases may also be formed, e.g. hemisulphate salts.

Pharmaceutically acceptable salts of compounds of the compounds of the invention may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002).

Prodrugs

The invention includes prodrugs of the compounds of Formula I. Prodrugs are derivatives of compounds of Formula I (which may have little or no pharmacological activity themselves), which can, when administered in vivo, be converted into compounds of Formula I.

Prodrugs can, for example, be produced by replacing functionalities present in the compounds of Formula I with appropriate moieties which are metabolised in vivo to form a compound of Formula I. The design of prodrugs is well-known in the art, as discussed in Bundgaard, *Design of Prodrugs* 1985 (Elsevier), *The Practice of Medicinal Chemistry* 2003, $2^{nd}$ Ed, 561-585 and Leinweber, *Drug Metab. Res.* 1987, 18: 379.

In vivo metabolism of prodrugs of compounds of Formula I may for example involve hydrolysis, oxidative metabolism or reductive metabolism of the prodrug. Examples of prodrugs of compounds of Formula I are amides and esters of those compounds that may be hydrolysed in vivo. For example, where the compound of Formula I contains a carboxylic acid group (—COOH), the hydrogen atom of the carboxylic acid group may be replaced in order to form an ester (e.g. the hydrogen atom may be replaced by $C_{1-6}$-alkyl). Where a compound contains an alcohol group (—OH), the hydrogen atom of the alcohol group may be replaced in order to form an ester (e.g. the hydrogen atom may be replaced by —C(O)$C_{1-6}$alkyl. Further examples of prodrugs of compounds of Formula I include pyridine N-oxides that may be reductively metabolised in vivo to form compounds of Formula I containing a pyridine ring.

Solvates

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a monohydrate, di-hydrate, tri-hydrate etc, depending on the number of water molecules present per molecule of substrate.

Isomers

It will be appreciated that the compounds of the present invention may exist in various isomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of Formula I as well as wholly or partially racemic mixtures of such enantiomers. Where appropriate, isomers can be separated from their mixtures by the application or adaptation of known methods (e.g. chromatographic techniques and recrystallisation techniques). Where appropriate, isomers can be prepared by the application or adaptation of known methods (e.g. asymmetric synthesis). In addition, it will be appreciated that in some instances, compounds of the invention may exist in tautomeric forms and the compounds of the present invention as hereinbefore defined include all tautomers and mixtures thereof.

Isotopes

The invention includes pharmaceutically acceptable isotopically-labelled compounds of Formula I wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, and sulphur, such as $^{35}$S. Certain isotopically-labelled compounds of Formula I, for example, those incorporating a radioactive isotope, are useful in drug and/or substrate tissue distribution studies. The radioactive isotopes $^3$H and $^{14}$C are particularly useful for this purpose in view of their ease of incorporation and ready means of detection. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labelled compounds of Formula I can generally be prepared by conventional techniques known to those skilled in the art or by processes analogous to those described herein using an appropriate isotopically-labelled reagent in place of the non-labelled reagent previously employed.

Pharmaceutical Compositions

For oral administration, the active ingredient may be presented as discrete units, such as tablets, capsules, powders, granulates, solutions, suspensions, and the like.

Formulations suitable for oral administration may also be designed to deliver the compounds of the invention in an immediate release manner or in a rate-sustaining manner, wherein the release profile can be delayed, pulsed, controlled, sustained, or delayed and sustained or modified in such a manner which optimises the therapeutic efficacy of the said compounds. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Liang and Chen, *Expert Opinion in Therapeutic Patents* 2001, 11(6): 981-986.

The formulation of tablets is discussed in H. Lieberman and L. Lachman, *Pharmaceutical Dosage Forms: Tablets* 1980, vol. 1 (Marcel Dekker, New York).

For administration intranasally or by inhalation, the active ingredient may be presented in the form of a dry powder from a dry powder inhaler or in the form of an aerosol spray of a solution or suspension from a pressurised container, pump, spray, atomiser or nebuliser.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

For parenteral administration, the compounds of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but not restricted to glucose, mannitol, sorbitol, etc.) salts, carbohydrates and buffering agents (preferably to a pH of from 3 to 9) may be used. For some applications, the compounds of the invention may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (e.g. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, for example, by lyophilisation, may readily be accomplished using standard pharmaceutical techniques well known to those skilled in the art.

The solubility of compounds of the invention used in the preparation of parenteral solutions may be increased by the use of appropriate formulation techniques, such as the incorporation of co-solvents and/or solubility-enhancing agents such as surfactants, micelle structures and cyclodextrins.

Mixed with such pharmaceutically acceptable excipients, e.g. as described in the standard reference, Gennaro, A. R. et al, *Remington: The Science and Practice of Pharmacy* (21st Edition, Lippincott Williams & Wilkins, 2005, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation or as an aerosol spray, in the form of a solution, suspension, or emulsion.

For making solid dosage units, the use of conventional additives such as fillers, colorants, polymeric binders and the like is contemplated. In general any pharmaceutically acceptable additive that does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described. In some embodiments, the one or more compounds of the present invention may be used in combination therapies for the treatment of the described conditions i.e., in conjunction with other therapeutic agents. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where a compound of the invention is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

In one embodiment, the invention provides a product comprising a compound of the invention and another therapeutic agent as a combined preparation for simultaneous, separate or sequential use in therapy. In one embodiment, the therapy is the treatment or prevention of disorders where a reduction of second messenger responses mediated by cyclic 3',5'-adenosine monophosphate (cAMP) is required. Products provided as a combined preparation include a composition comprising a compound of the invention and the other therapeutic agent together in the same pharmaceutical composition, or the compound of the invention and the other therapeutic agent in separate form, e.g. in the form of a kit.

In one embodiment, the invention provides a pharmaceutical composition comprising a compound of the invention and another therapeutic agent. Optionally, the pharmaceutical composition may comprise a pharmaceutically acceptable excipient, as described above.

In one embodiment, the invention provides a kit comprising two or more separate pharmaceutical compositions, at least one of which contains a compound of the invention. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Method of Manufacture & Method of Treatment

The invention also provides the use of a compound of the invention in the manufacture of a medicament for the treatment or prevention of disorders where a reduction of second messenger responses mediated by cyclic 3',5'-adenosine monophosphate (cAMP) is required, wherein the medicament is prepared for administration with another therapeutic agent. The invention also provides the use of another therapeutic agent in the manufacture of medicament for treating a disease or condition mediated by cAMP for the treatment or prevention of disorders where a reduction of second messenger responses mediated by cyclic 3',5'-adenosine monophosphate (cAMP) is required, wherein the medicament is prepared for administration with a compound of the invention.

The invention also provides a compound of the invention for use in the treatment or prevention of disorders where a reduction of second messenger responses mediated by cyclic 3',5'-adenosine monophosphate (cAMP) is required, wherein the compound of the invention is prepared for administration with another therapeutic agent. The invention also provides another therapeutic agent for use in the treatment or prevention of disorders where a reduction of second messenger responses mediated by cyclic 3',5'-adenosine monophosphate (cAMP) is required, wherein the other therapeutic agent is prepared for administration with a compound of the invention. The invention also provides a compound of the invention for use in for the treatment or prevention of disorders where a reduction of second messenger responses mediated by cyclic 3',5'-adenosine monophosphate (cAMP) is required, wherein the compound of the invention is administered with another therapeutic agent. The invention also provides another therapeutic agent for use in the treatment or prevention of disorders where a reduction of second messenger responses mediated by cyclic 3',5'-adenosine monophosphate (cAMP) is required, wherein the other therapeutic agent is administered with a compound of the invention.

The invention also provides the use of a compound of the invention in the manufacture of a medicament for the treatment or prevention of disorders where a reduction of second messenger responses mediated by cyclic 3',5'-adenosine monophosphate (cAMP) is required, wherein the patient has previously (e.g. within 24 hours) been treated with another therapeutic agent. The invention also provides the use of another therapeutic agent in the manufacture of a medicament for the treatment or prevention of disorders where a reduction of second messenger responses mediated by cyclic 3',5'-adenosine monophosphate (cAMP) is required, wherein the patient has previously (e.g. within 24 hours) been treated with a compound of the invention.

In one embodiment, the other therapeutic agent is:
(i) a presynaptic α-2 adrenergic receptor agonist, optionally clonidine, dexmedetomidine, or guanfacine;
(ii) a β-1 Adrenergic receptor antagonist ("beta-blocker"), optionally Atenolol, Metoprolol, Bisoprolol, Acebutolol, or Betaxolol.

EXAMPLES

The present invention will now be further described by way of the following non-limiting examples and with reference to the Tables and Figures:

Table 1 shows the structures of small molecule PDE4 long form activators, Examples 1 to 90, according to the present invention.

Table 2 shows enzyme assay data for PDE4D5, a long form of PDE4.

Table 3 shows enzyme assay data for PDE4B1, another long form of PDE4.

Table 4 shows enzyme assay data for PDE4A4, another long form of PDE4.

Table 5 shows enzyme assay data for PDE4B2, a short form of PDE4.

FIG. 1 shows dose-dependent activation of a PDE4 long form, PDE4D5, by Example 5.

Figure 2:
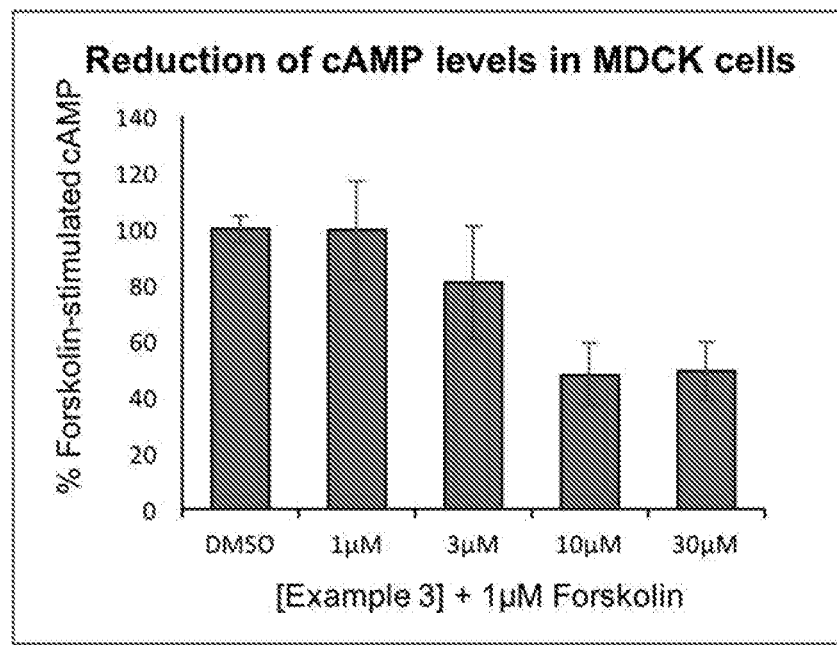
FIG. 2 shows a reduction in intracellular cAMP levels in MDCK cells treated with PDE4 long form activator, Example 3, for 40 min prior to treatment with forskolin (1 μM) for 20 min, using the method described in Experiment 2.

FIG. 2 shows a reduction in intracellular cAMP levels in Madin-Darby canine kidney (MDCK) cells treated with Example 3 for 40 min prior to treatment with forskolin (F) (1 μM) 30 for 20 min.

Figure 3:
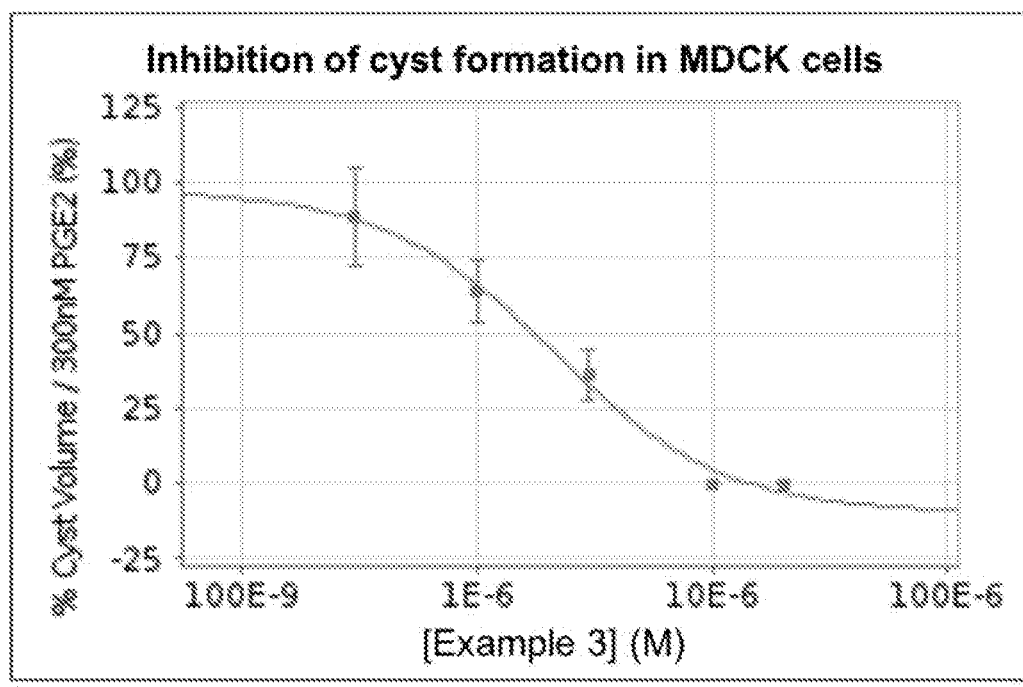
FIG. 3 shows inhibition of cyst formation in a 3D culture of MDCK cells treated with PDE4 long form activator, Example 3, using the method described in Experiment 3.

FIG. 3 shows inhibition of PGE2-stimulated cyst formation in a 3D culture of MDCK cells treated with PDE4 long form activator, Example 3.

Experimental Details

Preparation of PDE4 Long Form Activators
(Examples 1 to 90)

Reactions were monitored by thin layer chromatography (Merck Millipore TLC Silica Gel 60 $F_{254}$). Flash column chromatography was performed on Biotage Isolera® using pre-packed silica gel columns. NMR spectra were recorded using a Bruker 400 MHz spectrometer, using residual signal of deuterated solvent as internal reference, at 25° C. The following abbreviations are used in the assignment of NMR signals: s (singlet), d (doublet), t (triplet), q (quartet), spt (septet), m (multiplet), bs (broad singlet), dd (doublet of doublet), dt (doublet of triplet).

Example 1: 2-[3-(4-Chloro-3-fluorophenyl)-1-ethyl-1H-1,2,4-triazol-5-yl]-N-(3-fluorobenzyl) acetamide

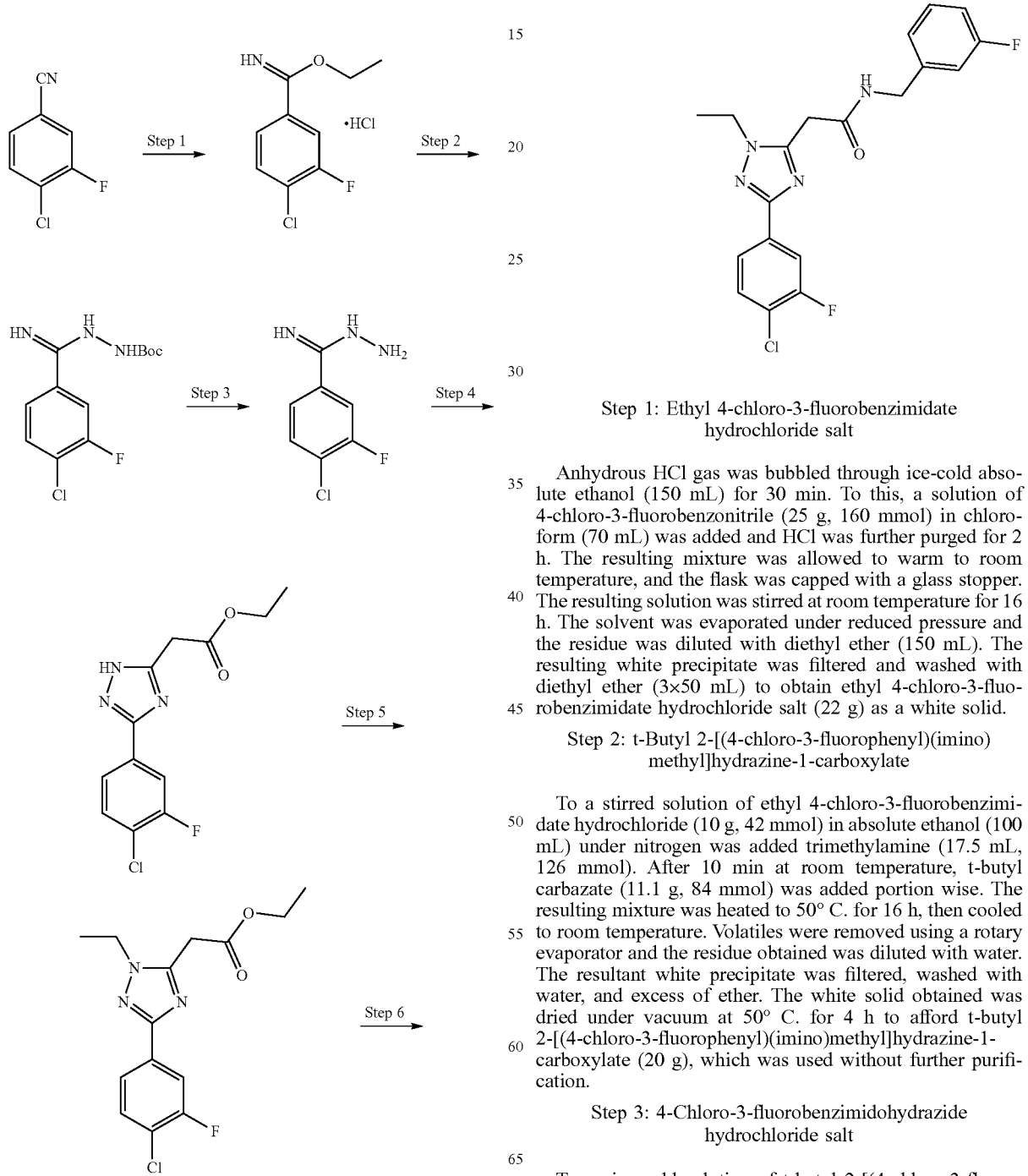

Step 1: Ethyl 4-chloro-3-fluorobenzimidate hydrochloride salt

Anhydrous HCl gas was bubbled through ice-cold absolute ethanol (150 mL) for 30 min. To this, a solution of 4-chloro-3-fluorobenzonitrile (25 g, 160 mmol) in chloroform (70 mL) was added and HCl was further purged for 2 h. The resulting mixture was allowed to warm to room temperature, and the flask was capped with a glass stopper. The resulting solution was stirred at room temperature for 16 h. The solvent was evaporated under reduced pressure and the residue was diluted with diethyl ether (150 mL). The resulting white precipitate was filtered and washed with diethyl ether (3×50 mL) to obtain ethyl 4-chloro-3-fluorobenzimidate hydrochloride salt (22 g) as a white solid.

Step 2: t-Butyl 2-[(4-chloro-3-fluorophenyl)(imino)methyl]hydrazine-1-carboxylate To a stirred solution of ethyl 4-chloro-3-fluorobenzimidate hydrochloride (10 g, 42 mmol) in absolute ethanol (100 mL) under nitrogen was added trimethylamine (17.5 mL, 126 mmol). After 10 min at room temperature, t-butyl carbazate (11.1 g, 84 mmol) was added portion wise. The resulting mixture was heated to 50° C. for 16 h, then cooled to room temperature. Volatiles were removed using a rotary evaporator and the residue obtained was diluted with water. The resultant white precipitate was filtered, washed with water, and excess of ether. The white solid obtained was dried under vacuum at 50° C. for 4 h to afford t-butyl 2-[(4-chloro-3-fluorophenyl)(imino)methyl]hydrazine-1-carboxylate (20 g), which was used without further purification.

Step 3: 4-Chloro-3-fluorobenzimidohydrazide hydrochloride salt

To an ice-cold solution of t-butyl 2-[(4-chloro-3-fluorophenyl)(imino)methyl]hydrazine-1-carboxylate (20 g, 69.7 mmol) in CH$_2$Cl$_2$/methanol (200 mL, 9:1) was added 4 M HCl in dioxane (87 mL, 348.5 mmol). The resulting mixture was stirred at room temperature for 20 h. All solvent was removed on rotary evaporator and the residue was diluted with ether (100 mL). The solid obtained was filtered and washed with ether (3×50 mL) to afford 4-chloro-3-fluorobenzimidohydrazide, hydrochloride salt (14 g) as a white solid.

Step 4: Ethyl 2-[3-(4-chloro-3-fluorophenyl)-1H-1,2,4-triazol-5-yl]acetate

To an ice-cold suspension of 4-chloro-3-fluorobenzimidohydrazide hydrochloride salt (150 g, 581 mmol) in acetonitrile (1.5 L) was slowly added diisopropyl ethylamine (429 mL, 2.33 mol). After 10 min of stirring, ethyl malonyl chloride (82.2 mL, 639 mmol) was added and the resulting mixture was stirred at room temperature for 16 h. Then the reaction mixture was concentrated under reduced pressure and the crude liquid obtained was transferred to a steel autoclave reactor. To this crude mass was added anhydrous sodium sulfate (20 g) and mixture of toluene/acetonitrile (1.75 L, 1:3 ratio). The resulting solution was heated for 8 h at 130° C. with 100 psi pressure of nitrogen gas. The reaction was cooled to room temperature and filtered through Celite®. The filtrate was diluted with water (1.0 L) and extracted with ethyl acetate (3×1 L). The combined organic layer was washed with brine, dried over anhydrous sodium sulfate and evaporated. The crude product obtained was purified by flash column chromatography, eluting with 5% to 10% methanol in dichloromethane, to afford ethyl 2-[3-(4-chloro-3-fluorophenyl)-1H-1,2,4-triazol-5-yl]acetate (60 g, 36%) as a white solid. $^1$H NMR: $\delta_H$ (400 MHz, DMSO-d6) 14.06 (1H, bs), 7.88-7.82 (2H, m), 7.72-7.68 (1H, m), 4.13 (2H, q, J 7.1), 3.93 (2H, s), 1.20 (3H, t, J 7.1).

Step 5: Ethyl 2-[3-(4-chloro-3-fluorophenyl)-1-ethyl-1H-1,2,4-triazol-5-yl]acetate Potassium carbonate (54 g, 400 mmol) was added to vigorously stirred solution of ethyl 2-[3-(4-chloro-3-fluorophenyl)-1H-1,2,4-triazol-5-yl]acetate (60 g, 200 mmol) in dry acetone (1.2 L). Ethyl iodide (24 mL, 300 mmol) was added dropwise and the resulting mixture was refluxed for 6 h. The reaction was cooled to room temperature and filtered through Celite®. The filtrate was concentrated and the crude product obtained was purified by flash column chromatography, by eluting with 50% to 80% ethyl acetate in petroleum ether, to afford ethyl 2-[3-(4-chloro-3-fluorophenyl)-1-ethyl-1H-1,2,4-triazol-5-yl]acetate (42.5 g, 69%) as a white solid. $^1$H NMR: $\delta_H$ (400 MHz, DMSO-d6) 7.85-7.79 (2H, m), 7.70-7.65 (1H, m), 4.22-4.10 (6H, m), 1.39 (3H, t, J 7.2), 1.21 (3H, t, J 7.1).

Step 6: 2-[3-(4-Chloro-3-fluorophenyl)-1-ethyl-1H-1,2,4-triazol-5-yl]acetic acid To an ice-cold solution of ethyl 2-[3-(4-chloro-3-fluorophenyl)-1-ethyl-1H-1,2,4-triazol-5-yl]acetate (42.5 g, 137 mmol) in THF/water (850 mL, 2:1) was added LiOH—H$_2$O (8.61 g, 204 mmol). The resulting solution was stirred at room temperature for 4 h. Volatiles were evaporated under vacuum and residue was acidified with 1.5 N HCl (pH 3-4) and filtered. The solid obtained was washed with water and dried in vacuum to obtain 2-[3-(4-chloro-3-fluorophenyl)-1-ethyl-1H-1,2,4-triazol-5-yl]acetic acid (35 g, 91%). $^1$H NMR: $\delta_H$ (400 MHz, DMSO-d6) 12.98 (1H, bs), 7.86-7.81 (2H, m), 7.68 (1H, t, J 8.0), 4.20 (2H, d, J 7.2), 4.01 (2H, s), 1.40 (3H, t, J 7.2).

Step 7: 2-[3-(4-Chloro-3-fluorophenyl)-1-ethyl-1H-1,2,4-triazol-5-yl]-N-(3-fluorobenzyl) acetamide To a stirred solution of 2-[3-(4-chloro-3-fluorophenyl)-1-ethyl-1H-1,2,4-triazol-5-yl]acetic acid (50 mg, 0.18 mmol) in dry dichloromethane (5 mL) was added triethylamine (0.07 mL, 0.53 mmol). Then 3-fluorobenzylamine (0.025 mL, 0.22 mmol) was added followed by propylphosphonic anhydride solution (50 wt. % in ethyl acetate; 0.2 mL, 0.35 mmol). The resulting mixture was stirred at room temperature for 16 h. The reaction mixture was diluted with dichloromethane (15 mL) and water (10 mL) and partitioned. The organic layer was washed with water (10 mL) and brine (10 mL). Then the organic layer was dried over anhydrous sodium sulfate, filtered and concentrated under reduced pressure. The crude solid was purified by flash column chromatography, by eluting with 60% to 70% ethyl acetate in petroleum ether to afford 2-[3-(4-chloro-3-fluorophenyl)-1-ethyl-1H-1,2,4-triazol-5-yl]-N-(3-fluorobenzyl)acetamide (20 mg, 29%) as an off-white solid. $^1$H NMR: $\delta_H$ (400 MHz, DMSO-d6) 8.85 (1H, t, J 6.0), 7.86-7.81 (2H, m), 7.68 (1H, t, J 8.0), 7.40-7.35 (1H, m), 7.17-7.15 (2H, m), 7.09 (1H, t, J 8.4), 4.35 (2H, d, J 6.0), 4.22 (2H, q, J 7.2), 3.93 (2H, s), 1.39 (3H, t, J 7.2).

Example 2: 2-[3-(4-Chloro-3-fluorophenyl)-1-ethyl-1H-1,2,4-triazol-5-yl]-N-(3-methoxybenzyl) acetamide The title compound was prepared according to the method of Example 1, using 3-methoxybenzylamine instead of 3-fluorobenzylamine in Step 7.

$^1$H NMR: $\delta_H$ (400 MHz, DMSO-d6) 8.78 (1H, t, J 5.6), 7.85-7.80 (2H, m), 7.68 (1H, t, J 8.0), 7.26 (1H, t, J 8.0), 6.89-6.83 (2H, m), 6.82-6.81 (1H, m), 4.29 (2H, d, J 5.6), 4.21 (2H, q, J7.2), 3.91 (2H, s), 3.74 (3H, s), 1.39 (3H, t, J 7.2).

Example 3: 2-[3-(4-Chloro-3-fluorophenyl)-1-ethyl-1H-1,2,4-triazol-5-yl]-N-((2,6-dimethylpyridin-4-yl)methyl)acetamide To an ice-cold solution of 2-[3-(4-chloro-3-fluorophenyl)-1-ethyl-1H-1,2,4-triazol-5-yl]acetic acid (prepared as described in Example 1; 300 mg, 1.06 mmol) in dry dichloromethane (3 mL) was added EDC.HCl (404 mg, 2.12 mmol), HOBt (243 mg, 1.59 mmol) and diisopropylethylamine (0.55 mL, 3.18 mmol). The resulting reaction mixture was stirred at room temperature for 15 min, then (2,6-dimethylpyridin-4-yl)methanamine (173 mg, 1.27 mmol) was added and further stirred at room temperature for 16 h. The reaction was diluted with ice water (10 mL) and extracted with dichloromethane (2×10 mL). The combined organic layers were washed with water and brine, dried over anhydrous sodium sulfate, filtered and concentrated under reduced pressure. The crude product was purified by flash column chromatography, to afford 2-[3-(4-chloro-3-fluorophenyl)-1-ethyl-1H-1,2,4-triazol-5-yl]-N-[(2,6-dimethylpyridin-4-yl)methyl]acetamide as a white solid (240 mg, 56%). $^1$H NMR: $\delta_H$ (400 MHz, DMSO-d6) 8.82 (1H, t, J 5.7), 7.85-7.80 (2H, m), 7.70-7.66 (1H, m), 6.93 (2H, s), 4.26-4.23 (2H, m), 4.20 (2H, q, J 7.2), 3.93 (2H, s), 2.37 (6H, s), 1.39 (3H, t, J 7.2).

General Procedure 1: Amide Coupling Procedure Using EDC and HOBt

To an ice-cold solution of carboxylic acid (1 equiv.) in dry dichloromethane was added EDC.HCl (2.0 equiv.), HOBt (1.5 equiv.) and diisopropylethylamine (3 equiv.). The resulting reaction mixture was stirred at room temperature for 15 min, then the amine (1.2 equiv.) was added and the reaction further stirred at room temperature for 4 to 16 h (monitored by TLC). The reaction was diluted with ice water and extracted with dichloromethane (2-3 times). The combined organic layers were washed with water and brine. The organic layer was dried over anhydrous sodium sulfate, filtered and concentrated under reduced pressure. The crude product was purified by flash column chromatography to afford the desired product as a white solid.

Example 4: 2-[3-(4-Chloro-3-fluorophenyl)-1-ethyl-1H-1,2,4-triazol-5-yl]-N-[(1H-indazol-7-yl)methyl]acetamide The title compound was prepared according to General Procedure 1, using 2-[3-(4-chloro-3-fluorophenyl)-1-ethyl-1H-1,2,4-triazol-5-yl]acetic acid and (1H-indazol-7-yl)methanamine.
$^1$H NMR: $\delta_H$ (400 MHz, DMSO-d6) 13.05 (1H, s), 8.88 (1H, t, J 5.6), 8.11 (1H, s), 7.86-7.80 (2H, m), 7.71-7.68 (2H, m), 7.31-7.29 (1H, m), 7.10-7.29 (1H, m), 4.63 (2H, d, J 5.6), 4.20 (2H, q, J 7.2), 3.97 (2H, s), 1.39 (3H, t, J 7.2).

Example 5: 2-[3-(4-Chloro-3-fluorophenyl)-1-ethyl-1H-1,2,4-triazol-5-yl]-N-(3,5-dichlorobenzyl)acetamide The title compound was prepared according to General Procedure 1, using 2-[3-(4-chloro-3-fluorophenyl)-1-ethyl-1H-1,2,4-triazol-5-yl]acetic acid and 3,5-dichlorobenzylamine.
$^1$H NMR: $\delta_H$ (400 MHz, DMSO-d6) 8.87 (1H, t, J 5.8), 7.86-7.81 (2H, m), 7.67 (1H, t, J 7.8), 7.49 (1H, s), 7.36 (2H, s), 4.33 (2H, d, J 5.8), 4.21 (2H, q, J 7.0), 3.93 (2H, s), 1.38 (3H, t, J 7.0).

Example 6: 2-[3-(4-Chloro-3-fluorophenyl)-1-ethyl-1H-1,2,4-triazol-5-yl]-N-(5-methyl-1,2-oxazol-3-yl)acetamide The title compound was prepared according to General Procedure 1, using 2-[3-(4-chloro-3-fluorophenyl)-1-ethyl-1H-1,2,4-triazol-5-yl]acetic acid and 5-methyl-1,2-oxazol-3-yl amine.
$^1$H NMR: $\delta_H$ (400 MHz, DMSO-d6) 11.36 (1H, s), 7.85-7.80 (2H, m), 7.70-7.66 (1H, m), 6.60 (1H, s), 4.23 (2H, q, J 7.1), 4.14 (2H, s), 2.33 (3H, s), 1.41 (3H, t, J 7.1).

Example 7: 2-[3-(4-Chloro-3-fluorophenyl)-1-ethyl-1H-1,2,4-triazol-5-yl]-N-[(1H-indazol-5-yl)methyl]acetamide The title compound was prepared according to General Procedure 1, using 2-[3-(4-chloro-3-fluorophenyl)-1-ethyl-1H-1,2,4-triazol-5-yl]acetic acid and (1H-indazol-5-yl)methanamine.
$^1$H NMR: $\delta_H$ (400 MHz, DMSO-d6) 13.04 (1H, s), 8.82 (1H, t, J 5.2), 8.02 (1H, s), 7.85-7.81 (2H, m), 7.69-7.67 (2H, m), 7.52-7.50 (1H, m), 7.32-7.30 (1H, m), 4.41 (2H, d, J 5.2), 4.22 (2H, q, J 7.2), 3.91 (2H, s), 1.39 (3H, t, J 7.2).

Example 8: 2-[3-(4-Chloro-3-fluorophenyl)-1-ethyl-1H-1,2,4-triazol-5-yl]-N-(pyrazin-2-yl)acetamide The title compound was prepared according to General Procedure 1, using 2-[3-(4-chloro-3-fluorophenyl)-1-ethyl-1H-1,2,4-triazol-5-yl]acetic acid and 2-aminopyrazine.
$^1$H NMR: $\delta_H$ (400 MHz, DMSO-d6) 11.24 (1H, s), 9.29 (1H, s), 8.46-8.44 (1H, m), 8.41 (1H, d, J 2.6), 7.86-7.80 (2H, m), 7.70-7.66 (1H, m), 4.27-4.24 (4H, m), 1.43 (3H, t, J 7.2).

Example 9: 2-[3-(4-Chloro-3-fluorophenyl)-1-ethyl-1H-1,2,4-triazol-5-yl]-N-[(2-oxo-2,3-dihydro-1H-benzo[d]imidazol-5-yl)methyl]acetamide The title compound was prepared according to the method of Example 3, using 5-(amino methyl)-1,3-dihydro-2H-benzo[d]imidazol-2-one instead of (2,6-dimethylpyridin-4-yl)methanamine.
$^1$H NMR: $\delta_H$ (400 MHz, DMSO-d6) 10.60 (1H, s), 10.57 (1H, s), 8.74 (1H, t, J 5.6), 7.84-7.80 (2H, m), 7.70-7.66 (1H, m), 6.89-6.87 (3H, m), 4.26-4.23 (2H, m), 4.21 (2H, q, J 7.2), 3.88 (2H, s), 1.39 (3H, t, J 7.2).

Example 10: 2-[3-(4-Chloro-3-fluorophenyl)-1-ethyl-1H-1,2,4-triazol-5-yl]-N-[(3-chloro-5-methylphenyl)methyl]acetamide The title compound was prepared according to the method of Example 3, using 3-chloro-5-methylbenzylamine instead of (2,6-dimethylpyridin-4-yl)methanamine.
$^1$H NMR: $\delta_H$ (400 MHz, DMSO-d6) 8.82 (1H, t, J 5.9), 7.86-7.81 (2H, m), 7.70-7.66 (1H, m), 7.16 (2H, s), 7.06 (1H, s), 4.29 (2H, d, J 5.9), 4.22 (2H, q, J 7.2), 3.92 (2H, s), 2.28 (3H, s), 1.39 (3H, t, J 7.2).

Example 11: 2-[3-(4-Chloro-3-fluorophenyl)-1-ethyl-1H-1,2,4-triazol-5-yl]-N-[(3-fluoro-5-methylphenyl)methyl]acetamide The title compound was prepared according to the method of Example 3, using 3-fluoro-5-methylbenzylamine instead of (2,6-dimethylpyridin-4-yl)methanamine.
$^1$H NMR: $\delta_H$ (400 MHz, DMSO-d6) 8.72 (1H, t, J 5.6), 7.84-7.80 (2H, m), 7.71-7.67 (1H, m), 7.22-7.15 (2H, m), 7.10-7.06 (1H, m), 4.33 (2H, d, J 5.6), 4.22 (2H, q, J 7.2), 3.92 (2H, s), 2.19 (3H, s), 1.39 (3H, t, J 7.2).

Example 12: 2-[3-(4-Chloro-3-fluorophenyl)-1-ethyl-1H-1,2,4-triazol-5-yl]-N-[(3,5-dimethylphenyl)methyl]acetamide The title compound was prepared according to the method of Example 3, using 3,5-dimethylbenzylamine instead of (2,6-dimethylpyridin-4-yl)methanamine.
$^1$H NMR: $\delta_H$ (400 MHz, DMSO-da) 8.72 (1H, t, J 5.6), 7.84-7.80 (2H, m), 7.70-7.66 (1H, m), 6.88 (3H, s), 4.37-4.15 (4H, m), 3.90 (2H, s), 2.23 (6H, s), 1.39 (3H, t, J 7.2).

Example 13: 2-[3-(4-Chloro-3-fluorophenyl)-1-ethyl-1H-1,2,4-triazol-5-yl]-N-[(2,3-difluorophenyl)methyl]acetamide The title compound was prepared according to the method of Example 3, using 2,3-difluorobenzylamine instead of (2,6-dimethylpyridin-4-yl)methanamine.

¹H NMR: δ$_H$ (400 MHz, DMSO-d6) 8.88 (1H, t, J 5.6), 7.84-7.80 (2H, m), 7.70-7.66 (1H, m), 7.39-7.32 (1H, m), 7.26-7.16 (2H, m), 4.40 (2H, d, J 5.6), 4.20 (2H, q, J 7.2), 3.92 (2H, s), 1.38 (3H, t, J 7.2).

Example 14: 2-[3-(4-Chloro-3-fluorophenyl)-1-ethyl-1H-1,2,4-triazol-5-yl]-N-[(3-ethoxyphenyl)methyl]acetamide The title compound was prepared according to the method of Example 3, using 3-ethoxybenzylamine instead of (2,6-dimethylpyridin-4-yl)methanamine.

¹H NMR: δ$_H$ (400 MHz, DMSO-d6) 8.77 (1H, t, J 5.6), 7.84-7.80 (2H, m), 7.70-7.66 (1H, m), 7.22 (1H, t, J 8.0), 6.86-6.79 (3H, m), 4.28 (2H, d, J 5.6), 4.21 (2H, q, J 7.2), 3.97 (2H, q, J 7.0), 3.91 (2H, s), 1.39 (3H, t, J 7.2), 1.28 (3H, t, J 7.0).

Example 15: 2-[3-(4-Chloro-3-fluorophenyl)-1-ethyl-1H-1,2,4-triazol-5-yl]-N-[(3,5-dimethoxyphenyl)methyl]acetamide The title compound was prepared according to the method of Example 3, using 3,5-dimethoxybenzylamine instead of (2,6-dimethylpyridin-4-yl)methanamine.

¹H NMR: δ$_H$ (400 MHz, DMSO-d6) 8.77 (1H, t, J 5.9), 7.85-7.81 (2H, m), 7.70-7.66 (1H, m), 6.47 (2H, d, J 2.2), 6.38 (1H, t, J 2.2), 4.26-4.20 (4H, m), 3.92 (2H, s), 3.71 (6H, s), 1.40 (3H, t, J 7.2).

Example 16: 2-[3-(4-Chloro-3-fluorophenyl)-1-ethyl-1H-1,2,4-triazol-5-yl]-N-[(4-methoxyphenyl)methyl]acetamide The title compound was prepared according to the method of Example 3, using 4-methoxybenzylamine instead of (2,6-dimethylpyridin-4-yl)methanamine.

¹H NMR: δ$_H$ (400 MHz, DMSO-d6) 8.71 (1H, t, J 5.6), 7.84-7.79 (2H, m), 7.69-7.65 (1H, m), 7.22 (2H, d, J 8.4), 6.89 (2H, d, J 8.4), 4.23-4.19 (4H, m), 3.88 (2H, s), 3.73 (3H, s), 1.38 (3H, t, J 7.2).

Example 17: 2-[3-(4-Chloro-3-fluorophenyl)-1-ethyl-1H-1,2,4-triazol-5-yl]-N-[(6-methoxypyridin-3-yl)methyl]acetamide The title compound was prepared according to the method of Example 3, using (6-methoxypyridin-3-yl)methanamine instead of (2,6-dimethylpyridin-4-yl)methanamine.

¹H NMR: δ$_H$ (400 MHz, DMSO-d6) 8.75 (1H, t, J 5.6), 8.10 (1H, d, J 2.4), 7.83-7.78 (2H, m), 7.69 (1H, t, J 8.4), 7.63-7.61 (1H, m), 6.78 (1H, d, J 8.4), 4.23 (2H, d, J 5.6), 4.18 (2H, q, J 7.8), 3.86 (2H, s), 3.81 (3H, s), 1.36 (3H, t, J 7.2).

Example 18: 2-[3-(4-Chloro-3-fluorophenyl)-1-methyl-1H-1,2,4-triazol-5-yl]-N-[(3,5-dichlorophenyl)methyl]acetamide

Step 1: Ethyl 2-[3-(4-Chloro-3-fluorophenyl)-1-methyl-1H-1,2,4-triazol-5-yl]acetate Potassium carbonate (1.95 g, 14.1 mmol) was added to vigorously stirred solution of ethyl 2-[3-(4-chloro-3-fluorophenyl)-1H-1,2,4-triazol-5-yl]acetate (2.0 g, 7.1 mmol) in dry acetone (40 mL). Methyl iodide (0.7 mL, 10.6 mmol) was added dropwise and the resulting mixture was refluxed for 5 h. The reaction was cooled to room temperature and filtered through Celite®. The filtrate was concentrated and the crude product obtained was purified by column chromatography, eluting with 50% to 80% ethyl acetate in petroleum ether, to afford ethyl 2-[3-(4-chloro-3-fluorophenyl)-1-methyl-1H-1,2,4-triazol-5-yl]acetate (1.5 g, 72%) as a white solid. ¹H NMR: δ$_H$ (400 MHz, DMSO-d6) 7.83-7.79 (2H, m), 7.70-7.66 (1H, m), 4.15-4.11 (4H, m), 3.86 (3H, s), 1.21 (3H, t, J 7.0).

Step 2: 2-[3-(4-Chloro-3-fluorophenyl)-1-methyl-1H-1,2,4-triazol-5-yl]acetic acid To an ice-cold solution of ethyl 2-[3-(4-chloro-3-fluorophenyl)-1-methyl-1H-1,2,4-triazol-5-yl]acetate (1.5 g, 5.0 mmol) in THF/water (20 mL, 4:1) was added LiOH—H$_2$O (422 mg, 10.0 mmol). The resulting solution was stirred at room temperature for 4 h. The mixture was concentrated under vacuum and the residue was acidified with 1.5 N HCl (pH 3-4) and filtered. The solid obtained was washed with water and dried under vacuum to obtain 2-[3-(4-chloro-3-fluorophenyl)-1-methyl-1H-1,2,4-triazol-5-yl]acetic acid (1.0 g, 76%). H NMR: δ$_H$(400 MHz, DMSO-d6) 12.93 (1H, bs), 7.82-7.78 (2H, m), 7.67 (1H, t, J 8.0), 4.00 (2H, s), 3.85 (3H, m).

Step 3: 2-[3-(4-Chloro-3-fluorophenyl)-1-methyl-1H-1,2,4-triazol-5-yl]-N-[(3,5-dichlorophenyl)methyl]acetamide The title compound was prepared according to the method of Example 3, using 2-[3-(4-chloro-3-fluorophenyl)-1-methyl-1H-1,2,4-triazol-5-yl]acetic acid instead of 2-[3-(4-chloro-3-fluorophenyl)-1-ethyl-1H-1,2,4-triazol-5-yl]acetic acid and 3,5-dichlorobenzylamine instead of (2,6-dimethylpyridin-4-yl)methanamine.

¹H NMR: δ$_H$ (400 MHz, DMSO-d5) 8.85 (1H, t, J 5.8), 7.85-7.80 (2H, m), 7.67 (11H, t, J 8.0), 7.49 (1H, s), 7.36 (2H, s), 4.33 (2H, d, J 5.8), 3.93 (2H, s), 3.88 (3H, s).

Example 19: 2-[3-(4-Chloro-3-fluorophenyl)-1-methyl-1H-1,2,4-triazol-5-yl]-N-[(3-methoxyphenyl)methyl]acetamide The title compound was prepared according to the method of Example 18, using 3-methoxybenzylamine instead of 3,5-dichlorobenzylamine.

¹H NMR: δ$_H$ (400 MHz, DMSO-d6) 8.78 (1H, t, J 5.8), 7.85-7.80 (2H, m), 7.71-7.67 (1H, m), 7.25 (1H, t, J 8.0), 6.89-6.82 (3H, m), 4.29 (2H, d, J 5.8), 3.92 (2H, s), 3.90 (3H, s), 3.73 (3H, s).

Example 20: 2-[3-(4-Chloro-3-fluorophenyl)-1-methyl-1H-1,2,4-triazol-5-yl]-N-[(3-fluorophenyl)methyl]acetamide The title compound was prepared according to the method of Example 18, using 3-fluorobenzylamine instead of 3,5-dichlorobenzylamine.

¹H NMR: δ$_H$ (400 MHz, DMSO-d6) 8.84 (1H, t, J 5.9), 7.86-7.80 (2H, m), 7.71-7.67 (1H, m), 7.40-7.35 (1H, m), 7.16-7.11 (2H, m), 7.09-7.06 (1H, m), 4.35 (2H, d, J 5.9), 3.93 (2H, s), 3.89 (3H, s).

Example 21: 2-[3-(4-Chloro-3-fluorophenyl)-1-methyl-1H-1,2,4-triazol-5-yl]-N-[(1H-indazol-5-yl)methyl]acetamide The title compound was prepared according to the method of Example 18, using (1H-indazol-5-yl)methanamine instead of 3,5-dichlorobenzylamine.

$^1$H NMR: $\delta_H$ (400 MHz, DMSO-d6) 13.04 (1H, s), 8.80 (1H, t, J 5.4), 8.03 (1H, s), 7.85-7.80 (2H, m), 7.71-7.67 (2H, m), 7.52-7.50 (1H, m), 7.32-7.30 (1H, m), 4.41 (2H, d, J 5.4), 3.92 (2H, s), 3.88 (3H, s).

Example 22: 2-[3-(4-Chloro-3-fluorophenyl)-1-(2-methoxyethyl)-1H-1,2,4-triazol-5-yl]-N-[(3,5-dichlorophenyl)methyl]acetamide

Step 1: Ethyl 2-[3-(4-chloro-3-fluorophenyl)-1-(2-methoxyethyl)-1H-1,2,4-triazol-5-yl]acetate Potassium carbonate (1.95 g, 14.1 mmol) was added to vigorously stirred solution of ethyl 2-[3-(4-chloro-3-fluorophenyl)-1H-1,2,4-triazol-5-yl]acetate (2.0 g, 7.1 mmol) and potassium iodide (50 mg) in dry acetone (40 mL). 2-Methoxyethyl bromide (0.8 mL, 8.5 mmol) was added dropwise and the resulting mixture was refluxed for 16 h. The reaction was cooled to room temperature and filtered through Celite®. The filtrate was concentrated and the crude product obtained was purified by column chromatography, eluting with 50% to 80% ethyl acetate in petroleum ether, to afford ethyl 2-[3-(4-chloro-3-fluorophenyl)-1-(2-methoxyethyl)-1H-1,2,4-triazol-5-yl]acetate (1.4 g, 58%) as a white solid. $^1$H NMR: $\delta_H$ (400 MHz, DMSO-d6) 7.85-7.81 (2H, m), 7.71-7.67 (1H, m), 4.37 (2H, t, J 5.3), 4.15 (2H, d, J 7.2), 4.08 (2H, s), 3.70 (2H, t, J 5.3), 3.23 (3H, s), 1.21 (3H, t, J 7.2).

Step 2: 2-[3-(4-Chloro-3-fluorophenyl)-1-(2-methoxyethyl)-1H-1,2,4-triazol-5-yl]acetic acid To an ice-cold solution of ethyl 2-[3-(4-chloro-3-fluorophenyl)-1-(2-methoxyethyl)-1H-1,2,4-triazol-5-yl]acetate (1.4 g, 4.0 mmol) in THF/water (15 mL, 3:1) was added LiOH—H$_2$O (270 mg, 6.0 mmol). The resulting solution was stirred at room temperature for 5 h. The mixture was concentrated under vacuum and the residue was acidified with 1.5 N HCl (pH 3-4) and filtered. The solid obtained was washed with water and dried under vacuum to obtain 2-[3-(4-chloro-3-fluorophenyl)-1-(2-methoxyethyl)-1H-1,2,4-triazol-5-yl]acetic acid (1.2 g, 93%). $^1$H NMR: $\delta_H$ (400 MHz, DMSO-d6) 12.96 (1H, bs), 7.85-7.80 (2H, m), 7.71-7.67 (1H, m), 4.36 (2H, t, J 5.3), 3.98 (2H, s), 3.70 (2H, t, J 5.3), 3.24 (3H, s).

Step 3: 2-[3-(4-Chloro-3-fluorophenyl)-1-(2-methoxyethyl)-1H-1,2,4-triazol-5-yl]-N-[(3,5-dichlorophenyl)methyl]acetamide The title compound was prepared according to the method of Example 3, using 2-[3-(4-chloro-3-fluorophenyl)-1-(2-methoxyethyl)-1H-1,2,4-triazol-5-yl]acetic acid instead of 2-[3-(4-chloro-3-fluorophenyl)-1-ethyl-1H-1,2,4-triazol-5-yl]acetic acid and 3,5-dichlorobenzylamine instead of (2,6-dimethylpyridin-4-yl)methanamine.

$^1$H NMR: $\delta_H$ (400 MHz, DMSO-d6) 8.83 (1H, t, J 6.0), 7.86-7.83 (2H, m), 7.70-7.68 (1H, m), 7.49 (1H, s), 7.37 (2H, s), 4.38 (2H, t, J 5.4), 4.34 (2H, q, J 6.0), 3.91 (2H, s), 3.71 (2H, t, J 5.4), 2.97 (3H, s).

Example 23: 2-[3-(4-Chloro-3-fluorophenyl)-1-(2-hydroxyethyl)-1H-1,2,4-triazol-5-yl]-N-[(3,5-dichlorophenyl)methyl]acetamide To an ice-cold solution of 2-[3-(4-chloro-3-fluorophenyl)-1-(2-methoxyethyl)-1H-1,2,4-triazol-5-yl]-N-[(3,5-dichlorophenyl)methyl]acetamide (75 mg, 0.16 mmol, 1.0 equi.) in anhydrous dichloromethane was added BBr$_3$ in dichloromethane (1M; 2.0 equi.). The resulting mixture was stirred at room temperature for 2 h. The reaction was quenched by slow addition of saturated sodium bicarbonate solution and extracted with dichloromethane (3 times). The combined organic layer was washed with water and brine. The organic layer was then dried over anhydrous sodium sulfate, filtered and concentrated under reduced pressure. The crude solid was purified by flash column chromatography, eluting with 80% ethyl acetate in petroleum ether to afford 2-[3-(4-chloro-3-fluorophenyl)-1-(2-hydroxyethyl)-1H-1,2,4-triazol-5-yl]-N-[(3,5-dichlorophenyl)methyl]acetamide as a white solid (20 mg, 27%).

$^1$H NMR: $\delta_H$ (400 MHz, DMSO-d6) 8.84 (1H, t, J 6.0), 7.87-7.81 (2H, m), 7.70-7.66 (1H, m), 7.49 (1H, s), 7.36 (2H, s), 5.00 (1H, t, J 5.2), 4.34 (2H, t, J 6.0), 4.27 (2H, t, J 5.2), 3.94 (2H, s), 3.78-3.75 (2H, m).

Example 24: 2-[3-(4-Chloro-3-fluorophenyl)-1-ethyl-1H-1,2,4-triazol-5-yl]-N-[(3-fluorophenyl)methyl]propanamide

Step 1: Ethyl 2-[3-(4-chloro-3-fluorophenyl)-1-ethyl-1H-1,2,4-triazol-5-yl]propanoate To an ice-cold solution of ethyl 2-[3-(4-chloro-3-fluorophenyl)-1-ethyl-1H-1,2,4-triazol-5-yl]acetate (prepared as described in Example 1; 0.2 g, 0.64 mmol) in THF (20 mL) was added dropwise 2M LDA in THF (0.64 mL). After 15 min, methyl iodide (0.05 mL, 0.78 mmol) was added and the resulting mixture was stirred at room temperature for 6 h. The reaction was then diluted with aqueous ammonium chloride and extracted with ethyl acetate (3×20 mL). The organic layer was washed with water and brine. The organic layer was dried over anhydrous sodium sulfate, filtered and concentrated under reduced pressure. The crude solid was purified by flash column chromatography, eluting with 10% to 50% ethyl acetate in petroleum ether, to afford ethyl 2-[3-(4-chloro-3-fluorophenyl)-1-ethyl-1H-1,2,4-triazol-5-yl]propanoate (0.15 g, 33%) as a white solid. $^1$H NMR: $\delta_H$ (400 MHz, DMSO-d6) 7.85-7.81 (2H, m), 7.71-7.66 (1H, m), 4.37 (1H, q, J 7.2), 4.25-4.10 (4H, m), 1.52 (3H, d J7.2), 1.41 (3H, t, J 7.2), 1.16 (3H, t, J 7.2).

Step 2: 2-[3-(4-Chloro-3-fluorophenyl)-1-ethyl-1H-1,2,4-triazol-5-yl]-N-[(3-fluorophenyl)methyl]propanamide To a degassed solution of ethyl 2-(3-(4-chloro-3-fluorophenyl)-1-ethyl-1H-1,2,4-triazol-5-yl)propanoate (70 mg, 0.22 mmol) and triethylamine (0.08 mL, 0.83 mmol) in dry toluene (7 mL) was added DABAL-Me$_3$ (56 mg, 0.22 mmol), followed by 3-fluorobenzylamine (32 mg, 0.26 mmol). The resulting mixture was heated in a sealed-tube at 110° C. for 1 h. The reaction was cooled to room temperature and diluted with ethyl acetate. The organic layer was washed with dilute aqueous HCl and brine. The organic layer was then dried over anhydrous sodium sulfate, filtered and concentrated under reduced pressure. The crude solid was purified by flash column chromatography, eluting with 50% to 80% ethyl acetate in petroleum ether to afford 2-[3-(4-chloro-3-fluorophenyl)-1-ethyl-1H-1,2,4-triazol-5-yl]-N-[(3-fluorophenyl)methyl]propanamide (10 mg, 12%).

$^1$H NMR: $\delta_H$ (400 MHz, DMSO-d6) 8.67 (1H, t, J 6.0), 7.86-7.82 (2H, m), 7.68 (1H, t, J 8.0), 7.38-7.32 (1H, m), 7.12-7.04 (3H, m), 4.41-4.35 (1H, m), 4.29-4.24 (1H, m), 4.19-4.11 (3H, m), 1.53 (3H, d, J 6.8), 1.33 (3H, t, J 7.2).

Example 25: 2-[3-(4-Chloro-3-fluorophenyl)-1-methanesulfonyl-1H-1,24-triazol-5-yl]-N-[(3-fluorophenyl)methyl]acetamide

Step 1: Ethyl 2-[3-(4-chloro-3-fluorophenyl)-1-methylsulfonyl-1H-1,2,4-triazol-5-yl]acetate To an ice-cold solution of ethyl 2-[3-(4-chloro-3-fluorophenyl)-1H-1,2,4-triazol-5-yl]acetate (prepared as described in Example 1; 0.5 g, 1.77 mmol) and trimethylamine (0.5 mL) in $CH_2Cl_2$ (10 mL) was added methane sulfonyl chloride (0.2 mL, 2.65 mmol). The resulting mixture was stirred at room temperature for 2 h. Then the reaction was diluted with ice-water and extracted with dichloromethane (2×10 mL). The organic layer was washed with saturated sodium bicarbonate (20 mL) and brine (20 mL). The organic layer was then dried over anhydrous sodium sulfate, filtered and concentrated under reduced pressure. The crude product obtained was used without further purification.

Step 2: 2-[3-(4-Chloro-3-fluorophenyl)-1-methylsulfonyl-1H-1,2,4-triazol-5-yl]-N-[(3-fluorophenyl)methyl]acetamide To a degassed solution of ethyl 2-[3-(4-chloro-3-fluorophenyl)-1-methylsulfonyl-1H-1,2,4-triazol-5-yl]acetate (80 mg, 0.22 mmol) and triethylamine (0.08 mL, 0.83 mmol) in dry toluene (7 mL) was added DABAL-Me$_3$ (56 mg, 0.22 mmol), followed by 3-fluorobenzylamine (33 mg, 0.27 mmol). The resulting mixture was heated in a sealed tube at 110° C. for 1.5 h. The reaction was cooled to room temperature and diluted with ethyl acetate. The organic layer was washed with dilute aqueous HCl and brine. The organic layer was dried over anhydrous sodium sulfate, filtered and concentrated under reduced pressure. The crude solid was purified by flash column chromatography, eluting with 50% to 70% ethyl acetate in petroleum ether to afford 2-[3-(4-chloro-3-fluorophenyl)-1-methylsulfonyl-1H-1,2,4-triazol-5-yl]-N-[(3-fluorophenyl)methyl]acetamide (5 mg).

$^1$H NMR: $\delta_H$ (400 MHz, DMSO-d6) 8.85 (1H, t, J 5.6), 7.97-7.90 (2H, m), 7.81-7.77 (1H, m), 7.41-7.36 (1H, m), 7.17-7.06 (3H, m), 4.36 (2H, d, J 5.6), 4.20 (2H, s), 3.72 (3H, s).

Example 26: 2-[3-(4-Chloro-3-fluorophenyl)-1-(cyclopropylmethyl)-1H-1,2,4-triazol-5-yl]-N-[(2,6-dimethylpyridin-4-yl)methyl]acetamide

Step 1: Ethyl 2-(3-(4-chloro-3-fluorophenyl)-1-(cyclopropylmethyl)-1H-1,2,4-triazol-5-yl)acetate Potassium carbonate (3.7 g, 27 mmol) was added to vigorously stirred solution of ethyl 2-[3-(4-chloro-3-fluorophenyl)-1H-1,2,4-triazol-5-yl]acetate (2.5 g, 9 mmol) in dry acetone (40 mL). (Bromomethyl)cyclopropane (1.3 mL, 13 mmol) was added dropwise and the resulting mixture was refluxed for 5 h. The reaction was cooled to room temperature and filtered through Celite®. The filtrate was concentrated and the crude product obtained was used in the next step without further purification.

Step 2: 2-[3-(4-Chloro-3-fluorophenyl)-1-(cyclopropylmethyl)-1H-1,2,4-triazol-5-yl]acetic acid To an ice-cold solution of ethyl 2-[3-(4-chloro-3-fluorophenyl)-1-(cyclopropylmethyl)-1H-1,2,4-triazol-5-yl]acetate (3.13 g, 9.3 mmol) in THF/water (15 mL, 3:1) was added LiOH—H$_2$O (0.58 g, 13.9 mmol). The resulting solution was stirred at room temperature for 3 h. The mixture was concentrated under vacuum and residue was acidified with 1.5 N HCl (pH 3-4) and filtered. The solid obtained was washed with water and dried under vacuum to obtain 2-[3-(4-chloro-3-fluorophenyl)-1-(cyclopropylmethyl)-1H-1,2,4-triazol-5-yl]acetic acid (2.7 g).

$^1$H NMR: $\delta_H$ (400 MHz, DMSO-d6) 7.85-7.80 (2H, m), 7.67-7.62 (1H, m), 4.00 (2H, d, J 9.6), 3.44 (2H, s), 1.36-1.31 (1H, m), 0.53-0.41 (4H, m).

Step 3: 2-[3-(4-Chloro-3-fluorophenyl)-1-(cyclopropylmethyl)-1H-1,2,4-triazol-5-yl]-N-[(2,6-dimethylpyridin-4-yl)methyl]acetamide The title compound was prepared according to the method of Example 3, using 2-[3-(4-chloro-3-fluorophenyl)-1-(cyclopropylmethyl)-1H-1,2,4-triazol-5-yl]acetic acid instead of 2-[3-(4-chloro-3-fluorophenyl)-1-ethyl-1H-1,2,4-triazol-5-yl]acetic acid.

$^1$H NMR: $\delta_H$ (400 MHz, DMSO-d6) 8.84 (1H, t, J 5.7), 7.86-7.82 (2H, m), 7.72-7.68 (1H, m), 6.94 (2H, s), 4.27 (2H, d, J 5.7), 4.20 (2H, d, J 7.1), 3.94 (2H, s), 2.34 (6H, s), 1.33-1.24 (1H, m), 0.52-0.43 (4H, m).

Example 27: 2-[3-(4-Chloro-3-fluorophenyl)-1-(cyclopropylmethyl)-1H-1,2,4-triazol-5-yl]-N-[(1H-indazol-5-yl)methyl]acetamide The title compound was prepared according to the method of Example 26, using (1H-indazol-5-yl)methanamine instead of (2,6-dimethylpyridin-4-yl)methanamine.

$^1$H NMR: $\delta_H$ (400 MHz, DMSO-d6) 13.03 (1H, s), 8.81 (1H, t, J 5.6), 8.02 (1H, s), 7.86-7.81 (2H, m), 7.71-7.68 (2H, m), 7.50 (1H, d, J 8.6), 7.31 (1H, d, J 8.6), 4.40 (2H, d, J 5.6), 4.05 (2H, d, J 7.1), 3.91 (2H, s), 1.33-1.30 (1H, m), 0.52-0.46 (2H, m), 0.44-0.42 (2H, m).

Example 28: N-[(3,5-Dichlorophenyl)methyl]-2-{1-ethyl-3-[4-(trifluoromethoxy)phenyl]-1H-1,2,4-triazol-5-yl}acetamide

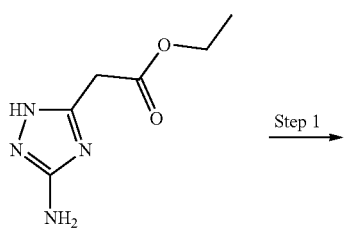

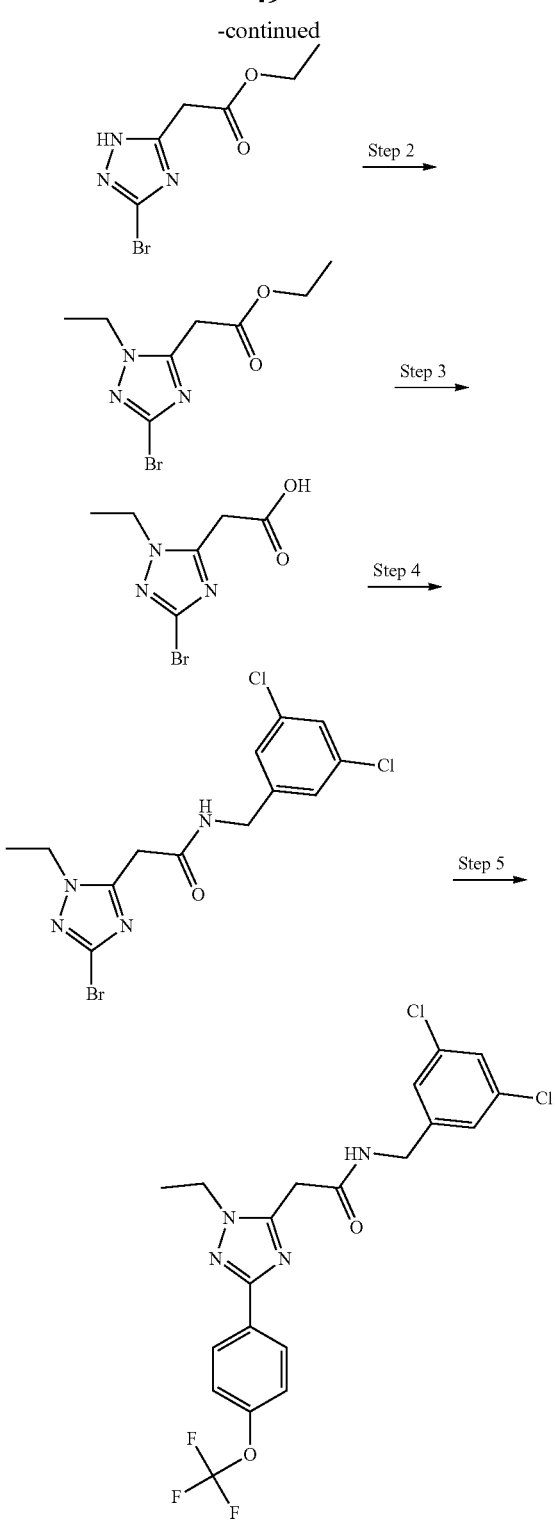

Step 1: Ethyl 2-(3-bromo-1H-1,2,4-triazol-5-yl)acetate

To an ice-cold vigorously stirred suspension of ethyl 2-(3-amino-1H-1,2,4-triazol-5-yl)acetate (3.0 g, 17.4 mmol; prepared as described in *Eur. J. Med. Chem.* 2009, 44, 117-123) in 1 M sulphuric acid (42 mL) was added dropwise a solution of NaNO$_2$ (1.8 g, 24.0 mmol) in water (30 mL). After 30 min of stirring at −5° C. to 0° C., cuprous bromide (0.72 g, 5.1 mmol) and potassium bromide (4.2 g, 34.8 mmol) were added. The resulting mixture was stirred at room temperature for 5 h. The reaction mixture was extracted with ethyl acetate (3×150 mL) and the combined organic layer was washed with water and brine. The organic layer was dried over anhydrous sodium sulfate, filtered and concentrated under reduced pressure. The crude solid was purified by flash column chromatography, eluting with 80% ethyl acetate in petroleum ether to afford ethyl 2-(3-bromo-1H-1,2,4-triazol-5-yl)acetate (900 mg, 23%) as a pale syrup.

Step 2: Ethyl 2-(3-bromo-1-ethyl-1H-1,2,4-triazol-5-yl)acetate

To a solution of ethyl 2-(3-bromo-1H-1,2,4-triazol-5-yl)acetate (900 mg, 3.8 mmol) in acetone (20 mL) was added potassium carbonate (1.32 g, 9.6 mmol) and ethyl iodide (0.5 mL, 5.8 mmol). The resulting mixture was stirred at room temperature for 16 h. The mixture was then concentrated under reduced pressure and the residue was diluted with water. This aqueous solution was extracted with ethyl acetate (3×100 mL) and the combined organic layer was washed with water and brine. The organic layer was then dried over anhydrous sodium sulfate, filtered and concentrated under reduced pressure. The crude product was mixture of regio-isomers, which was used without further purification for the next step.

Step 3: 2-(3-Bromo-1-ethyl-1H-1,2,4-triazol-5-yl)acetic acid

To an ice-cold solution of ethyl 2-(3-bromo-1-ethyl-1H-1,2,4-triazol-5-yl)acetate (800 mg) in THF/water (16 mL, 2:1) was added LiOH.H$_2$O (200 mg). The resulting solution was stirred at room temperature for 1 h. The mixture was then concentrated under reduced pressure and the residue was acidified with 1.5 N HCl (pH 4-5) and filtered. The solid obtained was washed with water and dried under vacuum to obtain crude 2-(3-bromo-1-ethyl-1H-1,2,4-triazol-5-yl)acetic acid along with another regio-isomer, which was used without further purification.

Step 4: 2-(3-Bromo-1-ethyl-1H-1,2,4-triazol-5-yl)-N-(3,5-dichlorobenzyl)acetamide To an ice-cold solution of crude 2-(3-bromo-1-ethyl-1H-1,2,4-triazol-5-yl)acetic acid (720 mg, 3.1 mmol) in dry dichloromethane (10 mL) was added EDC.HCl (1.2 g 6.1 mmol), HOBt (0.7 g, 4.6 mmol) and diisopropylethylamine (2.2 mL, 12.3 mmol). The resulting reaction mixture was stirred at room temperature for 15 min, then 3,5-dichlorobenzylamine (0.7 g, 5.2 mmol) was added and further stirred at room temperature for 16 h. The reaction was diluted with ice water and extracted dichloromethane (3×70 mL). The combined organic layer was washed with water and brine. The organic layer was dried over anhydrous sodium sulfate, filtered and concentrated under reduced pressure. The crude product was used in the next step without further purification.

Step 5: N-[(3,5-Dichlorophenyl)methyl]-2-{1-ethyl-3-[4-(trifluoromethoxy)phenyl]-1H-1,2,4-triazol-5-yl}acetamide To a degassed solution in a microwave tube of 2-(3-bromo-1-ethyl-1H-1,2,4-triazol-5-yl)-N-(3,5-dichlorobenzyl)acetamide (1 equiv.), 4-(trifluoromethoxy)phenylboronic acid (1.2 equiv.) and potassium carbonate (3 equiv.) in dioxane/water (9:1) was added 1,1'-bis(diphenylphosphino)ferrocene-palladium(II)dichloride dichloromethane complex (10 mol %). The reaction was heated at 120° C. in microwave for 1 h. Then the reaction was diluted with ethyl acetate and filtered through Celite® The residue was washed with ethyl acetate. The filtrate was evaporated under reduced pressure and the crude product was purified by flash column chromatography followed by preparative HPLC to afford the required product. $^1$H NMR: $\delta_H$ (400 MHz, DMSO-d6) 8.86 (1H, t, J 5.9), 8.08 (2H, d, J 8.8), 7.49 (1H, s), 7.43 (2H, d, J 8.8), 7.35 (2H, s), 4.34 (2H, d, J 5.9), 4.20 (2H, q, J 7.2), 3.93 (2H, s), 1.39 (3H, t, J7.2).

Example 29: 2-[3-(4-Chloro-3-methoxyphenyl)-1-ethyl-1H-1,2,4-triazol-5-yl]-N-[(3,5-dichlorophenyl)methyl]acetamide The title compound was prepared according to the method of Example 28, using 4-chloro-3-methoxyphenylboronic acid instead of 4-(trifluoromethoxy)phenylboronic acid in Step 5.
$^1$H NMR: $\delta_H$ (400 MHz, DMSO-d6) 8.87 (1H, t, J 5.6), 7.63-7.50 (4H, m), 7.35 (2H, s), 4.34 (2H, d, J 5.6), 4.21 (2H, q, J 7.2), 3.94 (2H, s), 3.93 (3H, s), 1.38 (3H, t, J 7.2).

Example 30: 2-[3-(4-Cyanophenyl)-1-ethyl-1H-1,2,4-triazol-5-yl]-N-[(3,5-dichlorophenyl)methyl]acetamide The title compound was prepared according to the method of Example 28, using 4-cyanophenylboronic acid instead of 4-(trifluoromethoxy)phenylboronic acid in Step 5.
$^1$H NMR: $\delta_H$ (400 MHz, DMSO-d6) 8.88 (1H, t, J 6.0), 8.14 (2H, d, J 8.4), 7.92 (2H, d, J 8.4), 7.50 (1H, d, J 1.8), 7.35 (2H, t, J 1.8), 4.34 (2H, d, J 6.0), 4.21 (2H, q, J 7.2), 3.96 (2H, s), 1.39 (3H, t, J 7.2).

Example 31: 2-[3-(4-Chloro-3-fluorophenyl)-1-ethyl-1H-1,2,4-triazol-5-yl]-N-[(2,6-dimethyl-1-oxidopyridin-4-yl)methyl]acetamide To a stirred solution of 2-[3-(4-chloro-3-fluorophenyl)-1-ethyl-1H-1,2,4-triazol-5-yl]-N-((2,6-dimethylpyridin-4-yl)methyl)acetamide (50 mg, 0.12 mmol) in dry dichloromethane (5 mL) was added mCPBA (24 mg, 0.14 mmol). The resulting solution was stirred at room temperature for 3 h. The reaction mixture was diluted with dichloromethane (15 mL) and saturated aqueous sodium bicarbonate solution (10 mL). The organic layer was separated and washed with water and brine. The organic layer was dried over anhydrous sodium sulfate, filtered and concentrated under reduced pressure. The crude solid was purified by flash column chromatography, eluting with ethyl acetate to afford 2-[3-(4-chloro-3-fluorophenyl)-1-ethyl-1H-1,2,4-triazol-5-yl]-N-[(2,6-dimethyl-1-oxidopyridin-4-yl)methyl]acetamide (30 mg, 58%). $^1$H NMR: $\delta_H$ (400 MHz, DMSO-d6) 8.84 (1H, t, J 5.7), 7.90-7.85 (2H, m), 7.71-7.67 (1H, m), 7.25 (2H, s), 4.26-4.20 (4H, m), 3.94 (2H, s), 2.34 (6H, s), 1.39 (3H, t, J 7.2).

Example 32: 2-[3-(4-Chloro-3-ethoxyphenyl)-1-ethyl-1H-1,2,4-triazol-5-yl]-N-[(3,5-dichlorophenyl)methyl]acetamide The title compound was prepared according to the method of Example 28, using 4-chloro-3-ethoxyphenylboronic acid instead of 4-(trifluoromethoxy)phenylboronic acid in Step 5.
$^1$H NMR: $\delta_H$ (400 MHz, DMSO-d6) 8.87 (1H, t, J 6.0), 7.61 (1H, d, J 1.6), 7.56 (1H, dd, J 8.0, 1.6), 7.51-7.48 (2H, m), 7.36 (2H, d, J 2.0), 4.34 (2H, d, J 6.0), 4.23-4.15 (4H, m), 3.94 (2H, s), 1.41-1.37 (6H, m).

Example 33: 2-{3-[4-Chloro-3-(2-methoxyethoxy)phenyl]-1-ethyl-1H-1,2,4-triazol-5-yl}-N-[(3,5-dichlorophenyl)methyl]acetamide The title compound was prepared according to the method of Example 28, using 4-chloro-3-(2-methoxyethoxy)phenylboronic acid instead of 4-(trifluoromethoxy)phenylboronic acid in Step 5. $^1$H NMR: $\delta_H$ (400 MHz, DMSO-d6) 8.88 (1H, t, J 5.9), 7.63 (1H, s), 7.57 (1H, d, J 8.2), 7.51-7.49 (2H, m), 7.36 (2H, d, J 1.4), 4.34 (2H, d, J 5.9), 4.26-4.20 (4H, m), 3.94 (2H, s), 3.74-3.72 (2H, m), 3.35 (3H, s), 1.33 (3H, t, J 7.2).

General Procedure 2: Amide Coupling Procedure Using Propylphosphonic Anhydride Solution To an ice-cold solution of carboxylic acid (1 equiv.), amine (1.2 equiv.) and propylphosphonic anhydride solution (T3P) (50 wt. % in ethyl acetate; 2 equiv.) in dry dichloromethane was added triethylamine (7 equiv.). The resulting reaction mixture was stirred at room temperature for 4 to 16 h (monitored by TLC). The reaction was diluted with ice water and extracted with dichloromethane (2-3 times). The combined organic layer was washed with water and brine. The organic layer was dried over anhydrous sodium sulfate, filtered and concentrated under reduced pressure. The crude product was purified by flash column chromatography to afford the desired product.

General Procedure for Synthesis of Chiral Amines

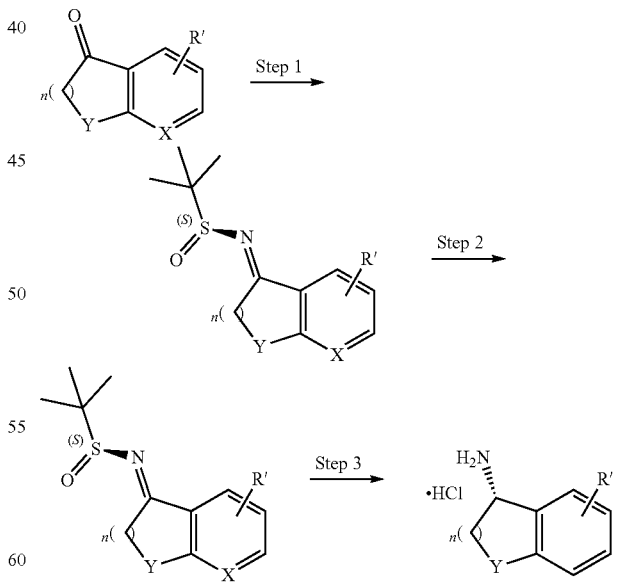

(In the above scheme, when utilised to synthesise a compound of Formula I, it will be appreciated that X may be C or N, Y may be C or a heteroatom, n is 1 or 2 and R' is absent or represents one or more substituents suitable to provide a compound of Formula I)

Step 1

To a stirred solution of ketone (1 equiv.) and (S)-2-methylpropane-2-sulfinamide (1 equiv.) in dry THF was added titanium (IV) ethoxide (1.8 equiv.). The resulting mixture was cautiously stirred at 100° C. for 2-3 h in a sealed tube. The reaction mixture was cooled to room temperature, diluted with brine and ethyl acetate. The resulting suspension was filtered through Celite® and the filter cake was washed with ethyl acetate. The organic layer was separated and dried over anhydrous sodium sulfate, filtered and concentrated under reduced pressure. The crude product was purified by flash column chromatography to afford the desired product.

(S)—N-(6,7-dihydro-5H-cyclopenta[b]pyridin-5-ylidene)-2-methylpropane-2-sulfinamide $^1$H NMR: $\delta_H$ (400 MHz, DMSO-d6) 8.75 (1H, dd, J 6.4, 1.5), 8.09-8.06 (1H, m), 7.44-7.40 (1H, m), 3.20-3.13 (4H, m), 1.27 (9H, s).

(S)—N-(6-chlorochroman-4-ylidene)-2-methylpropane-2-sulfinamide $^1$H NMR: $\delta_H$ (400 MHz, DMSO-d6) 7.81 (1H, d, J 2.7), 7.51 (1H, dd, J 8.7, 2.7), 7.05 (1H, d, J 8.7), 4.40-4.34 (2H, m), 3.35-3.25 (2H, m), 1.23 (9H, s).

Similarly (R)—N-(6-chlorochroman-4-ylidene)-2-methylpropane-2-sulfinamide was made using (R)-2-methylpropane-2-sulfinamide instead of (S)-2-methylpropane-2-sulfinamide (R)—N-(6-chlorochroman-4-ylidene)-2-methylpropane-2-sulfinamide $^1$H NMR: $\delta_H$ (400 MHz, CDCl$_3$) 7.93 (1H, d, J 2.6), 7.31 (1H, dd, J 8.8, 2.6), 6.90 (1H, d, J 8.8), 4.42-4.29 (2H, m), 3.56-3.48 (1H, m), 3.34-3.28 (1H, m), 1.24 (9H, s).

Step 2

The N-sulfinyl imine (1 equiv.) was dissolved in wet THF (2-3% water) and cooled to −50° C. Sodium borohydride (3.1 equiv) was added in a single portion. The mixture was then stirred for 30 min at −50° C., after which time the bath temperature was allowed to gradually rise to ambient temperature. The reaction was stirred at ambient temperature for 2-3 h (monitored by TLC). The mixture was concentrated under reduced pressure and diluted with dichloromethane. The mixture was dried over anhydrous sodium sulfate, filtered and concentrated under reduced pressure. The crude product was purified by flash column chromatography to separate the mixture of diastereoisomers to afford the required diastereoisomer with good purity.

(S)—N—((S)-6,7-dihydro-5H-cyclopenta[b]pyridin-5-yl)-2-methylpropane-2-sulfinamide $^1$H NMR: $\delta_H$ (400 MHz, DMSO-d6) 8.48 (1H, d, J 5.7), 7.97 (1H, d, J 7.6), 7.54-7.51 (1H, m), 5.99 (1H, d, J 9.2), 4.90-4.88 (1H, m), 3.25-3.17 (1H, m), 2.96-3.05 (1H, m), 2.68-2.55 (1H, m), 2.12-2.16 (1H, m), 1.17 (9H, s).

(S)—N—((S)-6-chlorochroman-4-yl)-2-methylpropane-2-sulfinamide $^1$H NMR: $\delta_H$ (400 MHz, DMSO-d6) 7.57 (1H, d, J 2.4), 7.18 (1H, dd, J 8.7, 2.4), 6.79 (1H, d, J8.7), 5.91 (1H, d, J 8.1), 4.49-4.42 (1H, m), 4.29-4.17 (2H, m), 2.05-1.94 (2H, m), 1.16 (9H, s).

Similarly (R)—N—((R)-6-chlorochroman-4-yl)-2-methylpropane-2-sulfinamide was Made Following this General Procedure (R)—N—((R)-6-chlorochroman-4-yl)-2-methylpropane-2-sulfinamide $^1$H NMR: $\delta_H$ (400 MHz, DMSO-d6) 7.57 (1H, d, J 2.6), 7.18 (1H, dd, J 8.7, 2.6), 6.78 (1H, d, J8.7), 5.90 (1H, d, J 8.0), 4.48-4.43 (1H, m), 4.27-4.20 (2H, m), 2.06-1.89 (2H, m), 1.16 (9H, s).

Step 3

To an ice-cold solution of sulfinamide (1 equiv.) in MeOH was added 4 N HCl in dioxane (1 mL/mmol). After all sulfinamide was consumed (by TLC; 0.5-1 h), the mixture was concentrated under reduced pressure. The residue was diluted with pentane and the yellow solid obtained was filtered and dried.

(S)-6,7-dihydro-5H-cyclopenta[b]pyridin-5-amine $^1$H NMR: $\delta_H$ (400 MHz, DMSO-d6) 8.77 (1H, d, J 5.4), 8.46 (1H, d, J 7.6), 7.86-7.82 (1H, m), 5.09-5.08 (1H, m), 3.55-3.51 (1H, m), 3.44-3.41 (1H, m), 2.92-2.87 (1H, m), 2.39-2.34 (1H, m).

(S)-6-Chlorochroman-4-amine $^1$H NMR: $\delta_H$ (400 MHz, DMSO-d6) 8.68 (3H, bs), 7.65 (1H, d, J 2.5), 7.32 (1H, dd, J 8.8, 2.5), 6.90 (1H, d, J 8.8), 4.52-4.51 (1H, m), 4.33-4.22 (2H, m), 2.34-2.21 (1H, m), 2.15-2.09 (1H, m).

(R)-6-Chlorochroman-4-amine $^1$H NMR: $\delta_H$ (400 MHz, DMSO-d6) 8.63 (3H, bs), 7.64 (1H, d, J 2.4), 7.33 (1H, dd, J 8.8, 2.4), 6.91 (1H, d, J 8.8), 4.54-4.50 (1H, m), 4.30-4.25 (2H, m), 2.27-2.23 (1H, m), 2.12-2.08 (1H, m).

Examples 34 to 42

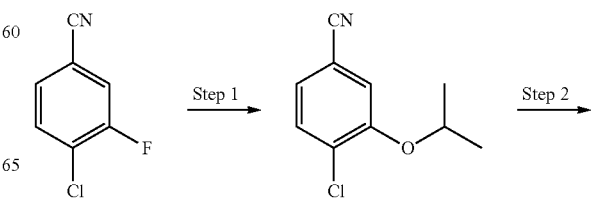

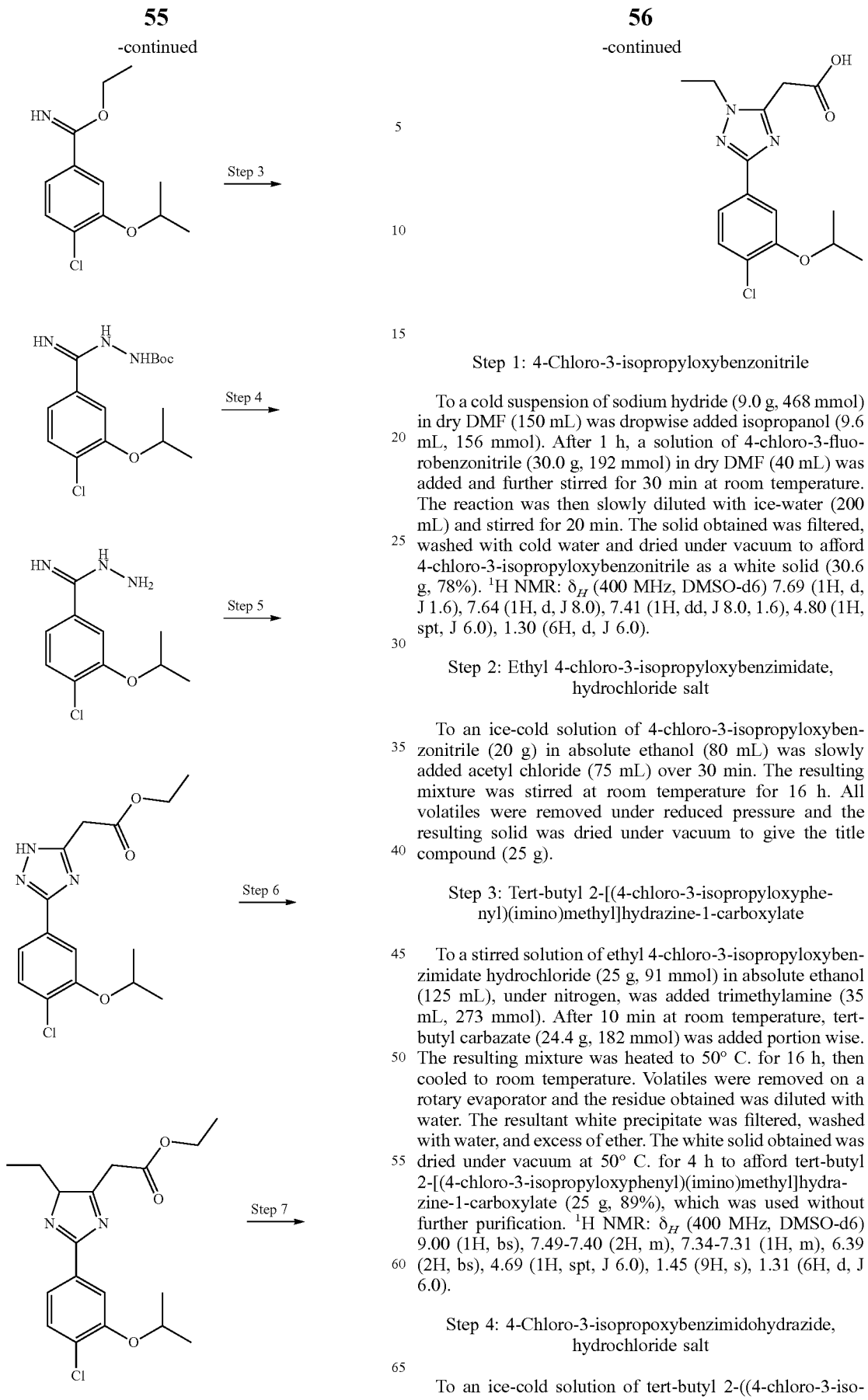

Step 1: 4-Chloro-3-isopropyloxybenzonitrile

To a cold suspension of sodium hydride (9.0 g, 468 mmol) in dry DMF (150 mL) was dropwise added isopropanol (9.6 mL, 156 mmol). After 1 h, a solution of 4-chloro-3-fluorobenzonitrile (30.0 g, 192 mmol) in dry DMF (40 mL) was added and further stirred for 30 min at room temperature. The reaction was then slowly diluted with ice-water (200 mL) and stirred for 20 min. The solid obtained was filtered, washed with cold water and dried under vacuum to afford 4-chloro-3-isopropyloxybenzonitrile as a white solid (30.6 g, 78%). $^1$H NMR: $\delta_H$ (400 MHz, DMSO-d6) 7.69 (1H, d, J 1.6), 7.64 (1H, d, J 8.0), 7.41 (1H, dd, J 8.0, 1.6), 4.80 (1H, spt, J 6.0), 1.30 (6H, d, J 6.0).

Step 2: Ethyl 4-chloro-3-isopropyloxybenzimidate, hydrochloride salt

To an ice-cold solution of 4-chloro-3-isopropyloxybenzonitrile (20 g) in absolute ethanol (80 mL) was slowly added acetyl chloride (75 mL) over 30 min. The resulting mixture was stirred at room temperature for 16 h. All volatiles were removed under reduced pressure and the resulting solid was dried under vacuum to give the title compound (25 g).

Step 3: Tert-butyl 2-[(4-chloro-3-isopropyloxyphenyl)(imino)methyl]hydrazine-1-carboxylate To a stirred solution of ethyl 4-chloro-3-isopropyloxybenzimidate hydrochloride (25 g, 91 mmol) in absolute ethanol (125 mL), under nitrogen, was added trimethylamine (35 mL, 273 mmol). After 10 min at room temperature, tert-butyl carbazate (24.4 g, 182 mmol) was added portion wise. The resulting mixture was heated to 50° C. for 16 h, then cooled to room temperature. Volatiles were removed on a rotary evaporator and the residue obtained was diluted with water. The resultant white precipitate was filtered, washed with water, and excess of ether. The white solid obtained was dried under vacuum at 50° C. for 4 h to afford tert-butyl 2-[(4-chloro-3-isopropyloxyphenyl)(imino)methyl]hydrazine-1-carboxylate (25 g, 89%), which was used without further purification. $^1$H NMR: $\delta_H$ (400 MHz, DMSO-d6) 9.00 (1H, bs), 7.49-7.40 (2H, m), 7.34-7.31 (1H, m), 6.39 (2H, bs), 4.69 (1H, spt, J 6.0), 1.45 (9H, s), 1.31 (6H, d, J 6.0).

Step 4: 4-Chloro-3-isopropoxybenzimidohydrazide, hydrochloride salt

To an ice-cold solution of tert-butyl 2-((4-chloro-3-isopropyloxyphenyl)(imino)methyl)hydrazine-1-carboxylate (25 g) in CH$_2$Cl$_2$ (200 mL) was added 4 M HCl in dioxane (71 mL). The resulting mixture was stirred at room temperature for 20 h. Then all solvent was removed on rotary evaporator and the residue was diluted with ether (100 mL). The solid obtained was filtered and washed with ether (3×50 mL) to afford 4-chloro-3-isopropyloxybenzimidohydrazide, hydrochloride salt (17.8 g) as a white solid. $^1$H NMR: δ$_H$ (300 MHz, DMSO-d6) 11.80 (1H, bs), 10.99 (1H, bs), 10.21 (1H, bs), 9.64 (1H, bs), 7.76-7.50 (2H, m), 7.35-7.32 (1H, m), 4.90 (1H, spt, J 6.0), 1.33 (6H, d, J 6.0).

Step 5: Ethyl 2-[3-(4-chloro-3-isopropoxyphenyl)-1H-1,2,4-triazol-5-yl]acetate

To an ice-cold suspension of 4-chloro-3-isopropyloxybenzimidohydrazide, hydrochloride salt, (7.5 g, 32.8 mmol) in acetonitrile (5 mL) was slowly added diisopropyl ethylamine (28.8 mL, 154 mmol). After 10 min of stirring, ethyl malonyl chloride (49.2 mL, 49.2 mmol) was added and the resulting mixture was stirred at room temperature for 16 h. Then the reaction mixture was concentrated under reduced pressure and crude liquid was dissolved in mixture of toluene/acetonitrile (20 mL, 1:3 ratio) and transferred to steel autoclave reactor. To this crude mass was added anhydrous sodium sulfate (0.5 g). The resulting solution was heated for 8 h at 130° C. with 100 psi pressure of nitrogen gas. The reaction was cooled to room temperature, filtered through Celite©. The filtrate was diluted with water (100 mL) and extracted with ethyl acetate (3×20 mL). The combined organic layer was washed with brine, dried over anhydrous sodium sulfate, filtered and concentrated under reduced pressure. The crude product obtained was purified by column chromatography, eluting with 5% to 10% methanol in dichloromethane, to afford ethyl 2-[3-(4-chloro-3-isopropyloxyphenyl)-1H-1,2,4-triazol-5-yl]acetate (3.0 g, 29%) as a white solid. $^1$H NMR: δ$_H$ (300 MHz, DMSO-d6) 14.00 (1H, bs), 7.62-7.46 (3H, m), 4.75-4.72 (1H, m), 4.15 (2H, q, J 7.2), 3.98 (2H, s), 1.32 (6H, d, J 6.0), 1.20 (3H, t, J 7.2).

Step 6: Ethyl 2-[3-(4-chloro-3-isopropoxyphenyl)-1-ethyl-1H-1,2,4-triazol-5-yl]acetate Potassium carbonate (2.12 g, 15.4 mmol) was added to a vigorously stirred solution of ethyl 2-[3-(4-chloro-3-isopropyloxyphenyl)-1H-1,2,4-triazol-5-yl]acetate (2.5 g, 7.7 mmol) in dry acetone (130 mL). Ethyl iodide (1.3 mL, 16.6 mmol) was added dropwise and the resulting mixture was refluxed for 16 h. The reaction was cooled to room temperature and filtered through Celite®. The filtrate was concentrated and the crude product obtained was purified by column chromatography, eluting with 50% to 80% ethyl acetate in petroleum ether, to afford ethyl 2-[3-(4-chloro-3-isopropyloxyphenyl)-1-ethyl-1H-1,2,4-triazol-5-yl]acetate (0.9 g, 33%) as a white solid. $^1$H NMR: δ$_H$ (300 MHz, DMSO-d6) 7.61 (1H, s), 7.54-7.46 (2H, m), 4.73-4.69 (1H, m), 4.19-4.11 (5H, m), 1.40-1.31 (9H, m), 1.19 (3H, t, J 7.1).

Step 7: 2-[3-(4-Chloro-3-isopropoxyphenyl)-1-ethyl-1H-1,2,4-triazol-5-yl]acetic acid To an ice-cold solution of ethyl 2-[3-(4-chloro-3-isopropyloxyphenyl)-1-ethyl-1H-1,2,4-triazol-5-yl]acetate (0.55 g, 1.56 mmol) in THF/methanol/water (12.5 mL, 2:2:1) was added LiOH—H$_2$O (124 mg, 3.12 mmol). The resulting solution was stirred at room temperature for 8 h. The mixture was concentrated under vacuum and the residue was acidified with 1.5 N HCl (to pH 3-4) and filtered. The solid obtained was washed with water and dried under vacuum to obtain 2-[3-(4-chloro-3-isopropyloxyphenyl)-1-ethyl-1H-1,2,4-triazol-5-yl]acetic acid (400 mg, 80%). $^1$H NMR: δ$_H$ (400 MHz, DMSO-d6) 12.95 (1H, bs), 7.63 (1H, s), 7.55-7.48 (2H, m), 4.73 (1H, spt, J 6.0), 4.20 (2H, d, J 7.1), 4.02 (2H, s), 1.39 (3H, t, J 7.1), 1.34 (6H, d, J 6.0).

Example 34: 2-[3-(4-Chloro-3-isopropyloxyphenyl)-1-ethyl-1H-1,2,4-triazol-5-yl]-N-[(3,5-dichlorophenyl)methyl]acetamide The title compound was prepared according to General Procedure 2, using 2-[3-(4-chloro-3-isopropyloxyphenyl)-1-ethyl-1H-1,2,4-triazol-5-yl]acetic acid and 3,5-dichlorobenzylamine. $^1$H NMR: δ$_H$ (400 MHz, DMSO-d6) 8.85 (1H, t, J 6.0), 7.62 (1H, s), 7.55 (1H, dd, J 8.0, 1.6), 7.49-7.47 (2H, m), 7.35 (2H, s), 4.70 (1H, spt, J 6.0), 4.33 (2H, d, J 6.0), 4.20 (2H, d, J 7.2), 3.93 (2H, s), 1.38 (3H, t, J 7.2), 1.32 (6H, d, J 6.0).

Example 35: 2-[3-(4-Chloro-3-isopropyloxyphenyl)-1-ethyl-1H-1,2,4-triazol-5-yl]-N-[(2,6-dimethylpyridin-4-yl)methyl]acetamide The title compound could be prepared according to the method of Example 3, using 2-[3-(4-chloro-3-isopropyloxyphenyl)-1-ethyl-1H-1,2,4-triazol-5-yl]acetic acid instead of 2-[3-(4-chloro-3-fluorophenyl)-1-ethyl-1H-1,2,4-triazol-5-yl]acetic acid. $^1$H NMR: δ$_H$ (400 MHz, DMSO-d6) 8.83 (1H, t, J 5.9), 7.64 (1H, d, J 1.6), 7.55 (1H, dd, J 8.2, 1.6), 7.50 (1H, d, J 8.2), 6.93 (2H, s), 4.70 (1H, spt, J 6.0), 4.26 (2H, d, J 5.9), 4.22 (2H, q, J 7.2), 3.94 (2H, s), 2.38 (6H, s), 1.39 (3H, t, J 7.2), 1.33 (6H, d, J 6.0).

Example 36: 2-[3-(4-Chloro-3-isopropyloxyphenyl)-1-ethyl-1H-1,2,4-triazol-5-yl]-N-[(1S)-2,3-dihydro-1H-inden-1-yl]acetamide The title compound was prepared according to General Procedure 1, using 2-[3-(4-chloro-3-isopropyloxyphenyl)-1-ethyl-1H-1,2,4-triazol-5-yl]acetic acid and (S)-1-aminoindane. $^1$H NMR: δ$_H$ (400 MHz, DMSO-d6) 8.71 (1H, d, J 8.0), 7.64 (1H, s), 7.55 (1H, d, J 8.0), 7.50 (1H, d, J 8.0), 7.29-7.20 (4H, m), 5.32-5.27 (1H, m), 4.73 (1H, spt, J 5.5), 4.23 (2H, q, J 7.2), 3.93-3.85 (2H, m), 3.00-2.85 (1H, m), 2.83-2.79 (1H, m), 2.43-2.39 (1H, m), 1.86-1.81 (1H, m), 1.43 (3H, t, J 7.2), 1.34 (6H, d, J 5.5).

Example 37: 2-[3-(4-Chloro-3-isopropyloxyphenyl)-1-ethyl-1H-1,2,4-triazol-5-yl]-N-[(3-cyanophenyl)methyl]acetamide The title compound was prepared according to General Procedure 2, using 2-[3-(4-chloro-3-isopropyloxyphenyl)-1-ethyl-1H-1,2,4-triazol-5-yl]acetic acid and 3-cyanobenzylamine. $^1$H NMR: δ$_H$ (400 MHz, DMSO-d6) 8.88 (1H, t, J 5.8), 7.75 (2H, s), 7.67 (1H, d, J 7.8), 7.58 (1H, s), 7.56-7.54 (2H, m), 7.49 (1H, d, J 8.2), 4.70 (1H, spt, J 6.0), 4.38 (2H, d, J 5.8), 4.20 (2H, q, J 7.1), 3.94 (2H, s), 1.38 (3H, t, J 7.1), 1.33 (6H, d, J 6.0).

Example 38: 2-[3-(4-Chloro-3-isopropyloxyphenyl)-1-ethyl-1H-1,2,4-triazol-5-yl]-N-[(1H-indazol-5-yl)methyl]acetamide The title compound was prepared according to General Procedure 1, using 2-[3-(4-chloro-3-isopropyloxyphenyl)-1- ethyl-1H-1,2,4-triazol-5-yl]acetic acid and 1-(1H-indazol-5-yl)methylamine. ¹H NMR: δ$_H$ (400 MHz, DMSO-d6) 13.03 (1H, s), 8.81 (1H, t, J 5.7), 8.01 (1H, s), 7.67 (1H, s), 7.64 (1H, d, J 1.6), 7.55 (1H, dd, J 8.2, 1.6), 7.51-7.48 (2H, m), 7.31 (1H, dd, J 8.6, 1.4), 4.71 (1H, spt, J 6.0), 4.40 (2H, d, J 5.7), 4.21 (2H, q, J 7.2), 3.91 (2H, s), 1.39 (3H, t, J 7.2), 1.33 (6H, d, J 6.0).

Example 39: 2-[3-(4-Chloro-3-isopropyloxyphenyl)-1-ethyl-1H-1,2,4-triazol-5-yl]-N-[(4S)-3,4-dihydro-2H-1-benzopyran-4-yl]acetamide The title compound was prepared according to General Procedure 2, using 2-[3-(4-chloro-3-isopropyloxyphenyl)-1-ethyl-1H-1,2,4-triazol-5-yl]acetic acid and (S)-chroman-4-ylamine.
¹H NMR: δ$_H$ (400 MHz, DMSO-d6) 8.83 (1H, d, J 8.0), 7.64 (1H, d, J 1.6), 7.55 (1H, dd, J 8.4, 1.6), 7.50 (1H, d, J 8.4), 7.23 (1H, d, J 7.6), 7.18-7.16 (1H, m), 6.89 (1H, td, J 7.6, 0.8), 6.81 (1H, d, J 8.0), 5.02-5.00 (1H, m), 4.72 (1H, spt, J 6.0), 4.26-4.20 (4H, m), 3.94-3.88 (2H, m), 2.11-2.05 (1H, m), 1.96-1.90 (1H, m), 1.42 (3H, t, J 7.2), 1.34 (6H, d, J 6.0).

Example 40: N-[(4S)-6-Chloro-3,4-dihydro-2H-1-benzopyran-4-yl]-2-[3-(4-chloro-3-isopropyloxyphenyl)-1-ethyl-1H-1,2,4-triazol-5-yl]acetamide The title compound was prepared according to General Procedure 2, using 2-[3-(4-chloro-3-isopropyloxyphenyl)-1-ethyl-1H-1,2,4-triazol-5-yl]acetic acid and (S)-6-chloro-chroman-4-ylamine. ¹H NMR: δ$_H$ (400 MHz, DMSO-d6) 8.85 (1H, d, J 8.0), 7.64 (1H, s), 7.56 (1H, d, J 8.2), 7.49 (1H, d, J 8.2), 7.23-7.21 (2H, m), 6.84 (1H, d, J 8.4), 5.05-5.02 (1H, m), 4.72 (1H, spt, J 6.0), 4.29-4.21 (4H, m), 3.92 (2H, ABq, J 15.6), 2.09-2.07 (1H, m), 1.95-1.90 (1H, m), 1.43 (3H, t, J 7.2), 1.34 (6H, d, J 6.0).

Example 41: N-[(4R)-6-Chloro-3,4-dihydro-2H-1-benzopyran-4-yl]-2-[3-(4-chloro-3-isopropyloxyphenyl)-1-ethyl-1H-1,2,4-triazol-5-yl]acetamide The title compound was prepared according to General Procedure 2, using 2-[3-(4-chloro-3-isopropyloxyphenyl)-1-ethyl-1H-1,2,4-triazol-5-yl]acetic acid and (R)-6-chloro-chroman-4-ylamine. ¹H NMR: δ$_H$ (400 MHz, DMSO-d6) 8.84 (1H, d, J 8.4), 7.64 (1H, s), 7.56 (1H, d, J 8.2), 7.49 (1H, d, J 8.2), 7.23-7.21 (2H, m), 6.84 (1H, d, J 8.0), 5.04-5.02 (1H, m), 4.72 (1H, spt, J 6.0), 4.27-4.21 (4H, m), 3.92 (2H, ABq, J 16.0), 2.09-2.07 (1H, m), 1.95-1.90 (1H, m), 1.43 (3H, t, J 7.2), 1.34 (6H, d, J 6.0).

Example 42: 2-[3(4-Chloro-3-isopropyloxyphenyl)-1-ethyl-1H-1,2,4-triazol-5-yl]-N-[(5S)-5H,6H,7H-cyclopenta[b]pyridin-5-yl]acetamide The title compound was prepared according to General Procedure 1, using 2-[3-(4-chloro-3-isopropyloxyphenyl)-1-ethyl-1H-1,2,4-triazol-5-yl]acetic acid and (S)-6,7-dihydro-5H-cyclopenta[b]pyridin-5-amine. ¹H NMR: δ$_H$ (400 MHz, DMSO-d6) 8.78 (1H, d, J 8.0), 8.41 (1H, d, J 5.0), 7.65-7.63 (2H, m), 7.55 (1H, d, J 8.4), 7.50 (1H, d, J 8.4), 7.22-7.19 (1H, m), 5.32-5.29 (1H, m), 4.72 (1H, spt, J 6.0), 4.23 (2H, q, J 7.1), 3.89 (2H, s), 3.00-2.91 (3H, m), 1.92-1.87 (1H, m), 1.42 (3H, t, J 7.1), 1.34 (6H, d, J 3.0).

Examples 43 to 49

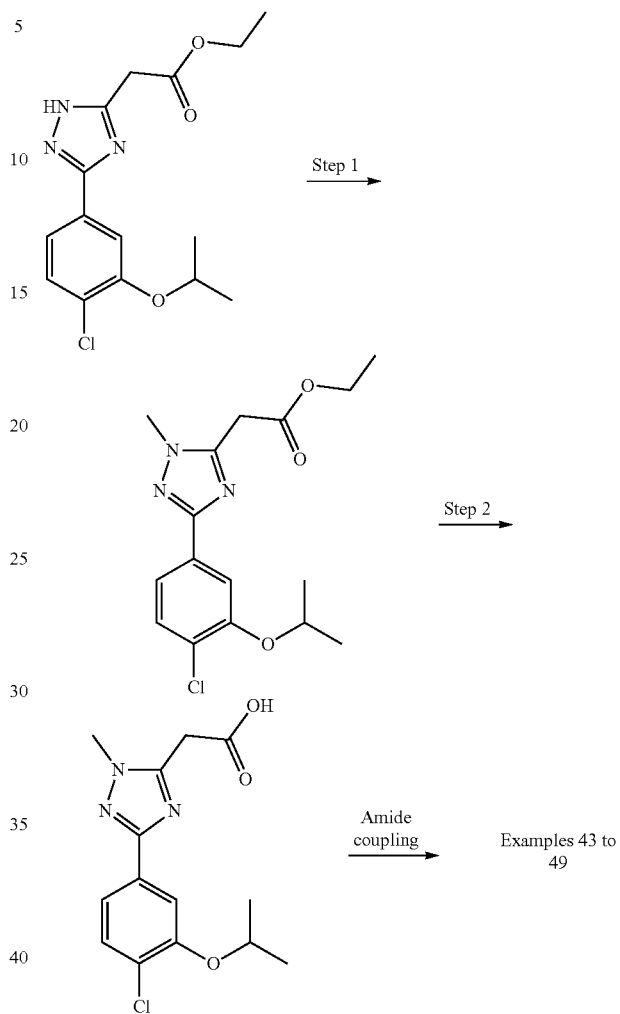

Step 1: Ethyl 2-[3-(4-chloro-3-isopropyloxyphenyl)-1-methyl-1H-1,2,4-triazol-5-yl]acetate Potassium carbonate (2.48 g, 18 mmol) was added to a vigorously stirred solution of ethyl 2-(3-(4-chloro-3-isopropoxyphenyl)-1H-1,2,4-triazol-5-yl)acetate (3.0 g, 9 mmol) in dry acetone (30 mL). Methyl iodide (0.97 mL, 13 mmol) was added dropwise and the resulting mixture was refluxed for 16 h. The reaction was cooled to room temperature and filtered through Celite®. The filtrate was concentrated under reduced pressure and the crude product obtained was purified by column chromatography, by eluting with 50% to 80% ethyl acetate in petroleum ether, to afford ethyl 2-(3-(4-chloro-3-isopropyloxyphenyl)-1-methyl-1H-1,2,4-triazol-5-yl)acetate (0.8 g, 26%) as a white solid. ¹H NMR: δ$_H$ (400 MHz, DMSO-d6) 7.62 (1H, d, J 1.2), 7.53 (1H, dd, J 8.2, 1.2), 7.49 (1H, d, J 1.2), 4.73 (1H, spt, J 6.0), 4.18-4.12 (4H, m), 3.86 (3H, s), 1.33 (6H, d, J 6.0), 1.22 (3H, t, J 7.1).

Step 2: 2-[3-(4-Chloro-3-isopropoxyphenyl)-1-methyl-1H-1,2,4-triazol-5-yl]acetic acid To an ice-cold solution of ethyl 2-(3-(4-chloro-3-isopropyloxyphenyl)-1-methyl-1H-1,2,4-triazol-5-yl)acetate (700 mg, 2.07 mmol) in THF/methanol/water (12.5 mL, 2:2:1) was added LiOH.H₂O (141 mg, 4.14 mmol). The resulting solution was stirred at room temperature for 2 h. Volatiles were evaporated under vacuum and residue was acidified with 1.5 N HCl (pH 3-4) and filtered. Solid obtained was washed with water and dried in vacuum to obtain 2-[3-(4-chloro-3-isopropyloxyphenyl)-1-methyl-1H-1,2,4-triazol-5-yl]acetic acid (600 mg, 94%). $^1$H NMR: $\delta_H$ (400 MHz, DMSO-d6) 7.62 (1H, s), 7.54-7.47 (2H, m), 4.74 (1H, spt, J 6.0), 4.00 (2H, s), 3.85 (3H, s), 1.33 (6H, d, J 6.0).

Example 43: 2-[3-(4-Chloro-3-isopropyloxyphenyl)-1-methyl-1H-1,2,4-triazol-5-yl]-N-[(3,5-dichlorophenyl)methyl]acetamide The title compound was prepared according to General Procedure 2, using 2-[3-(4-chloro-3-isopropyloxyphenyl)-1-methyl-1H-1,2,4-triazol-5-yl]acetic acid and 3,5-dichlorobenzylamine. $^1$H NMR: $\delta_H$ (400 MHz, DMSO-d6) 8.86 (1H, t, J 5.8), 7.62 (1H, s), 7.55-7.48 (3H, m), 7.36 (2H, s), 4.72 (1H, spt, J 6.0), 4.34 (2H, d, J 5.8), 3.94 (2H, s), 3.88 (3H, s), 1.33 (6H, d, J 6.0).

Example 44: 2-[3-(4-Chloro-3-isopropyloxyphenyl)-1-methyl-1H-1,2,4-triazol-5-yl]-N-(1S)-2,3-dihydro-1H-inden-1-yl]acetamide The title compound was prepared according to General Procedure 2, using 2-[3-(4-chloro-3-isopropyloxyphenyl)-1-methyl-1H-1,2,4-triazol-5-yl]acetic acid and (S)-1-aminoindane. $^1$H NMR: $\delta_H$ (400 MHz, DMSO-d6) 8.69 (1H, d, J 8.2), 7.63 (1H, d, J 1.4), 7.54 (1H, dd, J 8.2, 1.4), 7.50 (1H, d, J 8.2), 7.28-7.18 (4H, m), 5.32-5.26 (1H, m), 4.73 (1H, spt, J 6.0), 3.94-3.85 (5H, m), 3.00-2.93 (1H, m), 2.86-2.78 (1H, m), 2.43-2.33 (1H, m), 1.88-1.78 (1H, m), 1.34 (6H, d, J 6.0).

Example 45: 2-[3-(4-Chloro-3-isopropyloxyphenyl)-1-methyl-1H-1,2,4-triazol-5-yl]-N-[(2,6-dimethylpyridin-4-yl)methyl]acetamide The title compound was prepared according to the method of Example 3, using 2-[3-(4-chloro-3-isopropyloxyphenyl)-1-methyl-1H-1,2,4-triazol-5-yl]acetic acid instead of 2-[3-(4-chloro-3-fluorophenyl)-1-ethyl-1H-1,2,4-triazol-5-yl]acetic acid. $^1$H NMR: $\delta_H$ (400 MHz, DMSO-d6) 8.82 (1H, t, J 5.2), 7.63 (1H, s), 7.55-7.49 (2H, m), 6.94 (2H, s), 4.72 (1H, spt, J 5.9), 4.27 (2H, d, J 5.2), 3.95 (2H, s), 3.89 (3H, s), 2.36 (6H, s), 1.34 (6H, d, J 5.9).

Example 46: 2-[3-(4-Chloro-3-isopropyloxyphenyl)-1-methyl-1H-1,2,4-triazol-5-yl]-N-[(3-fluorophenyl)methyl]acetamide The title compound was prepared according to General Procedure 2, using 2-[3-(4-chloro-3-isopropyloxyphenyl)-1-methyl-1H-1,2,4-triazol-5-yl]acetic acid and 3-fluorobenzylamine. $^1$H NMR: $\delta_H$ (400 MHz, DMSO-dB) 8.84 (1H, t, J 5.9), 7.62 (1H, d, J 1.7), 7.54 (1H, dd, J 8.2, 1.7), 7.49 (1H, d, J 8.2), 7.41-7.35 (1H, m), 7.16-7.06 (3H, m), 4.73 (1H, spt, J 6.0), 4.35 (2H, d, J 5.9), 3.93 (2H, s), 3.88 (3H, s), 1.33 (6H, d, J 6.0).

Example 47: 2-[3-(4-Chloro-3-isopropyloxyphenyl)-1-methyl-1H-1,2,4-triazol-5-yl]-N-[(4R)-3,4-dihydro-2H-1-benzopyran-4-yl]acetamide The title compound was prepared according to General Procedure 2, using 2-[3-(4-chloro-3-isopropyloxyphenyl)-1-methyl-1H-1,2,4-triazol-5-yl]acetic acid and (R)-chroman-4-ylamine. $^1$H NMR: $\delta_H$ (400 MHz, DMSO-d6) 8.81 (1H, d, J 8.0), 7.63 (1H, s), 7.54 (1H, d, J 8.5), 7.50 (1H, d, J 8.5), 7.24-7.16 (2H, m), 6.91-6.87 (1H, m), 6.80 (1H, d, J 8.2), 5.04-5.01 (1H, m), 4.72 (1H, spt, J 6.0), 4.27-4.20 (2H, m), 3.94-3.84 (5H, m), 2.10-2.06 (1H, m), 1.95-1.91 (1H, m), 1.34 (6H, d, J 6.0)

Example 48: 2-[3-(4-Chloro-3-isopropyloxyphenyl)-1-methyl-1H-1,2,4-triazol-5-yl]-N-[(4S)-3,4-dihydro-2H-1-benzopyran-4-yl]acetamide The title compound was prepared according to General Procedure 2, using 2-[3-(4-chloro-3-isopropyloxyphenyl)-1-methyl-1H-1,2,4-triazol-5-yl]acetic acid and (S)-chroman-4-ylamine. $^1$H NMR: $\delta_H$ (400 MHz, DMSO-dB) 8.82 (1H, d, J 8.0), 7.63 (1H, s), 7.53 (1H, d, J 8.5), 7.50 (1H, d, J 8.5), 7.24-7.16 (2H, m), 6.91-6.87 (1H, m), 6.80 (1H, d, J 8.2), 5.04-5.01 (1H, m), 4.72 (1H, spt, J 6.0), 4.27-4.20 (2H, m), 3.94-3.84 (5H, m), 2.10-2.06 (1H, m), 1.95-1.91 (1H, m), 1.34 (6H, d, J 6.0)

Example 49: N-[(4R)-6-Chloro-3,4-dihydro-2H-1-benzopyran-4-yl]-2-[3-(4-chloro-3-isopropyloxyphenyl)-1-methyl-1H-1,2,4-triazol-5-yl]acetamide The title compound was prepared according to General Procedure 1, using 2-[3-(4-chloro-3-isopropyloxyphenyl)-1-methyl-1H-1,2,4-triazol-5-yl]acetic acid and (R)-6-chloro-chroman-4-ylamine. $^1$H NMR: $\delta_H$ (400 MHz, DMSO-d6) 8.84 (1H, d, J 7.6), 7.63 (1H, s), 7.54 (1H, d, J 8.3), 7.49 (1H, d, J 8.3), 7.23-7.21 (2H, m), 6.84 (1H, d, J 8.4), 5.04-5.02 (1H, m), 4.72 (1H, spt, J 6.0), 4.27-4.22 (2H, m), 3.98-3.85 (5H, m), 2.08-2.05 (1H, m), 1.95-1.90 (1H, m), 1.34 (6H, d, J 6.0).

Examples 50 to 53

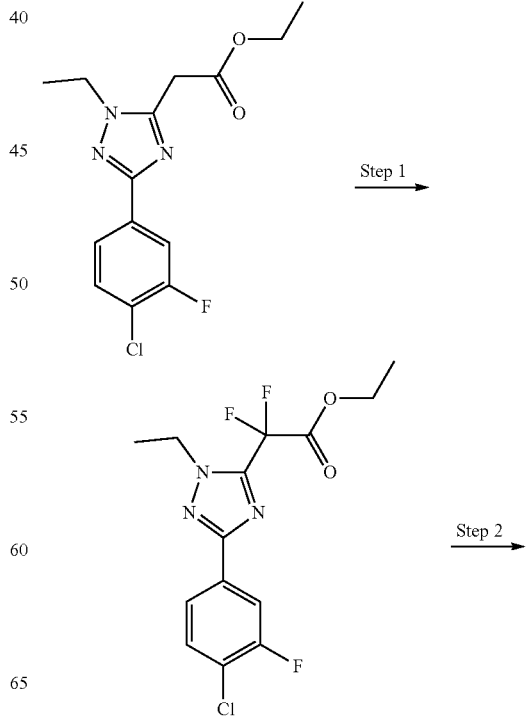

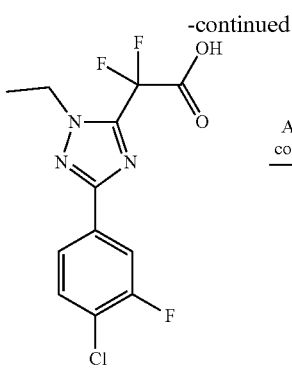

-continued

Amide coupling → Examples 50 to 53

Step 1: Ethyl 2-(3-(4-chloro-3-fluorophenyl)-1-ethyl-1H-1,2,4-triazol-5-yl)-2,2-difluoroacetate At −78° C. under inert atmosphere, a 1 M solution of KHMDS in THF (60 mL, 60 mmol) was added dropwise to a solution of ethyl 2-(3-(4-chloro-3-fluorophenyl)-1-ethyl-1H-1,2,4-triazol-5-yl)acetate (15 g, 48.1 mmol) and 18-crown-6 (32 g) in dry THF (150 mL). After 1h at −78° C., additional KHMDS solution (60 mL, 60 mmol) was added and further stirred for 45 min, followed by addition of N-fluorobenzenesulfonimide (38 g, 120 mmol) in THF (60 mL). After 1 h at −78° C., the reaction was slowly quenched with 1 M aqueous HCl, stirred at room temperature for 15 min and extracted with ethyl acetate (3×50 mL). The combined organic layer was washed with brine, dried over anhydrous sodium sulfate and concentrated under reduced pressure. The crude product obtained was purified by column chromatography, eluting with 10% to 15% ethyl acetate in petroleum ether, to afford ethyl 2-(3-(4-chloro-3-fluorophenyl)-1-ethyl-1H-1,2,4-triazol-5-yl)-2,2-difluoroacetate (9 g, 54%). $^1$H NMR: $\delta_H$ (400 MHz, DMSO-d6) 7.86-7.80 (2H, m), 7.75-7.71 (1H, m), 4.49-4.44 (4H, m), 1.47 (3H, t, J7.2), 1.31 (3H, t, J 6.8).

Step 2: 2-(3-(4-Chloro-3-fluorophenyl)-1-ethyl-1H-1,2,4-triazol-5-yl)-2,2-difluoroacetic acid To an ice-cold solution of ethyl 2-(3-(4-chloro-3-fluorophenyl)-1-ethyl-1H-1,2,4-triazol-5-yl)-2,2-difluoroacetate (9 g, 25 mmol) in THF/water (90 mL, 2:1) was added LiOH—H$_2$O (2.1 g, 50 mmol). The resulting solution was stirred at room temperature for 16h. Volatiles were evaporated under vacuum and residue was acidified with 1.5 N HCl (pH 3-4) and filtered. The solid obtained was washed with water and dried under vacuum to obtain 2-(3-(4-chloro-3-fluorophenyl)-1-ethyl-1H-1,2,4-triazol-5-yl)-2,2-difluoroacetic acid (7 g, 87%). $^1$H NMR: $\delta_H$ (400 MHz, DMSO-d6) 7.87-7.82 (2H, m), 7.74-7.70 (1H, m), 4.39 (2H, q, J 7.2), 1.45 (3H, t, J 7.2).

Example 50: 2-[3-(4-Chloro-3-fluorophenyl)-1-ethyl-1H-1,2,4-triazol-5-yl]-N-[(3,5-dichlorophenyl)methyl]-2,2-difluoroacetamide The title compound was prepared according to General Procedure 1, using 2-[3-(4-chloro-3-fluorophenyl)-1-ethyl-1H-1,2,4-triazol-5-yl]-2,2-difluoroacetic acid and 3,5-dichlorobenzylamine. $^1$H NMR: $\delta_H$ (400 MHz, DMSO-d6) 9.89 (1H, t, J 6.1), 7.87-7.82 (2H, m), 7.60-7.41 (1H, m), 7.55 (1H, t, J 1.9), 7.40 (2H, d, J 1.9), 4.49-4.42 (4H, m), 1.46 (3H, t, J 7.2).

Example 51: 2-[3-(4-Chloro-3-fluorophenyl)-1-ethyl-1H-1,2,4-triazol-5-yl]-N-[(2,6-dimethylpyridin-4-yl)methyl]-2,2-difluoroacetamide The title compound was prepared according to the method of Example 3, using 2-[3-(4-chloro-3-fluorophenyl)-1-ethyl-1H-1,2,4-triazol-5-yl]-2,2-difluoroacetic acid instead of 2-[3-(4-chloro-3-fluorophenyl)-1-ethyl-1H-1,2,4-triazol-5-yl]acetic acid. $^1$H NMR: $\delta_H$ (400 MHz, DMSO-d6) 9.87 (1H, t, J 6.0), 7.88-7.78 (2H, m), 7.76-7.74 (1H, m), 6.95 (2H, s), 4.45 (2H, q, J 7.2), 4.39 (2H, d, J 6.0), 2.37 (6H, s), 1.46 (3H, t, J 7.2).

Example 52: 2-[3-(4-Chloro-3-fluorophenyl)-1-ethyl-1H-1,2,4-triazol-5-yl]-2,2-difluoro-N-[(2-methyl-1H-1,3-benzimidazol-5-yl)methyl]acetamide The title compound was prepared according to General Procedure 1, using 2-[3-(4-chloro-3-fluorophenyl)-1-ethyl-1H-1,2,4-triazol-5-yl]-2,2-difluoroacetic acid and 1-(2-methyl-1H-1,3-benzimidazol-5-yl)methylamine. $^1$H NMR: $\delta_H$ (400 MHz, DMSO-d6) 12.15 (1H, s), 9.86 (1H, t, J 3.5), 7.90-7.70 (3H, m), 7.55 (1H, s), 7.46-7.35 (1H, m), 7.13-7.12 (1H, m), 4.52 (2H, d, J 3.5), 4.39 (2H, q, J 7.2), 2.47 (3H, s), 1.39 (3H, t, J 7.2).

Example 53: N-[(4S)-6-Chloro-3,4-dihydro-2H-1-benzopyran-4-yl]-2-[3-(4-chloro-3-fluorophenyl)-1-ethyl-1H-1,2,4-triazol-5-yl]-2,2-difluoroacetamide The title compound was prepared according to General Procedure 1, using 2-[3-(4-chloro-3-fluorophenyl)-1-ethyl-1H-1,2,4-triazol-5-yl]-2,2-difluoroacetic acid and (S)-6-chlorochroman-4-ylamine. $^1$H NMR: $\delta_H$ (400 MHz, DMSO-d6) 9.73 (1H, d, J 8.4), 7.91-7.86 (2H, m), 7.76-7.71 (1H, m), 7.25 (1H, d, J 2.0), 7.21 (1H, dd, J 8.4, 2.0), 6.83 (1H, d, J 8.4), 5.25-5.21 (1H, m), 4.46 (2H, q, J 7.2), 4.27-4.26 (2H, m), 2.32-2.03 (2H, m), 1.49 (3H, t, J 7.2).

Examples 54 to 56

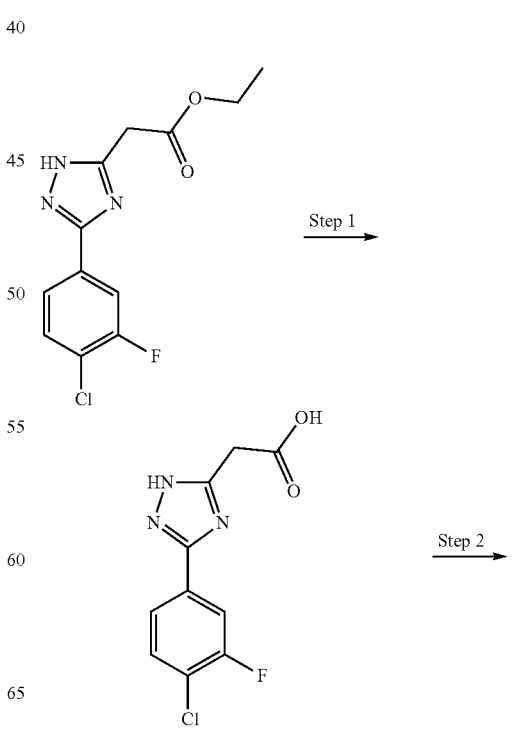

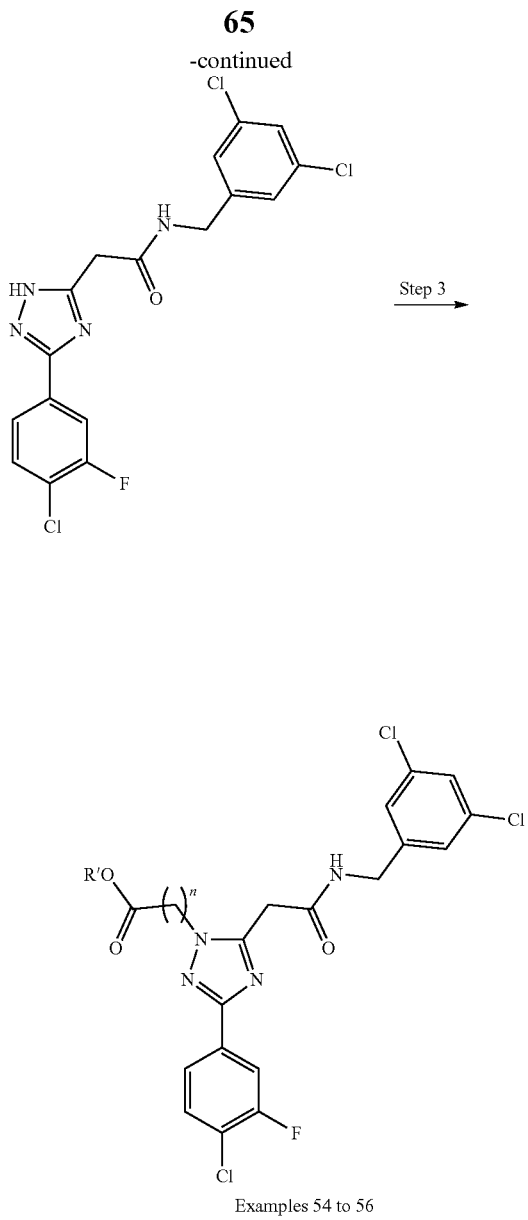

Examples 54 to 56

Step 1: 2-[3-(4-Chloro-3-fluorophenyl)-1H-1,2,4-triazol-5-yl]acetic acid

To an ice-cold solution of ethyl 2-[3-(4-chloro-3-fluorophenyl)-1H-1,2,4-triazol-5-yl]acetate (2.5 g, 8.8 mmol) in THF/water (20 mL, 3:1) was added LiOH—H$_2$O (0.74 g, 17.6 mmol). The resulting solution was stirred at room temperature for 16 h. The mixture was concentrated under vacuum and residue was acidified with 1.5 N HCl (pH 3-4) and filtered. The solid obtained was washed with water and dried under vacuum to obtain 2-[3-(4-chloro-3-fluorophenyl)-1H-1,2,4-triazol-5-yl]acetic acid (2.0 g, 80%) as a pale yellow solid. $^1$H NMR: δ$_H$ (400 MHz, DMSO-d6) 14.07 (1H, bs), 12.86 (1H, bs), 7.89-7.83 (2H, m), 7.69 (1H, s), 3.87 (2H, s).

Step 2: 2-[3-(4-Chloro-3-fluorophenyl)-1H-1,2,4-triazol-5-yl]-N-[(3,5-dichlorophenyl)methyl]acetamide To an ice-cold solution of 2-(3-(4-chloro-3-fluorophenyl)-1H-1,2,4-triazol-5-yl)acetic acid (2.0 g, 7.07 mmol) in dry dichloromethane (20 mL) was added EDC.HCl (2.71 g, 14.14 mmol), HOBt (1.64 g, 10.61 mmol) and diisopropylethylamine (5.2 mL, 28.3 mmol). The resulting reaction mixture was stirred at room temperature for 15 min, then 3,5-dichlorobenzylamine (1.12 mL, 8.48 mmol) was added and further stirred at room temperature for 16 h. The reaction was diluted with ice water and extracted with dichloromethane. The combined organic layer was washed with water and brine. The organic layer was dried over anhydrous sodium sulfate, filtered and concentrated under reduced pressure. The crude product was purified by flash column chromatography, eluting with 5% to 10% methanol in dichloromethane, to afford 2-[3-(4-chloro-3-fluorophenyl)-1H-1,2,4-triazol-5-yl]-N-[(3,5-dichlorophenyl)methyl] acetamide (1.0 g, 35%) as an off-white solid.

Step 3: Potassium carbonate (2 equiv.) was added to vigorously stirred solution of triazole (1 equiv.) in dry acetone. Halo ester (1.2 equiv.) was added dropwise and the resulting mixture was stirred at room temperature for 3-8 h (monitored by TLC). The reaction was filtered through Celite®. The filtrate was concentrated and the crude product obtained was purified by column chromatography, eluting with 5% to 8% methanol in dichloromethane, to afford the desired product as a solid.

Example 54: Methyl 2-[3-(4-chloro-3-fluorophenyl)-5-({[(3,5-dichlorophenyl)methyl]carbamoyl}methyl)-1H-1,2,4-triazol-1-yl]acetate The title compound was prepared using methyl bromoacetate as the halo ester in step 3. $^1$H NMR: δ$_H$ (400 MHz, DMSO-d6) 8.87 (1H, t, J 5.9), 7.88-7.81 (2H, m), 7.72-7.68 (1H, m), 7.50 (1H, t, J 1.8), 7.37 (2H, d, J 1.8), 5.30 (2H, s), 4.34 (2H, d, J 5.9), 3.93 (2H, s), 3.71 (3H, S).

Example 55: Methyl 3-[3-(4-chloro-3-fluorophenyl)-5-({[(3,5-dichlorophenyl)methyl]carbamoyl}methyl)-1H-1,2,4-triazol-1-yl]propanoate The title compound was prepared using methyl 3-bromopropionate as the halo ester in step 3. $^1$H NMR: δ$_H$ (400 MHz, DMSO-d6) 8.89 (1H, t, J 5.9), 7.85-7.79 (2H, m), 7.71-7.68 (1H, m), 7.50 (1H, t, J 1.8), 7.37 (2H, d, J 1.8), 4.43 (2H, t, J 6.8), 4.35 (2H, d, J 5.9), 3.98 (2H, s), 3.62 (3H, s), 2.96 (2H, t, J 6.8).

Example 56: Ethyl 4-[3-(4-chloro-3-fluorophenyl)-5-({[(3,5-dichlorophenyl)methyl]carbamoyl}methyl)-1H-1,2,4-triazol-1-yl]butanoate The title compound was prepared using ethyl 4-bromobutyrate as the halo ester in step 3. $^1$H NMR: δ$_H$ (400 MHz, DMSO-d6) 8.87 (1H, t, J 5.8), 7.87-7.81 (2H, m), 7.71-7.67 (1H, m), 7.50 (1H, t, J 1.6), 7.37 (2H, d, J 1.6), 4.35 (2H, d, J 5.8), 4.22 (2H, t, J 7.1), 4.03 (2H, q, J7.1), 3.93 (2H, s), 2.41-2.38 (2H, m), 2.09-2.05 (2H, m), 1.16 (3H, t, J 7.1).

Examples 57 to 59

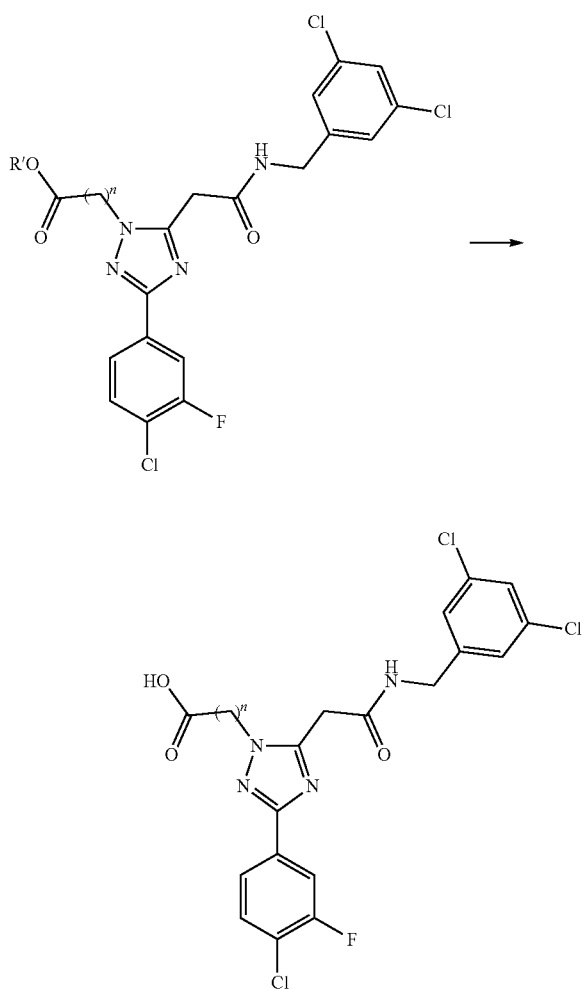

To an ice-cold solution of ester (1 equiv.) in THF/water (2:1) was added LiOH H$_2$O (2 equiv.). The resulting solution was stirred at room temperature for 1-6 h (monitored by TLC). The mixture was concentrated under vacuum and the residue was acidified with 1.5 N HCl (pH 4-5) and filtered. The solid obtained was extracted with dichloromethane and dried over anhydrous sodium sulfate. The crude product obtained was purified by column chromatography, eluting with 5% to 8% methanol in dichloromethane, to afford the desired product as a solid.

Example 57: 2-[3-(4-Chloro-3-fluorophenyl)-5-({[(3,5-dichlorophenyl)methyl]carbamoyl}methyl)-1H-1,2,4-triazol-1-yl]acetic acid The title compound was prepared from methyl 2-[3-(4-chloro-3-fluorophenyl)-5-({[(3,5-dichlorophenyl)methyl]carbamoyl}methyl)-1H-1,2,4-triazol-1-yl]acetate. $^1$H NMR: δ$_H$ (400 MHz, DMSO-d6) 9.36 (1H, bs), 7.87-7.82 (2H, m), 7.68 (1H, t, J 8.0), 7.45 (1H, s), 7.29 (2H, s), 4.86 (2H, s), 4.29 (2H, d, J 5.8), 3.84 (2H, s).

Example 58: 3-[3-(4-Chloro-3-fluorophenyl)-5-({[(3,5-dichlorophenyl)methyl]carbamoyl}methyl)-1H-1,2,4-triazol-1-yl]propanoic acid The title compound was prepared from methyl 3-[3-(4-chloro-3-fluorophenyl)-5-({[(3,5-dichlorophenyl)methyl]carbamoyl}methyl)-1H-1,2,4-triazol-1-yl]propanoate. $^1$H NMR: δ$_H$(400 MHz, DMSO-d6) 12.54 (1H, bs), 8.90 (1H, t, J 5.5), 7.86-7.80 (2H, m), 7.71-7.67 (1H, m), 7.50 (1H, s), 7.36 (2H, s), 4.40-4.34 (4H, m), 3.99 (2H, s), 2.89-2.86 (2H, m).

Example 59: 4-[3-(4-Chloro-3-fluorophenyl)-5-({[(3,5-dichlorophenyl)methyl]carbamoyl}methyl)-1H-1,2,4-triazol-1-yl]butanoic acid The title compound was prepared from ethyl 4-[3-(4-chloro-3-fluorophenyl)-5-({[(3,5-dichlorophenyl)methyl]carbamoyl}methyl)-1H-1,2,4-triazol-1-yl]butanoate. $^1$H NMR: δ$_H$ (400 MHz, DMSO-d6) 12.21 (1H, bs), 8.88 (1H, t, J 6.0), 7.87-7.82 (2H, m), 7.71-7.67 (1H, m), 7.50 (1H, s), 7.37 (2H, s), 4.35 (2H, d, J 6.0), 4.22 (2H, t, J 7.2), 3.93 (2H, s), 2.33-2.31 (2H, m), 2.07-2.01 (2H, m).

Example 60: 2-[3-(4-Chloro-3-fluorophenyl)-1-ethyl-1H-1,2,4-triazol-5-yl]-N-[(1R)-2,3-dihydro-1H-inden-1-yl]acetamide The title compound was prepared according to the method of Example 3, using (R)-1-aminoindane instead of (2,6-dimethylpyridin-4-yl)methanamine. $^1$H NMR: δ$_H$ (400 MHz, DMSO-d6) 8.71 (1H, d, J 8.4), 7.86-7.82 (2H, m), 7.72-7.68 (1H, m), 7.29-7.20 (4H, m), 5.30-5.27 (1H, m), 4.25 (2H, q, J 7.2), 3.91-3.89 (2H, m), 2.96-2.93 (1H, m), 2.85-2.83 (1H, m), 2.43-2.34 (1H, m), 1.85-1.82 (1H, m), 1.44 (3H, t, J 7.2).

Example 61: 2-[3-(4-Chloro-3-fluorophenyl)-1-ethyl-1H-1,2,4-triazol-5-yl]-N-[(1S)-2,3-dihydro-1H-inden-1-yl]acetamide The title compound was prepared according to the method of Example 3, using (S)-1-aminoindane instead of (2,6-dimethylpyridin-4-yl)methanamine. $^1$H NMR: δ$_H$ (400 MHz, DMSO-d6) 8.71 (1H, d, J 8.2), 7.86-7.82 (2H, m), 7.72-7.68 (1H, m), 7.29-7.21 (4H, m), 5.30-5.27 (1H, m), 4.25 (2H, q, J 7.2), 3.91-3.89 (2H, m), 2.96-2.94 (1H, m), 2.84-2.82 (1H, m), 2.43-2.34 (1H, m), 1.85-1.82 (1H, m), 1.43 (3H, t, J 7.2).

Example 62: 2-[3-(4-Chloro-3-fluorophenyl)-1-ethyl-1H-1,2,4-triazol-5-yl]-N-[(1R,2S)-2-hydroxy-2,3-dihydro-1H-inden-1-yl]acetamide The title compound was prepared according to the method of Example 3, using (1R,2S)-1-amino-2,3-dihydro-1H-inden-2-ol instead of (2,6-dimethylpyridin-4-yl)methanamine. $^1$H NMR: δ$_H$ (400 MHz, DMSO-d6) 8.52 (1H, d, J 8.6), 7.88-7.83 (2H, m), 7.72-7.68 (1H, m), 7.26-7.21 (4H, m), 5.22-5.19 (1H, m), 5.17 (1H, d, J 3.6), 4.48-4.46 (1H, m), 4.26 (2H, q, J 7.2), 4.03-4.01 (2H, m), 3.07 (1H, dd, J 15.8, 5.0), 2.84 (1H, d, J 16.5), 1.44 (3H, t, J 7.2).

Example 63: 2-[3-(4-Chloro-3-fluorophenyl)-1-ethyl-1H-1,2,4-triazol-5-yl]-N-[(1S,2R)-2-hydroxy-2,3-dihydro-1H-inden-1-yl]acetamide The title compound was prepared according to the method of Example 3, using (1S,2R)-1-amino-2,3-dihydro-1H-inden-2-ol instead of (2,6-dimethylpyridin-4-yl)methanamine. ¹H NMR: δ$_H$ (400 MHz, DMSO-d6) 8.52 (1H, d, J 8.3), 7.88-7.83 (2H, m), 7.72-7.68 (1H, m), 7.25-7.22 (4H, m), 5.22-5.19 (1H, m), 5.17 (1H, d, J 3.7), 4.48-4.46 (1H, m), 4.26 (2H, q, J 7.1), 4.03-4.01 (2H, m), 3.07 (1H, dd, J 16.3, 4.9), 2.84 (1H, d, J 16.3), 1.44 (3H, t, J 7.1).

Example 64: 2-[3-(4-Chloro-3-fluorophenyl)-1-ethyl-1H-1,2,4-triazol-5-yl]-N-[(1S,2S)-2-hydroxy-2,3-dihydro-1H-inden-1-yl]acetamide The title compound was prepared according to the method of Example 3, using (1S,2S)-1-amino-2,3-dihydro-1H-inden-2-ol instead of (2,6-dimethylpyridin-4-yl)methanamine. ¹H NMR: δ$_H$ (300 MHz, DMSO-d6) 8.66 (1H, d, J 8.4), 7.86-7.82 (2H, m), 7.72-7.66 (1H, m), 7.25-7.22 (4H, m), 5.34 (1H, d, J 5.4), 5.05-5.00 (1H, m), 4.29-4.19 (3H, m), 3.92-3.86 (2H, m), 3.16 (1H, dd, J 15.6, 7.2), 2.72 (1H, dd, J 15.6, 7.2), 1.44 (3H, t, J 7.2).

Example 65: 2-[3-(4-Chloro-3-fluorophenyl)-1-ethyl-1H-1,2,4-triazol-5-yl]-N-[(1R,2R)-2-hydroxy-2,3-dihydro-1H-inden-1-yl]acetamide The title compound was prepared according to the method of Example 3, using (1R,2R)-1-amino-2,3-dihydro-1H-inden-2-ol instead of (2,6-dimethylpyridin-4-yl)methanamine. ¹H NMR: δ$_H$ (400 MHz, DMSO-d6) 8.67 (1H, d, J 8.2), 7.87-7.83 (2H, m), 7.72-7.68 (1H, m), 7.25-7.22 (4H, m), 5.36 (1H, d, J 5.6), 5.06-5.02 (1H, m), 4.29-4.22 (3H, m), 3.92-3.88 (2H, m), 3.15 (1H, dd, J 15.3, 6.8), 2.72 (1H, dd, J 15.3, 6.8), 1.44 (3H, t, J 7.1).

Example 66: 2-[3-(4-Chloro-3-fluorophenyl)-1-ethyl-1H-1,2,4-triazol-5-yl]-N-(2,3-dihydro-1H-inden-2-yl)acetamide The title compound was prepared according to General Procedure 2, using 2-[3-(4-chloro-3-fluorophenyl)-1-ethyl-1H-1,2,4-triazol-5-yl]acetic acid and 2-aminoindane. ¹H NMR: δ$_H$ (400 MHz, DMSO-d6) 8.65 (1H, d, J 6.7), 7.84-7.79 (2H, m), 7.70-7.66 (1H, m), 7.26-7.24 (2H, m), 7.18-7.15 (2H, m), 4.47-4.45 (1H, m), 4.21 (2H, q, J 7.2), 3.83 (2H, s), 3.20 (2H, dd, J 16.0, 7.2), 2.81 (2H, dd, J 16.0, 5.2), 1.41 (3H, t, J 7.2).

Example 67: 2-[3-(4-Chloro-3-fluorophenyl)-1-ethyl-1H-1,2,4-triazol-5-yl]-N-[(1S,3R)-3-hydroxy-2,3-dihydro-1H-inden-1-yl]acetamide The title compound was prepared according to General Procedure 2, using 2-[3-(4-chloro-3-fluorophenyl)-1-ethyl-1H-1,2,4-triazol-5-yl]acetic acid and (1R,3S)-3-amino-2,3-dihydro-1H-inden-1-ol. ¹H NMR: δ$_H$ (400 MHz, DMSO-d6) 8.74 (1H, d, J 8.3), 7.87-7.83 (2H, m), 7.72-7.68 (1H, m), 7.38 (1H, d, J 6.6), 7.33-7.25 (3H, m), 5.56 (1H, d, J 5.8), 5.16-5.09 (1H, m), 5.00-4.96 (1H, m), 4.26 (2H, q, J 7.2), 3.98-3.88 (2H, m), 2.80-2.75 (1H, m), 1.71-1.64 (1H, m), 1.44 (3H, t, J 7.2).

Example 68: 2-[3-(4-Chloro-3-fluorophenyl)-1-ethyl-1H-1,2,4-triazol-5-yl]-N-[(1S,3S)-3-hydroxy-2,3-dihydro-1H-inden-1-yl]acetamide The title compound was prepared according to General Procedure 2, using 2-[3-(4-chloro-3-fluorophenyl)-1-ethyl-1H-1,2,4-triazol-5-yl]acetic acid and (1S,3S)-3-amino-2,3-dihydro-1H-inden-1-ol. ¹H NMR: δ$_H$ (400 MHz, DMSO-d6) 8.64 (1H, d, J 8.1), 7.85-7.81 (2H, m), 7.71-7.67 (1H, m), 7.40-7.38 (1H, m), 7.34-7.30 (3H, m), 5.46-5.41 (1H, m), 5.25 (1H, d, J 5.8), 5.19-5.16 (1H, m), 4.23 (2H, q, J 7.1), 3.87 (2H, s), 2.24-2.18 (1H, m), 2.14-2.08 (1H, m), 1.43 (3H, t, J 7.1).

Example 69: 2-[3-(4-Chloro-3-fluorophenyl)-1-ethyl-1H-1,2,4-triazol-5-yl]-N-[(1R,3R)-3-hydroxy-2,3-dihydro-1H-inden-1-yl]acetamide The title compound was prepared according to General Procedure 2, using 2-[3-(4-chloro-3-fluorophenyl)-1-ethyl-1H-1,2,4-triazol-5-yl]acetic acid and (1R,3R)-3-amino-2,3-dihydro-1H-inden-1-ol. ¹H NMR: δ$_H$ (400 MHz, DMSO-d6) 8.64 (1H, d, J 8.0), 7.86-7.81 (2H, m), 7.71-7.67 (1H, m), 7.40-7.38 (1H, m), 7.32-7.30 (3H, m), 5.46-5.41 (1H, m), 5.24 (1H, d, J 5.8), 5.19-5.16 (1H, m), 4.24 (2H, q, J 7.2), 3.87 (2H, s), 2.24-2.18 (1H, m), 2.14-2.08 (1H, m), 1.43 (3H, t, J 7.2).

Example 70: 2-[3-(4-Chloro-3-fluorophenyl)-1-ethyl-1H-1,2,4-triazol-5-yl]-N-[(1R,3S)-3-hydroxy-2,3-dihydro-1H-inden-1-yl]acetamide The title compound was prepared according to General Procedure 2, using 2-[3-(4-chloro-3-fluorophenyl)-1-ethyl-1H-1,2,4-triazol-5-yl]acetic acid and (1S,3R)-3-amino-2,3-dihydro-1H-inden-1-ol. ¹H NMR: δ$_H$ (400 MHz, DMSO-d6) 8.74 (1H, d, J 8.3), 7.87-7.82 (2H, m), 7.72-7.68 (1H, m), 7.38 (1H, d, J 6.6), 7.33-7.26 (3H, m), 5.57 (1H, d, J 5.8), 5.16-5.09 (1H, m), 5.00-4.95 (1H, m), 4.26 (2H, q, J 7.2), 3.98-3.88 (2H, m), 2.80-2.74 (1H, m), 1.71-1.64 (1H, m), 1.44 (3H, t, J 7.2).

Example 71: 2-[3-(4-Chloro-3-fluorophenyl)-1-(cyclopropylmethyl)-1H-1,2,4-triazol-5-yl]-N-[(5S)-5H,6H,7H-cyclopenta[b]pyridin-5-yl]acetamide The title compound was prepared according to General Procedure 2, using 2-[3-(4-chloro-3-fluorophenyl)-1-(cyclopropylmethyl)-1H-1,2,4-triazol-5-yl]acetic acid and (S)-6,7-dihydro-5H-cyclopenta[b]pyridin-5-amine. ¹H NMR: δ$_H$ (400 MHz, DMSO-d6) 8.76 (1H, d, J 7.6), 8.40 (1H, d, J 4.8), 7.84-7.81 (2H, m), 7.71-7.63 (2H, m), 7.20 (1H, dd, J 7.6, 5.2), 5.33-5.28 (1H, m), 4.09 (2H, d, J 7.2), 3.89 (2H, s), 3.03-2.85 (2H, m), 2.43-2.39 (1H, m), 1.93-1.83 (1H, m), 1.37-1.31 (1H, m), 0.56-0.43 (4H, m).

Example 72: 2-[3-(4-Chloro-3-fluorophenyl)-1-(cyclopropylmethyl)-1H-1,2,4-triazol-5-yl]-N-[(1S)-2,3-dihydro-1H-inden-1-yl]acetamide The title compound was prepared according to General Procedure 1, using 2-[3-(4-chloro-3-fluorophenyl)-1-(cyclopropylmethyl)-1H-1,2,4-triazol-5-yl]acetic acid and (S)-1-aminoindane. ¹H NMR: δ$_H$ (400 MHz, DMSO-d6) 8.69 (1H, d, J 8.0), 7.86-7.81 (2H, m), 7.72-7.68 (1H, m), 7.30-7.20 (4H, m), 5.29-5.27 (1H, m), 4.10 (2H, d, J 7.2), 3.91-3.88 (2H, m), 2.98-2.92 (1H, m), 2.86-2.80 (1H, m), 2.40-2.32 (1H, m), 1.85-1.80 (1H, m), 1.37-1.34 (1H, m), 0.56-0.43 (4H, m).

Example 73: 2-[3-(4-Chloro-3-fluorophenyl)-1-ethyl-1H-1,2,4-triazol-5-yl]-N-[(2-oxo-2,3-dihydro-1,3-benzoxazol-5-yl)methyl]acetamide The title compound was prepared according to General Procedure 1, using 2-[3-(4-chloro-3-fluorophenyl)-1-ethyl- 1H-1,2,4-triazol-5-yl]acetic acid and 1-(2-oxo-2,3-dihydro-1,3-benzoxazol-5-yl)methanamine. $^1$H NMR: $\delta_H$ (400 MHz, DMSO-d6) 11.63 (1H, bs), 8.81 (1H, t, J 5.8), 7.84-7.81 (2H, m), 7.70-7.66 (1H, m), 7.23 (1H, d, J 8.6), 7.03-7.02 (2H, m), 4.31 (2H, d, J 5.8), 4.20 (2H, q, J 7.1), 3.90 (2H, s), 1.39 (3H, t, J 7.1).

Example 74: 2-[3-(4-Chloro-3-fluorophenyl)-1-ethyl-1H-1,2,4-triazol-5-yl]-N-[(4S)-3,4-dihydro-2H-1-benzopyran-4-yl]acetamide The title compound was prepared according to General Procedure 1, using 2-[3-(4-chloro-3-fluorophenyl)-1-ethyl-1H-1,2,4-triazol-5-yl]acetic acid and (S)-chroman-4-ylamine. H NMR: $\delta_H$ (400 MHz, DMSO-d6) 8.82 (1H, d, J 7.5), 7.86-7.81 (2H, m), 7.72-7.68 (1H, m), 7.24 (1H, d, J 7.6), 7.20-7.16 (1H, m), 6.92-6.88 (1H, m), 6.80 (1H, d, J 8.0), 5.02-5.00 (1H, m), 4.24-4.21 (4H, m), 3.90-3.88 (2H, m), 2.08-2.06 (1H, m), 1.94-1.91 (1H, m), 1.43 (3H, t, J 7.2).

Example 75: 2-[3-(4-Chloro-3-fluorophenyl)-1-ethyl-1H-1,2,4-triazol-5-yl]-N-[(4R)-3,4-dihydro-2H-1-benzopyran-4-yl]acetamide The title compound was prepared according to General Procedure 1, using 2-[3-(4-chloro-3-fluorophenyl)-1-ethyl-1H-1,2,4-triazol-5-yl]acetic acid and (R)-chroman-4-ylamine. $^1$H NMR: $\delta_H$ (400 MHz, DMSO-d6) 8.82 (1H, d, J 8.0), 7.86-7.81 (2H, m), 7.72-7.68 (1H, m), 7.24 (1H, d, J 7.6), 7.20-7.16 (1H, m), 6.91 (1H, td, J 7.6, 1.2), 6.80 (1H, dd, J 8.0, 0.8), 5.04-5.00 (1H, m), 4.26-4.18 (4H, m), 3.95-3.85 (2H, m), 2.08-2.05 (1H, m), 1.95-1.90 (1H, m), 1.43 (3H, t, J 7.2).

Example 76: N-[(4S)-6-Chloro-3,4-dihydro-2H-1-benzopyran-4-yl]-2-[3-(4-chloro-3-fluorophenyl)-1-ethyl-1H-1,2,4-triazol-5-yl]acetamide The title compound was prepared according to General Procedure 1, using 2-[3-(4-chloro-3-fluorophenyl)-1-ethyl-1H-1,2,4-triazol-5-yl]acetic acid and (S)-6-chlorochroman-4-ylamine. $^1$H NMR: $\delta_H$ (400 MHz, DMSO-d6) 8.85 (1H, d, J 8.1), 7.86-7.83 (2H, m), 7.70-7.67 (1H, m), 7.25-7.20 (2H, m), 6.84 (1H, d, J 8.6), 5.06-5.01 (1H, m), 4.29-4.20 (4H, m), 3.92 (2H, ABq, J 15.9), 2.10-2.07 (1H, m), 1.95-1.90 (1H, m), 1.43 (3H, t, J 7.2).

Example 77: N-[(4R)-6-Chloro-3,4-dihydro-2H-1-benzopyran-4-yl]-2-[3-(4-chloro-3-fluorophenyl)-1-ethyl-1H-1,2,4-triazol-5-yl]acetamide The title compound was prepared according to General Procedure 1, using 2-[3-(4-chloro-3-fluorophenyl)-1-ethyl-1H-1,2,4-triazol-5-yl]acetic acid and (R)-6-chlorochroman-4-ylamine. $^1$H NMR: $\delta_H$ (400 MHz, DMSO-d6) 8.85 (1H, d, J 8.1), 7.88-7.82 (2H, m), 7.71-7.67 (1H, m), 7.25-7.20 (2H, m), 6.84 (1H, d, J 8.6), 5.06-5.01 (1H, m), 4.27-4.22 (4H, m), 3.92 (2H, ABq, J 15.9), 2.10-2.07 (1H, m), 1.95-1.90 (1H, m), 1.43 (3H, t, J 7.2).

Example 78: N-[(4S)-6-Chloro-3,4-dihydro-2H-1-benzopyran-4-yl]-2-[3-(4-chloro-3-fluorophenyl)-1-(cyclopropylmethyl)-1H-1,2,4-triazol-5-yl]acetamide The title compound was prepared according to General Procedure 1, using 2-[3-(4-chloro-3-fluorophenyl)-1-(cyclopropylmethyl)-1H-1,2,4-triazol-5-yl]acetic acid and (S)-6-chlorochroman-4-ylamine. $^1$H NMR: $\delta_H$ (400 MHz, DMSO-d6) 8.83 (1H, d, J 8.4), 7.87-7.82 (2H, m), 7.70-7.66 (1H, m), 7.25 (1H, d, J 2.4), 7.21 (1H, dd, J 8.8, 2.4), 6.83 (1H, d, J 8.8), 5.06-5.01 (1H, m), 4.26-4.21 (2H, m), 4.09 (2H, d, J 7.2), 3.95-3.85 (2H, m), 2.07-1.88 (2H, m), 1.36-1.31 (1H, m), 0.56-0.47 (4H, m).

Example 79: 2-[3-(4-Chloro-3-fluorophenyl)-1-ethyl-1H-1,2,4-triazol-5-yl]-N-{pyrazolo[1,5-a]pyridin-3-yl}acetamide

Step 1: t-butyl pyrazolo[1,5-a]pyridin-3-ylcarbamate

To a solution of pyrazolo[1,5-a]pyridine-3-carboxylic acid (2 g, 12.3 mmol) and DPPA (4.3 mL, 18.4 mmol) in dry THF (15 mL) was added diisopropylethyl amine (4.3 mL, 24.6 mmol). The resulting solution was stirred at room temperature for 16 h. Then dry tBuOH (10 mL) was added and the resulting mixture was stirred at 75° C. for 16 h. The reaction was cooled to room temperature, diluted with water (15 mL) and extracted with ethyl acetate (2×20 mL). The combined organic layers were dried over anhydrous sodium sulfate and concentrated under reduced pressure. The crude residue was purified by column chromatography, eluting with 25% to 30% ethyl acetate in hexane, to afford t-butyl pyrazolo[1,5-a]pyridin-3-ylcarbamate (700 mg, 25%) as a pale yellow liquid. $^1$H NMR: $\delta_H$ (400 MHz, DMSO-d6) 9.21 (1H, bs), 8.50 (1H, d, J 7.2), 8.05 (1H, s), 7.70 (1H, d, J 8.8), 7.10-7.07 (1H, m), 6.80-6.77 (1H, m), 1.48 (9H, s).

Step 2: Pyrazolo[1,5-a]pyridin-3-amine, hydrochloride salt

To a cold solution of tert-butyl pyrazolo[1,5-a]pyridin-3-ylcarbamate (0.5 g, 2.1 mmol) in dichloromethane (5 mL) was added 4M HCl in dioxane (1.5 mL) and stirred at room temperature for 3 h. Then all volatiles were removed under reduced pressure and the residue was triturated with ether and filtered. The solid obtained was dried to afford pyrazolo[1,5-a]pyridin-3-amine, hydrochloride salt (230 mg, 92%) as an off-white solid. $^1$H NMR: $\delta_H$ (400 MHz, DMSO-d6) 10.70 (3H, bs), 8.71 (1H, dt, J 7.0, 1.0), 8.13 (1H, s), 7.82 (1H, dt, J 9.0, 1.2), 7.39 (1H, ddd, J 9.0, 6.8, 1.0), 7.02 (1H, td, J 6.8, 1.2).

Step 3: 2-[3-(4-Chloro-3-fluorophenyl)-1-ethyl-1H-1,2,4-triazol-5-yl]-N-{pyrazolo[1,5-a]pyridin-3-yl}acetamide The title compound was prepared according to General Procedure 1, using 2-[3-(4-chloro-3-fluorophenyl)-1-ethyl-1H-1,2,4-triazol-5-yl]acetic acid and pyrazolo[1,5-a]pyridin-3-amine. $^1$H NMR: $\delta_H$ (400 MHz, DMSO-d6) 10.45 (1H, s), 8.59 (1H, dt, J 7.0, 1.0), 8.24 (1H, s), 7.88-7.82 (2H, m), 7.77 (1H, dt, J 9.0, 1.2), 7.71-7.66 (1H, m), 7.20 (1H, ddd, J 9.0, 6.6, 1.0), 6.87 (1H, td, J 6.6, 1.2), 4.29 (2H, d, J 7.2), 4.15 (2H, s), 1.45 (3H, t, J 7.2).

Example 80: 2-[3-(4-Chloro-3-fluorophenyl)-1-ethyl-1H-1,2,4-triazol-5-yl]-N-[(2,6-diethylpyridin-4-yl)methyl]acetamide

Step 1: 2,6-Diethylisonicotinonitrile

Zinc cyanide (546 mg, 4.67 mmol) was added to a degassed solution of 4-bromo-2,6-diethylpyridine (500 mg, 10.8 mmol) and tetrakis(triphenylphoshpine) palladium (137 mg, 0.17 mmol) in dry DMF (5 mL). The resulting reaction mixture was heated at 100° C. for 16 h. The mixture was cooled to room temperature, diluted with ethyl acetate (15 mL) and filtered through Celite®. The filter cake was washed with ethyl acetate (2×10 mL). The combined organic filtrate was washed with water (10 mL) and saturated aqueous NaCl, dried over anhydrous sodium sulfate, filtered, and concentrated under reduced pressure. The crude product was purified by flash chromatography, eluting with 40% to 60% ethyl acetate in petroleum ether, to afford 2,6-diethylisonicotinonitrile (270 mg, 73%). $^1$H NMR: $\delta_H$ (300 MHz, DMSO-d6) 7.56 (2H, s), 2.77 (4H, q, J 7.5), 1.23 (6H, t, J 7.5).

Step 2: (2,6-Diethylpyridin-4-yl)methanamine

A mixture of 2,6-diethylisonicotinonitrile (270 mg) and 10% Pd/C (27 mg) in ethanol (12 mL) was stirred under a hydrogen atmosphere for 16 h. Then the reaction mixture was filtered through Celite® and the residue was washed with ethanol (2×15 mL). The filtrate was concentrated under reduced pressure and the crude (2,6-diethylpyridin-4-yl)methanamine (120 mg) was used without further purification. $^1$H NMR: $\delta_H$ (300 MHz, DMSO-d6) 7.00 (2H, s), 3.66 (2H, s), 2.65 (4H, q, J 7.5), 1.19 (6H, t, J 7.5).

Step 3: 2-[3-(4-Chloro-3-fluorophenyl)-1-ethyl-1H-1,2,4-triazol-5-yl]-N-[(2,6-diethylpyridin-4-yl)methyl]acetamide The title compound was prepared according to General Procedure 1, using 2-[3-(4-chloro-3-fluorophenyl)-1-ethyl-1H-1,2,4-triazol-5-yl]acetic acid and (2,6-diethylpyridin-4-yl)methanamine. $^1$H NMR: $\delta_H$ (400 MHz, DMSO-d6) 8.84 (1H, t, J 5.6), 7.85-7.81 (2H, m), 7.71-7.67 (1H, m), 6.95 (2H, s), 4.29 (2H, d, J 5.6), 4.23 (2H, q, J 7.2), 3.94 (2H, s), 2.66 (4H, q, J 7.6), 1.39 (3H, t, J 7.2), 1.17 (6H, t, J 7.6).

Example 81: 2-[3-(4-Chloro-3-fluorophenyl)-1-ethyl-1H-1,2,4-triazol-5-yl]-N-[(4,6-dimethylpyridin-2-yl)methyl]acetamide Step 1: 2,4-Dimethylpyridine 1-oxide To an ice-cold solution of 2,4-dimethylpyridine (10 g, 93.4 mmol) in dry dichloromethane (50 mL) was portion wise added mCPBA (32 g). After 16 h at room temperature, the mixture was diluted with saturated sodium bicarbonate and stirred vigorously. This mixture was then extracted with dichloromethane (2×50 mL). The combined organic layers were dried over anhydrous sodium sulfate, filtered and concentrated under reduced pressure to obtain crude 2,4-dimethylpyridine 1-oxide as a pale yellow liquid, which was used in the next step without further purification.

Step 2: 4,6-Dimethylpicolinonitrile

To a solution of 2,4-dimethylpyridine 1-oxide (500 mg, 4.06 mmol) in dry dichloromethane (10 mL) was added TMSCN (0.4 mL, 4.06 mmol). After 15 min at room temperature, dimethylcarbamoyl chloride (0.37 mL, 4.06 mmol) was added and further stirred at room temperature for 20 h. The mixture was diluted with saturated sodium bicarbonate and extracted with dichloromethane (2×15 mL). The combined organic layers were dried over anhydrous sodium sulfate, filtered and concentrated under reduced pressure. The crude residue was purified by column chromatography, by eluting with 25% to 30% ethyl acetate in hexane, to afford 4,6-dimethylpicolinonitrile (130 mg, 25%). $^1$H NMR: $\delta_H$ (400 MHz, DMSO-d6) 7.70 (1H, s), 7.45 (1H, s), 2.47 (3H, s), 2.34 (3H, s).

Step 3: (4,6-Dimethylpyridin-2-yl)methanamine

A mixture of 4,6-dimethylpicolinonitrile (120 mg, 0.9 mmol) and 10% Pd/C (25 mg) in ethanol (10 mL) was stirred under a hydrogen atmosphere for 16 h. The reaction mixture was filtered through Celite® and the residue was washed with ethanol (2×10 mL). The filtrate was concentrated under reduced pressure and the crude (4,6-dimethylpyridin-2-yl)methanamine (80 mg) was used without further purification. $^1$H NMR: $\delta_H$ (400 MHz, DMSO-d6) 7.03 (1H, s), 6.93 (1H, s), 3.65 (2H, s), 2.35 (3H, s), 2.23 (3H, s).

Step 4: 2-[3-(4-Chloro-3-fluorophenyl)-1-ethyl-1H-1,2,4-triazol-5-yl]-N-[(4,6-dimethylpyridin-2-yl)methyl]acetamide The title compound was prepared according to General Procedure 2, using 2-[3-(4-chloro-3-fluorophenyl)-1-ethyl-1H-1,2,4-triazol-5-yl]acetic acid and (4,6-dimethylpyridin-2-yl) methanamine. $^1$H NMR: $\delta_H$ (400 MHz, DMSO-d6) 8.85 (1H, t, J 5.9), 7.86-7.82 (2H, m), 7.71-7.67 (1H, m), 6.96 (2H, s), 4.32 (2H, d, J 5.9), 4.23 (2H, q, J 7.2), 3.95 (2H, s), 2.50 (3H, s), 2.24 (3H, s), 1.39 (3H, t, J 7.2).

Example 82: 2-[3-(4-Chloro-3-isopropyloxyphenyl)-1-ethyl-1H-1,2,4-triazol-5-yl]-N-[(4,6-dimethylpyridin-2-yl)methyl]acetamide The title compound was prepared according to General Procedure 2, using 2-[3-(4-chloro-3-isopropyloxyphenyl)-1-ethyl-1H-1,2,4-triazol-5-yl]acetic acid and (4,6-dimethylpyridin-2-yl) methanamine. $^1$H NMR: $\delta_H$ (400 MHz, DMSO-d6) 8.84 (1H, t, J 5.9), 7.63 (1H, s), 7.56-7.48 (2H, m), 6.96 (1H, s), 6.95 (1H, s), 4.73-4.70 (1H, m), 4.32 (2H, d, J 5.9), 4.22 (2H, q, J 7.0), 3.95 (2H, s), 2.40 (3H, s), 2.33 (3H, s), 1.39 (3H, t, J 7.0), 1.33 (6H, d, J 6.0).

Example 83: 2-[3-(4-Chloro-3-fluorophenyl)-1-ethyl-1H-1,2,4-triazol-5-yl]-N-{[2-(trifluoromethyl)pyridin-4-yl]methyl}acetamide Step 1: 2-(Trifluoromethyl)isonicotinonitrile Zinc cyanide (2.71 g, 23.2 mmol) was added to a degassed solution of 4-chloro-2-(trifluoromethyl)pyridine (3 g, 16.6 mmol), DPPF (0.73 g, 1.32 mmol) and Pd$_2$(dba)$_3$ (0.76 g, 0.83 mmol) in dry DMF (30 mL). The reaction mixture was heated at 100° C. for 16 h. The mixture was cooled to room temperature, diluted with ethyl acetate (35 mL) and filtered through Celite®. The filter cake was washed with ethyl acetate (2×30 mL). The combined organic filtrate was washed with water (30 mL) and saturated aqueous NaCl, dried over anhydrous sodium sulfate, filtered, and concentrated under reduced pressure. The crude product was purified by flash chromatography, eluting with 40% to 60% ethyl acetate in petroleum ether, to afford 2-(trifluoromethyl)isonicotinonitrile (1 g, 35%).

Step 2: Tert-butyl {[2-(trifluoromethyl)pyridin-4-yl]methyl}carbamate

To an ice-cold solution of 2-(trifluoromethyl)isonicotinonitrile (100 mg, 0.58 mmol) and Boc-anhydride (152 mg, 0.7 mmol) in dry methanol (5 mL) were added NiCl$_2$ (150 mg, 1.16 mmol) and sodium borohydride (116 mg, 2.91 mmol). The resulting mixture was stirred at room temperature for 16 h, then concentrated under reduced pressure and diluted with ethyl acetate (15 mL). The resulting suspension was filtered through Celite® and the residue was washed with ethyl acetate (2×5 mL). The filtrate was concentrated and the crude residue was purified by column chromatography, eluting with 45% to 55% ethyl acetate in hexane, to afford tert-butyl {[2-(trifluoromethyl)pyridin-4-yl]methyl}carbamate (100 mg).

Step 3: [2-(Trifluoromethyl)pyridin-4-yl]methanamine, hydrochloride salt

To a cold solution of tert-butyl {[2-(trifluoromethyl)pyridin-4-yl]methyl}carbamate (100 mg) in dichloromethane (5 mL) was added 4M HCl in dioxane (0.1 mL). The mixture was stirred at room temperature for 2 h, then concentrated under reduced pressure and the residue was triturated with ether and filtered. The solid obtained was dried to afford [2-(trifluoromethyl)pyridin-4-yl]methanamine, hydrochloride salt (60 mg).

Step 4: 2-[3-(4-Chloro-3-fluorophenyl)-1-ethyl-1H-1,2,4-triazol-5-yl]-N-{[2-(trifluoromethyl) pyridin-4-yl]methyl}acetamide The title compound was prepared according to General Procedure 2, using 2-[3-(4-chloro-3-fluorophenyl)-1-ethyl-1H-1,2,4-triazol-5-yl]acetic acid and [2-(trifluoromethyl)pyridin-4-yl]methanamine. $^1$H NMR: $\delta_H$ (400 MHz, DMSO-d6) 8.98 (1H, t, J 5.7), 8.72 (1H, d, J 4.7), 7.85-7.80 (3H, m), 7.71-7.65 (2H, m), 4.48 (2H, d, J 5.7), 4.21 (2H, q, J 7.2), 3.98 (2H, s), 1.38 (3H, t, J 7.2).

Example 84: 2-[3-(4-Chloro-3-fluorophenyl)-1-ethyl-1H-1,2,4-triazol-5-yl]-N-{[2-(difluoromethyl) pyridin-4-yl]methyl}acetamide Step 1: 2-(Difluoromethyl)isonicotinonitrile To a solution of isonicotinonitrile (2 g, 19 mmol) and difluoroacetic acid (2.4 mL, 38 mmol) in acetonitrile/water (90 mL, 2:1) were added potassium persulfate (25.6 g, 95 mmol) and silver nitrate (1.61 g, 9.5 mmol). The resulting mixture was heated at 80° C. for 16 h and then cooled to room temperature. The reaction was diluted with saturated sodium bicarbonate solution (30 mL) and extracted with ethyl acetate (2×50 mL). The combined organic layers were dried over anhydrous sodium sulfate, filtered and concentrated under reduced pressure. The crude product obtained was purified by column chromatography, eluting with 5% to 8% ethyl acetate in hexane, to afford the desired product as a pale yellow liquid (1.6 g, 54%).

Step 2: Tert-butyl {[2-(difluoromethyl)pyridin-4-yl]methyl}carbamate

To an ice-cold solution of 2-(difluoromethyl)isonicotinonitrile (1 g, 6.4 mmol) and Boc-anhydride (1.69 g, 7.7 mmol) in dry methanol (15 mL) were added NiCl$_2$ (1.65 g, 12.8 mmol) and sodium borohydride (1.2 g, 32 mmol). The resulting mixture was stirred at room temperature for 16 h, concentrated and diluted with ethyl acetate (50 mL). This suspension was filtered through Celite® and the residue was washed with ethyl acetate (2×10 mL). The filtrate was concentrated and the crude residue was purified by column chromatography, eluting with 25% to 30% ethyl acetate in hexane, to afford tert-butyl {[2-(difluoromethyl)pyridin-4-yl]methyl}carbamate (0.48 g, 47%). $^1$H NMR: $\delta_H$ (400 MHz, DMSO-d6) 8.61 (1H, d, J 4.9), 7.60-7.54 (2H, m), 7.42 (1H, d, J 4.9), 6.95 (1H, t, J 55.0), 4.24 (2H, d, J 6.1), 1.39 (9H, s).

Step 3: [2-(Difluoromethyl)pyridin-4-yl]methanamine

To a cold solution of tert-butyl {[2-(difluoromethyl)pyridin-4-yl]methyl}carbamate (0.48 g, 1.86 mmol) in dichloromethane (5 mL) was added 4M HCl in dioxane (5 mL). The mixture was stirred at room temperature for 2 h, then concentrated under reduced pressure and the residue was triturated with ether and filtered. The solid obtained was dried to afford [2-(difluoromethyl)pyridin-4-yl]methanamine, hydrochloride salt (280 mg) as a pale yellow solid. $^1$H NMR: $\delta_H$ (400 MHz, DMSO-d6) 8.71 (1H, d, J 5.0), 8.66 (3H, bs), 7.86 (1H, s), 7.69 (1H, d, J 5.0), 6.99 (1H, t, J 55.0), 4.19-4.15 (2H, m).

Step 4: 2-[3-(4-Chloro-3-fluorophenyl)-1-ethyl-1H-1,2,4-triazol-5-yl]-N—([2-(difluoromethyl) pyridin-4-yl]methyl)acetamide The title compound was prepared according to General Procedure 2, using 2-[3-(4-chloro-3-fluorophenyl)-1-ethyl-1H-1,2,4-triazol-5-yl]acetic acid and [2-(difluoromethyl)pyridin-4-yl]methanamine. $^1$H NMR: $\delta_H$ (400 MHz, DMSO-d6) 8.95 (1H, t, J 5.9), 8.62 (1H, d, J 5.0), 7.85-7.80 (2H, m), 7.70-7.68 (1H, m), 7.60 (1H, s), 7.51 (1H, d, J 4.8), 6.93 (1H, t, J 55.0), 4.44 (2H, d, J 5.9), 4.20 (2H, q, J 7.2), 3.97 (2H, s), 1.38 (3H, t, J 7.2).

Example 85: N-{[2,6-Bis(difluoromethyl)pyridin-4-yl]methyl}-2-[3-(4-chloro-3-fluorophenyl)-1-ethyl-1H-1,2,4-triazol-5-yl]acetamide Step 1: Dimethyl 4-bromopyridine-2,6-dicarboxylate Chelidamic acid (5 g, 27 mmol) was mixed with phosphorus pentabromide (58 g, 135 mmol) and heated to 80° C. for 2 h. The resulting mixture was cooled to room temperature, chloroform (50 mL) was added and the mixture was filtered. The filtrate was cooled to 0° C., methanol (90 mL) was added in small portions and the resulting suspension was filtered off and dried under vacuum at 50° C. to afford dimethyl 4-bromopyridine-2,6-dicarboxylate (7 g, 93%). $^1$H NMR: $\delta_H$ (300 MHz, DMSO-d6) 8.43 (2H, s), 3.93 (6H, s).

Step 2: (4-Bromopyridine-2,6-diyl)dimethanol

A mixture of dimethyl 4-bromopyridine-2,6-dicarboxylate (9 g, 33 mmol) and sodium borohydride (3 g, 132 mmol) in dry ethanol (90 mL) was heated under inert atmosphere at 60° C. for 3 h. The mixture was concentrated under reduced pressure, the residue was dissolved in ethyl acetate (50 mL) and washed with water. The organic layer was dried over anhydrous sodium sulfate, filtered, and concentrated under reduced pressure. The crude product was purified by flash chromatography, eluting with 40% to 60% ethyl acetate in petroleum ether, to afford (4-bromopyridine-2,6-diyl)dimethanol (7 g, 97%). $^1$H NMR: $\delta_H$ (300 MHz, DMSO-d6) 7.51 (2H, s), 5.34 (2H, t, J 5.7), 4.52 (4H, d, J 5.7).

Step 3: 4-Bromopyridine-2,6-dicarbaldehyde

Dess-Martin periodinane (24.5 g, 54 mmol) was added to bromopyridine-2,6-diyl)dimethanol (4 g, 18 mmol) in dry dichloromethane (50 mL). The resulting suspension was stirred at room temperature for 2 h and then filtered through Celite® The residue was washed with dichloromethane (2×15 mL) and the filtrate was concentrated. The crude product obtained was purified by flash column chromatography, by eluting with 30% ethyl acetate in petroleum ether, to afford 4-bromopyridine-2,6-dicarbaldehyde (2.6 g, 68%). $^1$H NMR: $\delta_H$ (300 MHz, DMSO-d6) 10.04 (2H, s), 8.37 (2H, s).

Step 4: 4-Bromo-2,6-bis(difluoromethyl)pyridine

To a solution of 4-bromopyridine-2,6-dicarbaldehyde (1.2 g, 5.6 mmol) in dichloromethane (12 mL) at −78° C., was added DAST (2.94 mL, 22 mmol). The resulting mixture was stirred at room temperature for 3 h. The mixture was diluted with dichloromethane (15 mL), water (15 mL) and partitioned. The organic layer was dried over anhydrous sodium sulfate, filtered and concentrated under reduced pressure. The crude product was purified by flash chromatography, eluting with 10% ethyl acetate in hexane, to give 4-bromo-2,6-bis(difluoromethyl)pyridine (0.9 g, 62%). $^1$H NMR: $\delta_H$ (300 MHz, DMSO-d6) 8.27 (2H, s), 7.05 (2H, t, J 54.3).

Step 5: 2,6-Bis(difluoromethyl)isonicotinonitrile

Zinc cyanide (1.26 g, 10 mmol) was added to a degassed solution of 4-bromo-2,6-bis(difluoromethyl)pyridine (1.4 g, 5 mmol) and tetrakis(triphenylphoshpine) palladium (258 mg, 0.5 mmol) in dry DMF (15 mL). The resulting reaction mixture was heated at 100° C. for 16 h. The mixture was cooled to room temperature, diluted with ethyl acetate (15 mL) and filtered through Celite®. The filter cake was washed with ethyl acetate (2×10 mL). The combined organic filtrate was washed with water (10 mL) and saturated aqueous NaCl, dried over anhydrous sodium sulfate, filtered and concentrated under reduced pressure. The crude product was purified by flash chromatography, eluting with 50% ethyl acetate in petroleum ether to afford 2,6-bis(difluoromethyl)isonicotinonitrile (300 mg, 31%). $^1$H NMR: $\delta_H$ (300 MHz, DMSO-d6) 8.44 (2H, s), 7.13 (2H, t, J 54.3).

Step 6: [2,6-Bis(difluoromethyl)pyridin-4-yl]methanamine

A mixture of 2,6-bis(difluoromethyl)isonicotinonitrile (300 mg) and 10% Pd/C (30 mg) in ethanol (13 mL) was stirred under a hydrogen atmosphere for 16 h. The reaction mixture was filtered through Celite® and the residue was washed with ethanol (2×15 mL). The filtrate was concentrated under reduced pressure and the crude [2,6-bis(difluoromethyl)pyridin-4-yl]methanamine (150 mg) was used without further purification.

Step 7: N-{[2,6-Bis(difluoromethyl)pyridin-4-yl]methyl}-2-[3-(4-chloro-3-fluorophenyl)-1-ethyl-1H-1,2,4-triazol-5-yl]acetamide The title compound was prepared according to General Procedure 1, using 2-[3-(4-chloro-3-fluorophenyl)-1-ethyl-1H-1,2,4-triazol-5-yl]acetic acid and [2,6-bis(difluoromethyl)pyridin-4-yl]methanamine. $^1$H NMR: $\delta_H$ (400 MHz, DMSO-d6) 9.03 (1H, t, J 6.0), 7.86-7.80 (4H, m), 7.70-7.66 (1H, m), 7.04 (2H, t, J 54.7), 4.53 (2H, d, J 6.0), 4.21 (2H, q, J 7.2), 4.00 (2H, s), 1.38 (3H, t, J 7.2).

Example 86: 2-[3-(4-Chloro-3-fluorophenyl)-1-ethyl-1H-1,2,4-triazol-5-yl]-N-[1-(2,6-dimethylpyridin-4-yl)cyclopropyl]acetamide

Step 1: 1-(2,6-Dimethylpyridin-4-yl)cyclopropan-1-amine

To a solution of 2,6-dimethylisonicotinonitrile (200 mg, 1.51 mmol) in diethyl ether (3 mL), at −78° C., were added ethyl magnesium bromide (3.33 mL, 3.33 mmol) and titanium isopropoxide (0.47 mL, 1.66 mmol). After 2 h at −78° C., BF$_3$.OEt$_2$ (0.42 mL, 3.03 mmol) was added and allowed to stir at room temperature for 14 h. The reaction was quenched with saturated ammonium chloride solution (3 mL), NaOH solution was added to maintain pH 10-12 and the mixture was extracted with ethyl acetate (3×10 mL). The combined organic filtrate was washed with water (30 mL) and saturated aqueous NaCl, dried over anhydrous sodium sulfate, filtered and concentrated under reduced pressure. The crude product was purified by flash chromatography, eluting with 40% to 60% ethyl acetate in petroleum ether to afford 1-(2,6-dimethylpyridin-4-yl)cyclopropan-1-amine (150 mg). $^1$H NMR: $\delta_H$ (400 MHz, CDCl$_3$) 6.83 (2H, s), 2.57 (6H, s), 1.20-1.17 (2H, m), 1.08-1.05 (2H, m).

Step 2: 2-[3-(4-Chloro-3-fluorophenyl)-1-ethyl-1H-1,2,4-triazol-5-yl]-N-[1-(2,6-dimethylpyridin-4-yl)cyclopropyl]acetamide The title compound was prepared according to General Procedure 1, using 2-[3-(4-chloro-3-fluorophenyl)-1-ethyl-1H-1,2,4-triazol-5-yl]acetic acid and 1-(2,6-dimethylpyridin-4-yl) cyclopropan-1-amine. $^1$H NMR: $\delta_H$ (400 MHz, DMSO-d6) 9.04 (1H, s), 7.87-7.83 (2H, m), 7.72-7.68 (1H, m), 6.77 (2H, s), 4.21 (2H, q, J 7.2), 3.92 (2H, s), 2.33 (6H, s), 1.39 (3H, t, J7.2), 1.28-1.23 (4H, m).

Example 87: 2-[3-(4-Chloro-3-fluorophenyl)-1-(cyclopropylmethyl)-1H-1,2,4-triazol-5-yl]-N-[1-(2,6-dimethylpyridin-4-yl)cyclopropyl]acetamide The title compound was prepared according to General Procedure 1, using 2-[3-(4-chloro-3-fluorophenyl)-1-(cyclopropylmethyl)-1H-1,2,4-triazol-5-yl]acetic acid and 1-(2,6-dimethylpyridin-4-yl)cyclopropan-1-amine. $^1$H NMR: $\delta_H$ (400 MHz, DMSO-d6) 9.04 (1H, s), 7.88-7.84 (2H, m), 7.73-7.69 (1H, m), 6.78 (2H, s), 4.07 (2H, d, J 7.1), 3.91 (2H, s), 2.33 (6H, s), 1.32-1.21 (5H, m), 0.53-0.43 (4H, m).

Example 88: 2-[3-(4-Chloro-3-fluorophenyl)-1-ethyl-1H-1,2,4-triazol-5-yl]-N-{[2,6-di($^2$H$_3$)methylpyridin-4-yl]methyl}acetamide

Step 1: 2,6-Bis(methyl-d3)isonicotinonitrile

To a degassed solution of 2,6-dimethylisonicotinonitrile (2 g, 14 mmol) and benzoic acid (0.9 g, 7 mmol) in dioxane (20 mL) (sealed-tube) was added D$_2$O (20 mL). The resulting mixture was stirred at 100° C. for 4 days. The reaction mixture was allowed to cool to room temperature and extracted with ethyl acetate. The combined organic layers were dried over anhydrous sodium sulfate, concentrated under reduced pressure and dried under vacuum to afford 2,6-bis(methyl-d3)isonicotinonitrile (1.8 g with ~94% D, 86%). $^1$H NMR: $\delta_H$ (400 MHz, CDCl$_3$) 7.21 (2H, s).

Step 2: [2,6-Bis(methyl-d3)pyridin-4-yl]methanamine

A solution of 2,6-bis(methyl-d3)isonicotinonitrile (5 g) in ethanol (50 mL) was added to a suspension of 10% Pd/C (1 g) in ethanol (10 mL). The reaction vessel was subjected to hydrogen pressure (10 Kg) and stirred at room temperature for 24 h. The reaction mixture was filtered through Celite®. The filter cake was washed with ethanol and the filtrate was concentrated to give a yellow solid of [2,6-bis(methyl-d3) pyridin-4-yl]methanamine (3.8 g). $^1$H NMR: $\delta_H$ (400 MHz, CDCl$_3$) 6.94 (2H, s), 3.83 (2H, s).

Step 3: 2-[3-(4-Chloro-3-fluorophenyl)-1-ethyl-1H-1,2,4-triazol-5-yl]-N-{[2,6-di($^2$H$_3$) methylpyridin-4-yl]methyl}acetamide The title compound was prepared according to General Procedure 1, using 2-[3-(4-chloro-3-fluorophenyl)-1-ethyl-1H-1,2,4-triazol-5-yl]acetic acid and [2,6-bis(methyl-d3) pyridin-4-yl]methanamine. $^1$H NMR: $\delta_H$ (400 MHz, CDCl$_3$) 8.14 (1H, t, J 5.6), 7.83 (1H, dd, J 9.6, 1.6), 7.79-7.77 (1H, m), 7.49-7.45 (1H, m), 6.87 (2H, s), 4.48 (2H, d, J 5.6), 4.25 (2H, q, J 7.2), 3.86 (2H, s), 1.53 (3H, t, J 7.2).

Example 89: 2-[3-(4-Chloro-3-fluorophenyl)-1-ethyl-1H-1,2,4-triazol-5-yl]-N-{[2,6-di($^2$H$_3$) methylpyridin-4-yl]methyl}-2,2-difluoroacetamide The title compound was prepared according to General Procedure 1, using 2-[3-(4-chloro-3-fluorophenyl)-1-ethyl-1H-1,2,4-triazol-5-yl]-2,2-difluoroacetic acid and [2,6-bis(methyl-d3)pyridin-4-yl]methanamine. $^1$H NMR: $\delta_H$ (400 MHz, DMSO-d6) 9.87 (1H, s), 7.88-7.83 (2H, m), 7.77-7.73 (1H, m), 6.95 (2H, s), 4.47-4.39 (4H, m), 1.46 (3H, t, J 7.2).

Example 90: 2-[3-(4-Chloro-3-fluorophenyl)-1-ethyl-1H-1,2,4-triazol-5-yl]-N-[(2,6-dimethylpyridin-4-yl)($^2$H$_2$)methyl]($^2$H$_2$)acetamide To a degassed solution of 2-(3-(4-chloro-3-fluorophenyl)-1-ethyl-1H-1,2,4-triazol-5-yl)-N-[(2,6-dimethylpyridin-4-yl)methyl]acetamide (300 mg, 0.75 mmol) and benzoic acid (92 mg, 0.75 mmol) in dioxane (2 mL) (sealed-tube) was added D$_2$O (2 mL). The resulting mixture was stirred at 100° C. for 24 h. The reaction mixture was allowed to cool to room temperature and extracted with ethyl acetate. The combined organic layers were dried over anhydrous sodium sulfate, concentrated under reduced pressure and dried under vacuum to afford the title compound (220 mg with ~98% D, 72%). $^1$H NMR: $\delta_H$ (400 MHz, CDCl$_3$) 8.06 (1H, bs), 7.83 (1H, dd, J 10.0, 2.0), 7.79 (1H, ddd, J 8.2, 2.0, 1.2), 7.48-7.45 (1H, m), 6.87 (2H, s), 4.25 (2H, q, J 7.2), 2.49 (6H, s), 1.53 (3H, t, J 7.2).

Biological Assays

Cell Culture

HEK 293 and MDCK cells (Public Health England, Cell Culture Collections) were maintained in DMEM supplemented with 10% (v/v) fetal bovine serum (Seralab), 2 mM L-glutamine, 1,000 U penicillin and 1,000 µg streptomycin (Life Technologies); termed complete media. Clonal HEK 293 cell lines were maintained in complete media supplemented with 0.6 mg/mL G418 (Enzo Life Sciences).

Experiment 1: Identification of PDE4 Long Form Activators of the Present Invention Using Full-Length Human PDE4 Isoforms PDE4D5, PDE4B1, PDE4A4 and PDE4B2

(Marchmont, R. J. and Houslay, M. D. *Biochem. J.* 187: 381-92, 1980)

Cell Line Generation

HEK 293 cells were transfected with pDEST™ PDE4 expression vectors using Lipofectamine LTX/Plus reagent (Invitrogen) as outlined by the manufacturer and clonal isolates expanded to obtain cell lines that stably expressed the full-length human PDE4D5, PDE4B1 and PDE4A4 long isoforms and the full length human PDE4B2 short isoform. These were called the HEK-PDE4D5, HEK-PDE4B1, HEK-PDE4A4 and HEK-PDE4B2 cell lines, respectively.

Lysate Preparation (Using PDE4D5 as a Typical Example)

HEK-PDE4D5 cells were seeded out in 100 mm plates and incubated at 37° C. in an atmosphere of 5% CO$_2$, 95% air. Cell lysates were prepared using KHEM buffer [50 mM KCl, 10 mM EGTA, 50 mM HEPES (pH 7.2), 1.92 mM MgCl$_2$].

To prepare the cell lysates, the 100 mm plates containing the cells were placed on ice and washed with ice-cold PBS (phosphate buffered saline, pH 7.4). KHEM buffer (500 µl) was added to the cells. Cells were then scraped off the plate and triturated using a needle (BD Microlance™ 0.8, 40 mm). The lysed cells were then centrifuged at 2000 rpm for 10 minutes to remove cell debris and the supernatant (cell lysate containing recombinant PDE4D5) was transferred to a fresh tube and kept on ice.

Cytosol Fraction Preparation (Using PDE4D5 as a Typical Example)

The cell lysate containing recombinant PDE4D5 was transferred into a centrifuge tube and placed into an ultracentrifuge (BECKMAN COULTER) and spun at high speed (100,000 g) for 30 minutes at 4° C. The cytosol fraction was then collected and its protein amount determined using a BCA protein assay.

PDE Assay—(Using PDE4D5 as a Typical Example)

PDE assays were performed in thin walled V-bottomed 96-well plates. The assays were performed at a final concentration of 10 mM Tris/5 mM MgCl$_2$ plus PDE4D5 cell lysate cytosol fraction, containing over-expressed PDE4D5, with and without test compound. The lysate/compound mix were incubated together for 15 min at room temperature on an orbital shaker prior to addition of [$^3$H] cAMP (final concentration 1 µM [$^3$H] cAMP; Perkin Elmer) to a final volume of 50 µl per reaction. The reactions were then incubated for 10 minutes at 30° C., terminated by heating for 2 min at 95° C. and allowed to cool. Snake venom (12.5 µl of 1 mg/ml; *Crotalus atrox*, Sigma) was then added and the plates were agitated and incubated for a further 15 minutes at 30° C. Dowex ion exchange resin (Sigma, chloride form, 200-400 mesh; 200 µl; prepared as a 1:1 Dowex: water stock, thoroughly re-suspended and diluted 2:1 with ethanol) was then added to each well and the plates incubated for 15 min at room temperature on an orbital shaker ensuring sufficient agitation for resin suspension (550 RPM). The reaction mixture was then transferred to a 96 well filter plate (Millipore; 0.45 µM pore size) and filtered into a receiving 96-well plate to remove the dowex suspension. 30 µL of the filtered solution was then transferred to the wells of an Opti-plate (Perkin Elmer) 96 well assay plate and 120 µl of Microscint 40 scintillation fluid was added. The plate was then placed on an orbital shaker for 10 min at high speed (900 RPM) to mix the sample with scintillation fluid prior to quantitation using a plate based scintillation counter (TopCount).

The % increase in counts in the presence of test compound at a particular concentration indicates the % increase in enzyme activity at that concentration.

Data are shown in FIG. 1 and Tables 2 to 5.

Experiment 2: Reduction of Intracellular cAMP Levels in MDCK Cells by PDE4 Long Form Activators MDCK cells were seeded at 100,000 cells per well, and left to adhere overnight. The cells were then treated with the test compound for 40 minutes, prior to stimulation with forskolin (1 µM, Sigma) for 20 minutes. Media was aspirated, and hydrochloric acid (0.1 M) was added to lyse the cells. The cAMP assay (Enzo Life Sciences) was performed according to the manufacturer's instructions.

Compounds of the present invention reduced intracellular cAMP levels in forskolin stimulated MDCK cells. Data for Example 3 are shown in FIG. 2.

Experiment 3: Inhibition of In Vitro Cyst Formation in MDCK Cells Treated with PDE4 Long Form Activators In this study, the well-established three-dimensional (3D) MDCK cell model is used to investigate the effects of PDE4 long form activators on the formation of kidney cysts and evaluate their potential in the treatment of polycystic kidney diseases. 3D cysts are generated based on the method of Mao et al. (Mao, Z., Streets, A. J., Ong, A. C. M. *Am. J. Physiol. Renal Physiol.* 300(6): F1375-F1384, 2011), with some modifications.

Type 1 collagen (Invitrogen) is first prepared on ice by neutralising an acidic stock solution (3 mg/ml) with 17 mM NaOH and diluting it to 1 mg/ml with DMEM, supplemented with 2% (v/v) FBS, 2 mM L-glutamine, 1,000 U penicillin and 1,000 µg streptomycin (DMEM-2% FBS). A primary collagen layer is first added to each well and allowed to solidify at 37° C. prior to seeding MDCK cells (50,000 cells/well) in a secondary collagen layer and allowed to solidify at 37° C. DMEM-2% (v/v) FBS is added along with the test compound indicated in the presence of 300 nM prostaglandin E2 (Sigma Aldrich) in duplicate wells per condition. Media is replenished every 3 days for 10 days at which time the test compound and prostaglandin E2 are added.

Phase-contrast images are obtained on the Motic microscope (×4 magnification). 8 images are taken per condition and the cyst diameter measured (up to 150 cyst measurements per well). Cyst spheroid volume is calculated using the formula $4/3\pi r^3$ where r is the radius of the spheroid. A mean cyst volume is then calculated per well. The mean cyst volume and standard deviation between the duplicate wells is then calculated and expressed as a % Cyst Volume compared to the vehicle only (DMSO+300 nM PGE2) control wells. PDE4 long form activators inhibit in vitro cyst formation in MDCK cells. Data for Example 3 are shown in FIG. 3.

Experiment 4: Inhibition of proliferation of LNCaP human prostate cancer cells

In this study, the potential utility of PDE4 long form activators in the treatment of prostate cancer is studied using the LNCaP human prostate cancer cell line. The experiments are carried out according to the method described by Henderson et al. (Henderson, D. J. P., Byrne, A., Dulla, K., Jenster, G., Hoffmann, R., Baillie, G. S., Houslay, M. D. *Br. J. Cancer* 110: 1278-1287, 2014).

LNCaP Cell Culture

Androgen-sensitive (AS) LNCaP cells are maintained in RPMI1640 supplemented with 10% FBS (Seralabs), 2 mM L-glutamine and 1,000U penicillin-streptomycin. LNCaP androgen-insensitive (AI) cells are generated by culturing the LNCaP-AS cells in RPMI1640 supplemented with 10% charcoal stripped FBS, 2 mM L-glutamine and 1,000U penicillin-streptomycin for a minimum of four weeks. All tissue culture reagents are from Life Technologies.

Xcelligence (Roche) Proliferation Assay

Cell proliferation is measured as a function of changing electrical impedance. Values are represented by cell index number, a dimensionless unit of measurement representing the cell status, which increases as cells adhere to 96-well electrode plates and divide.

LNCaP AI/AS cells are plated at a density of 25,000 cells per well in a 96-well electrode plate (in triplicate), in the presence/absence of various concentrations of test compound.

Cell indices are measured every 10 minutes for up to 100 hours, analysed using RTCA software and normalised to the cell index of vehicle-treated cells (n=3).

PDE4 long form activators inhibit the proliferation of AS and AI LNCaP human prostate cancer cells.

TABLE 1

Small molecule PDE4 long form activators (Examples 1 to 90), according to the present invention

| Compound | Chemical name | Molecular weight (Daltons) | Chemical Structure |
|---|---|---|---|
| Example 1 | 2-[3-(4-chloro-3-fluorophenyl)-1-ethyl-1H-1,2,4-triazol-5-yl]-N-(3-fluorobenzyl)acetamide | 390.8 | 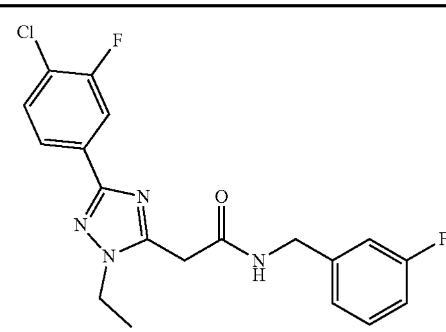 |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 2 | 2-[3-(4-chloro-3-fluorophenyl)-1-ethyl-1H-1,2,4-triazol-5-yl]-N-(3-methoxybenzyl)acetamide | 402.9 | 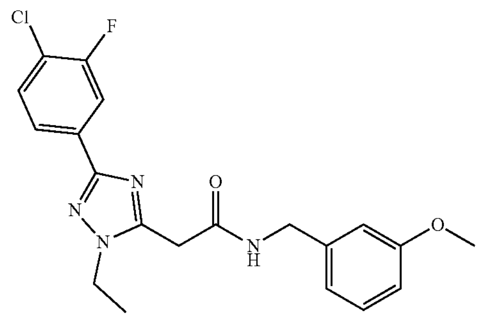 [SMILES: CCn1nc(-c2ccc(Cl)c(F)c2)nc1CC(=O)NCc1cccc(OC)c1] |
| Example 3 | 2-[3-(4-chloro-3-fluorophenyl)-1-ethyl-1H-1,2,4-triazol-5-yl]-N-[(2,6-dimethylpyridin-4-yl)methyl]acetamide | 401.9 | 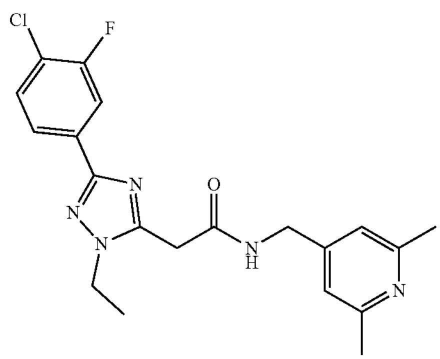 [SMILES: CCn1nc(-c2ccc(Cl)c(F)c2)nc1CC(=O)NCc1cc(C)nc(C)c1] |
| Example 4 | 2-[3-(4-chloro-3-fluorophenyl)-1-ethyl-1H-1,2,4-triazol-5-yl]-N-[(1H-indazol-7-yl)methyl]acetamide | 412.9 | 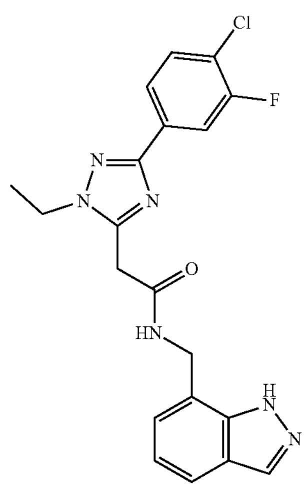 [SMILES: CCn1nc(-c2ccc(Cl)c(F)c2)nc1CC(=O)NCc1cccc2cn[nH]c12] |
| Example 5 | 2-[3-(4-chloro-3-fluorophenyl)-1-ethyl-1H-1,2,4-triazol-5-yl]-N-(3,5-dichlorobenzyl)acetamide | 441.7 | 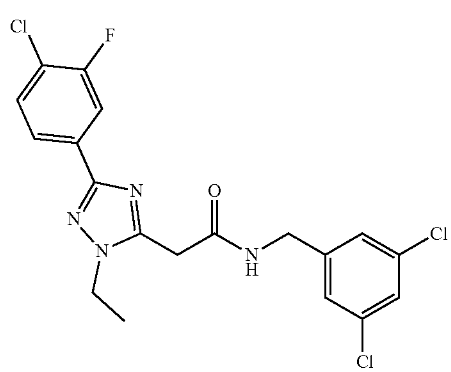 [SMILES: CCn1nc(-c2ccc(Cl)c(F)c2)nc1CC(=O)NCc1cc(Cl)cc(Cl)c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 6 | 2-[3-(4-chloro-3-fluorophenyl)-1-ethyl-1H-1,2,4-triazol-5-yl]-N-(5-methyl-1,2-oxazol-3-yl)acetamide | 363.8 | 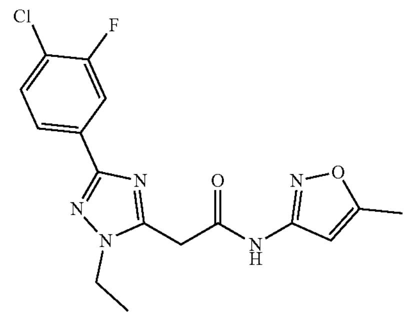 [SMILES: CCn1nc(-c2ccc(Cl)c(F)c2)nc1CC(=O)Nc1cc(C)on1] |
| Example 7 | 2-[3-(4-chloro-3-fluorophenyl)-1-ethyl-1H-1,2,4-triazol-5-yl]-N-[(1H-indazol-5-yl)methyl]acetamide | 412.9 | 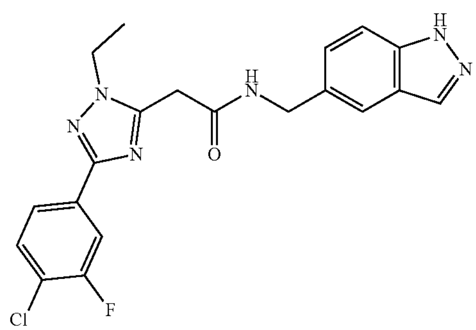 [SMILES: CCn1nc(-c2ccc(Cl)c(F)c2)nc1CC(=O)NCc1ccc2[nH]ncc2c1] |
| Example 8 | 2-[3-(4-chloro-3-fluorophenyl)-1-ethyl-1H-1,2,4-triazol-5-yl]-N-(pyrazin-2-yl)acetamide | 360.8 | 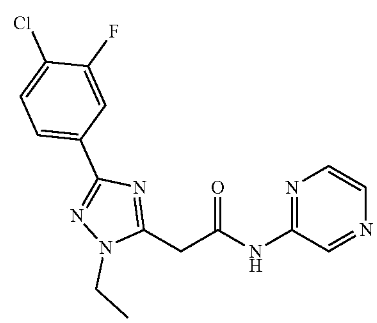 [SMILES: CCn1nc(-c2ccc(Cl)c(F)c2)nc1CC(=O)Nc1cnccn1] |
| Example 9 | 2-[3-(4-chloro-3-fluorophenyl)-1-ethyl-1H-1,2,4-triazol-5-yl]-N-[(2-oxo-2,3-dihydro-1H-benzo[d]imidazol-5-yl)methyl]acetamide | 428.9 | 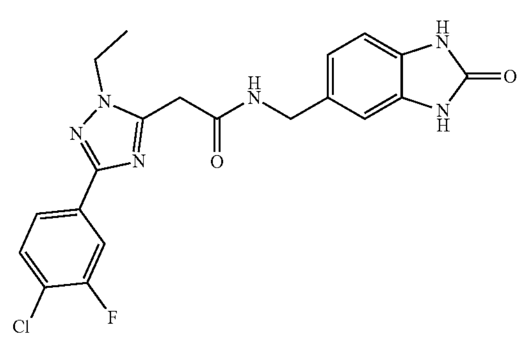 [SMILES: CCn1nc(-c2ccc(Cl)c(F)c2)nc1CC(=O)NCc1ccc2[nH]c(=O)[nH]c2c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 10 | 2-[3-(4-chloro-3-fluorophenyl)-1-ethyl-1H-1,2,4-triazol-5-yl]-N-[(3-chloro-5-methylphenyl)methyl]acetamide | 421.3 | 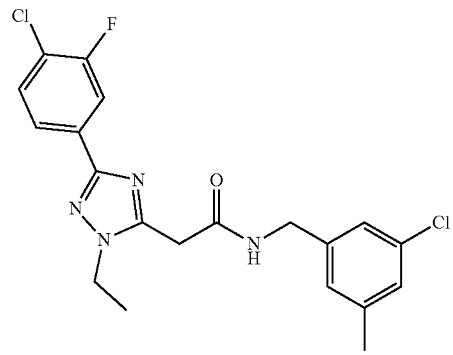 [SMILES: CCn1nc(-c2ccc(Cl)c(F)c2)nc1CC(=O)NCc1cc(C)cc(Cl)c1] |
| Example 11 | 2-[3-(4-chloro-3-fluorophenyl)-1-ethyl-1H-1,2,4-triazol-5-yl]-N-[(3-fluoro-5-methylphenyl)methyl]acetamide | 404.9 | 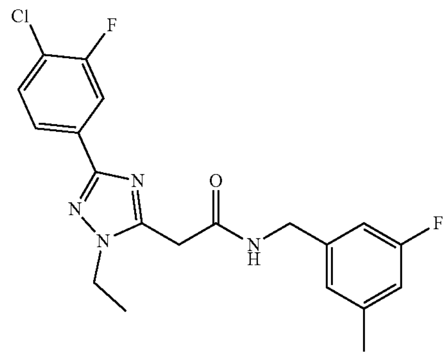 [SMILES: CCn1nc(-c2ccc(Cl)c(F)c2)nc1CC(=O)NCc1cc(C)cc(F)c1] |
| Example 12 | 2-[3-(4-chloro-3-fluorophenyl)-1-ethyl-1H-1,2,4-triazol-5-yl]-N-[(3,5-dimethylphenyl)methyl]acetamide | 400.9 | 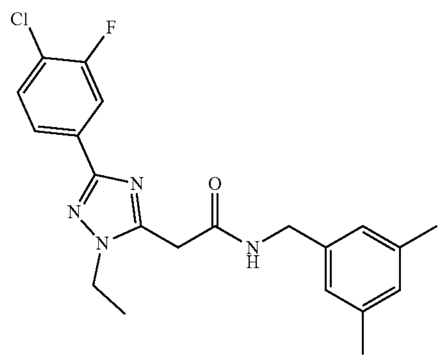 |
| Example 13 | 2-[3-(4-chloro-3-fluorophenyl)-1-ethyl-1H-1,2,4-triazol-5-yl]-N-[(2,3-difluorophenyl)methyl]acetamide | 408.8 | 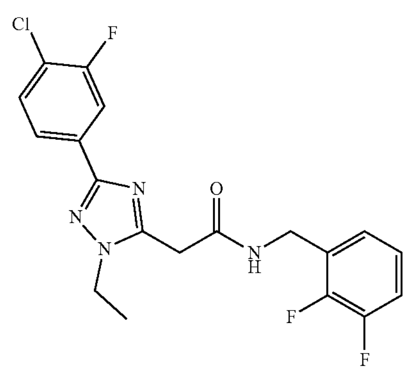 [SMILES: CCn1nc(-c2ccc(Cl)c(F)c2)nc1CC(=O)NCc1cccc(F)c1F] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 14 | 2-[3-(4-chloro-3-fluorophenyl)-1-ethyl-1H-1,2,4-triazol-5-yl]-N-[(3-ethoxyphenyl)methyl]acetamide | 416.9 | 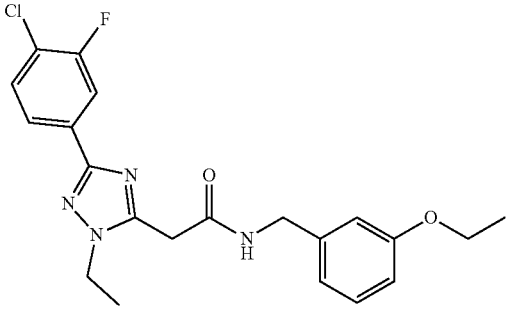 [SMILES: CCOc1cccc(CNC(=O)Cc2nc(-c3ccc(Cl)c(F)c3)nn2CC)c1] |
| Example 15 | 2-[3-(4-chloro-3-fluorophenyl)-1-ethyl-1H-1,2,4-triazol-5-yl]-N-[(3,5-dimethoxyphenyl)methyl]acetamide | 432.9 | 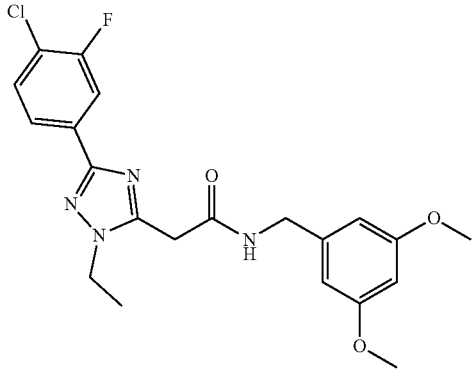 [SMILES: CCn1nc(-c2ccc(Cl)c(F)c2)nc1CC(=O)NCc1cc(OC)cc(OC)c1] |
| Example 16 | 2-[3-(4-chloro-3-fluorophenyl)-1-ethyl-1H-1,2,4-triazol-5-yl]-N-[(4-methoxyphenyl)methyl]acetamide | 402.9 | 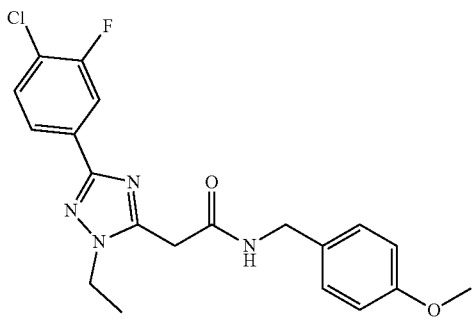 [SMILES: CCn1nc(-c2ccc(Cl)c(F)c2)nc1CC(=O)NCc1ccc(OC)cc1] |
| Example 17 | 2-[3-(4-chloro-3-fluorophenyl)-1-ethyl-1H-1,2,4-triazol-5-yl]-N-[(6-methoxypyridin-3-yl)methyl]acetamide | 403.8 | 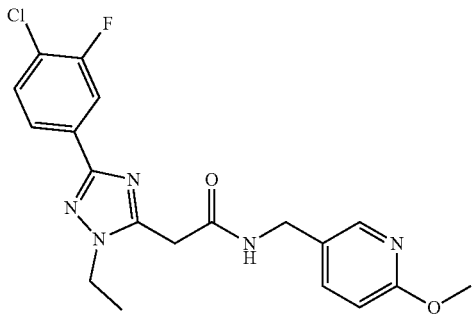 [SMILES: CCn1nc(-c2ccc(Cl)c(F)c2)nc1CC(=O)NCc1ccc(OC)nc1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 18 | 2-[3-(4-chloro-3-fluorophenyl)-1-methyl-1H-1,2,4-triazol-5-yl]-N-[(3,5-dichlorophenyl)methyl]acetamide | 427.7 | 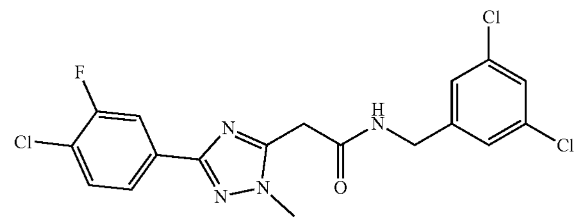 [SMILES: Cn1nc(-c2ccc(Cl)c(F)c2)nc1CC(=O)NCc1cc(Cl)cc(Cl)c1] |
| Example 19 | 2-[3-(4-chloro-3-fluorophenyl)-1-methyl-1H-1,2,4-triazol-5-yl]-N-[(3-methoxyphenyl)methyl]acetamide | 388.8 | 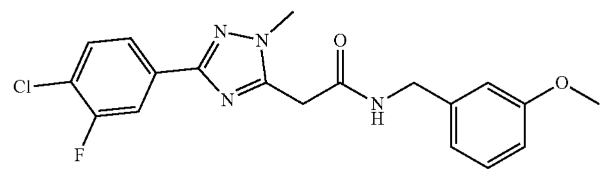 [SMILES: COc1cccc(CNC(=O)Cc2nc(-c3ccc(Cl)c(F)c3)nn2C)c1] |
| Example 20 | 2-[3-(4-chloro-3-fluorophenyl)-1-methyl-1H-1,2,4-triazol-5-yl]-N-[(3-fluorophenyl)methyl]acetamide | 376.8 | 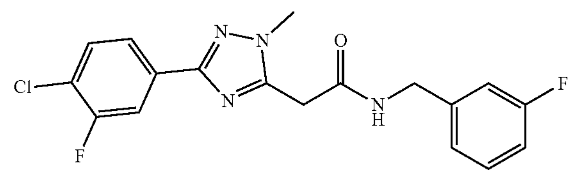 [SMILES: Cn1nc(-c2ccc(Cl)c(F)c2)nc1CC(=O)NCc1cccc(F)c1] |
| Example 21 | 2-[3-(4-chloro-3-fluorophenyl)-1-methyl-1H-1,2,4-triazol-5-yl]-N-[(1H-indazol-5-yl)methyl]acetamide | 398.8 | 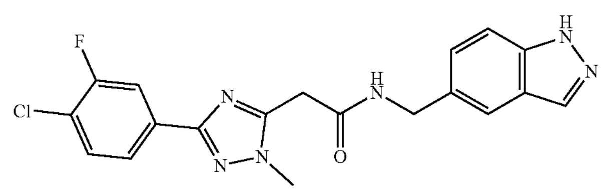 [SMILES: Cn1nc(-c2ccc(Cl)c(F)c2)nc1CC(=O)NCc1ccc2[nH]ncc2c1] |
| Example 22 | 2-[3-(4-chloro-3-fluorophenyl)-1-(2-methoxyethyl)-1H-1,2,4-triazol-5-yl]-N-[(3,5-dichlorophenyl)methyl]acetamide | 471.7 | 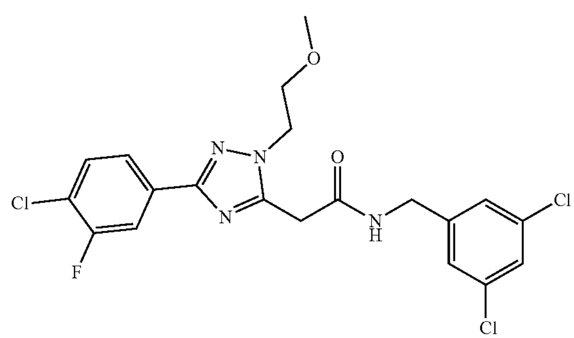 [SMILES: COCCn1nc(-c2ccc(Cl)c(F)c2)nc1CC(=O)NCc1cc(Cl)cc(Cl)c1] |
| Example 23 | 2-[3-(4-chloro-3-fluorophenyl)-1-(2-hydroxyethyl)-1H-1,2,4-triazol-5-yl]-N-[(3,5-dichlorophenyl)methyl]acetamide | 457.7 | 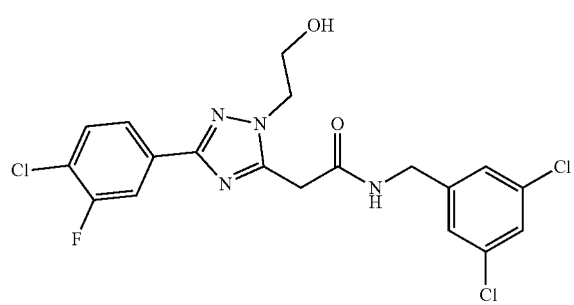 [SMILES: O=C(Cc1nc(-c2ccc(Cl)c(F)c2)nn1CCO)NCc1cc(Cl)cc(Cl)c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 24 | 2-[3-(4-chloro-3-fluorophenyl)-1-ethyl-1H-1,2,4-triazol-5-yl]-N-[(3-fluorophenyl)methyl]propanamide | 404.9 | 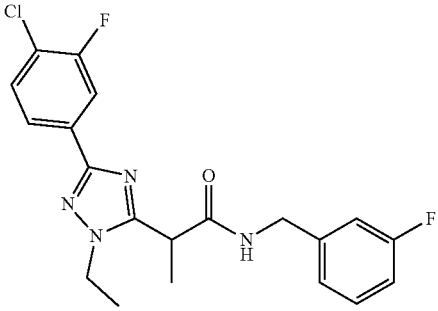 [SMILES: CCn1nc(-c2ccc(Cl)c(F)c2)nc1C(C)C(=O)NCc1cccc(F)c1] |
| Example 25 | 2-[3-(4-chloro-3-fluorophenyl)-1-methanesulfonyl-1H-1,2,4-triazol-5-yl]-N-[(3-fluorophenyl)methyl]acetamide | 440.9 | 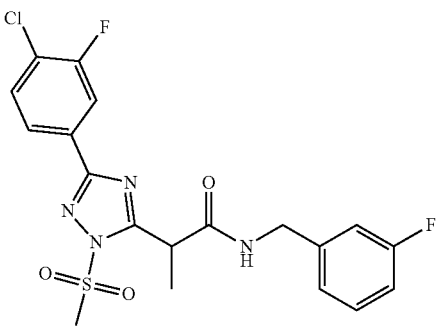 [SMILES: CC(C(=O)NCc1cccc(F)c1)c1nc(-c2ccc(Cl)c(F)c2)nn1S(C)(=O)=O] |
| Example 26 | 2-[3-(4-chloro-3-fluorophenyl)-1-(cyclopropylmethyl)-1H-1,2,4-triazol-5-yl]-N-[(2,6-dimethylpyridin-4-yl)methyl]acetamide | 427.9 | 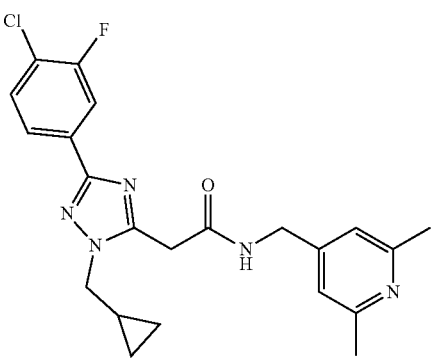 [SMILES: Cc1cc(CNC(=O)Cc2nc(-c3ccc(Cl)c(F)c3)nn2CC2CC2)cc(C)n1] |
| Example 27 | 2-[3-(4-chloro-3-fluorophenyl)-1-(cyclopropylmethyl)-1H-1,2,4-triazol-5-yl]-N-[(1H-indazol-5-yl)methyl]acetamide | 438.9 | 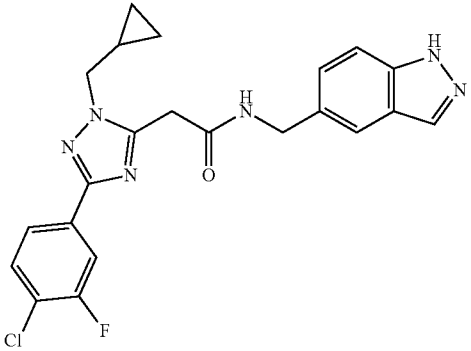 [SMILES: O=C(Cc1nc(-c2ccc(Cl)c(F)c2)nn1CC1CC1)NCc1ccc2[nH]ncc2c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 28 | N-[(3,5-dichlorophenyl)methyl]-2-{1-ethyl-3-[4-(trifluoromethoxy)phenyl]-1H-1,2,4-triazol-5-yl}acetamide | 473.3 | 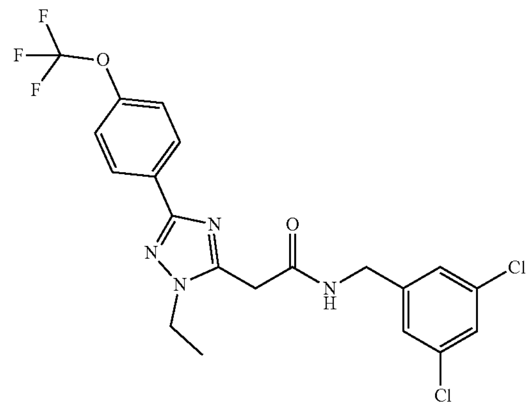 [SMILES: CCn1nc(-c2ccc(OC(F)(F)F)cc2)nc1CC(=O)NCc1cc(Cl)cc(Cl)c1] |
| Example 29 | 2-[3-(4-chloro-3-methoxyphenyl)-1-ethyl-1H-1,2,4-triazol-5-yl]-N-[(3,5-dichlorophenyl)methyl]acetamide | 453.8 | 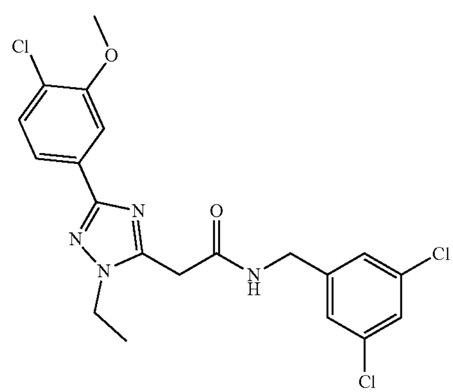 [SMILES: CCn1nc(-c2ccc(Cl)c(OC)c2)nc1CC(=O)NCc1cc(Cl)cc(Cl)c1] |
| Example 30 | 2-[3-(4-cyanophenyl)-1-ethyl-1H-1,2,4-triazol-5-yl]-N-[(3,5-dichlorophenyl)methyl]acetamide | 414.3 | 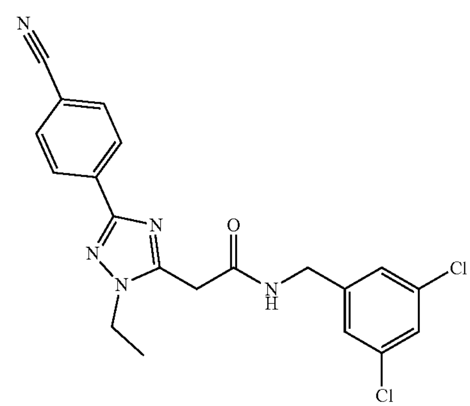 [SMILES: CCn1nc(-c2ccc(C#N)cc2)nc1CC(=O)NCc1cc(Cl)cc(Cl)c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 31 | 2-[3-(4-chloro-3-fluorophenyl)-1-ethyl-1H-1,2,4-triazol-5-yl]-N-[(2,6-dimethyl-1-oxidopyridin-4-yl)methyl]acetamide | 417.9 | 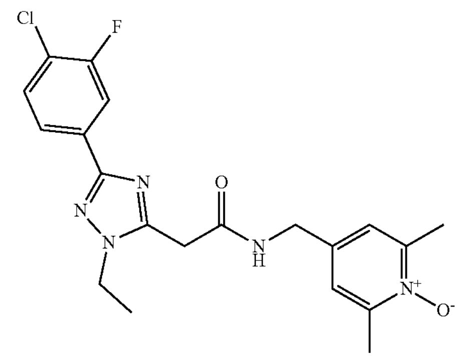 [SMILES: CCn1nc(-c2ccc(Cl)c(F)c2)nc1CC(=O)NCc1cc(C)[n+]([O-])c(C)c1] |
| Example 32 | 2-[3-(4-chloro-3-ethoxyphenyl)-1-ethyl-1H-1,2,4-triazol-5-yl]-N-[(3,5-dichlorophenyl)methyl]acetamide | 467.8 | 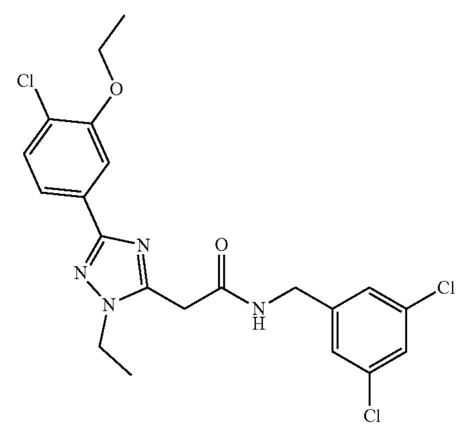 [SMILES: CCOc1cc(-c2nc(CC(=O)NCc3cc(Cl)cc(Cl)c3)n(CC)n2)ccc1Cl] |
| Example 33 | 2-{3-[4-chloro-3-(2-methoxyethoxy)phenyl]-1-ethyl-1H-1,2,4-triazol-5-yl}-N-[(3,5-dichlorophenyl)methyl]acetamide | 497.8 | 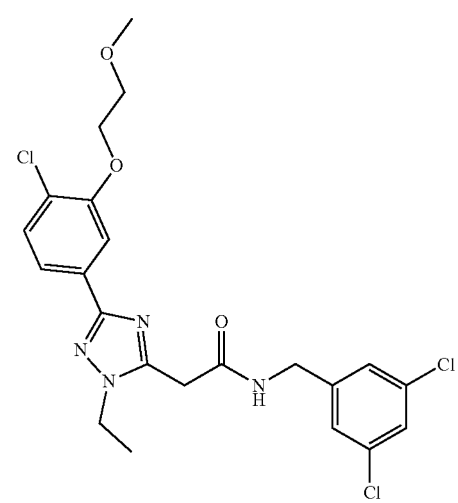 [SMILES: CCn1nc(-c2ccc(Cl)c(OCCOC)c2)nc1CC(=O)NCc1cc(Cl)cc(Cl)c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 34 | 2-[3-(4-chloro-3-isopropyloxyphenyl)-1-ethyl-1H-1,2,4-triazol-5-yl]-N-[(3,5-dichlorophenyl)methyl]acetamide | 481.8 | 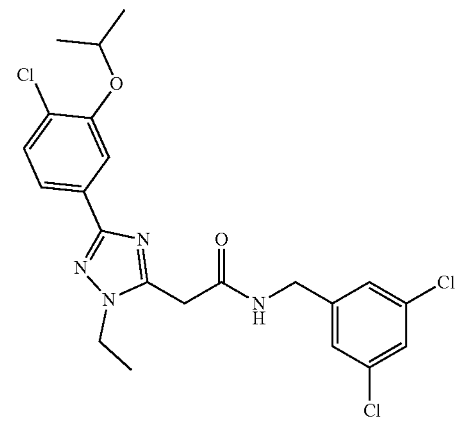 [SMILES: CCn1nc(-c2ccc(Cl)c(OC(C)C)c2)nc1CC(=O)NCc1cc(Cl)cc(Cl)c1] |
| Example 35 | 2-[3-(4-chloro-3-isopropyloxyphenyl)-1-ethyl-1H-1,2,4-triazol-5-yl]-N-[(2,6-dimethylpyridin-4-yl)methyl]acetamide | 442.0 | 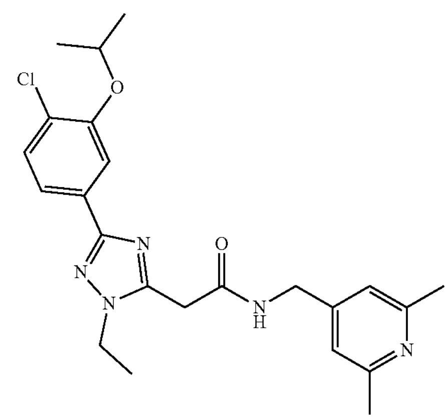 [SMILES: CCn1nc(-c2ccc(Cl)c(OC(C)C)c2)nc1CC(=O)NCc1cc(C)nc(C)c1] |
| Example 36 | 2-[3-(4-chloro-3-isopropyloxyphenyl)-1-ethyl-1H-1,2,4-triazol-5-yl]-N-[(1S)-2,3-dihydro-1H-inden-1-yl]acetamide | 439.0 | 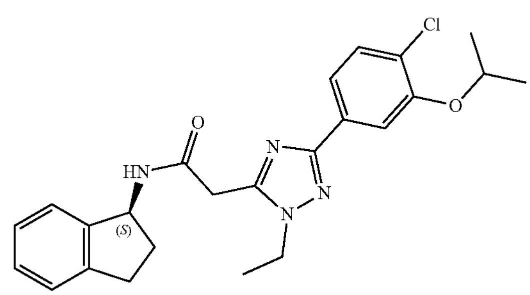 |
| Example 37 | 2-[3-(4-chloro-3-isopropyloxyphenyl)-1-ethyl-1H-1,2,4-triazol-5-yl]-N-[(3-cyanophenyl)methyl]acetamide | 437.9 | 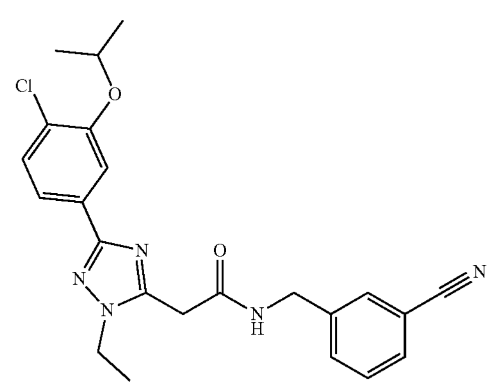 [SMILES: CCn1nc(-c2ccc(Cl)c(OC(C)C)c2)nc1CC(=O)NCc1cccc(C#N)c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 38 | 2-[3-(4-chloro-3-isopropyloxyphenyl)-1-ethyl-1H-1,2,4-triazol-5-yl]-N-[(1H-indazol-5-yl)methyl]acetamide | 452.9 | 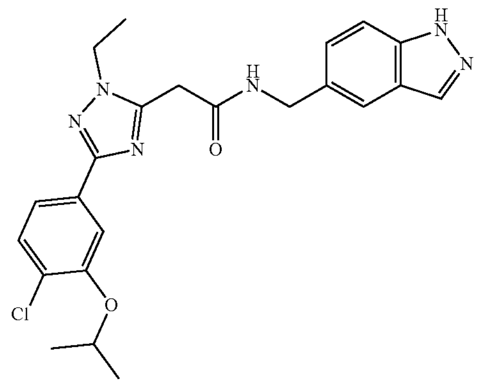 [SMILES: CCn1nc(-c2ccc(Cl)c(OC(C)C)c2)nc1CC(=O)NCc1ccc2[nH]ncc2c1] |
| Example 39 | 2-[3-(4-chloro-3-isopropyloxyphenyl)-1-ethyl-1H-1,2,4-triazol-5-yl]-N-[(4S)-3,4-dihydro-2H-1-benzopyran-4-yl]acetamide | 455.0 | 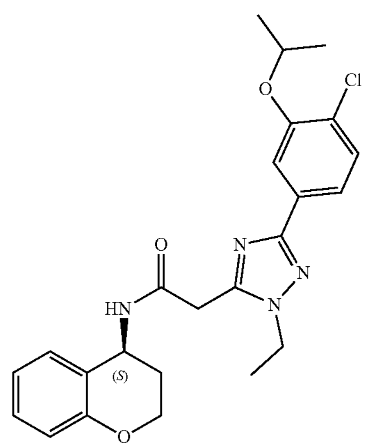 |
| Example 40 | N-[(4S)-6-chloro-3,4-dihydro-2H-1-benzopyran-4-yl]-2-[3-(4-chloro-3-isopropyloxyphenyl)-1-ethyl-1H-1,2,4-triazol-5-yl]acetamide | 489.4 | 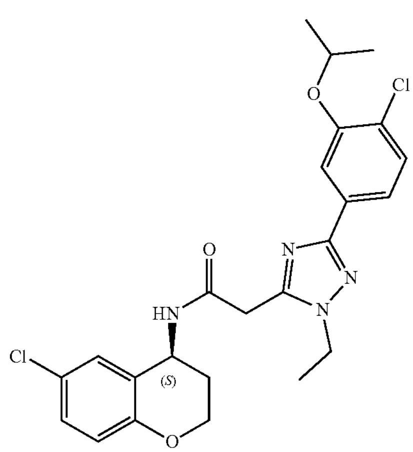 |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 41 | N-[(4R)-6-chloro-3,4-dihydro-2H-1-benzopyran-4-yl]-2-[3-(4-chloro-3-isopropyloxyphenyl)-1-ethyl-1H-1,2,4-triazol-5-yl]acetamide | 489.4 | 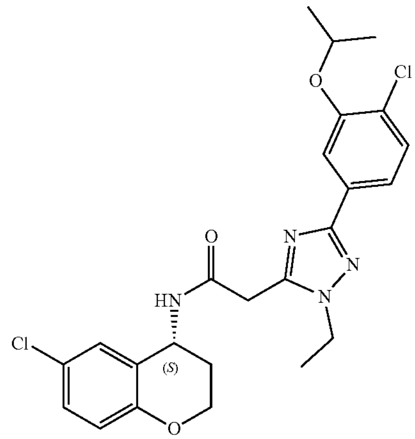 |
| Example 42 | 2-[3(4-chloro-3-isopropyloxyphenyl)-1-ethyl-1H-1,2,4-triazol-5-yl]-N-[(5S)-5H,6H,7H-cyclopenta[b]pyridin-5-yl]acetamide | 439.9 | 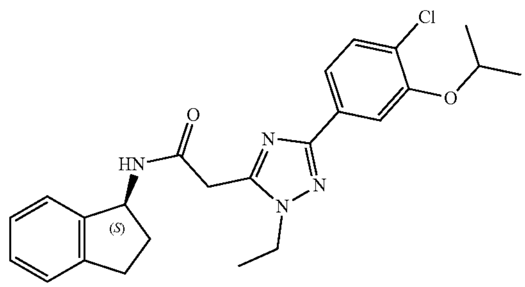 |
| Example 43 | 2-[3-(4-chloro-3-isopropyloxyphenyl)-1-methyl-1H-1,2,4-triazol-5-yl]-N-[(3,5-dichlorophenyl)methyl]acetamide | 467.8 | 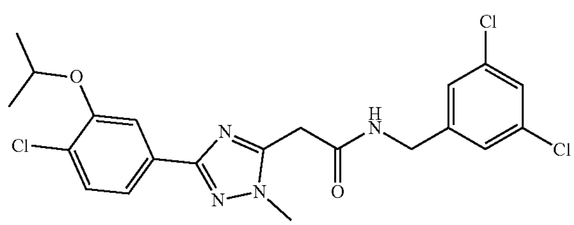 [SMILES: CC(C)Oc1cc(-c2nc(CC(=O)NCc3cc(Cl)cc(Cl)c3)n(C)n2)ccc1Cl] |
| Example 44 | 2-[3-(4-chloro-3-isopropyloxyphenyl)-1-methyl-1H-1,2,4-triazol-5-yl]-N-[(1S)-2,3-dihydro-1H-inden-1-yl]acetamide | 424.9 | 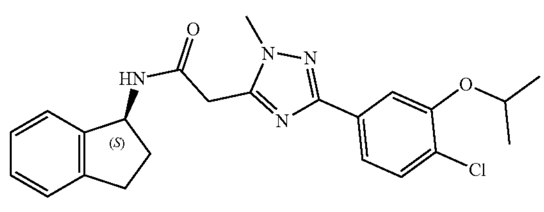 |
| Example 45 | 2-[3-(4-chloro-3-isopropyloxyphenyl)-1-methyl-1H-1,2,4-triazol-5-yl]-N-[(2,6-dimethylpyridin-4-yl)methyl]acetamide | 427.9 | 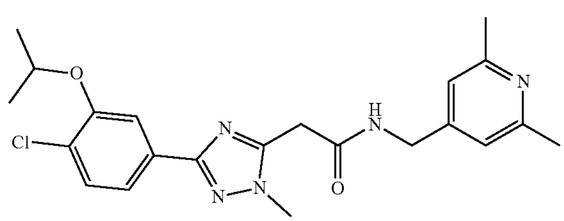 [SMILES: Cc1cc(CNC(=O)Cc2nc(-c3ccc(Cl)c(OC(C)C)c3)nn2C)cc(C)n1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 46 | 2-[3-(4-chloro-3-isopropyloxyphenyl)-1-methyl-1H-1,2,4-triazol-5-yl]-N-[(3-fluorophenyl)methyl]acetamide | 416.9 | 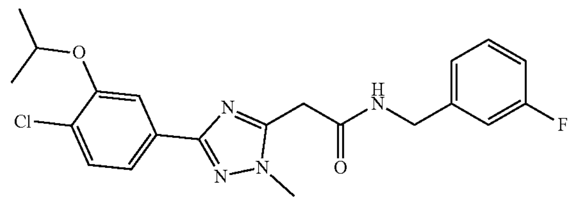 [SMILES: CC(C)Oc1cc(-c2nc(CC(=O)NCc3cccc(F)c3)n(C)n2)ccc1Cl] |
| Example 47 | 2-[3-(4-chloro-3-isopropyloxyphenyl)-1-methyl-1H-1,2,4-triazol-5-yl]-N-[(4R)-3,4-dihydro-2H-1-benzopyran-4-yl]acetamide | 440.9 | 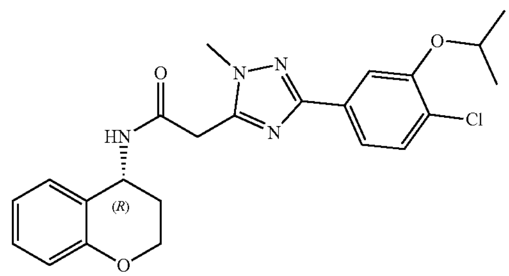 |
| Example 48 | 2-[3-(4-chloro-3-isopropyloxyphenyl)-1-methyl-1H-1,2,4-triazol-5-yl]-N-[(4S)-3 dihydro-2H-1-benzopyran-4-yl]acetamide | 440.9 | 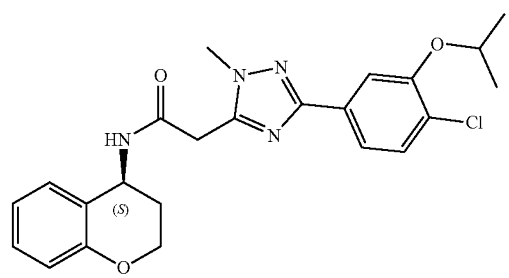 |
| Example 49 | N-[(4R)-6-chloro-3,4-dihydro-2H-1-benzopyran-4-yl]-2-[3-(4-chloro-3-isopropyloxyphenyl)-1-methyl-1H-1,2,4-triazol-5-yl]acetamide | 475.4 | 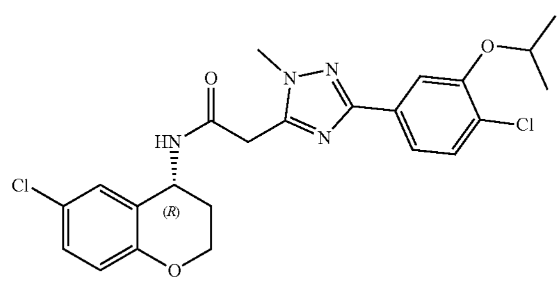 |
| Example 50 | 2-[3-(4-chloro-3-fluorophenyl)-1-ethyl-1H-1,2,4-triazol-5-yl]-N-[(3,5-dichlorophenyl)methyl]-2,2-difluoroacetamide | 477.7 | 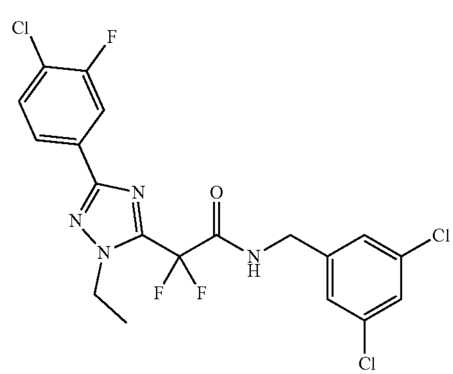 [SMILES: CCn1nc(-c2ccc(Cl)c(F)c2)nc1C(F)(F)C(=O)NCc1cc(Cl)cc(Cl)c1] |

TABLE 1-continued

Small molecule PDE4 long form activators (Examples 1 to 90), according to the present invention

| Compound | Chemical name | Molecular weight (Daltons) | Chemical Structure |
| --- | --- | --- | --- |
| Example 51 | 2-[3-(4-chloro-3-fluorophenyl)-1-ethyl-1H-1,2,4-triazol-5-yl]-N-[(2,6-dimethylpyridin-4-yl)methyl]-2,2-difluoroacetamide | 437.9 | 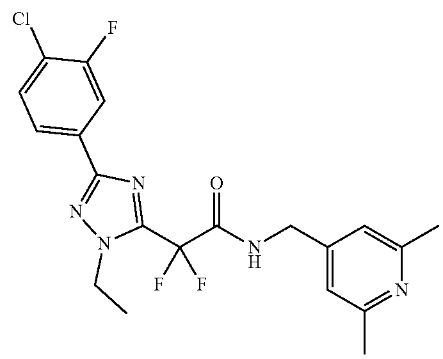 [SMILES: CCn1nc(-c2ccc(Cl)c(F)c2)nc1C(F)(F)C(=O)NCc1cc(C)nc(C)c1] |
| Example 52 | 2-[3-(4-chloro-3-fluorophenyl)-1-ethyl-1H-1,2,4-triazol-5-yl]-2,2-difluoro-N-[(2-methyl-1H-1,3-benzimidazol-5-yl)methyl]acetamide | 462.9 | 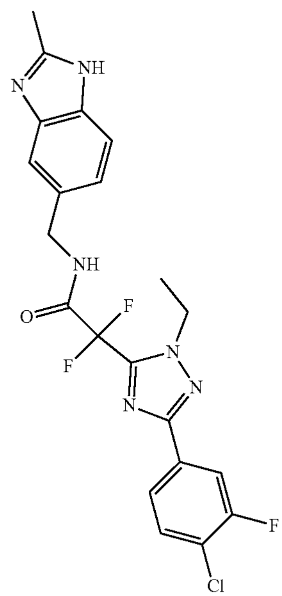 [SMILES: CCn1nc(-c2ccc(Cl)c(F)c2)nc1C(F)(F)C(=O)NCc1ccc2[nH]c(C)nc2c1] |
| Example 53 | N-[(4S)-6-chloro-3,4-dihydro-2H-1-benzopyran-4-yl]-2-[3-(4-chloro-3-fluorophenyl)-1-ethyl-1H-1,2,4-triazol-5-yl]-2,2-difluoroacetamide | 485.3 | 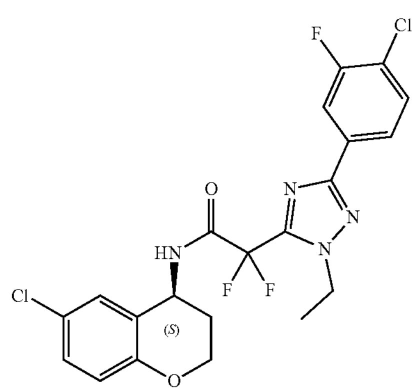 |

TABLE 1-continued

Small molecule PDE4 long form activators (Examples 1 to 90), according to the present invention

| Compound | Chemical name | Molecular weight (Daltons) | Chemical Structure |
| --- | --- | --- | --- |
| Example 54 | methyl 2-[3-(4-chloro-3-fluorophenyl)-5-({[(3,5-dichlorophenyl)methyl]carbamoyl}methyl)-1H-1,2,4-triazol-1-yl]acetate | 485.7 | 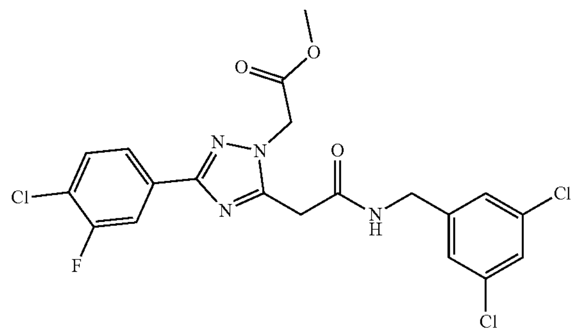 [SMILES: COC(=O)Cn1nc(-c2ccc(Cl)c(F)c2)nc1CC(=O)NCc1cc(Cl)cc(Cl)c1] |
| Example 55 | methyl 3-[3-(4-chloro-3-fluorophenyl)-5-({[(3,5-dichlorophenyl)methyl]carbamoyl}methyl)-1H-1,2,4-triazol-1-yl]propanoate | 499.8 | 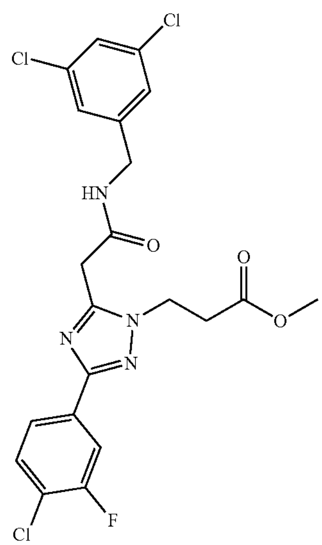 [SMILES: COC(=O)CCn1nc(-c2ccc(Cl)c(F)c2)nc1CC(=O)NCc1cc(Cl)cc(Cl)c1] |
| Example 56 | ethyl 4-[3-(4-chloro-3-fluorophenyl)-5-({[(3,5-dichlorophenyl)methyl]carbamoyl}methyl)-1H-1,2,4-triazol-1-yl]butanoate | 527.8 | 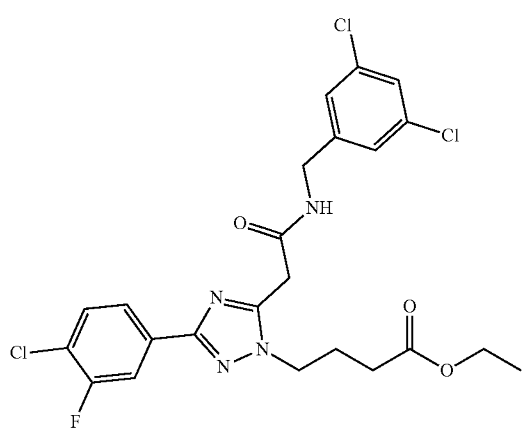 [SMILES: CCOC(=O)CCCn1nc(-c2ccc(Cl)c(F)c2)nc1CC(=O)NCc1cc(Cl)cc(Cl)c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 57 | 2-[3-(4-chloro-3-fluorophenyl)-5-({[(3,5-dichlorophenyl)methyl]carbamoyl}methyl)-1H-1,2,4-triazol-1-yl]acetic acid | 471.7 | 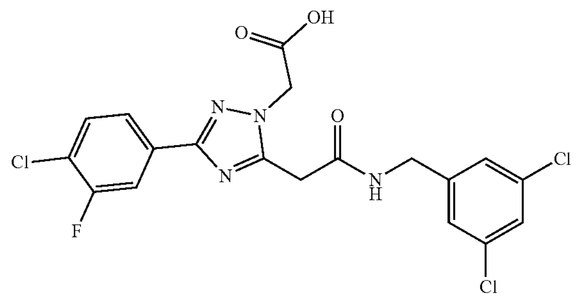 [SMILES: O=C(O)Cn1nc(-c2ccc(Cl)c(F)c2)nc1CC(=O)NCc1cc(Cl)cc(Cl)c1] |
| Example 58 | 3-[3-(4-chloro-3-fluorophenyl)-5-({[(3,5-dichlorophenyl)methyl]carbamoyl}methyl)-1H-1,2,4-triazol-1-yl]propanoic acid | 485.7 | 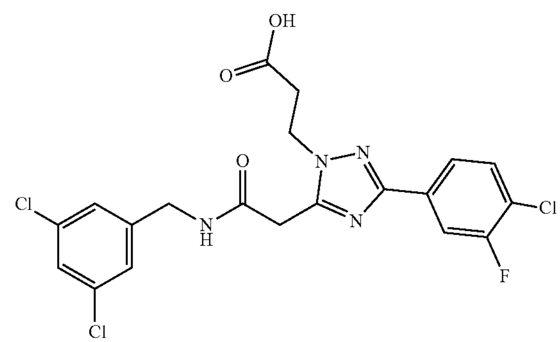 [SMILES: O=C(O)CCn1nc(-c2ccc(Cl)c(F)c2)nc1CC(=O)NCc1cc(Cl)cc(Cl)c1] |
| Example 59 | 4-[3-(4-chloro-3-fluorophenyl)-5-({[(3,5-dichlorophenyl)methyl]carbamoyl}methyl)-1H-1,2,4-triazol-1-yl]butanoic acid | 499.8 | 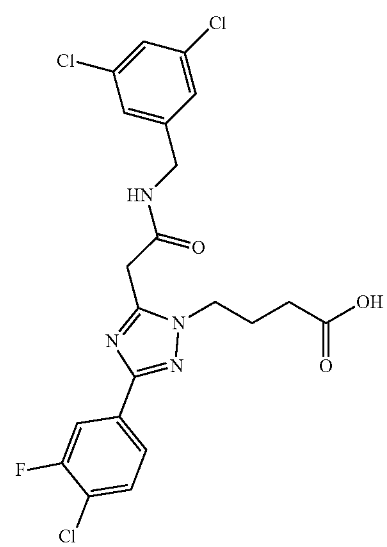 [SMILES: O=C(O)CCCn1nc(-c2ccc(Cl)c(F)c2)nc1CC(=O)NCc1cc(Cl)cc(Cl)c1] |
| Example 60 | 2-[3-(4-chloro-3-fluorophenyl)-1-ethyl-1H-1,2,4-triazol-5-yl]-N-[(1R)-2,3-dihydro-1H-inden-1-yl]acetamide | 398.9 | 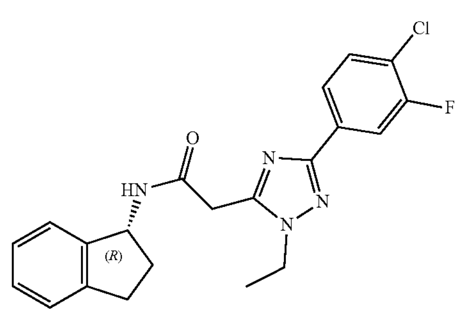 |

TABLE 1-continued

Small molecule PDE4 long form activators (Examples 1 to 90), according to the present invention

| Compound | Chemical name | Molecular weight (Daltons) | Chemical Structure |
| --- | --- | --- | --- |
| Example 61 | 2-[3-(4-chloro-3-fluorophenyl)-1-ethyl-1H-1,2,4-triazol-5-yl]-N-[(1S)-2,3-dihydro-1H-inden-1-yl]acetamide | 398.9 | 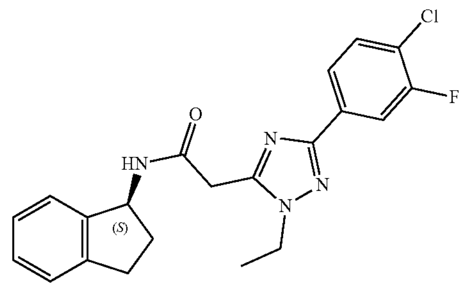 |
| Example 62 | 2-[3-(4-chloro-3-fluorophenyl)-1-ethyl-1H-1,2,4-triazol-5-yl]-N-[(1R,2S)-2-hydroxy-2,3-dihydro-1H-inden-1-yl]acetamide | 414.9 | 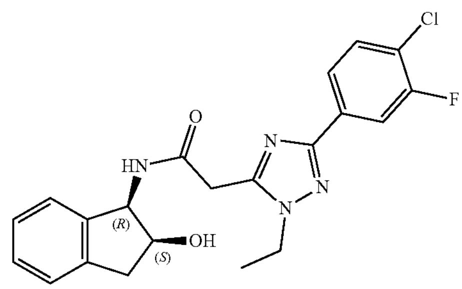 |
| Example 63 | 2-[3-(4-chloro-3-fluorophenyl)-1-ethyl-1H-1,2,4-triazol-5-yl]-N-[(1S,2R)-2-hydroxy-2,3-dihydro-1H-inden-1-yl]acetamide | 414.9 | 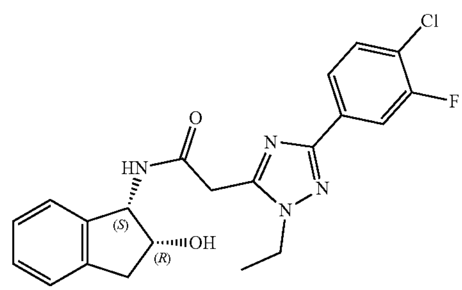 |
| Example 64 | 2-[3-(4-chloro-3-fluorophenyl)-1-ethyl-1H-1,2,4-triazol-5-yl]-N-[(1S,2S)-2-hydroxy-2,3-dihydro-1H-inden-1-yl]acetamide | 414.9 | 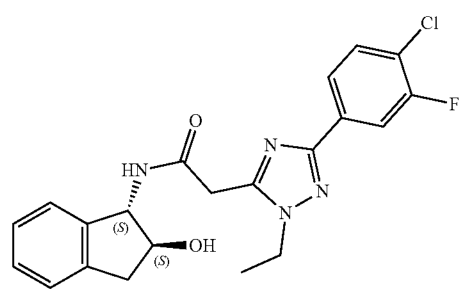 |
| Example 65 | 2-[3-(4-chloro-3-fluorophenyl)-1-ethyl-1H-1,2,4-triazol-5-yl]-N-[(1R,2R)-2-hydroxy-2,3-dihydro-1H-inden-1-yl]acetamide | 414.9 | 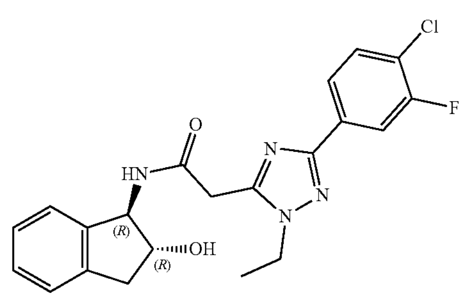 |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 66 | 2-[3-(4-chloro-3-fluorophenyl)-1-ethyl-1H-1,2,4-triazol-5-yl]-N-(2,3-dihydro-1H-inden-2-yl)acetamide | 398.9 | 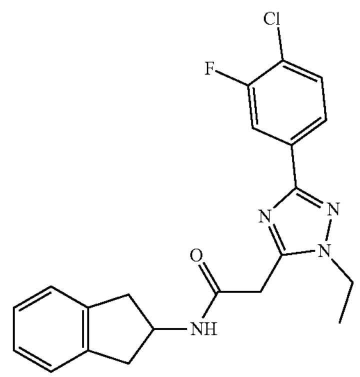 [SMILES: CCn1nc(-c2ccc(Cl)c(F)c2)nc1CC(=O)NC1Cc2ccccc2C1] |
| Example 67 | 2-[3-(4-chloro-3-fluorophenyl)-1-ethyl-1H-1,2,4-triazol-5-yl]-N-[(1S,3R)-3-hydroxy-2,3-dihydro-1H-inden-1-yl]acetamide | 414.9 | 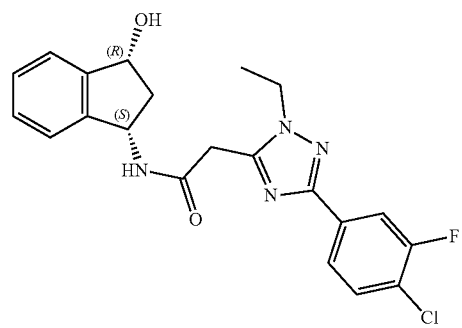 |
| Example 68 | 2-[3-(4-chloro-3-fluorophenyl)-1-ethyl-1H-1,2,4-triazol-5-yl]-N-[(1S,3S)-3-hydroxy-2,3-dihydro-1H-inden-1-yl]acetamide | 414.9 | 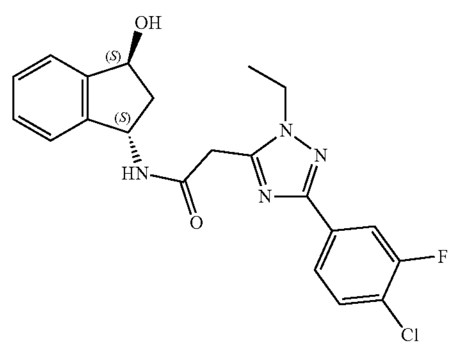 |
| Example 69 | 2-[3-(4-chloro-3-fluorophenyl)-1-ethyl-1H-1,2,4-triazol-5-yl]-N-[(1R,3R)-3-hydroxy-2,3-dihydro-1H-inden-1-yl]acetamide | 414.9 | 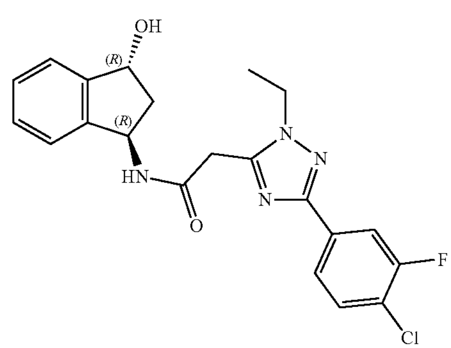 |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 70 | 2-[3-(4-chloro-3-fluorophenyl)-1-ethyl-1H-1,2,4-triazol-5-yl]-N-[(1R,3S)-3-hydroxy-2,3-dihydro-1H-inden-1-yl]acetamide | 414.9 | 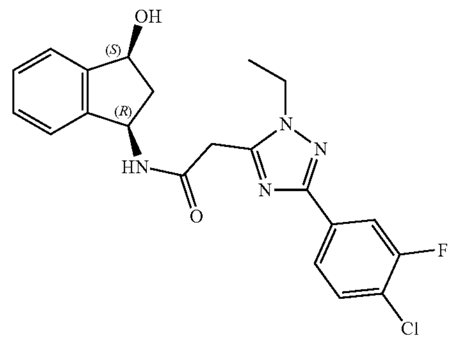 |
| Example 71 | 2-[3-(4-chloro-3-fluorophenyl)-1-(cyclopropylmethyl)-1H-1,2,4-triazol-5-yl]-N-[(5S)-5H,6H,7H-cyclopenta[b]pyridin-5-yl]acetamide | 425.9 | 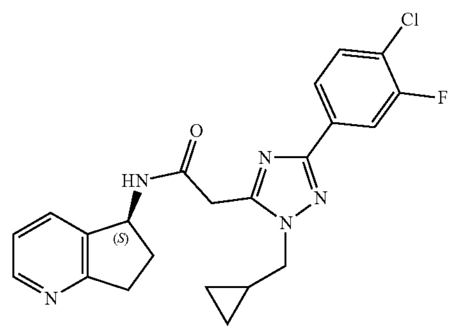 |
| Example 72 | 2-[3-(4-chloro-3-fluorophenyl)-1-(cyclopropylmethyl)-1H-1,2,4-triazol-5-yl]-N-[(1S)-2,3-dihydro-1H-inden-1-yl]acetamide | 424.9 | 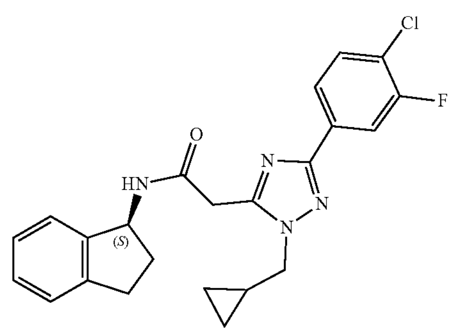 |
| Example 73 | 2-[3-(4-chloro-3-fluorophenyl)-1-ethyl-1H-1,2,4-triazol-5-yl]-N-[(2-oxo-2,3-dihydro-1,3-benzoxazol-5-yl)methyl]acetamide | 429.8 | 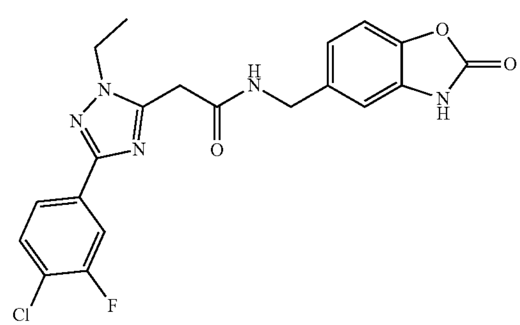 [SMILES: CCn1nc(-c2ccc(Cl)c(F)c2)nc1CC(=O)NCc1ccc2oc(=O)[nH]c2c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 74 | 2-[3-(4-chloro-3-fluorophenyl)-1-ethyl-1H-1,2,4-triazol-5-yl]-N-[(4S)-3,4-dihydro-2H-1-benzopyran-4-yl]acetamide | 414.9 | 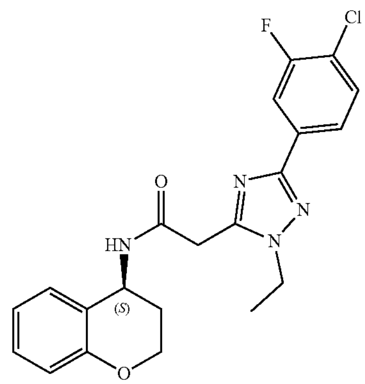 |
| Example 75 | 2-[3-(4-chloro-3-fluorophenyl)-1-ethyl-1H-1,2,4-triazol-5-yl]-N-[(4R)-3,4-dihydro-2H-1-benzopyran-4-yl]acetamide | 414.9 | 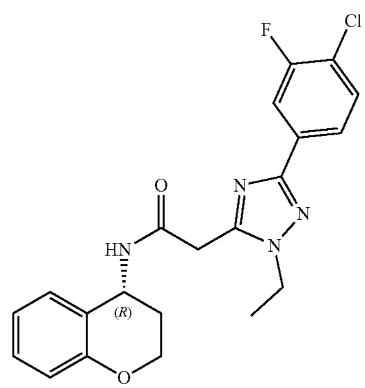 |
| Example 76 | N-[(4S)-6-chloro-3,4-dihydro-2H-1-benzopyran-4-yl]-2-[3-(4-chloro-3-fluorophenyl)-1-ethyl-1H-1,2,4-triazol-5-yl]acetamide | 449.3 | 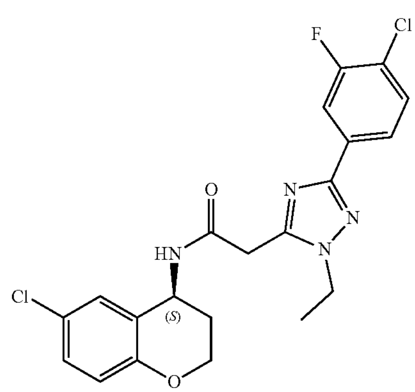 |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 77 | N-[(4R)-6-chloro-3,4-dihydro-2H-1-benzopyran-4-yl]-2-[3-(4-chloro-3-fluorophenyl)-1-ethyl-1H-1,2,4-triazol-5-yl]acetamide | 449.3 | 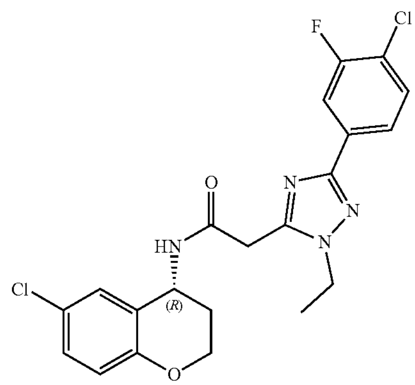 |
| Example 78 | N-[(4S)-6-chloro-3,4-dihydro-2H-1-benzopyran-4-yl]-2-[3-(4-chloro-3-fluorophenyl)-1-(cyclopropylmethyl)-1H-1,2,4-triazol-5-yl]acetamide | 475.4 | 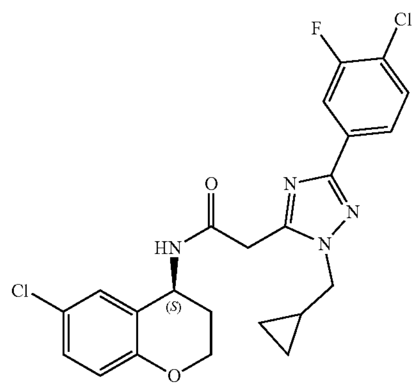 |
| Example 79 | 2-[3-(4-chloro-3-fluorophenyl)-1-ethyl-1H-1,2,4-triazol-5-yl]-N-{pyrazolo[1,5-a]pyridin-3-yl}acetamide | 398.8 | 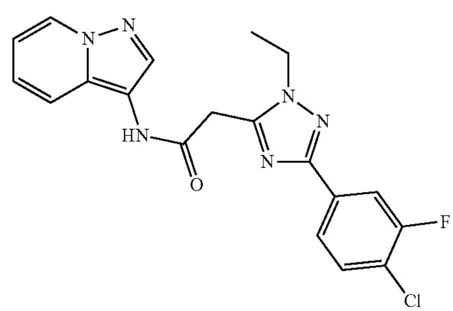 [SMILES: CCn1nc(-c2ccc(Cl)c(F)c2)nc1CC(=O)Nc1cnn2ccccc12] |
| Example 80 | 2-[3-(4-chloro-3-fluorophenyl)-1-ethyl-1H-1,2,4-triazol-5-yl]-N-[(2,6-diethylpyridin-4-yl)methyl]acetamide | 429.9 | 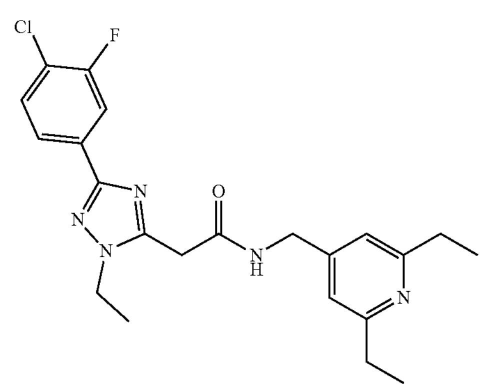 [SMILES: CCc1cc(CNC(=O)Cc2nc(-c3ccc(Cl)c(F)c3)nn2CC)cc(CC)n1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 81 | 2-[3-(4-chloro-3-fluorophenyl)-1-ethyl-1H-1,2,4-triazol-5-yl]-N-[(4,6-dimethylpyridin-2-yl)methyl]acetamide | 401.9 | 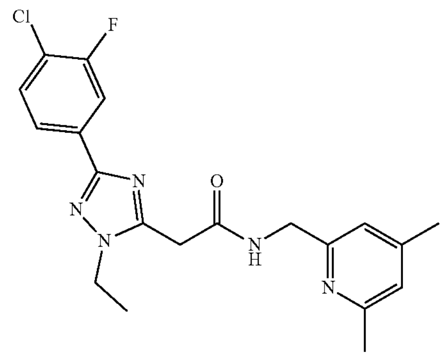 [SMILES: CCn1nc(-c2ccc(Cl)c(F)c2)nc1CC(=O)NCc1cc(C)cc(C)n1] |
| Example 82 | 2-[3-(4-chloro-3-isopropyloxyphenyl)-1-ethyl-1H-1,2,4-triazol-5-yl]-N-[(4,6-dimethylpyridin-2-yl)methyl]acetamide | 442.0 | 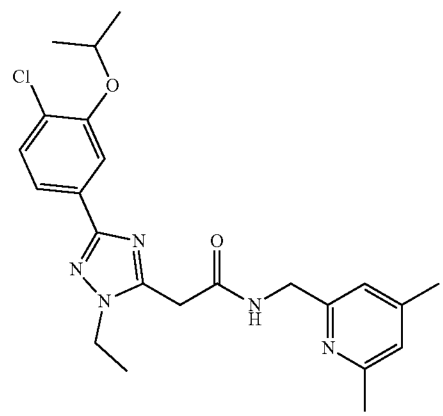 [SMILES: CCn1nc(-c2ccc(Cl)c(OC(C)C)c2)nc1CC(=O)NCc1cc(C)cc(C)n1] |
| Example 83 | 2-[3-(4-chloro-3-fluorophenyl)-1-ethyl-1H-1,2,4-triazol-5-yl]-N-{[2-(trifluoromethyl)pyridin-4-yl]methyl}acetamide | 441.8 | 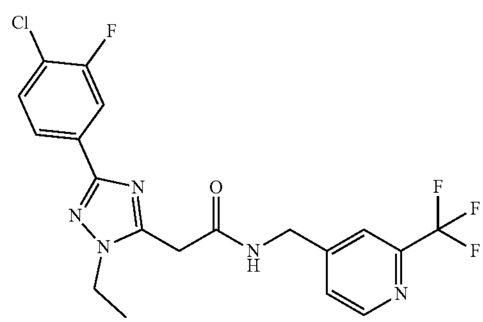 [SMILES: CCn1nc(-c2ccc(Cl)c(F)c2)nc1CC(=O)NCc1ccnc(C(F)(F)F)c1] |
| Example 84 | 2-[3-(4-chloro-3-fluorophenyl)-1-ethyl-1H-1,2,4-triazol-5-yl]-N-{[2-(difluoromethyl)pyridin-4-yl]methyl}acetamide | 423.8 | 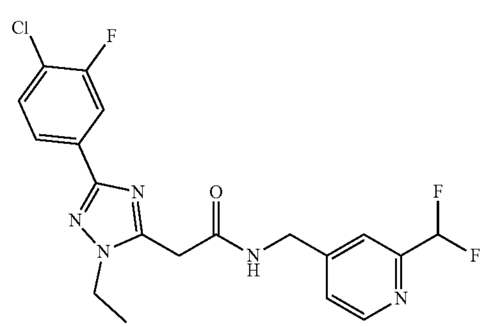 [SMILES: CCn1nc(-c2ccc(Cl)c(F)c2)nc1CC(=O)NCc1ccnc(C(F)F)c1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 85 | N-{[2,6-bis(difluoromethyl)pyridin-4-yl]methyl}-2-[3-(4-chloro-3-fluorophenyl)-1-ethyl-1H-1,2,4-triazol-5-yl]acetamide | 473.8 | 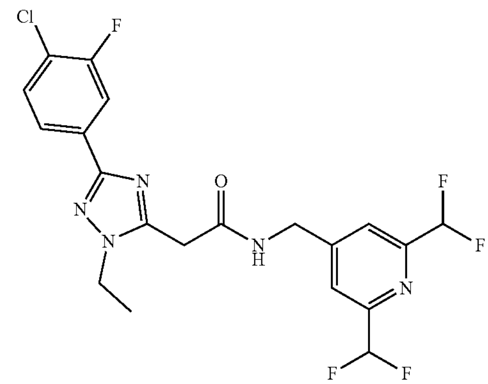 [SMILES: CCn1nc(-c2ccc(Cl)c(F)c2)nc1CC(=O)NCc1cc(C(F)F)nc(C(F)F)c1] |
| Example 86 | 2-[3-(4-chloro-3-fluorophenyl)-1-ethyl-1H-1,2,4-triazol-5-yl]-N-[1-(2,6-dimethylpyridin-4-yl)cyclopropyl]acetamide | 427.9 | 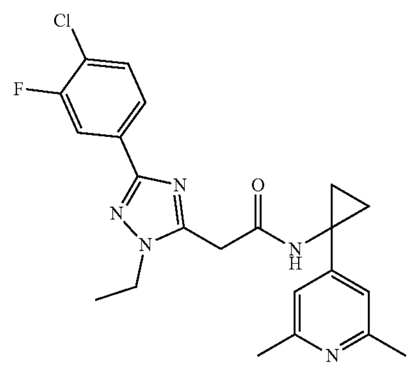 [SMILES: CCn1nc(-c2ccc(Cl)c(F)c2)nc1CC(=O)NC1(c2cc(C)nc(C)c2)CC1] |
| Example 87 | 2-[3-(4-chloro-3-fluorophenyl)-1-(cyclopropylmethyl)-1H-1,2,4-triazol-5-yl]-N-[1-(2,6-dimethylpyridin-4-yl)cyclopropyl]acetamide | 454.0 | 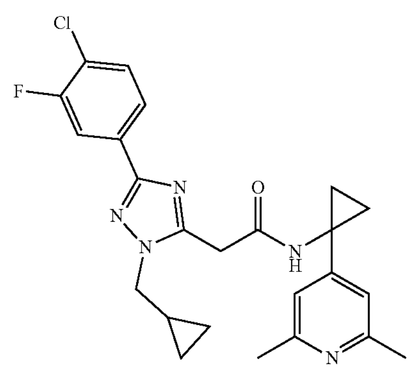 [SMILES: Cc1cc(C2(NC(=O)Cc3nc(-c4ccc(Cl)c(F)c4)nn3CC3CC3)CC2)cc(C)n1] |
| Example 88 | 2-[3-(4-chloro-3-fluorophenyl)-1-ethyl-1H-1,2,4-triazol-5-yl]-N-{[2,6-di($^2$H$_3$)methylpyridin-4-yl]methyl}acetamide | 407.9 | 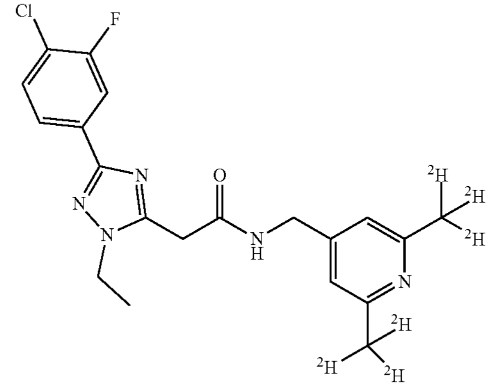 [SMILES: [2H]C([2H])([2H])c1cc(CNC(=O)Cc2nc(-c3ccc(Cl)c(F)c3)nn2CC)cc(C([2H])([2H])[2H])n1] |

TABLE 1-continued

Small molecule PDE4 long form activators (Examples 1 to 90), according to the present invention

| Compound | Chemical name | Molecular weight (Daltons) | Chemical Structure |
|---|---|---|---|
| Example 89 | 2-[3-(4-chloro-3-fluorophenyl)-1-ethyl-1H-1,2,4-triazol-5-yl]-N-{[2,6-di($^2$H$_3$)methylpyridin-4-yl]methyl}-2,2-difluoroacetamide | 443.9 | 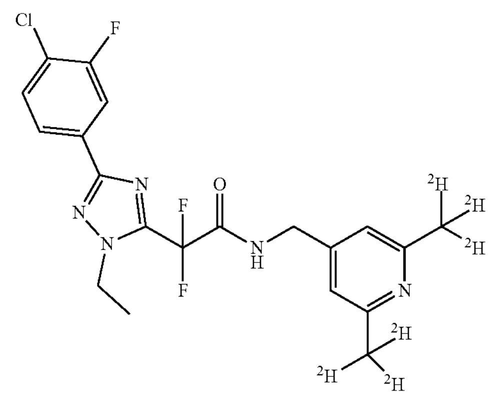 [SMILES: [2H]C([2H])([2H])c1cc(CNC(=O)C(F)(F)c2nc(-c3ccc(Cl)c(F)c3)nn2CC)cc(C([2H])([2H])[2H])n1] |
| Example 90 | 2-[3-(4-chloro-3-fluorophenyl)-1-ethyl-1H-1,2,4-triazol-5-yl]-N-[(2,6-dimethylpyridin-4-yl)($^2$H$_2$)methyl]($^2$H$_2$)acetamide | 405.9 | 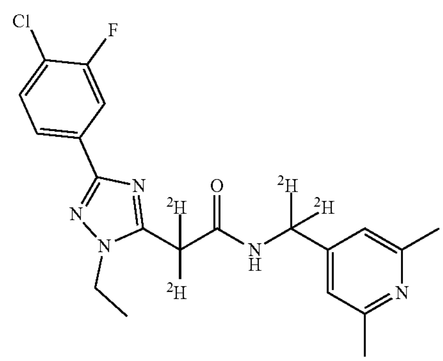 [SMILES: [2H]C([2H])(NC(=O)C([2H])([2H])c1nc(-c2ccc(Cl)c(F)c2)nn1CC)c1cc(C)nc(C)c1] |

TABLE 2

Enzyme assay data for PDE4D5, a long form of PDE4 Using the method described in Experiment 1, the following PDE4D5 activation data were obtained for compounds of the present invention.

| Compound | % increase in PDE4D5 activity at 30 μM* |
|---|---|
| Example 3 | 73.2 |
| Example 4 | 32.2 |
| Example 5 | 56.1 |
| Example 6 | 38.5 |
| Example 7 | 94.1 |
| Example 8 | 49.6 |
| Example 9 | 55.6 |
| Example 10 | 136 |
| Example 11 | 52.8 |
| Example 12 | 71.6 |
| Example 13 | 28.4 |
| Example 14 | 142 |
| Example 15 | 61.5 |
| Example 16 | 44.7 |
| Example 17 | 26.8 |
| Example 18 | 77.8 |
| Example 19 | 87.8 |
| Example 20 | 78.6 |
| Example 21 | 60.8 |
| Example 22 | 99.9 |
| Example 23 | 53.8 |
| Example 24 | 72.2 |
| Example 25 | 69.9 |
| Example 26 | 87.5 |
| Example 27 | 106 |
| Example 28 | 46.3 |
| Example 29 | 104 |
| Example 30 | 45.9 |

TABLE 2-continued

Enzyme assay data for PDE4D5, a long form of PDE4 Using the method described in Experiment 1, the following PDE4D5 activation data were obtained for compounds of the present invention.

| Compound | % increase in PDE4D5 activity at 30 μM* |
|---|---|
| Example 32 | 42.8 |
| Example 33 | 82.3 |
| Example 34 | 108 |
| Example 35 | 28.5 |
| Example 36 | 33.0 |
| Example 37 | 40.2 |
| Example 38 | 81.6 |
| Example 40 | 48.5 |
| Example 42 | 40.0 |
| Example 44 | 45.0 |
| Example 46 | 26.2 |
| Example 48 | 45.2 |
| Example 50 | 36.7 |
| Example 52 | 73.8 |
| Example 54 | 97.2 |
| Example 56 | 155 |
| Example 58 | 128 |
| Example 62 | 49.8 |
| Example 66 | 92.1 |
| Example 68 | 51.3 |
| Example 72 | 92.0 |
| Example 74 | 55.3 |
| Example 78 | 79.1 |
| Example 80 | 58.9 |
| Example 82 | 34.3 |
| Example 83 | 89.6 |
| Example 84 | 32.2 |
| Example 86 | 37.3 |

*Measured as mean % increase in counts over basal activity

TABLE 3

Enzyme assay data for PDE4B1, another long form of PDE4 Using the method described in Experiment 1, the following PDE4B1 activation data were obtained for compounds of the present invention.

| Compound | % increase in PDE4B1 activity at 30 μM* |
|---|---|
| Example 1 | 79.1 |
| Example 2 | 99.4 |

*Measured as mean % increase in counts over basal activity

TABLE 4

Enzyme assay data for PDE4A4, another long form of PDE4 Using the method described in Experiment 1, the following PDE4A4 activation data were obtained for compounds of the present invention.

| Compound | % increase in PDE4A4 activity at 30 μM* |
|---|---|
| Example 22 | 92.5 |
| Example 34 | 75.5 |

*Measured as mean % increase in counts over basal activity

TABLE 5

Enzyme assay data for PDE4B2, a short form of PDE4 Using the method described in Experiment 1, the following PDE4B2 data were obtained for compounds of the present invention.

| Compound | % increase in PDE4B2 activity at 30 μM* |
|---|---|
| Example 3 | −10.9 |
| Example 22 | −2.9 |
| Example 29 | 3.4 |
| Example 33 | −9.4 |
| Example 34 | −4.4 |
| Example 40 | 1.6 |

*Measured as mean % increase in counts over basal activity

The invention claimed is:

1. A compound of Formula I:

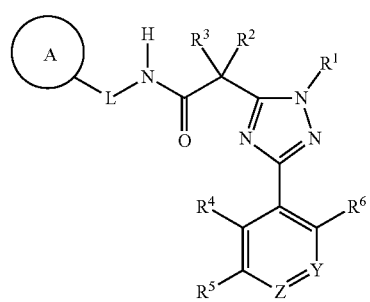

Formula I or a pharmaceutically acceptable salt or derivative thereof, wherein:

$R^1$ is (C1-6)alkyl, (C3-7)cycloalkyl, —C(O)X or —S(O)$_2$X, the (C1-6)alkyl and (C3-7)cycloalkyl groups being optionally substituted with one or more substituents independently selected from OH, (C1-4)alkyloxy, (C1-4)alkylsulfonyl, C(O)—NR$^9$R$^{10}$, C(O)—OR$^9$, S(O)$_2$—NR$^9$R$^{10}$, CN and halogen, the (C1-4)alkyloxy and (C1-4)alkylsulfonyl groups being optionally substituted with one or more fluoros;

X, when present, is (C1-6)alkyl or NR$^9$R$^{10}$, the (C1-6) alkyl group being optionally substituted with one or more substituents independently selected from OH, (C1-4)alkyloxy, CN and halogen;

R$^2$ and R$^3$ are independently selected from H, fluoro and (C1-4)alkyl, the (C1-4)alkyl being optionally substituted with one or more fluoros;

L is a linker —CR$^7$R$^8$— or L is absent;

R$^7$ and R$^8$ are independently selected from H and (C1-4) alkyl or R$^7$ and R$^8$, together with the carbon atom to which they are bonded, form a cyclopropyl, cyclobutyl or cyclopentyl group;

A is selected from a 6-membered heteroaromatic ring that contains one to three N atoms, a 5-membered heteroaromatic ring that contains 1 to 3 heteroatoms selected from O, S and N, a fused 10-membered bicyclic aromatic ring system or heteroaromatic ring system that contains one to three N atoms, a fused 9-membered bicyclic heteroaromatic ring system that contains 1 to 3 heteroatoms selected from O, S and N, and a fused 9- or 10-membered bicyclic ring system that contains an aromatic or heteroaromatic ring fused to a non-aromatic carbocyclic or heterocyclic ring;

wherein A is optionally substituted with one or more substituents independently selected from (C1-4)alkyl, (C1-4)alkyloxy, (C1-4)alkylsulfonyl, C(O)—NR$^9$R$^{10}$, S(O)$_2$—NR$^9$R$^{10}$, OH, CN and halogen, the (C1-4) alkyl, (C1-4)alkyloxy and (C1-4)alkylsulfonyl groups being optionally substituted with one or more fluoros;

R$^4$ and R$^6$ are independently selected from H, (C1-4)alkyl, (C1-4)alkyloxy, CN and halogen, the (C1-4)alkyl and (C1-4)alkyloxy groups being optionally substituted with one or more fluoros;

R$^5$ is selected from H, (C1-4)alkyl, (C1-4)alkyloxy, —O—(CH$_2$)$_n$—O—(CH$_2$)$_m$CH$_3$, CN and halogen, the (C1-4)alkyl, (C1-4)alkyloxy and —O—(CH$_2$)$_n$—O—(CH$_2$)$_m$CH$_3$ groups being optionally substituted with OH or one or more fluoros;

Y and Z are independently selected from N and CR$^{11}$;

each R$^{11}$, when present, is independently selected from H, (C1-4)alkyl, (C1-4)alkyloxy, —O—(CH$_2$)$_n$—O—(CH$_2$)$_m$CH$_3$, (C1-4)alkylsulfonyl, CN and halogen, the (C1-4)alkyl, (C1-4)alkyloxy, (C1-4)alkylsulfonyl and —O—(CH$_2$)$_n$—O—(CH$_2$)$_m$CH$_3$, groups being optionally substituted with OH or one or more fluoros;

each n is, independently, 1, 2, 3 or 4;

each m is, independently, 0 or 1; and each R$^9$ and R$^{10}$, when present, is independently selected from H and (C1-6)alkyl.

2. A compound or a pharmaceutically acceptable salt or derivative thereof of claim 1, wherein:

R$^1$ is (C1-6)alkyl, (C3-7)cycloalkyl, —C(O)X or —S(O)$_2$ X, the (C1-6)alkyl and (C3-7)cycloalkyl groups being optionally substituted with one or more substituents independently selected from OH, (C1-4)alkyloxy, (C1-4)alkylsulfonyl, C(O)—NR$^9$R$^{10}$, C(O)—OR$^9$, S(O)$_2$—NR$^9$R$^{10}$, CN and halogen, the (C1-4)alkyloxy and (C1-4)alkylsulfonyl groups being optionally substituted with one or more fluoros;

X, when present, is (C1-6)alkyl or NR$^9$R$^{10}$, the (C1-6) alkyl group being optionally substituted with one or more substituents independently selected from OH, (C1-4)alkyloxy, CN and halogen;

R$^2$ and R$^3$ are independently selected from H and (C1-4) alkyl;

L is a linker —CR$^7$R$^8$— where R$^7$ and R$^8$ are independently selected from H and (C1-4)alkyl or L is absent;

A is selected from a 6-membered heteroaromatic ring that contains one to three N atoms, a 5-membered heteroaromatic ring that contains 1 to 3 heteroatoms selected from O, S and N, a fused 10-membered bicyclic aromatic ring system or heteroaromatic ring system that contains one to three N atoms, and a fused 9-membered bicyclic heteroaromatic ring system that contains 1 to 3 heteroatoms selected from O, S and N;

wherein A is optionally substituted with one or more substituents independently selected from (C1-4)alkyl, (C1-4)alkyloxy, (C1-4)alkylsulfonyl, C(O)—NR$^9$R$^{10}$, S(O)$_2$—NR$^9$R$^{10}$, NR$^9$R$^{10}$, OH, CN and halogen, the (C1-4)alkyl, (C1-4)alkyloxy and (C1-4)alkylsulfonyl groups being optionally substituted with one or more fluoros;

R$^4$ and R$^6$ are independently selected from H, (C1-4)alkyl, (C1-4)alkyloxy, CN and halogen, the (C1-4)alkyl and (C1-4)alkyloxy groups being optionally substituted with one or more fluoros;

R$^5$ is selected from H, (C1-4)alkyl, (C1-4)alkyloxy, CN and halogen, the (C1-4)alkyl and (C1-4)alkyloxy groups being optionally substituted with OH or one or more fluoros;

Y and Z are independently selected from N and CR$^{11}$;

each R$^{11}$, when present, is independently selected from H, (C1-4)alkyl, (C1-4)alkyloxy, (C1-4)alkylsulfonyl, CN and halogen, the (C1-4)alkyl, (C1-4)alkyloxy and (C1-4)alkylsulfonyl groups being optionally substituted with OH or one or more fluoros; and each R$^9$ and R$^{10}$, when present, is independently selected from H and (C1-6)alkyl.

3. A compound or pharmaceutically acceptable salt or derivative of claim 1, wherein R$^1$ is (C1-6)alkyl or (C3-7) cycloalkyl, the (C1-6)alkyl and (C3-7)cycloalkyl groups being optionally substituted with 1 to 3 substituents independently selected from OH, (C1-4)alkyloxy, CN and halogen, the (C1-4)alkyloxy group being optionally substituted with one or more fluoros.

4. A compound or pharmaceutically acceptable salt or derivative of claim 1, wherein R$^1$ is (C1-4)alkyl, optionally substituted with 1 to 3 substituents independently selected from OH and (C1-2)alkyloxy.

5. A compound or pharmaceutically acceptable salt or derivative of claim 1, wherein R$^2$ and R$^3$ are both H, R$^2$ and R$^3$ are both F or one of R$^2$ and R$^3$ is H and the other is methyl.

6. A compound or pharmaceutically acceptable salt or derivative of claim 1, wherein R$^5$ is selected from H, (C1-3)alkyl, (C1-3)alkyloxy, —O—(CH$_2$)$_{n'}$—O—(CH$_2$)$_{m'}$ CH$_3$, CN and halogen, the (C1-3)alkyl, (C1-3)alkyloxy and —O—(CH$_2$)$_{n'}$—O—(CH$_2$)$_{m'}$CH$_3$ groups being optionally substituted with one or more fluoros, wherein n' is 1 or 2 and m' is 0.

7. A compound or pharmaceutically acceptable salt or derivative of claim 1, wherein R$^4$, R$^5$ and R$^6$ are, independently, H or F.

8. A compound or pharmaceutically acceptable salt or derivative of claim 1, wherein R$^4$ and R$^6$ are H.

9. A compound or pharmaceutically acceptable salt or derivative of claim 1, wherein Y and Z are both CR$^{11}$ or one of Y and Z is N and the other of Y and Z is CR$^{11}$.

10. A compound or pharmaceutically acceptable salt or derivative of claim 1, wherein Y and Z are both $CR^{11}$.

11. A compound or pharmaceutically acceptable salt or derivative of claim 1, wherein each $R^{11}$, when present, is independently selected from H, (C1-3)alkyl, (C1-3)alkyloxy, —O—$(CH_2)_{n'}$—O—$(CH_2)_{m'}CH_3$, CN and halogen, the (C1-3)alkyl, (C1-3)alkyloxy and —O—$(CH_2)_{n'}$—O—$(CH_2)_{m'}CH_3$ groups being optionally substituted with one or more fluoros, wherein n' is 1 or 2 and m' is 0.

12. A compound or pharmaceutically acceptable salt or derivative of claim 1, wherein at least one instance of $R^5$ and $R^{11}$ is not H.

13. A compound or pharmaceutically acceptable salt or derivative of claim 12, wherein at least one instance of $R^5$ and $R^{11}$ is H.

14. A compound or pharmaceutically acceptable salt or derivative of claim 1, wherein Y and Z are both $CR^{11}$, $R^5$ is H and (a) each instance of $R^{11}$ is independently selected from (C1-4)alkyl, (C1-4)alkyloxy, —O—$(CH_2)_n$—O—$(CH_2)_m CH_3$, CN and halogen, the (C1-4)alkyl, (C1-4)alkyloxy, and —O—$(CH_2)_n$—O—$(CH_2)_m CH_3$ groups being optionally substituted with one or more fluoros; or (b) one instance of $R^{11}$ is H and the other instance of $R^{11}$ is selected from ((C1-4)alkyl, (C1-4)alkyloxy, —O—$(CH_2)_n$—O—$(CH_2)_m CH_3$, CN and halogen, the (C1-4)alkyl, (C1-4)alkyloxy, and —O—$(CH_2)_n$—O—$(CH_2)_m CH_3$ groups being optionally substituted with one or more fluoros.

15. A compound or pharmaceutically acceptable salt or derivative of claim 14, wherein Y and Z are both $CR^{11}$, $R^5$ is H and (a) each instance of $R^{11}$ is independently selected from (C1-2)alkyl, (C1-2)alkyloxy, CN and halogen, the (C1-2)alkyl and (C1-2)alkyloxy groups being optionally substituted with one or more fluoros; or (b) one instance of $R^{11}$ is H and the other instance of $R^{11}$ is selected from (C1-2)alkyl, (C1-2)alkyloxy, CN and halogen, the (C1-2) alkyl and (C1-2)alkyloxy groups being optionally substituted with one or more fluoros.

16. A compound or pharmaceutically acceptable salt or derivative of claim 1, wherein Z is $CR^{11a}$ and $R^{11a}$ is selected from (C1-2)alkyl, (C1-2)alkyloxy, CN and halogen, the (C1-2)alkyl and (C1-2)alkyloxy groups being optionally substituted with one or more fluoros.

17. A compound or pharmaceutically acceptable salt or derivative of claim 1, wherein L is a linker —$CR^7R^8$— and $R^7$ and $R^8$ are both H.

18. A compound or pharmaceutically acceptable salt or derivative of claim 1, wherein A is:

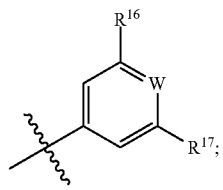

$R^{16}$ and $R^{17}$ are, independently selected from H, (C1-2) alkyl, (C1-2)alkyloxy, OH and halogen, the (C1-2)alkyl and (C1-2)alkyloxy groups being optionally substituted with one or more fluoros;
W is N; and
$R^{18}$ is selected from H, (C1-2)alkyl, (C1-2)alkyloxy, OH and halogen, the (C1-2)alkyl and (C1-2)alkyloxy groups being optionally substituted with one or more fluoros.

19. A compound or pharmaceutically acceptable salt or derivative of claim 1, wherein A is a benzimidazole, indazole, isoxazole, pyridine, indane, chromane or 7-aza-2,3-dihydro-1H-indene wherein A is optionally substituted as defined in any of the preceding claims.

20. A compound or pharmaceutically acceptable salt or derivative of claim 1, wherein one or more hydrogen atoms are replaced by $^2H$.

21. A compound selected from:
2-[3-(4-chloro-3-fluorophenyl)-1-ethyl-1H-1,2,4-triazol-5-yl]-N-(3-fluorobenzyl)acetamide;
2-[3-(4-chloro-3-fluorophenyl)-1-ethyl-1H-1,2,4-triazol-5-yl]-N-(3-methoxybenzyl)acetamide;
2-[3-(4-chloro-3-fluorophenyl)-1-ethyl-1H-1,2,4-triazol-5-yl]-N-[(2,6-dimethylpyridin-4-yl)methyl]acetamide;
2-[3-(4-chloro-3-fluorophenyl)-1-ethyl-1H-1,2,4-triazol-5-yl]-N-[(1H-indazol-7-yl)methyl]acetamide;
2-[3-(4-chloro-3-fluorophenyl)-1-ethyl-1H-1,2,4-triazol-5-yl]-N-(3,5-dichlorobenzyl)acetamide;
2-[3-(4-chloro-3-fluorophenyl)-1-ethyl-1H-1,2,4-triazol-5-yl]-N-(5-methyl-1,2-oxazol-3-yl)acetamide;
2-[3-(4-chloro-3-fluorophenyl)-1-ethyl-1H-1,2,4-triazol-5-yl]-N-[(1H-indazol-5-yl)methyl]acetamide;
2-[3-(4-chloro-3-fluorophenyl)-1-ethyl-1H-1,2,4-triazol-5-yl]-N-(pyrazin-2-yl)acetamide;
2-[3-(4-chloro-3-fluorophenyl)-1-ethyl-1H-1,2,4-triazol-5-yl]-N-[(2-oxo-2,3-dihydro-1H-benzo[d]imidazol-5-yl]methyl)acetamide;
2-[3-(4-chloro-3-fluorophenyl)-1-ethyl-1H-1,2,4-triazol-5-yl]-N-[(3-chloro-5-methylphenyl)methyl] acetamide;
2-[3-(4-chloro-3-fluorophenyl)-1-ethyl-1H-1,2,4-triazol-5-yl]-N-[(3-fluoro-5-methylphenyl)methyl] acetamide;
2-[3-(4-chloro-3-fluorophenyl)-1-ethyl-1H-1,2,4-triazol-5-yl]-N-[(3,5-dimethylphenyl)methyl] acetamide;
2-[3-(4-chloro-3-fluorophenyl)-1-ethyl-1H-1,2,4-triazol-5-yl]-N-[(2,3-difluorophenyl)methyl] acetamide;
2-[3-(4-chloro-3-fluorophenyl)-1-ethyl-1H-1,2,4-triazol-5-yl]-N-[(3-ethoxyphenyl)methyl] acetamide;
2-[3-(4-chloro-3-fluorophenyl)-1-ethyl-1H-1,2,4-triazol-5-yl]-N-[(3,5-dimethoxyphenyl)methyl] acetamide;
2-[3-(4-chloro-3-fluorophenyl)-1-ethyl-1H-1,2,4-triazol-5-yl]-N-[(4-methoxyphenyl)methyl] acetamide;
2-[3-(4-chloro-3-fluorophenyl)-1-ethyl-1H-1,2,4-triazol-5-yl]-N-[(6-methoxypyridin-3-yl)methyl] acetamide;
2-[3-(4-chloro-3-fluorophenyl)-1-methyl-1H-1,2,4-triazol-5-yl]-N-[(3,5-dichlorophenyl)methyl] acetamide;
2-[3-(4-chloro-3-fluorophenyl)-1-methyl-1H-1,2,4-triazol-5-yl]-N-[(3-methoxyphenyl)methyl] acetamide;
2-[3-(4-chloro-3-fluorophenyl)-1-methyl-1H-1,2,4-triazol-5-yl]-N-[(3-fluorophenyl)methyl] acetamide;
2-[3-(4-chloro-3-fluorophenyl)-1-methyl-1H-1,2,4-triazol-5-yl]-N-[(1H-indazol-5-yl)methyl] acetamide;
2-[3-(4-chloro-3-fluorophenyl)-1-(2-methoxyethyl)-1H-1,2,4-triazol-5-yl]-N-[(3,5-dichlorophenyl)methyl] acetamide;
2-[3-(4-chloro-3-fluorophenyl)-1-(2-hydroxyethyl)-1H-1,2,4-triazol-5-yl]-N-[(3,5-dichlorophenyl)methyl] acetamide;
2-[3-(4-chloro-3-fluorophenyl)-1-ethyl-1H-1,2,4-triazol-5-yl]-N-[(3-fluorophenyl)methyl] propanamide;
2-[3-(4-chloro-3-fluorophenyl)-1-methanesulfonyl-1H-1,2,4-triazol-5-yl]-N-[(3-fluorophenyl)methyl]acetamide;
2-[3-(4-chloro-3-fluorophenyl)-1-(cyclopropylmethyl)-1H-1,2,4-triazol-5-yl]-N-[(2,6-dimethylpyridin-4-yl) methyl]acetamide;

2-[3-(4-chloro-3-fluorophenyl)-1-(cyclopropylmethyl)-1H-1,2,4-triazol-5-yl]-N-[(1H-indazol-5-yl)methyl]acetamide;

N-[(3,5-dichlorophenyl)methyl]-2-{1-ethyl-3-[4-(trifluoromethoxy)phenyl]-1H-1,2,4-triazol-5-yl}acetamide;

2-[3-(4-chloro-3-methoxyphenyl)-1-ethyl-1H-1,2,4-triazol-5-yl]-N-[(3,5-dichlorophenyl)methyl] acetamide;

2-[3-(4-cyanophenyl)-1-ethyl-1H-1,2,4-triazol-5-yl]-N-[(3,5-dichlorophenyl)methyl]acetamide;

2-[3-(4-chloro-3-fluorophenyl)-1-ethyl-1H-1,2,4-triazol-5-yl]-N-[(2,6-dimethyl-1-oxidopyridin-4-yl)methyl]acetamide;

2-[3-(4-chloro-3-ethoxyphenyl)-1-ethyl-1H-1,2,4-triazol-5-yl]-N-[(3,5-dichlorophenyl)methyl]acetamide;

2-{3-[4-chloro-3-(2-methoxyethoxy)phenyl]-1-ethyl-1H-1,2,4-triazol-5-yl}-N-[(3,5-dichlorophenyl)methyl]acetamide;

2-[3-(4-chloro-3-isopropyloxyphenyl)-1-ethyl-1H-1,2,4-triazol-5-yl]-N-[(3,5-dichlorophenyl)methyl]acetamide;

2-[3-(4-chloro-3-isopropyloxyphenyl)-1-ethyl-1H-1,2,4-triazol-5-yl]-N-[(2,6-dimethylpyridin-4-yl)methyl]acetamide;

2-[3-(4-chloro-3-isopropyloxyphenyl)-1-ethyl-1H-1,2,4-triazol-5-yl]-N-[(1S)-2,3-dihydro-1H-inden-1-yl]acetamide;

2-[3-(4-chloro-3-isopropyloxyphenyl)-1-ethyl-1H-1,2,4-triazol-5-yl]-N-[(3-cyanophenyl)methyl]acetamide;

2-[3-(4-chloro-3-isopropyloxyphenyl)-1-ethyl-1H-1,2,4-triazol-5-yl]-N-[(1H-indazol-5-yl)methyl]acetamide;

2-[3-(4-chloro-3-isopropyloxyphenyl)-1-ethyl-1H-1,2,4-triazol-5-yl]-N-[(4S)-3,4-dihydro-2H-1-benzopyran-4-yl]acetamide;

N-[(4S)-6-chloro-3,4-dihydro-2H-1-benzopyran-4-yl]-2-[3-(4-chloro-3-isopropyloxyphenyl)-1-ethyl-1H-1,2,4-triazol-5-yl]acetamide;

N-[(4R)-6-chloro-3,4-dihydro-2H-1-benzopyran-4-yl]-2-[3-(4-chloro-3-isopropyloxyphenyl)-1-ethyl-1H-1,2,4-triazol-5-yl]acetamide;

2-[3(4-chloro-3-isopropyloxyphenyl)-1-ethyl-1H-1,2,4-triazol-5-yl]-N-[(5S)-5H,6H,7H-cyclopenta[b]pyridin-5-yl]acetamide;

2-[3-(4-chloro-3-isopropyloxyphenyl)-1-methyl-1H-1,2,4-triazol-5-yl]-N-[(3,5-dichlorophenyl)methyl]acetamide;

2-[3-(4-chloro-3-isopropyloxyphenyl)-1-methyl-1H-1,2,4-triazol-5-yl]-N-[(1S)-2,3-dihydro-1H-inden-1-yl]acetamide;

2-[3-(4-chloro-3-isopropyloxyphenyl)-1-methyl-1H-1,2,4-triazol-5-yl]-N-[(2,6-dimethylpyridin-4-yl)methyl]acetamide;

2-[3-(4-chloro-3-isopropyloxyphenyl)-1-methyl-1H-1,2,4-triazol-5-yl]-N-[(3-fluorophenyl)methyl]acetamide;

2-[3-(4-chloro-3-isopropyloxyphenyl)-1-methyl-1H-1,2,4-triazol-5-yl]-N-[(4R)-3,4-dihydro-2H-1-benzopyran-4-yl]acetamide;

2-[3-(4-chloro-3-isopropyloxyphenyl)-1-methyl-1H-1,2,4-triazol-5-yl]-N-[(4S)-3,4-dihydro-2H-1-benzopyran-4-yl]acetamide;

N-[(4R)-6-chloro-3,4-dihydro-2H-1-benzopyran-4-yl]-2-[3-(4-chloro-3-isopropyloxyphenyl)-1-methyl-1H-1,2,4-triazol-5-yl]acetamide;

2-[3-(4-chloro-3-fluorophenyl)-1-ethyl-1H-1,2,4-triazol-5-yl]-N-[(3,5-dichlorophenyl)methyl]-2,2-difluoroacetamide;

2-[3-(4-chloro-3-fluorophenyl)-1-ethyl-1H-1,2,4-triazol-5-yl]-N-[(2,6-dimethylpyridin-4-yl)methyl]-2,2-difluoroacetamide;

2-[3-(4-chloro-3-fluorophenyl)-1-ethyl-1H-1,2,4-triazol-5-yl]-2,2-difluoro-N-[(2-methyl-1H-1,3-benzimidazol-5-yl)methyl]acetamide;

N-[(4S)-6-chloro-3,4-dihydro-2H-1-benzopyran-4-yl]-2-[3-(4-chloro-3-fluorophenyl)-1-ethyl-1H-1,2,4-triazol-5-yl]-2,2-difluoroacetamide;

methyl 2-[3-(4-chloro-3-fluorophenyl)-5-({[(3,5-dichlorophenyl)methyl]carbamoyl}methyl)-1H-1,2,4-triazol-1-yl]acetate;

methyl 3-[3-(4-chloro-3-fluorophenyl)-5-({[(3,5-dichlorophenyl)methyl]carbamoyl}methyl)-1H-1,2,4-triazol-1-yl]propanoate;

ethyl 4-[3-(4-chloro-3-fluorophenyl)-5-({[(3,5-dichlorophenyl)methyl]carbamoyl}methyl)-1H-1,2,4-triazol-1-yl]butanoate;

2-[3-(4-chloro-3-fluorophenyl)-5-({[(3,5-dichlorophenyl)methyl] carbamoyl}methyl)-1H-1,2,4-triazol-1-yl]acetic acid;

3-[3-(4-chloro-3-fluorophenyl)-5-({[(3,5-dichlorophenyl)methyl] carbamoyl}methyl)-1H-1,2,4-triazol-1-yl]propanoic acid;

4-[3-(4-chloro-3-fluorophenyl)-5-({[(3,5-dichlorophenyl)methyl] carbamoyl}methyl)-1H-1,2,4-triazol-1-yl]butanoic acid;

2-[3-(4-chloro-3-fluorophenyl)-1-ethyl-1H-1,2,4-triazol-5-yl]-N-[(1R)-2,3-dihydro-1H-inden-1-yl]acetamide;

2-[3-(4-chloro-3-fluorophenyl)-1-ethyl-1H-1,2,4-triazol-5-yl]-N-[(1S)-2,3-dihydro-1H-inden-1-yl]acetamide;

2-[3-(4-chloro-3-fluorophenyl)-1-ethyl-1H-1,2,4-triazol-5-yl]-N-[(1R,2S)-2-hydroxy-2,3-dihydro-1H-inden-1-yl]acetamide;

2-[3-(4-chloro-3-fluorophenyl)-1-ethyl-1H-1,2,4-triazol-5-yl]-N-[(1S,2R)-2-hydroxy-2,3-dihydro-1H-inden-1-yl]acetamide;

2-[3-(4-chloro-3-fluorophenyl)-1-ethyl-1H-1,2,4-triazol-5-yl]-N-[(1S,2S)-2-hydroxy-2,3-dihydro-1H-inden-1-yl]acetamide;

2-[3-(4-chloro-3-fluorophenyl)-1-ethyl-1H-1,2,4-triazol-5-yl]-N-[(1R,2R)-2-hydroxy-2,3-dihydro-1H-inden-1-yl]acetamide;

2-[3-(4-chloro-3-fluorophenyl)-1-ethyl-1H-1,2,4-triazol-5-yl]-N-(2,3-dihydro-1H-inden-2-yl)acetamide;

2-[3-(4-chloro-3-fluorophenyl)-1-ethyl-1H-1,2,4-triazol-5-yl]-N-[(1S,3R)-3-hydroxy-2,3-dihydro-1H-inden-1-yl]acetamide;

2-[3-(4-chloro-3-fluorophenyl)-1-ethyl-1H-1,2,4-triazol-5-yl]-N-[(1S,3S)-3-hydroxy-2,3-dihydro-1H-inden-1-yl]acetamide;

2-[3-(4-chloro-3-fluorophenyl)-1-ethyl-1H-1,2,4-triazol-5-yl]-N-[(1R,3R)-3-hydroxy-2,3-dihydro-1H-inden-1-yl]acetamide;

2-[3-(4-chloro-3-fluorophenyl)-1-ethyl-1H-1,2,4-triazol-5-yl]-N-[(1R,3S)-3-hydroxy-2,3-dihydro-1H-inden-1-yl]acetamide;

2-[3-(4-chloro-3-fluorophenyl)-1-(cyclopropylmethyl)-1H-1,2,4-triazol-5-yl]-N-[(5S)-5H,6H,7H-cyclopenta[b]pyridin-5-yl]acetamide;

2-[3-(4-chloro-3-fluorophenyl)-1-(cyclopropylmethyl)-1H-1,2,4-triazol-5-yl]-N-[(1S)-2,3-dihydro-1H-inden-1-yl]acetamide;

2-[3-(4-chloro-3-fluorophenyl)-1-ethyl-1H-1,2,4-triazol-5-yl]-N-[(2-oxo-2,3-dihydro-1,3-benzoxazol-5-yl)methyl]acetamide;

2-[3-(4-chloro-3-fluorophenyl)-1-ethyl-1H-1,2,4-triazol-5-yl]-N-[(4S)-3,4-dihydro-2H-1-benzopyran-4-yl]acetamide;

2-[3-(4-chloro-3-fluorophenyl)-1-ethyl-1H-1,2,4-triazol-5-yl]-N-[(4R)-3,4-dihydro-2H-1-benzopyran-4-yl]acetamide;

N-[(4S)-6-chloro-3,4-dihydro-2H-1-benzopyran-4-yl]-2-[3-(4-chloro-3-fluorophenyl)-1-ethyl-1H-1,2,4-triazol-5-yl]acetamide;

N-[(4R)-6-chloro-3,4-dihydro-2H-1-benzopyran-4-yl]-2-[3-(4-chloro-3-fluorophenyl)-1-ethyl-1H-1,2,4-triazol-5-yl]acetamide;

N-[(4S)-6-chloro-3,4-dihydro-2H-1-benzopyran-4-yl]-2-[3-(4-chloro-3-fluorophenyl)-1-(cyclopropylmethyl)-1H-1,2,4-triazol-5-yl]acetamide;

2-[3-(4-chloro-3-fluorophenyl)-1-ethyl-1H-1,2,4-triazol-5-yl]-N-{pyrazolo[1,5-a]pyridin-3-yl}acetamide;

2-[3-(4-chloro-3-fluorophenyl)-1-ethyl-1H-1,2,4-triazol-5-yl]-N-[(2,6-diethylpyridin-4-yl)methyl]acetamide;

2-[3-(4-chloro-3-fluorophenyl)-1-ethyl-1H-1,2,4-triazol-5-yl]-N-[(4,6-dimethylpyridin-2-yl)methyl]acetamide;

2-[3-(4-chloro-3-isopropyloxyphenyl)-1-ethyl-1H-1,2,4-triazol-5-yl]-N-[(4,6-dimethylpyridin-2-yl)methyl]acetamide;

2-[3-(4-chloro-3-fluorophenyl)-1-ethyl-1H-1,2,4-triazol-5-yl]-N-{[2-(trifluoromethyl)pyridin-4-yl]methyl}acetamide;

2-[3-(4-chloro-3-fluorophenyl)-1-ethyl-1H-1,2,4-triazol-5-yl]-N-{[2-(difluoromethyl)pyridin-4-yl]methyl}acetamide;

N-{[2,6-bis(difluoromethyl)pyridin-4-yl]methyl}-2-[3-(4-chloro-3-fluorophenyl)-1-ethyl-1H-1,2,4-triazol-5-yl]acetamide;

2-[3-(4-chloro-3-fluorophenyl)-1-ethyl-1H-1,2,4-triazol-5-yl]-N-[1-(2,6-dimethylpyridin-4-yl)cyclopropyl]acetamide;

2-[3-(4-chloro-3-fluorophenyl)-1-(cyclopropylmethyl)-1H-1,2,4-triazol-5-yl]-N-[1-(2,6-dimethylpyridin-4-yl)cyclopropyl]acetamide;

2-[3-(4-chloro-3-fluorophenyl)-1-ethyl-1H-1,2,4-triazol-5-yl]-N-{[2,6-di($^{2}H_{3}$)methylpyridin-4-yl]methyl}acetamide;

2-[3-(4-chloro-3-fluorophenyl)-1-ethyl-1H-1,2,4-triazol-5-yl]-N-{[2,6-di($^{2}H_{3}$)methylpyridin-4-yl]methyl}-2,2-difluoroacetamide;

2-[3-(4-chloro-3-fluorophenyl)-1-ethyl-1H-1,2,4-triazol-5-yl]-N-[(2,6-dimethylpyridin-4-yl)($^{2}H_{2}$)methyl]($^{2}H_{2}$)acetamide;

and pharmaceutically acceptable salts thereof.

22. A pharmaceutical composition comprising a compound or a pharmaceutically acceptable salt or derivative as defined in claim 1, and a pharmaceutically acceptable excipient.

23. A compound or pharmaceutically acceptable salt or derivative of claim 6, wherein $R^5$ is selected from H, (C1-2)alkyl, (C1-2)alkyloxy, CN and halogen, the (C1-2) alkyl and (C1-2)alkyloxy groups being optionally substituted with one or more fluoros.

24. A compound or pharmaceutically acceptable salt or derivative of claim 11, wherein each $R^{11}$, when present, is independently selected from H, (C1-2)alkyl, (C1-2)alkyloxy, CN and halogen, the (C1-2)alkyl and (C1-2)alkyloxy groups being optionally substituted with one or more fluoros.

* * * * *